(12) United States Patent
Cronin et al.

(10) Patent No.: US 11,098,368 B2
(45) Date of Patent: Aug. 24, 2021

(54) ALK AND NTRK1 FUSION MOLECULES AND USES THEREOF

(71) Applicant: FOUNDATION MEDICINE, INC., Cambridge, MA (US)

(72) Inventors: Maureen T. Cronin, Boston, MA (US); Doron Lipson, Cambridge, MA (US); Roman Yelensky, Newton, MA (US)

(73) Assignee: FOUNDATION MEDICINE, INC., Cambridge, MA (US)

( * ) Notice: Subject to any disclaimer, the term of this patent is extended or adjusted under 35 U.S.C. 154(b) by 0 days.

(21) Appl. No.: 15/978,701

(22) Filed: May 14, 2018

(65) Prior Publication Data

US 2018/0346992 A1 Dec. 6, 2018

Related U.S. Application Data

(60) Division of application No. 14/257,607, filed on Apr. 21, 2014, now Pat. No. 10,000,814, which is a continuation of application No. PCT/US2012/061211, filed on Oct. 19, 2012.

(60) Provisional application No. 61/550,327, filed on Oct. 21, 2011.

(51) Int. Cl.
| | |
|---|---|
| *C12Q 1/6886* | (2018.01) |
| *C07K 14/47* | (2006.01) |
| *C12N 9/12* | (2006.01) |
| *A61K 31/4545* | (2006.01) |
| *C07K 16/40* | (2006.01) |
| *G01N 33/50* | (2006.01) |
| *G01N 33/574* | (2006.01) |
| *A61K 38/00* | (2006.01) |

(52) U.S. Cl.
CPC ........ *C12Q 1/6886* (2013.01); *A61K 31/4545* (2013.01); *C07K 14/4738* (2013.01); *C07K 14/4748* (2013.01); *C07K 16/40* (2013.01); *C12N 9/12* (2013.01); *C12N 9/1205* (2013.01); *G01N 33/5011* (2013.01); *G01N 33/57496* (2013.01); *A61K 38/00* (2013.01); *C12Y 207/10001* (2013.01)

(58) Field of Classification Search
CPC ............... A61K 31/4545; A61K 38/00; C07K 14/4738; C07K 14/4748; C07K 16/40; C12Q 1/6886; C12Y 207/10001; G01N 33/5011; G01N 33/57496; C12N 9/12; C12N 9/1205; A61P 35/00; A61P 35/04; A61P 43/00
See application file for complete search history.

(56) References Cited

U.S. PATENT DOCUMENTS

| | | | |
|---|---|---|---|
| 8,377,921 B2 * | 2/2013 | Michellys | C07D 417/12 514/210.18 |
| 10,000,814 B2 | 6/2018 | Cronin et al. | |
| 2002/0197679 A1 | 12/2002 | Tang et al. | |
| 2005/0287541 A1 | 12/2005 | Nakagawara et al. | |
| 2007/0010657 A1 | 1/2007 | Klocke et al. | |
| 2007/0059710 A1 | 3/2007 | Luke et al. | |
| 2007/0248605 A1 | 10/2007 | Hestir et al. | |
| 2008/0051462 A1 | 2/2008 | Fritz et al. | |
| 2008/0131375 A1 | 6/2008 | Gordon et al. | |
| 2008/0171689 A1 | 7/2008 | Williams et al. | |
| 2008/0226664 A1 | 9/2008 | Old et al. | |
| 2009/0130101 A1 | 5/2009 | Cohen | |
| 2009/0156475 A1 | 6/2009 | Rikova et al. | |
| 2009/0209496 A1 | 8/2009 | Chaplin et al. | |
| 2011/0118298 A1 | 5/2011 | Fritz et al. | |
| 2011/0150893 A1 | 6/2011 | Cho et al. | |
| 2012/0039805 A1 | 2/2012 | Lisanti et al. | |
| 2012/0208706 A1 | 8/2012 | Downing et al. | |
| 2013/0096021 A1 | 4/2013 | Chinnaiyan et al. | |
| 2014/0336236 A1 | 11/2014 | Cronin et al. | |
| 2015/0073036 A1 | 3/2015 | Hawryluk et al. | |
| 2015/0366866 A1 | 12/2015 | Ali et al. | |
| 2016/0009785 A1 | 1/2016 | Lipson et al. | |
| 2016/0010068 A1 | 1/2016 | Bastian et al. | |

FOREIGN PATENT DOCUMENTS

| | | |
|---|---|---|
| EP | 0698096 B1 | 2/1996 |
| EP | 0698096 B1 | 3/1997 |
| EP | 2057465 A2 | 5/2009 |
| WO | 9426889 A2 | 11/1994 |
| WO | 01027081 A1 | 4/2001 |
| WO | 03031568 A2 | 4/2003 |
| WO | 200413099 A1 | 2/2004 |
| WO | 2007060402 A1 | 5/2007 |
| WO | 2008021290 A2 | 2/2008 |
| WO | 2010081817 A1 | 7/2010 |
| WO | 2012092426 A1 | 7/2012 |
| WO | 2013059740 A1 | 4/2013 |
| WO | 2013076186 A1 | 5/2013 |
| WO | 2013087716 A2 | 6/2013 |
| WO | 2014018673 A2 | 1/2014 |
| WO | 2014036387 A2 | 3/2014 |
| WO | 2014071358 A2 | 5/2014 |
| WO | 2014071419 A2 | 5/2014 |
| WO | 2014113729 A2 | 7/2014 |
| WO | 2014130975 A1 | 8/2014 |

OTHER PUBLICATIONS

National Center for Biotechnology Information. PubChem Database. Ceritinib, CID=57379345, https://pubchem.ncbi.nlm.nih.gov/compound/Ceritinib (Create: Jul. 16, 2012; Accessed on Jul. 21, 2019) (Year: 2012).*

(Continued)

*Primary Examiner* — My-Chau T. Tran
(74) *Attorney, Agent, or Firm* — Morrison & Foerster LLP

(57) ABSTRACT

Novel ALK and NTRK1 fusion molecules and uses are disclosed.

30 Claims, 17 Drawing Sheets

Specification includes a Sequence Listing.

(56) References Cited

OTHER PUBLICATIONS

Wang et al., "Fusion of dynactin 1 to anaplastic lymphoma kinase in inflammatory myofibroblastic tumor", 2012, Human Pathology, 43(11), pp. 2047-2052. (Year: 2012).*
Wiesner et al., "Kinase fusions are frequent in Spitz tumours and spitzoid melanomas", 2014, Nature Communications, 5(3116), pp. 1-9 (DOI: 10.1038/ncomms4116) (Year: 2014).*
Vendrell et al., "Detection of known and novel ALK fusion transcripts in lung cancer patients using next-generation sequencing approaches", 2017, Sci. Rep., 7(12510), pp. 1-11. (https://doi.org/10.1038/s41598-017-12679-8). (Year: 2017).*
Weiss, GJ et al., "Phase I study of the safety, tolerability and pharmacokinetics of PHA-848125AC, a dual tropomyosin receptor kinase A and cyclin-dependent kinase inhibitor, in patients with advanced solid malignancies", Invest New Drugs, 30(6):2334-2343 ePub Dec. 2011, Dec. 2012.
Williams et al., "Oncogenic FGFR3 gene fusions in bladder cancer" Human Molecular Genetics, 22(4):795-803 (2013).
Wong et al. "Evaluation of a Congenital Infantile Fibrosarcoma by Comprehensive Genomic Profiling Reveals an LMNA NTRK1 Gene Fusion Responsive to Crizotinib" J Natl Cancer Inst (2016) vol. 108, No. 1, djv307, pp. 1-3.
Written Opinion for International Application No. PCT/US2013/068604 dated May 5, 2015.
Wu et al. "Identification of Targetable FGFR Gene Fusions in Diverse Cancers" Cancer Discovery (Jun. 2013) pp. 636-647.
Yoon et al. "Enhanced epidermal growth factor receptor activation in human cholangiocarcinoma cells" Journal of Hepatology (2004) pp. 808-814.
Albanese, C. et al., "Dual targeting of CDK and tropomyosin receptor kinase families by the oral inhibitor PHA-848125, an agent with broad-spectrum antitumor efficacy", Mol Cancer Ther 9(8):2243-54, Aug. 3, 2010.
Altorki et al. "Phase II Proof-of-Concept Study of Pazopanib Monotherapy in Treatment—Naive Patience With State I/II Resectable Non-Small-Cell Lung Cancer" Journal of Clinical Oncology (2010) vol. 28, No. 19, pp. 3131-3137.
Amatu et al. "NTRK gene fusions as novel targets of cancer therapy across multiple tumour types" ESMO Open (2016) vol. 1, e000023, pp. 1-9.
Avet-Loiseau et al. "High Incidence of Translocations t(11;14)(q13;q32) and t(4;14)(p16;q32) in Patients with Plasma Cell Malignancies" Cancer Research (1998) vol. 58, pp. 5640-5645.
Bai et al. "GP369, an FGFR2-IIIb-Specific Antibody, Exhibits Potent antitumor Activity against Human Cancers Driven by Activated FGFR2 Signaling" Cancer Research (2010) vol. 70 No. 19.
Brave et al. "Assessing the Activity of Cediranib, a VEGFR-2/3 Tyrosine Kinase Inhibitor, against VEGFR-1 and Members of the Structurally Related PDGFR Family" Molecular Cancer Therapeutics (2011) vol. 10 No. 5 pp. 861-873.
Byron et al. "Inhibition of Activated Fibroblast Growth Factor Receptor 2 in Endometrial Cancer Cells Induces Cell Death Despite PTEN Abrogation" Cancer Research (2008) vol. 68 No. 17.
Camidge et al. Optimizing the detection of lung cancer patients harboring anaplastic lymphoma kinase (ALK) gene rearrangements potentially suitable for ALK inhibitor treatment. Clin Cancer Res Nov. 14, 2010 vol. 16 No. 22 pp. 5581-5590. Especially p. 5586 col. 2 para 2-3.
Caneiro et al. "FGFR3-TACC3: A novel gene fusion in cervical cancer" Gynecologic Oncology Reports (2015), vol. 13, pp. 53-56.
Capelletti et al. "Identification of Recurrent FGFR3-TACC3 Fusion Oncogenes from Lung Adenocarcinoma" Clin Cancer Res (2014) vol. 20, pp. 6551-6558.
Chen et al. "FGFR3 as a therapeutic target of the small molecule inhibitor PKC412 in hematopoietic malignancies" Oncogene (2005) vol. 24, pp. 8259-8267.
Chiorean et al, "Imatinib Mesylate (STI-571), a c-Abl Kinase Inhibitor, Indirectly Blocks Receptor Tyrosine Kinase Activation and Induces Apoptosis in a Human Cholangiocarcinoma Cell Line" Gastroenterology (2003) vol. 124 No. 4.
Cho et al. "Enhanced Expression of Keratinocyte Growth Factor and Its Receptor Correlates with Venous Invasion in Pancreatic Cancer" The American Journal of Pathology (2007) vol. 170 No. 6.
ClinicalTrials.Gov Identifier No. NCT02568267, "Basket Study of Entrectinib (RXDX-101) for the Treatment of Patients With Solid Tumors Harboring NTRK 1/2/3/ (Trk A/B/C), ROS1, or ALK Gene Rearrangements (Fusions) (STARTRK-2)" Last Updated : Jan. 3, 2017; https://clinicaltrials.gov/ct2/show/NCT02568267?term=NTRK1+fusion+lung&rank=1; Retrieved Jan. 4, 2017.
ClinicalTrials.Gov Identifier No. NCT0257643.1, "Study of LOXO-101 in Subjects With NTRK Fusion Positive Solid Tumors (NAVIGATE)" Last Updated: Nov. 16, 2016; https://clinicaltrials.gov/ct2/show/NCT02576431?term=NTRK1+fusion+lung&rank=2; Retrieved Jan. 4, 2017.
Cohen, Roger B. et al., "A phase I dose-escalation study of danusertib (PHA-739358) administered as a 24-hour infusion with and without granulocyte colony-stimulating factor in a 14-day cycle in patients with advanced solid tumors", Clin Cancer Res 15(21):6694-701, ePub Oct. 13, 2009, Nov. 1, 2009.
Cole et al. "Inhibition of FGFR2 and FGFR1 increases cisplatin sensitivity in ovarian cancer" Cancer Biology & Therapy (2010) vol. 10 No. 5 pp. 495-504.
Cortes et al. "A Pivotal PhaM 2 Trial of Ponatinib in Patients with Chronic Myeloid Leukemia (CML) and Philadelphia Chromosome-Positive Acute Lymphoblastic Leukemia (Ph+ALL) ResIIItIInt or Intole111nt to DasatInIb or Nilotinib, or with the T315I BCR-ABL Mutation: 1Z-Month Follow-up of the Pace Trial" ASH Annual Meeting and Exposition (Dec. 9, 2012) Abstract No. 163.
Costa et al. "FGFR3-TACC3 fusion in solid tumors: mini review" Oncotarget (2016) vol. 7, No. 34, pp. 55924-55938.
Degrassi, A. et al., "Efficacy of PHA-848125, a cyclin-dependent kinase inhibitor, on the K-Ras(G12D) LA2 lung adenocarcinoma transgenic mouse model: evaluation by multimodality imaging", Mol Cancer Ther 9(3):673-81, Mar. 9, 2010.
Doebele et al. "An Oncogenic NTRK Fusion in a Patient with Soft-Tissue Sarcoma with Response to the Tropomyosin-Related Kinase Inhibitor LOXO-101" Cancer Discovery (2015) vol. 5, pp. 1049-1057.
Doebele et al., "NTRK1 Gene Fusions as a Novel Oncogene Target in Lung Cancer", 2013 ASCO Annual Meeting; Abstract No. 8023; Poster (May 31-Jun. 4, 2013).
Garcia-Mayoral et al. "The Structure of the C-Terminal KH Domains of KSRP Reveals a Noncanonical Motif Important for mRNA Degradation" Structure (2007) vol. 15 pp. 485-498.
Gartside et al. "Loss-of-Function Fibroblast Growth Factor Receptor-2 Mutations in Melanoma" Molecular Cancer Research (2009) vol. 7 No. 1 pp. 41-54.
GenBank Accession No. NM_000141 accessed Nov. 19, 2015 from http://www.ncbi.nlm.nih.gov/nuccore/189083823.
GenBank Accession No. NM_001012331 accessed Nov. 19, 2015 from <http://www.ncbi.nlm.nih.gov/nuccore/NM_001012331.1>.
Genbank Accession No. NM_001080512 accessed Nov. 19, 2015 from http://www.ncbi.nlm.nih.gov/nuccore/NM_001080512.2.
GenBank Accession No. NM_001127211 accessed Nov. 19, 2015 from http://www.ncbi.nlm.nih.gov/nuccore/385198090.
GenBank Accession No. NM_001144915 accessed on Nov. 17, 2015 from http://www.ncbi.nlm.nih.gov/nuccore/NM_001144915.1.
GenBank Accession No. NM_003787 accessed Nov. 19, 2015 from http://www.ncbi.nlm.nih.gov/nuccore/NM_003787.
GenBank Accession No. NM_004562 accessed Nov. 19, 2015 from http://www.ncbi.nlm.nih.gov/nuccore/NM_004562.2.
GenBank Accession No. NM_006342 accessed Nov. 19, 2015 from http://www.ncbi.nlm.nih.gov/nuccore/NM_006342.
GenBank Accession No. NM_022494 accessed Nov. 19, 2015 from http://www.ncbi.nlm.nih.gov/nuccore/NM_022494.2.
GenBank Accession No. NP_001012331 accessed Nov. 19, 2015 from http://www.ncbi.nlm.nih.gov/protein/59889558.
Gergely et al. "The TACC domain identifies a family of centrosomal proteins that can interact with microtubules" Proc Natl Acad Sci. (2000) vol. 97, pp. 14352-14357.

(56) References Cited

OTHER PUBLICATIONS

Gozgit et al "Ponatinib (AB24534), a Multitargeted Pan-FGFR Inhibitor with Activity in Multiple FGFR-Amplified or Mutated Cancer Models" Molecular Cancer Therapeutics (2012) vol. 11 No. 3 pp. 690-699.

Greco A, et al. "Characterization of the NTRK1 genomic region involved in chromosomal rearrangements generating TRK oncogenes." Genomics (1993) 18(2):397-400.

Greco A, et al. "TRK-T1 is a novel oncogene formed by the fusion of TPR and TRK genes in human papillary thyroid carcinomas." Oncogene (1992) 7(2):237-42.

Greco et al. Rearrangements of NTRK1 gene in papillary thyroid carcinoma. Mol Cell Endrocrinol May 28, 2010 vol. 321 No. 1 pp. 44-49. Especially p. 46 col. 2 para 3.

Greco, A. et al., "The DNA rearrangement that generates the TRK-T3 oncogene involves a novel gene on chromosome 3 whose product has a potential coiled-coil domain", Mol Cell Biol 15(11):6118-27, Nov. 1995.

Han, SY et al., "Evaluation of a multi-kinase inhibitor KRC-108 as an anti-tumor agent in vitro and in vivo", Invest New Drugs 30(2):518-23, ePub Nov. 16, 2010, Apr. 2012.

Huehne K, et al. "Novel missense, insertion and deletion mutations in the neurotrophic tyrosine kinase receptor type 1 gene (NTRK1) associated with congenital insensitivity to pain with anhidrosis." Neuromuscul Disord (2008) 18(2):159-66.

Huether et al.: "Sorafenib alone or as combination therapy for growth control of cholangiocarcinoma", Biochemical Pharmacology, Elsevier, US, vol. 73, No. 9, Mar. 24, 2007 (Mar. 24, 2007), pp. 1308-1317.

Indo Y, et al. "Structure and organization of the human TRKA gene encoding a high affinity receptor for nerve growth factor." Jpn J Hum Genet (1997) 42(2):343-51.

International Preliminary Report on Patentability and Written Opinion for International Application No. PCT/US2012/061211 dated Apr. 22, 2014.

International Preliminary Report on Patentability for International Application No. PCT/US2013/068604 dated May 5, 2015.

International Preliminary Report on Patentability from PCT/US14/12136 dated Mar. 18, 2015.

International Search Report and Written Opinion for International Application No. PCT/US2013/068457 dated Jul. 11, 2014.

International Search Report and Written Opinion for PCT/US2014/012136 dated Jul. 16, 2014.

International Search Report for International Application No. PCT/US2012/061211 dated Feb. 5, 2013.

International Search Report for International Application No. PCT/US2012/061211 dated May 2, 2013.

International Search Report for International Application No. PCT/US2013/068604 dated Nov. 7, 2014.

Iyer, R. et al., "Lestaurtinib enhances the antitumor efficacy of chemotherapy in murine xenograft models of neuroblastoma", Clin Cancer Res 16(5):1478-85, ePub Feb. 23, 2010, Mar. 1, 2010.

Keats et al. "In multiple myeloma, t(4;14)(p16;q32) is an adverse prognostic factor irrespective of FGFR3 expression" Blood (2003) vol. 101, No. 4, pp. 1520-1529.

Keegan et al. "Isolation of an additional member of the fibroblast growth factor receptor family, FGFR-3" Proc Natl Acad Sci. (1991) vol. 88, No. 4, pp. 1095-1099.

Kelleher et al. The emerging pathogenic and therapeutic importance of the anaplastic lymphoma kinase gene. Eur J Cancer Sep. 2010 vol. 46 No. 13 pp. 2357-2368. Especially p. 2365 table 6.

Ko et al. "Phase II study of telatinib (T) in combination with capecitabine (X) and cisplatin (P) as first-line treatment in patients (pts) with advanced cancer of the stomach (G) or gastro-esophageal junction (GEJ)." Journal of Clinical Oncology ASCO Annual Meeting Abstracts, vol. 28 No. 15; May 20 supplement (2010).

Landis et al "Cancer Statistics, 1998" Ca Cancer J Clin (1998) vol. 48 No. 1 pp. 6-29.

Lih et al. "N of 2 Responders With LMNA-NTRK1" J Natl Cancer Inst (2016) vol. 108, No. 1, djv376, pp. 1-2.

Lin et al., "Exon Array Profiling Detects EML4-ALK Fusion in Breast, Colorectal, and Non-Small Cell Lung Cancers" Mol Cancer Research (2009) vol. 7, No. 9, pp. 1466-1476.

Lorenzi et al. "FRAG1, a gene that potently activates fibroblast growth factor receptor by C-terminal fusion through chromosomal rearrangement" Proc. Natl. Acad. Sci. USA (1996) vol. 93 pp. 8956-8961.

Lorenzi et al. "Ligand-independent activation of fibroblast growth factor receptor-2 by carboxl terminal alterations" Oncogene (1997) vol. 15 pp. 817-826.

Marchetti et al., "Frequent Mutations in the Neurotrophic Tyrosine Receptor Kinase Gene Family in Large Cell Neuroendocrine Carcinoma of the Lung" Human Mutation (2008) vol. 29, No. 5, pp. 609-616.

Mardy et al., Congenital insensitivity to pain with anhidrosis: Novel mutations in the TRKA (NTRK1) gene encoding a high-affinity receptor for nerve growth factor, 1999, Am. J. Hum. Genet., 64, pp. 1570-1579.

Martin-Zanca D, et al. "A human oncogene formed by the fusion of truncated tropomyosin and protein tyrosine kinase sequences." Nature (1986) 319(6056):743-8.

Matsumoto et al. "FGFR2 gene amplification and clinicopathological features in gastric cancer" British Journal of Cancer (2012) vol. 106 No. 4 pp. 727-732.

McKay et al. "PP58 Novel potential therapeutic targets for cholangiocarcinoma identified by array comparitive hybridization" European Journal of Cancer (2009) vol. 7 No. 4.

Meulenbeld, Hielke J. et al., "Danusertib, an aurora kinase inhibitor," Expert Opinion Investigative Drugs. Mar. 2012, 21(3), pp. 383-393.

Miura Y, et al. "Mutation and polymorphism analysis of the TRKA (NTRK1) gene encoding a high-affinity receptor for nerve growth factor in congenital insensitivity to pain with anhidrosis (CIPA) families." Hum Genet (2000) 106(1):116-24.

Monk et al. "Phase II, Open-Label Study of Pazopanib or Lapatinib Monotherapy Compared With Pazopanib Plus Lapatinib Combination Therapy in Patients With Advanced and Recurrent Cervical Cancer" Journal of Clinical Oncology (2010) vol. 28, No. 22, pp. 3562-3569.

Muller-Tidow et al., Identification of Metastasis-Associated Receptor Tyrosine Kinases in Non-Small Cell Lung Cancer, 2005, Cancer Res., vol. 65, No. 5 pp. 1778-1782.

Narong and Leelawat "Basic fibroblast growth factor induces cholangiocarcinoma cell migration via activation of the MEK1/2 pathway" Oncology Letters (2011) pp. 821-825.

Notification of Transmittal of the International Search Report and Written Opinion of the International Searching Authority from corresponding PCT/US2013/068457 dated Jul. 11, 2014.

Patel et al "Cholangiocarcinoma—controversies and challenges" Nat Rev Gastroenterol Hepatol (2011) vol. 8 No. 4.

Patel et al. "Worldwide trends in mortality from biliary tract malignancies" BMC Cancer (2002) vol. 2 No. 10.

Perez-Pinera P, et al. "The Trk tyrosine kinase inhibitor K252a regulates growth of lung adenocarcinomas." Mol Cell Biochem (2007) 295(1-2):19-26.

Powers et al. "Fibroblast growth factors, their receptors and signaling" Endocrine-Related Cancer (2000) vol. 7 pp. 165-197.

Rao, R. et al., "Heat shock protein 90 inhibition depletes TrkA levels and signaling in human acute leukemia cells", Mol Cancer Ther 9(8):2232-42, ePub Jul. 27, 2010, Aug. 2010.

Reck et al. "A phase II double-blind study to investigate efficacy and safety of two doses of the triple angiokinase inhibitor BIBF 1120 in patients with relapsed advanced non-small-cell lung cancer" Annals of Oncology (2011) vol. 22, pp. 1374-1381.

Richelda et al. "A Novel Chromosomal Translocation t(4; 14)(p16. 3; q32) in Multiple Myeloma Involves the Fibroblast Growth Factor Receptor 3 Gene" Blood (1997) vol. 90, No. 10, pp. 4062-4070.

Santra et al. "A sibset of multiple myeloma harboring the t(4;14)(p16;q32) translocation lacks FGFR3 expression but maintains an IGH/MMSET fusion transcript" Blood (2003) vol. 101, No. 6, pp. 2374-2376.

(56) References Cited

OTHER PUBLICATIONS

Sartore-Bianchi et al. "Sensitivity to Entrectinib Associated With a Novel LMNA-NTRK1 Gene Fusion in Metastatic Colorectal Cancer" J Natl Cancer Inst (2016) vol. 108, No. 1, djv306, pp. 1-4.
Schneider et al., "The transforming acidic coiled coil 3 protein is essential for spindle-dependent chromosome alignment and mitotic survival" The Journal of Biological Chemistry, 282(40):29273-29283 (2007).
Singh et al "Transforming Fusions of FGFR and TACC Genes in Human Glioblastoma" Science (2012) vol. 337(6099) pp. 1231-1235.
Stewart et al. "Correlation of TACC3, FGFR3, MMSET and p21 expression with the t(4;14)(p16.3;q32) in multiple myeloma" British Journal of Haematology (2004) vol. 126, pp. 72-76.
Tacconelli, A. et al., "TrkA alternative splicing: a regulated tumor-promoting switch in human neuroblastoma", Cancer Cell 6(4):347-60, Oct. 2004.
Takeuchi et al. Multiplex reverse transcription—PCR screening for EML4-ALK fusion transcripts. Clin Cancer Res Oct. 15, 2008 vol. 14 No. 20 pp. 6618-6624. Especially p. 6619 col. 1 para.
Teixeira et al., "Recurrent Fusion Oncogenes in Carcinomas" Critical Reviews in Oncogenesis, 12(3-4):257-271 (2006).
Thress, K. et al., "Identification and preclinical characterization of AZ-23, a novel, selective, and orally bioavailable inhibitor of the Trk kinase pathway", Mol Cancer Ther 8(7):1818-27, ePub Jun. 9, 2009, Jul. 2009.
Toyokawa et al. "Co-expression of keratinocyte growth factor and K-sam is an independent prognostic factor in gastric carcinoma" Oncology Reports (2009) vol. 21 pp. 875-880.
Turner and Grose "Fibroblast growth factor signalling: from development to cancer" Nat Rev Cancer (2010) vol. 10 No. 2 pp. 116-129.
Turner et al "Fibroblast growth factor signalling: from development to cancer" Nature (2010) vol. 10, pp. 116-129.
Turner et al. "Integrative molecular profiling of triple negative breast cancers identifies amplicon drivers and potential therapeutic targets" Oncogene (2010) vol. 8 No. 29 pp. 2013-2023.
Undevia, SD et al., "Phase I clinical trial of CEP-2563 dihydrochloride, a receptor tyrosine kinase inhibitor, in patients with refractory solid tumors", Invest New Drugs 22(4):449-58, Nov. 2004.
University of Colorado Denver; "NTRK1: A new oncogene and target in lung cancer". Press Release, Public release date: Jun. 3, 2013.
Vaishnavi, Aria et al., "Oncogenic and drug-sensitive NTRK1 rearrangements in lung cancer", Nature Medicine, vol. 19, No. 11, pp. 1469-1472, ePub Oct. 27, 2013, Nov. 2013.
Wang et al "Mutations in Isocitrate Dehydrogenase 1 and 2 Occur Frequently in Intrahepatic Cholangiocarcinomas and Share Hypermethylation Targets with Glioblastomas" Oncogene (2013) vol. 32 No. 25.
Wang et al. Fusion of dynactin 1 to anaplastic lymphoma kinase in inflammatory myofibroblastic tumor. Hum Pathol ePub Jun. 1, 2012 vol. 43 No. 11 pp. 2047-2052. Especially abstract.
Ware et al. "Rapidly Acquired Resistance to EGFR Tyrosine Kinase Inhibitors in NSCLC Cell Lines through De-Repression of FGFR2 and FGFR3 Expression" PLOS One (2010) vol. 5, No. 11, pp. e14117.
Cappellen et al., "Frequent activating mutations of FGFR3 in human bladder and cervix carcinomas," Nature Genetics (1999) vol. 23, pp. 18-20.
Farago et al., "Durable Clinical Response to Entrectinib in NTRK1-Rearranged Non-Small Cell Lung Cancer" Journal of Thoracic Oncology (2015) vol. 10, No. 12, pp. 1670-1674.
Guagnano et al., "FGFR Genetic Alterations Predict for Sensitivity to NVP-BGJ398, a Selective Pan-FGFR Inhibitor," Cancer Discovery (2012) vol. 2, pp. 1118-1133.
Hyman et al. "The efficacy of larotrectinib (LOXO-101), a selective tropomyosin receptor kinase (TRK) inhibitor, in adult and pediatric TRK fusion cancers" Presentation from the ASCO Annual Meeting 2017.
Javle et al., "Biliary Cancer: Utility of Next-Generation Sequencing for Clinical Management," Cancer (2016) vol. 122, pp. 3838-3847.
Jiao et al., "Exome sequencing identifies frequest inactivating mutations in BAP1, ARID1A and PBRM in intrahepatic cholangiocarcinomas," Nature Genetics (2013) vol. 45, No. 12, pp. 1470-1473 and Supplementary Information.
Lee et al., "The potential role of comprehensive genomic profiling to guide targeted therapy for patients with biliary cancer," Ther Adv Gastroenterol (2017) vol. 10, No. 6, pp. 507-520.
Brambilla et al., "The new World Health Organization classification of lung tumours," Eur Respir J (2001) vol. 18, pp. 1059-1068.
Dhami et al., "Comprehensive genomic profiling aids in treatment of metastatic endometrial cancer," Cold Spring Harb Mol Case Stud (2018) vol. 4, Article a002089, 14 pages.
Kang et al., "microRNA-99b acts as a tumor suppressor in non-small cell lung cancer by directly targeting fibroblast growth factor receptor 3," Experimental and Therapeutic Medicine (2012) vol. 3, pp. 149-153.
Lam et al., "Expression profiling in lung adenocarcinomas with or without epidermal growth factor receptor (EGFR) gene mutation at exons 18-21 reveals expression signatures related to the EGFR pathway," Proc Amer Assoc Cancer Res (2005) vol. 46, Abstract 883.
Ou et al., "Emergence of FGFR3-TACC3 fusions as a potential by-pass resistance mechanism to EGFR tyrosine kinase inhibitors in EGFR mutated NSCLC patients," Lung Cancer (2017) vol. 111, pp. 61-67.
Woenckhaus et al., "Prognostic value of FHIT, CTNNB1, and MUC1 expression in non-small cell lung cancer," Human Pathology (2008) vol. 39, pp. 126-136.

* cited by examiner

FIG. 2A

```
atg gca cag agc aag agg cac gtg tac agc cgg acg ccc agc ggc agc agg atg agt gcg   60
 M   A   Q   S   K   R   H   V   Y   S   R   T   P   S   G   S   R   M   S   A   20 gag gca agc gcc cgg cct ctg cgg gtg ggc tcc cgt gta gag gtg att gga aaa ggc cac  120
 E   A   S   A   R   P   L   R   V   G   S   R   V   E   V   I   G   K   G   H   40 cga ggc act gtg gcc tat gtt gga gcc aca ctg ttt gcc act ggc aaa tgg gta ggc gtg  180
 R   G   T   V   A   Y   V   G   A   T   L   F   A   T   G   K   W   V   G   V   60 att ctg gat gaa gca aag ggc aaa aat gat gga act gtt caa ggc agg aag tac ttc act  240
 I   L   D   E   A   K   G   K   N   D   G   T   V   Q   G   R   K   Y   F   T   80 tgt gat gaa ggg cat ggc atc ttt gtg cgc cag tcc cag atc cag gta ttt gaa gat gga  300
 C   D   E   G   H   G   I   F   V   R   Q   S   Q   I   Q   V   F   E   D   G  100 gca gat act act tcc cca gag aca cct gat tct tct gct tca aaa gtc ctc aaa aga gag  360
 A   D   T   T   S   P   E   T   P   D   S   S   A   S   K   V   L   K   R   E  120 gga act gat aca act gca aag act agc aaa ctg cgg gga ctg aag cct aag aag gca ccg  420
 G   T   D   T   T   A   K   T   S   K   L   R   G   L   K   P   K   K   A   P  140 aca gcc cga aag acc aca act cgg cga ccc aag ccc acg cgc cca gcc agt act ggg gtg  480
 T   A   R   K   T   T   T   R   R   P   K   P   T   R   P   A   S   T   G   V  160 gct ggg gcc agt agc tcc ctg ggc ccc tct ggc tca gcg tca gca ggt gag ctg agc agc  540
 A   G   A   S   S   S   L   G   P   S   G   S   A   S   A   G   E   L   S   S  180 agt gag ccc agc acc ccg gct cag act ccg ctg gca gca ccc atc atc ccc acg ccg gtc  600
 S   E   P   S   T   P   A   Q   T   P   L   A   A   P   I   I   P   T   P   V  200 ctc acc tct cct gga gca gtc ccc ccg ctt cct tcc cca tcc aag gag gag gag gga cta  660
 L   T   S   P   G   A   V   P   P   L   P   S   P   S   K   E   E   E   G   L  220 agg gct cag gtg cgg gac ctg gag gag aaa cta gag acc ctg aga ctg aaa cgg gca gaa  720
 R   A   Q   V   R   D   L   E   E   K   L   E   T   L   R   L   K   R   A   E  240 gac aaa gca aag cta aaa gag ctg gag aaa cac aaa atc cag ctg gag cag gtg cag gaa  780
 D   K   A   K   L   K   E   L   E   K   H   K   I   Q   L   E   Q   V   Q   E  260 tgg aag agc aaa atg cag gag cag cag gcc gac ctg cag cgg cgc ctc aag gag gcg aga  840
 W   K   S   K   M   Q   E   Q   Q   A   D   L   Q   R   R   L   K   E   A   R  280 aag gaa gcc aag gag gcg ctg gag gca aag gaa cgc tat atg gag gag atg gct gat act  900
 K   E   A   K   E   A   L   E   A   K   E   R   Y   M   E   E   M   A   D   T  300 gct gat gcc att gag atg gcc act ttg gac aag gag atg gct gaa gag cgg gct gag tcc  960
 A   D   A   I   E   M   A   T   L   D   K   E   M   A   E   E   R   A   E   S  320
```

FIG. 2B

```
ctg cag cag gag gtg gag gca ctg aag gag cgg gtg gac gag ctc act act gac tta gag   1020
 L   Q   Q   E   V   E   A   L   K   E   R   V   D   E   L   T   T   D   L   E    340 atc ctc aag gct gag att gaa gag aag ggc tca gat ggc gct gca tcc agt tat cag ctc   1080
 I   L   K   A   E   I   E   E   K   G   S   D   G   A   A   S   S   Y   Q   L    360 aag cag ctt gag gag cag aat gcc cgc ctg aag gat gcc ctg gtg agg atg cgg gat ctt   1140
 K   Q   L   E   E   Q   N   A   R   L   K   D   A   L   V   R   M   R   D   L    380 tct tcc tca gag aag cag gag cat gtg aag ctc cag aag ctc atg gaa aag aag aac caa   1200
 S   S   S   E   K   Q   E   H   V   K   L   Q   K   L   M   E   K   K   N   Q    400 gag ctg gaa gtt gtg agg caa cag cgg gag cgt ctg cag gag gag cta agc cag gca gag   1260
 E   L   E   V   V   R   Q   Q   R   E   R   L   Q   E   E   L   S   Q   A   E    420 agc acc att gat gag ctc aag gag cag gtg gat gct gct ctg ggt gct gag gag atg gtg   1320
 S   T   I   D   E   L   K   E   Q   V   D   A   A   L   G   A   E   E   M   V    440 gag atg ctg aca gat cgg aac ctg aat ctg gaa gag aaa gtg cgc gag ttg agg gag act   1380
 E   M   L   T   D   R   N   L   N   L   E   E   K   V   R   E   L   R   E   T    460 gtg gga gac ttg gaa gcg atg aat gag atg aac gat gag ctg cag gag aat gca cgt gag   1440
 V   G   D   L   E   A   M   N   E   M   N   D   E   L   Q   E   N   A   R   E    480 aca gaa ctg gag ctg cgg gag cag ctg gac atg gca ggc gcg cgg gtt cgt gag gcc cag   1500
 T   E   L   E   L   R   E   Q   L   D   M   A   G   A   R   V   R   E   A   Q    500 aag cgt gtg gag gca gcc cag gag acg gtt gca gac tac cag cag acc atc aag aag tac   1560
 K   R   V   E   A   A   Q   E   T   V   A   D   Y   Q   Q   T   I   K   K   Y    520 cgc cag ctg acc gcc cat cta cag gat gtg aat cgg gaa ctg aca aac cag cag gaa gca   1620
 R   Q   L   T   A   H   L   Q   D   V   N   R   E   L   T   N   Q   Q   E   A    540 tct gtg gag agg caa cag cag cca cct cca gag acc ttt gac ttc aaa atc aag ttt gct   1680
 S   V   E   R   Q   Q   Q   P   P   P   E   T   F   D   F   K   I   K   F   A    560 gag act aag gcc cat gcc aag gca att gag atg gaa ttg agg cag atg gag gtg gcc cag   1740
 E   T   K   A   H   A   K   A   I   E   M   E   L   R   Q   M   E   V   A   Q    580 gcc aat cga cac atg tcc ctg ctg aca gcc ttc atg cct gac agc ttc ctt cgg cca ggt   1800
 A   N   R   H   M   S   L   L   T   A   F   M   P   D   S   F   L   R   P   G    600 ggg gac cat gac tgc gtt ctg gtg ctg ttg ctc atg cct cgt ctc att tgc aag gca gag   1860
 G   D   H   D   C   V   L   V   L   L   L   M   P   R   L   I   C   K   A   E    620 ctg atc cgg aag cag gcc cag gag aag ttt gaa cta agt gag aac tgt tca gag cgg cct   1920
 L   I   R   K   Q   A   Q   E   K   F   E   L   S   E   N   C   S   E   R   P    640
```

FIG. 2C

```
ggg ctg cga gga gct gct ggg gag caa ctc agc ttt gct gct gga ctg gtg tac tcg ctg   1980
 G   L   R   G   A   A   G   E   Q   L   S   F   A   A   G   L   V   Y   S   L    660 agc ctg ctg cag gcc acg cta cac cgc tat gag cat gcc ctc tct cag tgc agt gtg gat   2040
 S   L   L   Q   A   T   L   H   R   Y   E   H   A   L   S   Q   C   S   V   D    680 gtg tat aag aaa gtg ggc agc ctg tac cct gag atg agt gcc cat gag cgc tcc ttg gat   2100
 V   Y   K   K   V   G   S   L   Y   P   E   M   S   A   H   E   R   S   L   D    700 ttc ctc att gaa ctg ctg cac aag gat cag ctg gat gag act gtc aat gtg gag cct ctc   2160
 F   L   I   E   L   L   H   K   D   Q   L   D   E   T   V   N   V   E   P   L    720 acc aag gcc atc aag tac tat cag cat ctg tac agc atc cac ctt gcc gaa cag cct gag   2220
 T   K   A   I   K   Y   Y   Q   H   L   Y   S   I   H   L   A   E   Q   P   E    740 gac tgt act atg cag ctg gct gac cac att aag ttc acg cag agt gct ctg gac tgc atg   2280
 D   C   T   M   Q   L   A   D   H   I   K   F   T   Q   S   A   L   D   C   M    760 agt gtg gag gta gga cgg ctg cgt gcc ttc ttg cag ggt ggg cag gag gct aca gat att   2340
 S   V   E   V   G   R   L   R   A   F   L   Q   G   G   Q   E   A   T   D   I    780 gcc ctc ctg ctc cgg gat ctg gaa act tca tgc agt gac atc cgc cag ttc tgc aag aag   2400
 A   L   L   L   R   D   L   E   T   S   C   S   D   I   R   Q   F   C   K   K    800 atc cga agg cga atg cca ggg aca gat gct cct ggg atc cca gct gca ctg gcc ttt gga   2460
 I   R   R   R   M   P   G   T   D   A   P   G   I   P   A   A   L   A   F   G    820 cca cag gta tct gac acg ctc cta gac tgc agg aaa cac ttg acg tgg gtc gtg gct gtg   2520
 P   Q   V   S   D   T   L   L   D   C   R   K   H   L   T   W   V   V   A   V    840 ctg cag gag gtg gca gct gct gct gcc cag ctc att gcc cca ctg gca gag aat gag ggg   2580
 L   Q   E   V   A   A   A   A   A   Q   L   I   A   P   L   A   E   N   E   G    860 cta ctt gtg gct gct ctg gag gaa ctg gct ttc aaa gca agc gag cag atc tat ggg acc   2640
 L   L   V   A   A   L   E   E   L   A   F   K   A   S   E   Q   I   Y   G   T    880 ccc tcc agc agc ccc tat gag tgt ctg cgc cag tca tgc aac atc ctc atc agt acc atg   2700
 P   S   S   S   P   Y   E   C   L   R   Q   S   C   N   I   L   I   S   T   M    900 aac aag ctg gcc aca gcc atg cag gag ggg gag tat gat gca gag cgg ccc ccc agc aag   2760
 N   K   L   A   T   A   M   Q   E   G   E   Y   D   A   E   R   P   P   S   K    920 cct cca ccg gtt gaa ctg cgg gct gct gcc ctt cgt gca gag atc aca gat gct gaa ggc   2820
 P   P   P   V   E   L   R   A   A   A   L   R   A   E   I   T   D   A   E   G    940
```

FIG. 2D

```
ctg ggt ttg aag ctc gaa gat cga gag aca gtt att aag gag ttg aag aag tca ctc aag  2880
 L   G   L   K   L   E   D   R   E   T   V   I   K   E   L   K   K   S   L   K   960 att aag gga gag gag cta agt gag gcc aat gtg cgg ctg agc ctc ctg gag aag aag ttg  2940
 I   K   G   E   E   L   S   E   A   N   V   R   L   S   L   L   E   K   K   L   980 gac agt gct gcc aag gat gca gat gag cgc atc gag aaa gtc cag act cgg ctg gag gag  3000
 D   S   A   A   K   D   A   D   E   R   I   E   K   V   Q   T   R   L   E   E   1000 acc cag gca ctg ctg cga aag aag gag aaa gag ttt gag gag aca atg gat gca ctc cag  3060
 T   Q   A   L   L   R   K   K   E   K   E   F   E   E   T   M   D   A   L   Q   1020 gct gac atc gac cag ctg gag gca gag aag gca gaa cta aag cag cgt ctg aac agc cag  3120
 A   D   I   D   Q   L   E   A   E   K   A   E   L   K   Q   R   L   N   S   Q   1040 tcc aaa cgc acg att gag gga ctc cgg ggc cct cct cct tca ggc att gct act ctg gtc  3180
 S   K   R   T   I   E   G   L   R   G   P   P   P   S   G   I   A   T   L   V   1060 tct ggc att gct ggt gtg tac cgc cgg aag cac cag gag ctg caa gcc atg cag atg gag  3240
 S   G   I   A   G   V   Y   R   R   K   H   Q   E   L   Q   A   M   Q   M   E   1080 ctg cag agc cct gag tac aag ctg agc aag ctc cgc acc tcg acc atc atg acc gac tac  3300
 L   Q   S   P   E   Y   K   L   S   K   L   R   T   S   T   I   M   T   D   Y   1100 aac ccc aac tac tgc ttt gct ggc aag acc tcc tcc atc agt gac ctg aag gag gtg ccg  3360
 N   P   N   Y   C   F   A   G   K   T   S   S   I   S   D   L   K   E   V   P   1120 cgg aaa aac atc acc ctc att cgg ggt ctg ggc cat ggc gcc ttt ggg gag gtg tat gaa  3420
 R   K   N   I   T   L   I   R   G   L   G   H   G   A   F   G   E   V   Y   E   1140 ggc cag gtg tcc gga atg ccc aac gac cca agc ccc ctg caa gtg gct gtg aag acg ctg  3480
 G   Q   V   S   G   M   P   N   D   P   S   P   L   Q   V   A   V   K   T   L   1160 cct gaa gtg tgc tct gaa cag gac gaa ctg gat ttc ctc atg gaa gcc ctg atc atc agc  3540
 P   E   V   C   S   E   Q   D   E   L   D   F   L   M   E   A   L   I   I   S   1180 aaa ttc aac cac cag aac att gtt cgc tgc att ggg gtg agc ctg caa tcc ctg ccc cgg  3600
 K   F   N   H   Q   N   I   V   R   C   I   G   V   S   L   Q   S   L   P   R   1200 ttc atc ctg ctg gag ctc atg gcg ggg gga gac ctc aag tcc ttc ctc cga gag acc cgc  3660
 F   I   L   L   E   L   M   A   G   G   D   L   K   S   F   L   R   E   T   R   1220 cct cgc ccg agc cag ccc tcc tcc ctg gcc atg ctg gac ctt ctg cac gtg gct cgg gac  3720
 P   R   P   S   Q   P   S   S   L   A   M   L   D   L   L   H   V   A   R   D   1240 att gcc tgt ggc tgt cag tat ttg gag gaa aac cac ttc atc cac cga gac att gct gcc  3780
 I   A   C   G   C   Q   Y   L   E   E   N   H   F   I   H   R   D   I   A   A   1260
```

FIG. 2E

```
aga aac tgc ctc ttg acc tgt cca ggc cct gga aga gtg gcc aag att gga gac ttc ggg 3840
 R   N   C   L   L   T   C   P   G   P   G   R   V   A   K   I   G   D   F   G  1280 atg gcc cga gac atc tac agg gcg agc tac tat aga aag gga ggc tgt gcc atg ctg cca 3900
 M   A   R   D   I   Y   R   A   S   Y   Y   R   K   G   G   C   A   M   L   P  1300 gtt aag tgg atg ccc cca gag gcc ttc atg gaa gga ata ttc act tct aaa aca gac aca 3960
 V   K   W   M   P   P   E   A   F   M   E   G   I   F   T   S   K   T   D   T  1320 tgg tcc ttt gga gtg ctg cta tgg gaa atc ttt tct ctt gga tat atg cca tac ccc agc 4020
 W   S   F   G   V   L   L   W   E   I   F   S   L   G   Y   M   P   Y   P   S  1340 aaa agc aac cag gaa gtt ctg gag ttt gtc acc agt gga ggc cgg atg gac cca ccc aag 4080
 K   S   N   Q   E   V   L   E   F   V   T   S   G   G   R   M   D   P   P   K  1360 aac tgc cct ggg cct gta tac cgg ata atg act cag tgc tgg caa cat cag cct gaa gac 4140
 N   C   P   G   P   V   Y   R   I   M   T   Q   C   W   Q   H   Q   P   E   D  1380 agg ccc aac ttt gcc atc att ttg gag agg att gaa tac tgc acc cag gac ccg gat gta 4200
 R   P   N   F   A   I   I   L   E   R   I   E   Y   C   T   Q   D   P   D   V  1400 atc aac acc gct ttg ccg ata gaa tat ggt cca ctt gtg gaa gag gaa gag aaa gtg cct 4260
 I   N   T   A   L   P   I   E   Y   G   P   L   V   E   E   E   E   K   V   P  1420 gtg agg ccc aag gac cct gag ggg gtt cct cct ctc ctg gtc tct caa cag gca aaa cgg 4320
 V   R   P   K   D   P   E   G   V   P   P   L   L   V   S   Q   Q   A   K   R  1440 gag gag gag cgc agc cca gct gcc cca cca cct ctg cct acc acc tcc tct ggc aag gct 4380
 E   E   E   R   S   P   A   A   P   P   P   L   P   T   T   S   S   G   K   A  1460 gca aag aaa ccc aca gct gca gag atc tct gtt cga gtc cct aga ggg ccg gcc gtg gaa 4440
 A   K   K   P   T   A   A   E   I   S   V   R   V   P   R   G   P   A   V   E  1480 ggg gga cac gtg aat atg gca ttc tct cag tcc aac cct cct tcg gag ttg cac aag gtc 4500
 G   G   H   V   N   M   A   F   S   Q   S   N   P   P   S   E   L   H   K   V  1500 cac gga tcc aga aac aag ccc acc agc ttg tgg aac cca acg tac ggc tcc tgg ttt aca 4560
 H   G   S   R   N   K   P   T   S   L   W   N   P   T   Y   G   S   W   F   T  1520 gag aaa ccc acc aaa aag aat aat cct ata gca aag aag gag cca cac gac agg ggt aac 4620
 E   K   P   T   K   K   N   N   P   I   A   K   K   E   P   H   D   R   G   N  1540 ctg ggg ctg gag gga agc tgt act gtc cca cct aac gtt gca act ggg aga ctt ccg ggg 4680
 L   G   L   E   G   S   C   T   V   P   P   N   V   A   T   G   R   L   P   G  1560
```

FIG. 2F

```
gcc tca ctg ctc cta gag ccc tct tcg ctg act gcc aat atg aag gag gta cct ctg ttc   4740
 A   S   L   L   L   E   P   S   S   L   T   A   N   M   K   E   V   P   L   F    1580 agg cta cgt cac ttc cct tgt ggg aat gtc aat tac ggc tac cag caa cag ggc ttg ccc   4800
 R   L   R   H   F   P   C   G   N   V   N   Y   G   Y   Q   Q   Q   G   L   P    1600 tta gaa gcc gct act gcc cct gga gct ggt cat tac gag gat acc att ctg aaa agc aag   4860
 L   E   A   A   T   A   P   G   A   G   H   Y   E   D   T   I   L   K   S   K    1620 aat agc atg aac cag cct ggg ccc tga   4884   (SEQ ID NO: 6)
 N   S   M   N   Q   P   G   P   *    1628   (SEQ ID NO: 7)
```

FIG. 4A

```
atg gga gcc atc ggg ctc ctg tgg ctc ctg ccg ctg ctg ctt tcc acg gca gct gtg ggc   60
 M   G   A   I   G   L   L   W   L   L   P   L   L   L   S   T   A   A   V   G   20 tcc ggg atg ggg acc ggc cag cgc gcg ggc tcc cca gct gcg ggg ccg ccg ctg cag ccc  120
 S   G   M   G   T   G   Q   R   A   G   S   P   A   A   G   P   P   L   Q   P   40 cgg gag cca ctc agc tac tcg cgc ctg cag agg aag agt ctg gca gtt gac ttc gtg gtg  180
 R   E   P   L   S   Y   S   R   L   Q   R   K   S   L   A   V   D   F   V   V   60 ccc tcg ctc ttc cgt gtc tac gcc cgg gac cta ctg ctg cca cca tcc tcc tcg gag ctg  240
 P   S   L   F   R   V   Y   A   R   D   L   L   L   P   P   S   S   S   E   L   80 aag gct ggc agg ccc gag gcc cgc ggc tcg cta gct ctg gac tgc gcc ccg ctg ctc agg  300
 K   A   G   R   P   E   A   R   G   S   L   A   L   D   C   A   P   L   L   R  100 ttg ctg ggg ccg gcg ccg ggg gtc tcc tgg acc gcc ggt tca cca gcc ccg gca gag gcc  360
 L   L   G   P   A   P   G   V   S   W   T   A   G   S   P   A   P   A   E   A  120 cgg acg ctg tcc agg gtg ctg aag ggc ggc tcc gtg cgc aag ctc cgg cgt gcc aag cag  420
 R   T   L   S   R   V   L   K   G   G   S   V   R   K   L   R   R   A   K   Q  140 ttg gtg ctg gag ctg ggc gag gag gcg atc ttg gag ggt tgc gtc ggg ccc ccc ggg gag  480
 L   V   L   E   L   G   E   E   A   I   L   E   G   C   V   G   P   P   G   E  160 gcg gct gtg ggg ctg ctc cag ttc aat ctc agc gag ctg ttc agt tgg tgg att cgc caa  540
 A   A   V   G   L   L   Q   F   N   L   S   E   L   F   S   W   W   I   R   Q  180 ggc gaa ggg cga ctg agg atc cgc ctg atg ccc gag aag aag gcg tcg gaa gtg ggc aga  600
 G   E   G   R   L   R   I   R   L   M   P   E   K   K   A   S   E   V   G   R  200 gag gga agg ctg tcc gcg gca att cgc gcc tcc cag ccc cgc ctt ctc ttc cag atc ttc  660
 E   G   R   L   S   A   A   I   R   A   S   Q   P   R   L   L   F   Q   I   F  220 ggg act ggt cat agc tcc ttg gaa tca cca aca aac atg cct tct cct tct cct gat tat  720
 G   T   G   H   S   S   L   E   S   P   T   N   M   P   S   P   S   P   D   Y  240 ttt aca tgg aat ctc acc tgg ata atg aaa gac tcc ttc cct ttc ctg tct cat cgc agc  780
 F   T   W   N   L   T   W   I   M   K   D   S   F   P   F   L   S   H   R   S  260 cga tat ggt ctg gag tgc agc ttt gac ttc ccc tgt gag ctg gag tat tcc cct cca ctg  840
 R   Y   G   L   E   C   S   F   D   F   P   C   E   L   E   Y   S   P   P   L  280 cat gac ctc agg aac cag agc tgg tcc tgg cgc cgc atc ccc tcc gag gag gcc tcc cag  900
 H   D   L   R   N   Q   S   W   S   W   R   R   I   P   S   E   E   A   S   Q  300 atg gac ttg ctg gat ggg cct ggg gca gag cgt tct aag gag atg ccc aga ggc tcc ttt  960
 M   D   L   L   D   G   P   G   A   E   R   S   K   E   M   P   R   G   S   F  320
```

FIG. 4B

```
ctc ctt ctc aac acc tca gct gac tcc aag cac acc atc ctg agt ccg tgg atg agg agc    1020
 L   L   L   N   T   S   A   D   S   K   H   T   I   L   S   P   W   M   R   S     340 agc agt gag cac tgc aca ctg gcc gtc tcg gtg cac agg cac ctg cag ccc tct gga agg    1080
 S   S   E   H   C   T   L   A   V   S   V   H   R   H   L   Q   P   S   G   R     360 tac att gcc cag ctg ctg ccc cac aac gag gct gca aga gag atc ctc ctg atg ccc act    1140
 Y   I   A   Q   L   L   P   H   N   E   A   A   R   E   I   L   L   M   P   T     380 cca ggg aag cat ggt tgg aca gtg ctc cag gga aga atc ggg cgt cca gac aac cca ttt    1200
 P   G   K   H   G   W   T   V   L   Q   G   R   I   G   R   P   D   N   P   F     400 cga gtg gcc ctg gaa tac atc tcc agt gga aac cgc agc ttg tct gca gtg gac ttc ttt    1260
 R   V   A   L   E   Y   I   S   S   G   N   R   S   L   S   A   V   D   F   F     420 gcc ctg aag aac tgc agt gaa gga aca tcc cca ggc tcc aag atg gcc ctg cag agc tcc    1320
 A   L   K   N   C   S   E   G   T   S   P   G   S   K   M   A   L   Q   S   S     440 ttc act tgt tgg aat ggg aca gtc ctc cag ctt ggg cag gcc tgt gac ttc cac cag gac    1380
 F   T   C   W   N   G   T   V   L   Q   L   G   Q   A   C   D   F   H   Q   D     460 tgt gcc cag gga gaa gat gag agc cag atg tgc cgg aaa ctg cct gtg ggt ttt tac tgc    1440
 C   A   Q   G   E   D   E   S   Q   M   C   R   K   L   P   V   G   F   Y   C     480 aac ttt gaa gat ggc ttc tgt ggc tgg acc caa ggc aca ctg tca ccc cac act cct caa    1500
 N   F   E   D   G   F   C   G   W   T   Q   G   T   L   S   P   H   T   P   Q     500 tgg cag gtc agg acc cta aag gat gcc cgg ttc cag gac cac caa gac cat gct cta ttg    1560
 W   Q   V   R   T   L   K   D   A   R   F   Q   D   H   Q   D   H   A   L   L     520 ctc agt acc act gat gtc ccc gct tct gaa agt gct aca gtg acc agt gct acg ttt cct    1620
 L   S   T   T   D   V   P   A   S   E   S   A   T   V   T   S   A   T   F   P     540 gca ccg atc aag agc tct cca tgt gag ctc cga atg tcc tgg ctc att cgt gga gtc ttg    1680
 A   P   I   K   S   S   P   C   E   L   R   M   S   W   L   I   R   G   V   L     560 agg gga aac gtg tcc ttg gtg cta gtg gag aac aaa acc ggg aag gag caa ggc agg atg    1740
 R   G   N   V   S   L   V   L   V   E   N   K   T   G   K   E   Q   G   R   M     580 gtc tgg cat gtc gcc gcc tat gaa ggc ttg agc ctg tgg cag tgg atg gtg ttg cct ctc    1800
 V   W   H   V   A   A   Y   E   G   L   S   L   W   Q   W   M   V   L   P   L     600 ctc gat gtg tct gac agg ttc tgg ctg cag atg gtc gca tgg tgg gga caa gga tcc aga    1860
 L   D   V   S   D   R   F   W   L   Q   M   V   A   W   W   G   Q   G   S   R     620 gcc atc gtg gct ttt gac aat atc tcc atc agc ctg gac tgc tac ctc acc att agc gga    1920
 A   I   V   A   F   D   N   I   S   I   S   L   D   C   Y   L   T   I   S   G     640
```

FIG. 4C

```
gag gac aag atc ctg cag aat aca gca ccc aaa tca aga aac ctg ttt gag aga aac cca   1980
 E   D   K   I   L   Q   N   T   A   P   K   S   R   N   L   F   E   R   N   P    660 aac aag gag ctg aaa ccc ggg gaa aat tca cca aga cag acc ccc atc ttt gac cct aca   2040
 N   K   E   L   K   P   G   E   N   S   P   R   Q   T   P   I   F   D   P   T    680 gtt cat tgg ctg ttc acc aca tgt ggg gcc agc ggg ccc cat ggc ccc acc cag gca cag   2100
 V   H   W   L   F   T   T   C   G   A   S   G   P   H   G   P   T   Q   A   Q    700 tgc aac aac gcc tac cag aac tcc aac ctg agc gtg gag gtg ggg agc gag ggc ccc ctg   2160
 C   N   N   A   Y   Q   N   S   N   L   S   V   E   V   G   S   E   G   P   L    720 aaa ggc atc cag atc tgg aag gtg cca gcc acc gac acc tac agc atc tcg ggc tac gga   2220
 K   G   I   Q   I   W   K   V   P   A   T   D   T   Y   S   I   S   G   Y   G    740 gct gct ggc ggg aaa ggc ggg aag aac acc atg atg cgg tcc cac ggc gtg tct gtg ctg   2280
 A   A   G   G   K   G   G   K   N   T   M   M   R   S   H   G   V   S   V   L    760 ggc atc ttc aac ctg gag aag gat gac atg ctg tac atc ctg gtt ggg cag cag gga gag   2340
 G   I   F   N   L   E   K   D   D   M   L   Y   I   L   V   G   Q   Q   G   E    780 gac gcc tgc ccc agt aca aac cag tta atc cag aaa gtc tgc att gga gag aac aat gtg   2400
 D   A   C   P   S   T   N   Q   L   I   Q   K   V   C   I   G   E   N   N   V    800 ata gaa gaa gaa atc cgt gtg aac aga agc gtg cat gag tgg gca gga ggc gga gga gga   2460
 I   E   E   E   I   R   V   N   R   S   V   H   E   W   A   G   G   G   G   G    820 ggg ggt gga gcc acc tac gta ttt aag atg aag gat gga gtg ccg gtg ccc ctg atc att   2520
 G   G   G   A   T   Y   V   F   K   M   K   D   G   V   P   V   P   L   I   I    840 gca gcc gga ggt ggt ggc agg gcc tac ggg gcc aag aca gac acg ttc cac cca gag aga   2580
 A   A   G   G   G   R   A   Y   G   A   K   T   D   T   F   H   P   E   R    860 ctg gag aat aac tcc tcg gtt cta ggg cta aac ggc aat tcc gga gcc gca ggt ggt gga   2640
 L   E   N   N   S   S   V   L   G   L   N   G   N   S   G   A   A   G   G    880 ggt ggc tgg aat gat aac act tcc ttg ctc tgg gcc gga aaa tct ttg cag gag ggt gcc   2700
 G   G   W   N   D   N   T   S   L   L   W   A   G   K   S   L   Q   E   G   A    900 acc gga gga cat tcc tgc ccc cag gcc atg aag aag tgg ggg tgg gag aca aga ggg ggt   2760
 T   G   G   H   S   C   P   Q   A   M   K   K   W   G   W   E   T   R   G   G    920 ttc gga ggg ggt gga ggg ggg tgc tcc tca ggt gga gga ggc gga gga tat ata ggc ggc   2820
 F   G   G   G   G   G   G   C   S   S   G   G   G   G   G   Y   I   G   G    940 aat gca gcc tca aac aat gac ccc gaa atg gat ggg gaa gat ggg gtt tcc ttc atc agt   2880
 N   A   A   S   N   N   D   P   E   M   D   G   E   D   G   V   S   F   I   S    960 cca ctg ggc atc ctg tac acc cca gct tta aaa gtg atg gaa ggc cac ggg gaa gtg aat   2940
 P   L   G   I   L   Y   T   P   A   L   K   V   M   E   G   H   G   E   V   N    980
```

FIG. 4D

```
att aag cat tat cta aac tgc agt cac tgt gag gta gac gaa tgt cac atg gac cct gaa   3000
 I   K   H   Y   L   N   C   S   H   C   E   V   D   E   C   H   M   D   P   E   1000 agc cac aag gtc atc tgc ttc tgt gac cac ggg acg gtg ctg gct gag gat ggc gtc tcc   3060
 S   H   K   V   I   C   F   C   D   H   G   T   V   L   A   E   D   G   V   S   1020 tgc att gtg tca ccc acc ccg gag cca cac ctg cca ctc tcg ctg atc ctc tct gtg gtg   3120
 C   I   V   S   P   T   P   E   P   H   L   P   L   S   L   I   L   S   V   V   1040 acc tct gcc ctc gtg gcc gcc ctg gtc ctg gct ttc tcc ggc atc atg att gaa gaa cag   3180
 T   S   A   L   V   A   A   L   V   L   A   F   S   G   I   M   I   E   E   Q   1060 cag cga gga gcc atc cct ggg cag gct cca ggg tct gtg cca ggc cca ggg ctg gtg aag   3240
 Q   R   G   A   I   P   G   Q   A   P   G   S   V   P   G   P   G   L   V   K   1080 gac tca cca ctg ctg ctt cag cag atc tct gcc atg agg ctg cac atc tcc cag ctc cag   3300
 D   S   P   L   L   L   Q   Q   I   S   A   M   R   L   H   I   S   Q   L   Q   1100 cat gag aac agc atc ctc aag gga gcc cag atg aag gca tcc ttg gca tcc ctg ccc cct   3360
 H   E   N   S   I   L   K   G   A   Q   M   K   A   S   L   A   S   L   P   P   1120 ctg cat gtt gca aag cta tcc cat gag ggc cct ggc agt gag tta cca gct gga gcg ctg   3420
 L   H   V   A   K   L   S   H   E   G   P   G   S   E   L   P   A   G   A   L   1140 tat cgt aag acc agc cag ctg ctg gag aca ttg aat caa ttg agc aca cac acg cac gta   3480
 Y   R   K   T   S   Q   L   L   E   T   L   N   Q   L   S   T   H   T   H   V   1160 gta gac atc act cgc acc agc cct gct gcc aag agc ccg tcg cca caa ctt atg gag caa   3540
 V   D   I   T   R   T   S   P   A   A   K   S   P   S   A   Q   L   M   E   Q   1180 gtg gct cag ctt aag tcc ctg agt gac acc gtc gag aag ctc aag gat gag gtc ctc aag   3600
 V   A   Q   L   K   S   L   S   D   T   V   E   K   L   K   D   E   V   L   K   1200 gag aca gta tct cag cgc cct gga gcc aca gta ccc act gac ttt gcc acc ttc cct tca   3660
 E   T   V   S   Q   R   P   G   A   T   V   P   T   D   F   A   T   F   P   S   1220 tca gcc ttc ctc agg gcc aag gag gag cag cag gat gac aca gtc tac atg ggc aaa gtg   3720
 S   A   F   L   R   A   K   E   E   Q   Q   D   D   T   V   Y   M   G   K   V   1240 acc ttc tca tgt gcg gct ggt ttt gga cag cga cac cgg ctg gtg ctg acc cag gag cag   3780
 T   F   S   C   A   A   G   F   G   Q   R   H   R   L   V   L   T   Q   E   Q   1260 ctg cac cag ctt cac agt cgc ctc atc tcc taa                                        3813  (SEQ ID NO: 11)
 L   H   Q   L   H   S   R   L   I   S   *                                         1270  (SEQ ID NO: 12)
```

FIG. 7A

```
atg gag acc ccg tcc cag cgg cgc gcc acc cgc agc ggg gcg cag gcc agc tcc act ccg   60
 M   E   T   P   S   Q   R   R   A   T   R   S   G   A   Q   A   S   S   T   P   20 ctg tcg ccc acc cgc atc acc cgg ctg cag gag aag gag gac ctg cag gag ctc aat gat  120
 L   S   P   T   R   I   T   R   L   Q   E   K   E   D   L   Q   E   L   N   D   40 cgc ttg gcg gtc tac atc gac cgt gtg cgc tcg ctg gaa acg gag aac gca ggg ctg cgc  180
 R   L   A   V   Y   I   D   R   V   R   S   L   E   T   E   N   A   G   L   R   60 ctt cgc atc acc gag tct gaa aag gtg gtc agc cgc gag gtg tcc ggc atc aag gcc gcc  240
 L   R   I   T   E   S   E   K   V   V   S   R   E   V   S   G   I   K   A   A   80 tac gag gcc gag ctc ggg gat gcc cgc aag acc ctt gac tca gta gcc aag gag cgc gcc  300
 Y   E   A   E   L   G   D   A   R   K   T   L   D   S   V   A   K   E   R   A  100 cgc ctg cag ctg gag ctg agc aaa gtg cgt gag gag ttt aag gag ctg aaa gcg cgc aat  360
 R   L   Q   L   E   L   S   K   V   R   E   E   F   K   E   L   K   A   R   N  120 acc aag aag gag ggt gac ctg ata gct gct cag gct cgg ctg aag gac ctg gag gct ctg  420
 T   K   K   E   G   D   L   I   A   A   Q   A   R   L   K   D   L   E   A   L  140 ctg aac tcc aag gag gcc gca ctg agc act gct ctc agt gag aag cgc acg ctg gag ggc  480
 L   N   S   K   E   A   A   L   S   T   A   L   S   E   K   R   T   L   E   G  160 gag ctg cat gat ctg cgg ggc cag gtg gcc aag gtc tcc ttc tcg ccg gtg gac act aac  540
 E   L   H   D   L   R   G   Q   V   A   K   V   S   F   S   P   V   D   T   N  180 agc aca tct gga gac ccg gtg gag aag aag gac gaa aca cct ttt ggg gtc tcg gtg gct  600
 S   T   S   G   D   P   V   E   K   K   D   E   T   P   F   G   V   S   V   A  200 gtg ggc ctg gcc gtc ttt gcc tgc ctc ttc ctt tct acg ctg ctc ctt gtg ctc aac aaa  660
 V   G   L   A   V   F   A   C   L   F   L   S   T   L   L   V   L   N   K  220 tgt gga cgg aga aac aag ttt ggg atc aac cgc ccg gct gtg ctg gct cca gag gat ggg  720
 C   G   R   R   N   K   F   G   I   N   R   P   A   V   L   A   P   E   D   G  240 ctg gcc atg tcc ctg cat ttc atg aca ttg ggt ggc agc tcc ctg tcc ccc acc gag ggc  780
 L   A   M   S   L   H   F   M   T   L   G   G   S   L   S   P   T   E   G  260 aaa ggc tct ggg ctc caa ggc cac atc atc gag aac cca caa tac ttc agt gat gcc tgt  840
 K   G   S   G   L   Q   G   H   I   I   E   N   P   Q   Y   F   S   D   A   C  280 gtt cac cac atc aag cgc cgg gac atc gtg ctc aag tgg gag ctg ggg gag ggc gcc ttt  900
 V   H   H   I   K   R   R   D   I   V   L   K   W   E   L   G   E   G   A   F  300
```

FIG. 7B

```
ggg aag gtc ttc ctt gct gag tgc cac aac ctc ctg cct gag cag gac aag atg ctg gtg   960
 G   K   V   F   L   A   E   C   H   N   L   L   P   E   Q   D   K   M   L   V   320 gct gtc aag gca ctg aag gag gcg tcc gag agt gct cgg cag gac ttc caa cgt gag gct  1020
 A   V   K   A   L   K   E   A   S   E   S   A   R   Q   D   F   Q   R   E   A   340 gag ctg ctc acc atg ctg cag cac cag cac atc gtg cgc ttc ttc ggc gtc tgc acc gag  1080
 E   L   L   T   M   L   Q   H   Q   H   I   V   R   F   F   G   V   C   T   E   360 ggc cgc ccc ctg ctc atg gtc ttc gag tat atg cgg cac ggg gac ctc aac cgc ttc ctc  1140
 G   R   P   L   L   M   V   F   E   Y   M   R   H   G   D   L   N   R   F   L   380 cga tcc cat gga ccc gat gcc aag ctg ctg gct ggt ggg gag gat gtg gct cca ggc ccc  1200
 R   S   H   G   P   D   A   K   L   L   A   G   G   E   D   V   A   P   G   P   400 ctg ggt ctg ggg cag ctg ctg gcc gtg gct agc cag gtc gct gcg ggg atg gtg tac ctg  1260
 L   G   L   G   Q   L   L   A   V   A   S   Q   V   A   A   G   M   V   Y   L   420 gcg ggt ctg cat ttt gtg cac cgg gac ctg gcc aca cgc aac tgt cta gtg ggc cag gga  1320
 A   G   L   H   F   V   H   R   D   L   A   T   R   N   C   L   V   G   Q   G   440 ctg gtg gtc aag att ggt gat ttt ggc atg agc agg gat atc tac agc acc gac tat tac  1380
 L   V   V   K   I   G   D   F   G   M   S   R   D   I   Y   S   T   D   Y   Y   460 cgt gtg gga ggc cgc acc atg ctg ccc att cgc tgg atg ccg ccc gag agc atc ctg tac  1440
 R   V   G   G   R   T   M   L   P   I   R   W   M   P   P   E   S   I   L   Y   480 cgt aag ttc acc acc gag agc gac gtg tgg agc ttc ggc gtg gtg ctc tgg gag atc ttc  1500
 R   K   F   T   T   E   S   D   V   W   S   F   G   V   V   L   W   E   I   F   500 acc tac ggc aag cag ccc tgg tac cag ctc tcc aac acg gag gca atc gac tgc atc acg  1560
 T   Y   G   K   Q   P   W   Y   Q   L   S   N   T   E   A   I   D   C   I   T   520 cag gga cgt gag ttg gag cgg cca cgt gcc tgc cca cca gag gtc tac gcc atc atg cgg  1620
 Q   G   R   E   L   E   R   P   R   A   C   P   P   E   V   Y   A   I   M   R   540 ggc tgc tgg cag cgg gag ccc cag caa cgc cac agc atc aag gat gtg cac gcc cgg ctg  1680
 G   C   W   Q   R   E   P   Q   Q   R   H   S   I   K   D   V   H   A   R   L   560 caa gcc ctg gcc cag gca cct cct gtc tac ctg gat gtc ctg ggc tag (SEQ ID NO: 9)   1728
 Q   A   L   A   Q   A   P   P   V   Y   L   D   V   L   G   *   (SEQ ID NO: 10)  575
```

SEQUENCE LISTING

```
<160> NUMBER OF SEQ ID NOS: 13

<210> SEQ ID NO 1
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (16)..(185)
<223> OTHER INFORMATION: a, c, t, g, unknown or other

<400> SEQUENCE: 1
atcgcaccag cgtgtnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnncactg cggctcctca                                                 200

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000
```

<210> SEQ ID NO 5
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gttttggctt ggcctgggct gccctaatca ccaccccacc caattcacag tgtccaagca    60
gagaagcaat caa                                                      73

<210> SEQ ID NO 6
<211> LENGTH: 4887
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(4884)

<400> SEQUENCE: 6

| atg | gca | cag | agc | aag | agg | cac | gtg | tac | agc | cgg | acg | ccc | agc | ggc | agc | 48 |
| Met | Ala | Gln | Ser | Lys | Arg | His | Val | Tyr | Ser | Arg | Thr | Pro | Ser | Gly | Ser | |
| 1 | | | | 5 | | | | | 10 | | | | | 15 | | |

| agg | atg | agt | gcg | gag | gca | agc | gcc | cgg | cct | ctg | cgg | gtg | ggc | tcc | cgt | 96 |
| Arg | Met | Ser | Ala | Glu | Ala | Ser | Ala | Arg | Pro | Leu | Arg | Val | Gly | Ser | Arg | |
| | | | 20 | | | | | 25 | | | | | 30 | | | |

| gta | gag | gtg | att | gga | aaa | ggc | cac | cga | ggc | act | gtg | gcc | tat | gtt | gga | 144 |
| Val | Glu | Val | Ile | Gly | Lys | Gly | His | Arg | Gly | Thr | Val | Ala | Tyr | Val | Gly | |
| | | 35 | | | | | 40 | | | | | 45 | | | | |

| gcc | aca | ctg | ttt | gcc | act | ggc | aaa | tgg | gta | ggc | gtg | att | ctg | gat | gaa | 192 |
| Ala | Thr | Leu | Phe | Ala | Thr | Gly | Lys | Trp | Val | Gly | Val | Ile | Leu | Asp | Glu | |
| 50 | | | | | 55 | | | | | 60 | | | | | | |

| gca | aag | ggc | aaa | aat | gat | gga | act | gtt | caa | ggc | agg | aag | tac | ttc | act | 240 |
| Ala | Lys | Gly | Lys | Asn | Asp | Gly | Thr | Val | Gln | Gly | Arg | Lys | Tyr | Phe | Thr | |
| 65 | | | | 70 | | | | | 75 | | | | | 80 | | |

| tgt | gat | gaa | ggg | cat | ggc | atc | ttt | gtg | cgc | cag | tcc | cag | atc | cag | gta | 288 |
| Cys | Asp | Glu | Gly | His | Gly | Ile | Phe | Val | Arg | Gln | Ser | Gln | Ile | Gln | Val | |
| | | | | 85 | | | | | 90 | | | | | 95 | | |

| ttt | gaa | gat | gga | gca | gat | act | act | tcc | cca | gag | aca | cct | gat | tct | tct | 336 |
| Phe | Glu | Asp | Gly | Ala | Asp | Thr | Thr | Ser | Pro | Glu | Thr | Pro | Asp | Ser | Ser | |
| | | | 100 | | | | | 105 | | | | | 110 | | | |

| gct | tca | aaa | gtc | ctc | aaa | aga | gag | gga | act | gat | aca | act | gca | aag | act | 384 |
| Ala | Ser | Lys | Val | Leu | Lys | Arg | Glu | Gly | Thr | Asp | Thr | Thr | Ala | Lys | Thr | |
| | | 115 | | | | | 120 | | | | | 125 | | | | |

| agc | aaa | ctg | cgg | gga | ctg | aag | cct | aag | aag | gca | ccg | aca | gcc | cga | aag | 432 |
| Ser | Lys | Leu | Arg | Gly | Leu | Lys | Pro | Lys | Lys | Ala | Pro | Thr | Ala | Arg | Lys | |
| | 130 | | | | | 135 | | | | | 140 | | | | | |

| acc | aca | act | cgg | cga | ccc | aag | ccc | acg | cgc | cca | gcc | agt | act | ggg | gtg | 480 |
| Thr | Thr | Thr | Arg | Arg | Pro | Lys | Pro | Thr | Arg | Pro | Ala | Ser | Thr | Gly | Val | |
| 145 | | | | 150 | | | | | 155 | | | | | 160 | | |

| gct | ggg | gcc | agt | agc | tcc | ctg | ggc | ccc | tct | ggc | tca | gcg | tca | gca | ggt | 528 |
| Ala | Gly | Ala | Ser | Ser | Ser | Leu | Gly | Pro | Ser | Gly | Ser | Ala | Ser | Ala | Gly | |
| | | | | 165 | | | | | 170 | | | | | 175 | | |

| gag | ctg | agc | agc | agt | gag | ccc | agc | acc | ccg | gct | cag | act | ccg | ctg | gca | 576 |
| Glu | Leu | Ser | Ser | Ser | Glu | Pro | Ser | Thr | Pro | Ala | Gln | Thr | Pro | Leu | Ala | |
| | | | 180 | | | | | 185 | | | | | 190 | | | |

| gca | ccc | atc | atc | ccc | acg | ccg | gtc | ctc | acc | tct | cct | gga | gca | gtc | ccc | 624 |
| Ala | Pro | Ile | Ile | Pro | Thr | Pro | Val | Leu | Thr | Ser | Pro | Gly | Ala | Val | Pro | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 195 |     |     |     | 200 |     |     |     |     | 205 |     |     |     |     |     |      |
| ccg | ctt | cct | tcc | cca | tcc | aag | gag | gag | gag | gga | cta | agg | gct | cag | gtg | 672  |
| Pro | Leu | Pro | Ser | Pro | Ser | Lys | Glu | Glu | Glu | Gly | Leu | Arg | Ala | Gln | Val |      |
|     | 210 |     |     |     | 215 |     |     |     |     | 220 |     |     |     |     |     |      |
| cgg | gac | ctg | gag | gag | aaa | cta | gag | acc | ctg | aga | ctg | aaa | cgg | gca | gaa | 720  |
| Arg | Asp | Leu | Glu | Glu | Lys | Leu | Glu | Thr | Leu | Arg | Leu | Lys | Arg | Ala | Glu |      |
| 225 |     |     |     |     | 230 |     |     |     |     | 235 |     |     |     |     | 240 |      |
| gac | aaa | gca | aag | cta | aaa | gag | ctg | gag | aaa | cac | aaa | atc | cag | ctg | gag | 768  |
| Asp | Lys | Ala | Lys | Leu | Lys | Glu | Leu | Glu | Lys | His | Lys | Ile | Gln | Leu | Glu |      |
|     |     |     |     | 245 |     |     |     |     | 250 |     |     |     |     | 255 |     |      |
| cag | gtg | cag | gaa | tgg | aag | agc | aaa | atg | cag | gag | cag | cag | gcc | gac | ctg | 816  |
| Gln | Val | Gln | Glu | Trp | Lys | Ser | Lys | Met | Gln | Glu | Gln | Gln | Ala | Asp | Leu |      |
|     |     |     | 260 |     |     |     |     | 265 |     |     |     |     | 270 |     |     |      |
| cag | cgg | cgc | ctc | aag | gag | gcg | aga | aag | gaa | gcc | aag | gag | gcg | ctg | gag | 864  |
| Gln | Arg | Arg | Leu | Lys | Glu | Ala | Arg | Lys | Glu | Ala | Lys | Glu | Ala | Leu | Glu |      |
|     |     | 275 |     |     |     |     | 280 |     |     |     |     | 285 |     |     |     |      |
| gca | aag | gaa | cgc | tat | atg | gag | gag | atg | gct | gat | act | gct | gat | gcc | att | 912  |
| Ala | Lys | Glu | Arg | Tyr | Met | Glu | Glu | Met | Ala | Asp | Thr | Ala | Asp | Ala | Ile |      |
|     | 290 |     |     |     |     | 295 |     |     |     |     | 300 |     |     |     |     |      |
| gag | atg | gcc | act | ttg | gac | aag | gag | atg | gct | gaa | gag | cgg | gct | gag | tcc | 960  |
| Glu | Met | Ala | Thr | Leu | Asp | Lys | Glu | Met | Ala | Glu | Glu | Arg | Ala | Glu | Ser |      |
| 305 |     |     |     |     | 310 |     |     |     |     | 315 |     |     |     |     | 320 |      |
| ctg | cag | cag | gag | gtg | gag | gca | ctg | aag | gag | cgg | gtg | gac | gag | ctc | act | 1008 |
| Leu | Gln | Gln | Glu | Val | Glu | Ala | Leu | Lys | Glu | Arg | Val | Asp | Glu | Leu | Thr |      |
|     |     |     |     | 325 |     |     |     |     | 330 |     |     |     |     | 335 |     |      |
| act | gac | tta | gag | atc | ctc | aag | gct | gag | att | gaa | gag | aag | ggc | tca | gat | 1056 |
| Thr | Asp | Leu | Glu | Ile | Leu | Lys | Ala | Glu | Ile | Glu | Glu | Lys | Gly | Ser | Asp |      |
|     |     |     | 340 |     |     |     |     | 345 |     |     |     |     | 350 |     |     |      |
| ggc | gct | gca | tcc | agt | tat | cag | ctc | aag | cag | ctt | gag | gag | cag | aat | gcc | 1104 |
| Gly | Ala | Ala | Ser | Ser | Tyr | Gln | Leu | Lys | Gln | Leu | Glu | Glu | Gln | Asn | Ala |      |
|     |     | 355 |     |     |     |     | 360 |     |     |     |     | 365 |     |     |     |      |
| cgc | ctg | aag | gat | gcc | ctg | gtg | agg | atg | cgg | gat | ctt | tct | tcc | tca | gag | 1152 |
| Arg | Leu | Lys | Asp | Ala | Leu | Val | Arg | Met | Arg | Asp | Leu | Ser | Ser | Ser | Glu |      |
|     | 370 |     |     |     |     | 375 |     |     |     |     | 380 |     |     |     |     |      |
| aag | cag | gag | cat | gtg | aag | ctc | cag | aag | ctc | atg | gaa | aag | aag | aac | caa | 1200 |
| Lys | Gln | Glu | His | Val | Lys | Leu | Gln | Lys | Leu | Met | Glu | Lys | Lys | Asn | Gln |      |
| 385 |     |     |     |     | 390 |     |     |     |     | 395 |     |     |     |     | 400 |      |
| gag | ctg | gaa | gtt | gtg | agg | caa | cag | cgg | gag | cgt | ctg | cag | gag | gag | cta | 1248 |
| Glu | Leu | Glu | Val | Val | Arg | Gln | Gln | Arg | Glu | Arg | Leu | Gln | Glu | Glu | Leu |      |
|     |     |     |     | 405 |     |     |     |     | 410 |     |     |     |     | 415 |     |      |
| agc | cag | gca | gag | agc | acc | att | gat | gag | ctc | aag | gag | cag | gtg | gat | gct | 1296 |
| Ser | Gln | Ala | Glu | Ser | Thr | Ile | Asp | Glu | Leu | Lys | Glu | Gln | Val | Asp | Ala |      |
|     |     |     | 420 |     |     |     |     | 425 |     |     |     |     | 430 |     |     |      |
| gct | ctg | ggt | gct | gag | gag | atg | gtg | gag | atg | ctg | aca | gat | cgg | aac | ctg | 1344 |
| Ala | Leu | Gly | Ala | Glu | Glu | Met | Val | Glu | Met | Leu | Thr | Asp | Arg | Asn | Leu |      |
|     |     | 435 |     |     |     |     | 440 |     |     |     |     | 445 |     |     |     |      |
| aat | ctg | gaa | gag | aaa | gtg | cgc | gag | ttg | agg | gag | act | gtg | gga | gac | ttg | 1392 |
| Asn | Leu | Glu | Glu | Lys | Val | Arg | Glu | Leu | Arg | Glu | Thr | Val | Gly | Asp | Leu |      |
|     | 450 |     |     |     |     | 455 |     |     |     |     | 460 |     |     |     |     |      |
| gaa | gcg | atg | aat | gag | atg | aac | gat | gag | ctg | cag | gag | aat | gca | cgt | gag | 1440 |
| Glu | Ala | Met | Asn | Glu | Met | Asn | Asp | Glu | Leu | Gln | Glu | Asn | Ala | Arg | Glu |      |
| 465 |     |     |     |     | 470 |     |     |     |     | 475 |     |     |     |     | 480 |      |
| aca | gaa | ctg | gag | ctg | cgg | gag | cag | ctg | gac | atg | gca | ggc | gcg | cgg | gtt | 1488 |
| Thr | Glu | Leu | Glu | Leu | Arg | Glu | Gln | Leu | Asp | Met | Ala | Gly | Ala | Arg | Val |      |
|     |     |     |     | 485 |     |     |     |     | 490 |     |     |     |     | 495 |     |      |
| cgt | gag | gcc | cag | aag | cgt | gtg | gag | gca | gcc | cag | gag | acg | gtt | gca | gac | 1536 |
| Arg | Glu | Ala | Gln | Lys | Arg | Val | Glu | Ala | Ala | Gln | Glu | Thr | Val | Ala | Asp |      |
|     |     |     | 500 |     |     |     |     | 505 |     |     |     |     | 510 |     |     |      |
| tac | cag | cag | acc | atc | aag | aag | tac | cgc | cag | ctg | acc | gcc | cat | cta | cag | 1584 |

```
                                                            -continued
Tyr Gln Gln Thr Ile Lys Lys Tyr Arg Gln Leu Thr Ala His Leu Gln
    515                 520                 525 gat gtg aat cgg gaa ctg aca aac cag cag gaa gca tct gtg gag agg    1632
Asp Val Asn Arg Glu Leu Thr Asn Gln Gln Glu Ala Ser Val Glu Arg
530                 535                 540 caa cag cag cca cct cca gag acc ttt gac ttc aaa atc aag ttt gct    1680
Gln Gln Gln Pro Pro Pro Glu Thr Phe Asp Phe Lys Ile Lys Phe Ala
545                 550                 555                 560 gag act aag gcc cat gcc aag gca att gag atg gaa ttg agg cag atg    1728
Glu Thr Lys Ala His Ala Lys Ala Ile Glu Met Glu Leu Arg Gln Met
                565                 570                 575 gag gtg gcc cag gcc aat cga cac atg tcc ctg ctg aca gcc ttc atg    1776
Glu Val Ala Gln Ala Asn Arg His Met Ser Leu Leu Thr Ala Phe Met
            580                 585                 590 cct gac agc ttc ctt cgg cca ggt ggg gac cat gac tgc gtt ctg gtg    1824
Pro Asp Ser Phe Leu Arg Pro Gly Gly Asp His Asp Cys Val Leu Val
        595                 600                 605 ctg ttg ctc atg cct cgt ctc att tgc aag gca gag ctg atc cgg aag    1872
Leu Leu Leu Met Pro Arg Leu Ile Cys Lys Ala Glu Leu Ile Arg Lys
    610                 615                 620 cag gcc cag gag aag ttt gaa cta agt gag aac tgt tca gag cgg cct    1920
Gln Ala Gln Glu Lys Phe Glu Leu Ser Glu Asn Cys Ser Glu Arg Pro
625                 630                 635                 640 ggg ctg cga gga gct gct ggg gag caa ctc agc ttt gct gct gga ctg    1968
Gly Leu Arg Gly Ala Ala Gly Glu Gln Leu Ser Phe Ala Ala Gly Leu
                645                 650                 655 gtg tac tcg ctg agc ctg ctg cag gcc acg cta cac cgc tat gag cat    2016
Val Tyr Ser Leu Ser Leu Leu Gln Ala Thr Leu His Arg Tyr Glu His
            660                 665                 670 gcc ctc tct cag tgc agt gtg gat gtg tat aag aaa gtg ggc agc ctg    2064
Ala Leu Ser Gln Cys Ser Val Asp Val Tyr Lys Lys Val Gly Ser Leu
        675                 680                 685 tac cct gag atg agt gcc cat gag cgc tcc ttg gat ttc ctc att gaa    2112
Tyr Pro Glu Met Ser Ala His Glu Arg Ser Leu Asp Phe Leu Ile Glu
    690                 695                 700 ctg ctg cac aag gat cag ctg gat gag act gtc aat gtg gag cct ctc    2160
Leu Leu His Lys Asp Gln Leu Asp Glu Thr Val Asn Val Glu Pro Leu
705                 710                 715                 720 acc aag gcc atc aag tac tat cag cat ctg tac agc atc cac ctt gcc    2208
Thr Lys Ala Ile Lys Tyr Tyr Gln His Leu Tyr Ser Ile His Leu Ala
                725                 730                 735 gaa cag cct gag gac tgt act atg cag ctg gct gac cac att aag ttc    2256
Glu Gln Pro Glu Asp Cys Thr Met Gln Leu Ala Asp His Ile Lys Phe
            740                 745                 750 acg cag agt gct ctg gac tgc atg agt gtg gag gta gga cgg ctg cgt    2304
Thr Gln Ser Ala Leu Asp Cys Met Ser Val Glu Val Gly Arg Leu Arg
        755                 760                 765 gcc ttc ttg cag ggt ggg cag gag gct aca gat att gcc ctc ctg ctc    2352
Ala Phe Leu Gln Gly Gly Gln Glu Ala Thr Asp Ile Ala Leu Leu Leu
    770                 775                 780 cgg gat ctg gaa act tca tgc agt gac atc cgc cag ttc tgc aag aag    2400
Arg Asp Leu Glu Thr Ser Cys Ser Asp Ile Arg Gln Phe Cys Lys Lys
785                 790                 795                 800 atc cga agg cga atg cca ggg aca gat gct cct ggg atc cca gct gca    2448
Ile Arg Arg Arg Met Pro Gly Thr Asp Ala Pro Gly Ile Pro Ala Ala
                805                 810                 815 ctg gcc ttt gga cca cag gta tct gac acg ctc cta gac tgc agg aaa    2496
Leu Ala Phe Gly Pro Gln Val Ser Asp Thr Leu Leu Asp Cys Arg Lys
            820                 825                 830
```

-continued

| | | |
|---|---|---|
| cac ttg acg tgg gtc gtg gct gtg ctg cag gag gtg gca gct gct gct<br>His Leu Thr Trp Val Val Ala Val Leu Gln Glu Val Ala Ala Ala Ala<br>            835                    840                   845 | 2544 |
| gcc cag ctc att gcc cca ctg gca gag aat gag ggg cta ctt gtg gct<br>Ala Gln Leu Ile Ala Pro Leu Ala Glu Asn Glu Gly Leu Leu Val Ala<br>850                     855                    860 | 2592 |
| gct ctg gag gaa ctg gct ttc aaa gca agc gag cag atc tat ggg acc<br>Ala Leu Glu Glu Leu Ala Phe Lys Ala Ser Glu Gln Ile Tyr Gly Thr<br>865                   870                   875                 880 | 2640 |
| ccc tcc agc agc ccc tat gag tgt ctg cgc cag tca tgc aac atc ctc<br>Pro Ser Ser Ser Pro Tyr Glu Cys Leu Arg Gln Ser Cys Asn Ile Leu<br>                    885                   890                 895 | 2688 |
| atc agt acc atg aac aag ctg gcc aca gcc atg cag gag ggg gag tat<br>Ile Ser Thr Met Asn Lys Leu Ala Thr Ala Met Gln Glu Gly Glu Tyr<br>            900                    905                    910 | 2736 |
| gat gca gag cgg ccc ccc agc aag cct cca ccg gtt gaa ctg cgg gct<br>Asp Ala Glu Arg Pro Pro Ser Lys Pro Pro Pro Val Glu Leu Arg Ala<br>                   915                    920                 925 | 2784 |
| gct gcc ctt cgt gca gag atc aca gat gct gaa ggc ctg ggt ttg aag<br>Ala Ala Leu Arg Ala Glu Ile Thr Asp Ala Glu Gly Leu Gly Leu Lys<br>930                     935                    940 | 2832 |
| ctc gaa gat cga gag aca gtt att aag gag ttg aag aag tca ctc aag<br>Leu Glu Asp Arg Glu Thr Val Ile Lys Glu Leu Lys Lys Ser Leu Lys<br>945                   950                   955                 960 | 2880 |
| att aag gga gag gag cta agt gag gcc aat gtg cgg ctg agc ctc ctg<br>Ile Lys Gly Glu Glu Leu Ser Glu Ala Asn Val Arg Leu Ser Leu Leu<br>                   965                    970                 975 | 2928 |
| gag aag aag ttg gac agt gct gcc aag gat gca gat gag cgc atc gag<br>Glu Lys Lys Leu Asp Ser Ala Ala Lys Asp Ala Asp Glu Arg Ile Glu<br>            980                    985                    990 | 2976 |
| aaa gtc cag act cgg ctg gag gag   acc cag gca ctg ctg   cga aag aag<br>Lys Val Gln Thr Arg Leu Glu Glu   Thr Gln Ala Leu Leu   Arg Lys Lys<br>                 995                    1000                  1005 | 3024 |
| gag aaa gag ttt gag gag aca   atg gat gca ctc cag   gct gac atc<br>Glu Lys Glu Phe Glu Glu Thr   Met Asp Ala Leu Gln   Ala Asp Ile<br>    1010                    1015                  1020 | 3069 |
| gac cag ctg gag gca gag aag   gca gaa cta aag cag   cgt ctg aac<br>Asp Gln Leu Glu Ala Glu Lys   Ala Glu Leu Lys Gln   Arg Leu Asn<br>    1025                    1030                  1035 | 3114 |
| agc cag tcc aaa cgc acg att   gag gga ctc cgg ggc   cct cct cct<br>Ser Gln Ser Lys Arg Thr Ile   Glu Gly Leu Arg Gly   Pro Pro Pro<br>    1040                    1045                  1050 | 3159 |
| tca ggc att gct act ctg gtc   tct ggc att gct ggt   gtg tac cgc<br>Ser Gly Ile Ala Thr Leu Val   Ser Gly Ile Ala Gly   Val Tyr Arg<br>    1055                    1060                  1065 | 3204 |
| cgg aag cac cag gag ctg caa   gcc atg cag atg gag   ctg cag agc<br>Arg Lys His Gln Glu Leu Gln   Ala Met Gln Met Glu   Leu Gln Ser<br>    1070                    1075                  1080 | 3249 |
| cct gag tac aag ctg agc aag   ctc cgc acc tcg acc   atc atg acc<br>Pro Glu Tyr Lys Leu Ser Lys   Leu Arg Thr Ser Thr   Ile Met Thr<br>    1085                    1090                  1095 | 3294 |
| gac tac aac ccc aac tac tgc   ttt gct ggc aag acc   tcc tcc atc<br>Asp Tyr Asn Pro Asn Tyr Cys   Phe Ala Gly Lys Thr   Ser Ser Ile<br>    1100                    1105                  1110 | 3339 |
| agt gac ctg aag gag gtg ccg   cgg aaa aac atc acc   ctc att cgg<br>Ser Asp Leu Lys Glu Val Pro   Arg Lys Asn Ile Thr   Leu Ile Arg<br>    1115                    1120                  1125 | 3384 |
| ggt ctg ggc cat ggc gcc ttt   ggg gag gtg tat gaa   ggc cag gtg<br>Gly Leu Gly His Gly Ala Phe   Gly Glu Val Tyr Glu   Gly Gln Val<br>    1130                    1135                  1140 | 3429 |

| | | | | | | | | | | | |
|---|---|---|---|---|---|---|---|---|---|---|---|
| tcc | gga | atg | ccc | aac | gac | cca | agc | ccc | ctg | caa | gtg | gct | gtg | aag | 3474 |
| Ser | Gly | Met | Pro | Asn | Asp | Pro | Ser | Pro | Leu | Gln | Val | Ala | Val | Lys | |
| | 1145 | | | | 1150 | | | | | 1155 | | | | | |

| acg | ctg | cct | gaa | gtg | tgc | tct | gaa | cag | gac | gaa | ctg | gat | ttc | ctc | 3519 |
| Thr | Leu | Pro | Glu | Val | Cys | Ser | Glu | Gln | Asp | Glu | Leu | Asp | Phe | Leu | |
| 1160 | | | | | 1165 | | | | | 1170 | | | | | |

| atg | gaa | gcc | ctg | atc | atc | agc | aaa | ttc | aac | cac | cag | aac | att | gtt | 3564 |
| Met | Glu | Ala | Leu | Ile | Ile | Ser | Lys | Phe | Asn | His | Gln | Asn | Ile | Val | |
| 1175 | | | | | 1180 | | | | | 1185 | | | | | |

| cgc | tgc | att | ggg | gtg | agc | ctg | caa | tcc | ctg | ccc | cgg | ttc | atc | ctg | 3609 |
| Arg | Cys | Ile | Gly | Val | Ser | Leu | Gln | Ser | Leu | Pro | Arg | Phe | Ile | Leu | |
| | 1190 | | | | 1195 | | | | | 1200 | | | | | |

| ctg | gag | ctc | atg | gcg | ggg | gga | gac | ctc | aag | tcc | ttc | ctc | cga | gag | 3654 |
| Leu | Glu | Leu | Met | Ala | Gly | Gly | Asp | Leu | Lys | Ser | Phe | Leu | Arg | Glu | |
| 1205 | | | | | 1210 | | | | | 1215 | | | | | |

| acc | cgc | cct | cgc | ccg | agc | cag | ccc | tcc | tcc | ctg | gcc | atg | ctg | gac | 3699 |
| Thr | Arg | Pro | Arg | Pro | Ser | Gln | Pro | Ser | Ser | Leu | Ala | Met | Leu | Asp | |
| 1220 | | | | | 1225 | | | | | 1230 | | | | | |

| ctt | ctg | cac | gtg | gct | cgg | gac | att | gcc | tgt | ggc | tgt | cag | tat | ttg | 3744 |
| Leu | Leu | His | Val | Ala | Arg | Asp | Ile | Ala | Cys | Gly | Cys | Gln | Tyr | Leu | |
| | 1235 | | | | 1240 | | | | | 1245 | | | | | |

| gag | gaa | aac | cac | ttc | atc | cac | cga | gac | att | gct | gcc | aga | aac | tgc | 3789 |
| Glu | Glu | Asn | His | Phe | Ile | His | Arg | Asp | Ile | Ala | Ala | Arg | Asn | Cys | |
| 1250 | | | | | 1255 | | | | | 1260 | | | | | |

| ctc | ttg | acc | tgt | cca | ggc | cct | gga | aga | gtg | gcc | aag | att | gga | gac | 3834 |
| Leu | Leu | Thr | Cys | Pro | Gly | Pro | Gly | Arg | Val | Ala | Lys | Ile | Gly | Asp | |
| 1265 | | | | | 1270 | | | | | 1275 | | | | | |

| ttc | ggg | atg | gcc | cga | gac | atc | tac | agg | gcg | agc | tac | tat | aga | aag | 3879 |
| Phe | Gly | Met | Ala | Arg | Asp | Ile | Tyr | Arg | Ala | Ser | Tyr | Tyr | Arg | Lys | |
| | 1280 | | | | 1285 | | | | | 1290 | | | | | |

| gga | ggc | tgt | gcc | atg | ctg | cca | gtt | aag | tgg | atg | ccc | cca | gag | gcc | 3924 |
| Gly | Gly | Cys | Ala | Met | Leu | Pro | Val | Lys | Trp | Met | Pro | Pro | Glu | Ala | |
| 1295 | | | | | 1300 | | | | | 1305 | | | | | |

| ttc | atg | gaa | gga | ata | ttc | act | tct | aaa | aca | gac | aca | tgg | tcc | ttt | 3969 |
| Phe | Met | Glu | Gly | Ile | Phe | Thr | Ser | Lys | Thr | Asp | Thr | Trp | Ser | Phe | |
| 1310 | | | | | 1315 | | | | | 1320 | | | | | |

| gga | gtg | ctg | cta | tgg | gaa | atc | ttt | tct | ctt | gga | tat | atg | cca | tac | 4014 |
| Gly | Val | Leu | Leu | Trp | Glu | Ile | Phe | Ser | Leu | Gly | Tyr | Met | Pro | Tyr | |
| | 1325 | | | | 1330 | | | | | 1335 | | | | | |

| ccc | agc | aaa | agc | aac | cag | gaa | gtt | ctg | gag | ttt | gtc | acc | agt | gga | 4059 |
| Pro | Ser | Lys | Ser | Asn | Gln | Glu | Val | Leu | Glu | Phe | Val | Thr | Ser | Gly | |
| 1340 | | | | | 1345 | | | | | 1350 | | | | | |

| ggc | cgg | atg | gac | cca | ccc | aag | aac | tgc | cct | ggg | cct | gta | tac | cgg | 4104 |
| Gly | Arg | Met | Asp | Pro | Pro | Lys | Asn | Cys | Pro | Gly | Pro | Val | Tyr | Arg | |
| | 1355 | | | | 1360 | | | | | 1365 | | | | | |

| ata | atg | act | cag | tgc | tgg | caa | cat | cag | cct | gaa | gac | agg | ccc | aac | 4149 |
| Ile | Met | Thr | Gln | Cys | Trp | Gln | His | Gln | Pro | Glu | Asp | Arg | Pro | Asn | |
| 1370 | | | | | 1375 | | | | | 1380 | | | | | |

| ttt | gcc | atc | att | ttg | gag | agg | att | gaa | tac | tgc | acc | cag | gac | ccg | 4194 |
| Phe | Ala | Ile | Ile | Leu | Glu | Arg | Ile | Glu | Tyr | Cys | Thr | Gln | Asp | Pro | |
| | 1385 | | | | 1390 | | | | | 1395 | | | | | |

| gat | gta | atc | aac | acc | gct | ttg | ccg | ata | gaa | tat | ggt | cca | ctt | gtg | 4239 |
| Asp | Val | Ile | Asn | Thr | Ala | Leu | Pro | Ile | Glu | Tyr | Gly | Pro | Leu | Val | |
| 1400 | | | | | 1405 | | | | | 1410 | | | | | |

| gaa | gag | gaa | gag | aaa | gtg | cct | gtg | agg | ccc | aag | gac | cct | gag | ggg | 4284 |
| Glu | Glu | Glu | Glu | Lys | Val | Pro | Val | Arg | Pro | Lys | Asp | Pro | Glu | Gly | |
| | 1415 | | | | 1420 | | | | | 1425 | | | | | |

| gtt | cct | cct | ctc | ctg | gtc | tct | caa | cag | gca | aaa | cgg | gag | gag | gag | 4329 |
| Val | Pro | Pro | Leu | Leu | Val | Ser | Gln | Gln | Ala | Lys | Arg | Glu | Glu | Glu | |

```
cgc agc cca gct gcc cca cca cct ctg cct acc acc tcc tct ggc     4374
Arg Ser Pro Ala Ala Pro Pro Leu Pro Thr Thr Ser Ser Gly
    1445                1450                1455 aag gct gca aag aaa ccc aca gct gca gag atc tct gtt cga gtc     4419
Lys Ala Ala Lys Lys Pro Thr Ala Ala Glu Ile Ser Val Arg Val
1460                1465                1470 cct aga ggg ccg gcc gtg gaa ggg gga cac gtg aat atg gca ttc     4464
Pro Arg Gly Pro Ala Val Glu Gly Gly His Val Asn Met Ala Phe
    1475                1480                1485 tct cag tcc aac cct cct tcg gag ttg cac aag gtc cac gga tcc     4509
Ser Gln Ser Asn Pro Pro Ser Glu Leu His Lys Val His Gly Ser
1490                1495                1500 aga aac aag ccc acc agc ttg tgg aac cca acg tac ggc tcc tgg     4554
Arg Asn Lys Pro Thr Ser Leu Trp Asn Pro Thr Tyr Gly Ser Trp
    1505                1510                1515 ttt aca gag aaa ccc acc aaa aag aat aat cct ata gca aag aag     4599
Phe Thr Glu Lys Pro Thr Lys Lys Asn Asn Pro Ile Ala Lys Lys
1520                1525                1530 gag cca cac gac agg ggt aac ctg ggg ctg gag gga agc tgt act     4644
Glu Pro His Asp Arg Gly Asn Leu Gly Leu Glu Gly Ser Cys Thr
    1535                1540                1545 gtc cca cct aac gtt gca act ggg aga ctt ccg ggg gcc tca ctg     4689
Val Pro Pro Asn Val Ala Thr Gly Arg Leu Pro Gly Ala Ser Leu
1550                1555                1560 ctc cta gag ccc tct tcg ctg act gcc aat atg aag gag gta cct     4734
Leu Leu Glu Pro Ser Ser Leu Thr Ala Asn Met Lys Glu Val Pro
    1565                1570                1575 ctg ttc agg cta cgt cac ttc cct tgt ggg aat gtc aat tac ggc     4779
Leu Phe Arg Leu Arg His Phe Pro Cys Gly Asn Val Asn Tyr Gly
1580                1585                1590 tac cag caa cag ggc ttg ccc tta gaa gcc gct act gcc cct gga     4824
Tyr Gln Gln Gln Gly Leu Pro Leu Glu Ala Ala Thr Ala Pro Gly
    1595                1600                1605 gct ggt cat tac gag gat acc att ctg aaa agc aag aat agc atg     4869
Ala Gly His Tyr Glu Asp Thr Ile Leu Lys Ser Lys Asn Ser Met
1610                1615                1620 aac cag cct ggg ccc tga                                          4887
Asn Gln Pro Gly Pro
    1625
```

<210> SEQ ID NO 7
<211> LENGTH: 1628
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Met Ala Gln Ser Lys Arg His Val Tyr Ser Arg Thr Pro Ser Gly Ser
1               5                   10                  15

Arg Met Ser Ala Glu Ala Ser Ala Arg Pro Leu Arg Val Gly Ser Arg
            20                  25                  30

Val Glu Val Ile Gly Lys Gly His Arg Gly Thr Val Ala Tyr Val Gly
        35                  40                  45

Ala Thr Leu Phe Ala Thr Gly Lys Trp Val Gly Val Ile Leu Asp Glu
    50                  55                  60

Ala Lys Gly Lys Asn Asp Gly Thr Val Gln Gly Arg Lys Tyr Phe Thr
65                  70                  75                  80
```

```
Cys Asp Glu Gly His Gly Ile Phe Val Arg Gln Ser Gln Ile Gln Val
                 85                  90                  95

Phe Glu Asp Gly Ala Asp Thr Thr Ser Pro Glu Thr Pro Asp Ser Ser
            100                 105                 110

Ala Ser Lys Val Leu Lys Arg Glu Gly Thr Asp Thr Thr Ala Lys Thr
        115                 120                 125

Ser Lys Leu Arg Gly Leu Lys Pro Lys Ala Pro Thr Ala Arg Lys
130                 135                 140

Thr Thr Thr Arg Arg Pro Lys Pro Thr Arg Pro Ala Ser Thr Gly Val
145                 150                 155                 160

Ala Gly Ala Ser Ser Leu Gly Pro Ser Gly Ser Ala Ser Ala Gly
            165                 170                 175

Glu Leu Ser Ser Ser Glu Pro Ser Thr Pro Ala Gln Thr Pro Leu Ala
            180                 185                 190

Ala Pro Ile Ile Pro Thr Pro Val Leu Thr Ser Pro Gly Ala Val Pro
        195                 200                 205

Pro Leu Pro Ser Pro Ser Lys Glu Glu Gly Leu Arg Ala Gln Val
210                 215                 220

Arg Asp Leu Glu Glu Lys Leu Glu Thr Leu Arg Leu Lys Arg Ala Glu
225                 230                 235                 240

Asp Lys Ala Lys Leu Lys Glu Leu Glu Lys His Lys Ile Gln Leu Glu
            245                 250                 255

Gln Val Gln Glu Trp Lys Ser Lys Met Gln Glu Gln Ala Asp Leu
            260                 265                 270

Gln Arg Arg Leu Lys Glu Ala Arg Glu Ala Lys Glu Ala Leu Glu
            275                 280                 285

Ala Lys Glu Arg Tyr Met Glu Glu Met Ala Asp Thr Ala Asp Ala Ile
290                 295                 300

Glu Met Ala Thr Leu Asp Lys Glu Met Ala Glu Arg Ala Glu Ser
305                 310                 315                 320

Leu Gln Gln Glu Val Glu Ala Leu Lys Glu Arg Val Asp Glu Leu Thr
                325                 330                 335

Thr Asp Leu Glu Ile Leu Lys Ala Glu Ile Glu Glu Lys Gly Ser Asp
            340                 345                 350

Gly Ala Ala Ser Ser Tyr Gln Leu Lys Gln Leu Glu Glu Gln Asn Ala
        355                 360                 365

Arg Leu Lys Asp Ala Leu Val Arg Met Arg Asp Leu Ser Ser Ser Glu
    370                 375                 380

Lys Gln Glu His Val Lys Leu Gln Lys Leu Met Glu Lys Lys Asn Gln
385                 390                 395                 400

Glu Leu Glu Val Val Arg Gln Gln Arg Glu Arg Leu Gln Glu Glu Leu
                405                 410                 415

Ser Gln Ala Glu Ser Thr Ile Asp Glu Leu Lys Glu Gln Val Asp Ala
            420                 425                 430

Ala Leu Gly Ala Glu Glu Met Val Glu Met Leu Thr Asp Arg Asn Leu
        435                 440                 445

Asn Leu Glu Glu Lys Val Arg Glu Leu Arg Glu Thr Val Gly Asp Leu
450                 455                 460

Glu Ala Met Asn Glu Met Asn Asp Glu Leu Gln Glu Asn Ala Arg Glu
465                 470                 475                 480

Thr Glu Leu Glu Leu Arg Glu Gln Leu Asp Met Ala Gly Ala Arg Val
                485                 490                 495
```

-continued

```
Arg Glu Ala Gln Lys Arg Val Glu Ala Ala Gln Glu Thr Val Ala Asp
            500                 505                 510
Tyr Gln Gln Thr Ile Lys Lys Tyr Arg Gln Leu Thr Ala His Leu Gln
        515                 520                 525
Asp Val Asn Arg Glu Leu Thr Asn Gln Gln Glu Ala Ser Val Glu Arg
    530                 535                 540
Gln Gln Gln Pro Pro Glu Thr Phe Asp Phe Lys Ile Lys Phe Ala
545                 550                 555                 560
Glu Thr Lys Ala His Ala Lys Ala Ile Glu Met Glu Leu Arg Gln Met
                565                 570                 575
Glu Val Ala Gln Ala Asn Arg His Met Ser Leu Leu Thr Ala Phe Met
            580                 585                 590
Pro Asp Ser Phe Leu Arg Pro Gly Gly Asp His Asp Cys Val Leu Val
        595                 600                 605
Leu Leu Leu Met Pro Arg Leu Ile Cys Lys Ala Glu Leu Ile Arg Lys
    610                 615                 620
Gln Ala Gln Glu Lys Phe Glu Leu Ser Glu Asn Cys Ser Glu Arg Pro
625                 630                 635                 640
Gly Leu Arg Gly Ala Ala Gly Glu Gln Leu Ser Phe Ala Ala Gly Leu
                645                 650                 655
Val Tyr Ser Leu Ser Leu Leu Gln Ala Thr Leu His Arg Tyr Glu His
            660                 665                 670
Ala Leu Ser Gln Cys Ser Val Asp Val Tyr Lys Lys Val Gly Ser Leu
        675                 680                 685
Tyr Pro Glu Met Ser Ala His Glu Arg Ser Leu Asp Phe Leu Ile Glu
    690                 695                 700
Leu Leu His Lys Asp Gln Leu Asp Glu Thr Val Asn Val Glu Pro Leu
705                 710                 715                 720
Thr Lys Ala Ile Lys Tyr Tyr Gln His Leu Tyr Ser Ile His Leu Ala
                725                 730                 735
Glu Gln Pro Glu Asp Cys Thr Met Gln Leu Ala Asp His Ile Lys Phe
            740                 745                 750
Thr Gln Ser Ala Leu Asp Cys Met Ser Val Glu Val Gly Arg Leu Arg
        755                 760                 765
Ala Phe Leu Gln Gly Gly Gln Glu Ala Thr Asp Ile Ala Leu Leu Leu
    770                 775                 780
Arg Asp Leu Glu Thr Ser Cys Ser Asp Ile Arg Gln Phe Cys Lys Lys
785                 790                 795                 800
Ile Arg Arg Arg Met Pro Gly Thr Asp Ala Pro Gly Ile Pro Ala Ala
                805                 810                 815
Leu Ala Phe Gly Pro Gln Val Ser Asp Thr Leu Leu Asp Cys Arg Lys
            820                 825                 830
His Leu Thr Trp Val Ala Val Leu Gln Glu Val Ala Ala Ala Ala
        835                 840                 845
Ala Gln Leu Ile Ala Pro Leu Ala Glu Asn Glu Gly Leu Leu Val Ala
    850                 855                 860
Ala Leu Glu Glu Leu Ala Phe Lys Ala Ser Glu Gln Ile Tyr Gly Thr
865                 870                 875                 880
Pro Ser Ser Ser Pro Tyr Glu Cys Leu Arg Gln Ser Cys Asn Ile Leu
                885                 890                 895
Ile Ser Thr Met Asn Lys Leu Ala Thr Ala Met Gln Glu Gly Glu Tyr
            900                 905                 910
Asp Ala Glu Arg Pro Pro Ser Lys Pro Pro Pro Val Glu Leu Arg Ala
```

```
            915                 920                 925
Ala Ala Leu Arg Ala Glu Ile Thr Asp Ala Glu Gly Leu Gly Leu Lys
    930                 935                 940

Leu Glu Asp Arg Glu Thr Val Ile Lys Glu Leu Lys Lys Ser Leu Lys
945                 950                 955                 960

Ile Lys Gly Glu Glu Leu Ser Glu Ala Asn Val Arg Leu Ser Leu Leu
                965                 970                 975

Glu Lys Lys Leu Asp Ser Ala Ala Lys Asp Ala Asp Glu Arg Ile Glu
            980                 985                 990

Lys Val Gln Thr Arg Leu Glu Glu Thr Gln Ala Leu Leu Arg Lys Lys
        995                 1000                1005

Glu Lys Glu Phe Glu Glu Thr Met Asp Ala Leu Gln Ala Asp Ile
    1010                1015                1020

Asp Gln Leu Glu Ala Glu Lys Ala Glu Leu Lys Gln Arg Leu Asn
    1025                1030                1035

Ser Gln Ser Lys Arg Thr Ile Glu Gly Leu Arg Gly Pro Pro Pro
    1040                1045                1050

Ser Gly Ile Ala Thr Leu Val Ser Gly Ile Ala Gly Val Tyr Arg
    1055                1060                1065

Arg Lys His Gln Glu Leu Gln Ala Met Gln Met Glu Leu Gln Ser
    1070                1075                1080

Pro Glu Tyr Lys Leu Ser Lys Leu Arg Thr Ser Thr Ile Met Thr
    1085                1090                1095

Asp Tyr Asn Pro Asn Tyr Cys Phe Ala Gly Lys Thr Ser Ser Ile
    1100                1105                1110

Ser Asp Leu Lys Glu Val Pro Arg Lys Asn Ile Thr Leu Ile Arg
    1115                1120                1125

Gly Leu Gly His Gly Ala Phe Gly Glu Val Tyr Glu Gly Gln Val
    1130                1135                1140

Ser Gly Met Pro Asn Asp Pro Ser Pro Leu Gln Val Ala Val Lys
    1145                1150                1155

Thr Leu Pro Glu Val Cys Ser Glu Gln Asp Glu Leu Asp Phe Leu
    1160                1165                1170

Met Glu Ala Leu Ile Ile Ser Lys Phe Asn His Gln Asn Ile Val
    1175                1180                1185

Arg Cys Ile Gly Val Ser Leu Gln Ser Leu Pro Arg Phe Ile Leu
    1190                1195                1200

Leu Glu Leu Met Ala Gly Gly Asp Leu Lys Ser Phe Leu Arg Glu
    1205                1210                1215

Thr Arg Pro Arg Pro Ser Gln Pro Ser Ser Leu Ala Met Leu Asp
    1220                1225                1230

Leu Leu His Val Ala Arg Asp Ile Ala Cys Gly Cys Gln Tyr Leu
    1235                1240                1245

Glu Glu Asn His Phe Ile His Arg Asp Ile Ala Ala Arg Asn Cys
    1250                1255                1260

Leu Leu Thr Cys Pro Gly Pro Gly Arg Val Ala Lys Ile Gly Asp
    1265                1270                1275

Phe Gly Met Ala Arg Asp Ile Tyr Arg Ala Ser Tyr Tyr Arg Lys
    1280                1285                1290

Gly Gly Cys Ala Met Leu Pro Val Lys Trp Met Pro Pro Glu Ala
    1295                1300                1305

Phe Met Glu Gly Ile Phe Thr Ser Lys Thr Asp Thr Trp Ser Phe
    1310                1315                1320
```

Gly Val Leu Leu Trp Glu Ile Phe Ser Leu Gly Tyr Met Pro Tyr
    1325                1330                1335

Pro Ser Lys Ser Asn Gln Glu Val Leu Glu Phe Val Thr Ser Gly
    1340                1345                1350

Gly Arg Met Asp Pro Pro Lys Asn Cys Pro Gly Pro Val Tyr Arg
    1355                1360                1365

Ile Met Thr Gln Cys Trp Gln His Gln Pro Glu Asp Arg Pro Asn
    1370                1375                1380

Phe Ala Ile Ile Leu Glu Arg Ile Glu Tyr Cys Thr Gln Asp Pro
    1385                1390                1395

Asp Val Ile Asn Thr Ala Leu Pro Ile Glu Tyr Gly Pro Leu Val
    1400                1405                1410

Glu Glu Glu Glu Lys Val Pro Val Arg Pro Lys Asp Pro Glu Gly
    1415                1420                1425

Val Pro Pro Leu Leu Val Ser Gln Gln Ala Lys Arg Glu Glu Glu
    1430                1435                1440

Arg Ser Pro Ala Ala Pro Pro Pro Leu Pro Thr Thr Ser Ser Gly
    1445                1450                1455

Lys Ala Ala Lys Lys Pro Thr Ala Ala Glu Ile Ser Val Arg Val
    1460                1465                1470

Pro Arg Gly Pro Ala Val Glu Gly Gly His Val Asn Met Ala Phe
    1475                1480                1485

Ser Gln Ser Asn Pro Pro Ser Glu Leu His Lys Val His Gly Ser
    1490                1495                1500

Arg Asn Lys Pro Thr Ser Leu Trp Asn Pro Thr Tyr Gly Ser Trp
    1505                1510                1515

Phe Thr Glu Lys Pro Thr Lys Lys Asn Asn Pro Ile Ala Lys Lys
    1520                1525                1530

Glu Pro His Asp Arg Gly Asn Leu Gly Leu Glu Gly Ser Cys Thr
    1535                1540                1545

Val Pro Pro Asn Val Ala Thr Gly Arg Leu Pro Gly Ala Ser Leu
    1550                1555                1560

Leu Leu Glu Pro Ser Ser Leu Thr Ala Asn Met Lys Glu Val Pro
    1565                1570                1575

Leu Phe Arg Leu Arg His Phe Pro Cys Gly Asn Val Asn Tyr Gly
    1580                1585                1590

Tyr Gln Gln Gln Gly Leu Pro Leu Glu Ala Ala Thr Ala Pro Gly
    1595                1600                1605

Ala Gly His Tyr Glu Asp Thr Ile Leu Lys Ser Lys Asn Ser Met
    1610                1615                1620

Asn Gln Pro Gly Pro
    1625

<210> SEQ ID NO 8
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ataaaaattt aaagaaatta gctgggcata ggggtcccca ggggaggatg aggcaggtct    60
ggagacct                                                              68

-continued

<210> SEQ ID NO 9
<211> LENGTH: 1728
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(1725)

<400> SEQUENCE: 9

```
atg gag acc ccg tcc cag cgg cgc gcc acc cgc agc ggg gcg cag gcc         48
Met Glu Thr Pro Ser Gln Arg Arg Ala Thr Arg Ser Gly Ala Gln Ala
1               5                   10                  15 agc tcc act ccg ctg tcg ccc acc cgc atc acc cgg ctg cag gag aag         96
Ser Ser Thr Pro Leu Ser Pro Thr Arg Ile Thr Arg Leu Gln Glu Lys
            20                  25                  30 gag gac ctg cag gag ctc aat gat cgc ttg gcg gtc tac atc gac cgt        144
Glu Asp Leu Gln Glu Leu Asn Asp Arg Leu Ala Val Tyr Ile Asp Arg
        35                  40                  45 gtg cgc tcg ctg gaa acg gag aac gca ggg ctg cgc ctt cgc atc acc        192
Val Arg Ser Leu Glu Thr Glu Asn Ala Gly Leu Arg Leu Arg Ile Thr
    50                  55                  60 gag tct gaa gag gtg gtc agc cgc gag gtg tcc ggc atc aag gcc gcc        240
Glu Ser Glu Glu Val Val Ser Arg Glu Val Ser Gly Ile Lys Ala Ala
65                  70                  75                  80 tac gag gcc gag ctc ggg gat gcc cgc aag acc ctt gac tca gta gcc        288
Tyr Glu Ala Glu Leu Gly Asp Ala Arg Lys Thr Leu Asp Ser Val Ala
                85                  90                  95 aag gag cgc gcc cgc ctg cag ctg gag ctg agc aaa gtg cgt gag gag        336
Lys Glu Arg Ala Arg Leu Gln Leu Glu Leu Ser Lys Val Arg Glu Glu
            100                 105                 110 ttt aag gag ctg aaa gcg cgc aat acc aag aag gag ggt gac ctg ata        384
Phe Lys Glu Leu Lys Ala Arg Asn Thr Lys Lys Glu Gly Asp Leu Ile
        115                 120                 125 gct gct cag gct cgg ctg aag gac ctg gag gct ctg ctg aac tcc aag        432
Ala Ala Gln Ala Arg Leu Lys Asp Leu Glu Ala Leu Leu Asn Ser Lys
    130                 135                 140 gag gcc gca ctg agc act gct ctc agt gag aag cgc acg ctg gag ggc        480
Glu Ala Ala Leu Ser Thr Ala Leu Ser Glu Lys Arg Thr Leu Glu Gly
145                 150                 155                 160 gag ctg cat gat ctg cgg ggc cag gtg gcc aag gtc tcc ttc tcg ccg        528
Glu Leu His Asp Leu Arg Gly Gln Val Ala Lys Val Ser Phe Ser Pro
                165                 170                 175 gtg gac act aac agc aca tct gga gac ccg gtg gag aag aag gac gaa        576
Val Asp Thr Asn Ser Thr Ser Gly Asp Pro Val Glu Lys Lys Asp Glu
            180                 185                 190 aca cct ttt ggg gtc tcg gtg gct gtg ggc ctg gcc gtc ttt gcc tgc        624
Thr Pro Phe Gly Val Ser Val Ala Val Gly Leu Ala Val Phe Ala Cys
        195                 200                 205 ctc ttc ctt tct acg ctg ctc ctt gtg ctc aac aaa tgt gga cgg aga        672
Leu Phe Leu Ser Thr Leu Leu Leu Val Leu Asn Lys Cys Gly Arg Arg
    210                 215                 220 aac aag ttt ggg atc aac cgc ccg gct gtg ctg gct cca gag gat ggg        720
Asn Lys Phe Gly Ile Asn Arg Pro Ala Val Leu Ala Pro Glu Asp Gly
225                 230                 235                 240 ctg gcc atg tcc ctg cat ttc atg aca ttg ggt ggc agc tcc ctg tcc        768
Leu Ala Met Ser Leu His Phe Met Thr Leu Gly Gly Ser Ser Leu Ser
                245                 250                 255 ccc acc gag ggc aaa ggc tct ggg ctc caa ggc cac atc atc gag aac        816
Pro Thr Glu Gly Lys Gly Ser Gly Leu Gln Gly His Ile Ile Glu Asn
```

```
                    Pro Thr Glu Gly Lys Gly Ser Gly Leu Gln Gly His Ile Ile Glu Asn
                                260             265                 270 cca caa tac ttc agt gat gcc tgt gtt cac cac atc aag cgc cgg gac        864
Pro Gln Tyr Phe Ser Asp Ala Cys Val His His Ile Lys Arg Arg Asp
            275                 280                 285 atc gtg ctc aag tgg gag ctg ggg gag ggc gcc ttt ggg aag gtc ttc        912
Ile Val Leu Lys Trp Glu Leu Gly Glu Gly Ala Phe Gly Lys Val Phe
    290                 295                 300 ctt gct gag tgc cac aac ctc ctg cct gag cag gac aag atg ctg gtg        960
Leu Ala Glu Cys His Asn Leu Leu Pro Glu Gln Asp Lys Met Leu Val
305                 310                 315                 320 gct gtc aag gca ctg aag gag gcg tcc gag agt gct cgg cag gac ttc       1008
Ala Val Lys Ala Leu Lys Glu Ala Ser Glu Ser Ala Arg Gln Asp Phe
                325                 330                 335 caa cgt gag gct gag ctg ctc acc atg ctg cag cac cag cac atc gtg       1056
Gln Arg Glu Ala Glu Leu Leu Thr Met Leu Gln His Gln His Ile Val
            340                 345                 350 cgc ttc ttc ggc gtc tgc acc gag ggc cgc ccc ctc atg gtc ttc           1104
Arg Phe Phe Gly Val Cys Thr Glu Gly Arg Pro Leu Leu Met Val Phe
        355                 360                 365 gag tat atg cgg cac ggg gac ctc aac cgc ttc ctc cga tcc cat gga       1152
Glu Tyr Met Arg His Gly Asp Leu Asn Arg Phe Leu Arg Ser His Gly
370                 375                 380 ccc gat gcc aag ctg ctg gct ggt ggg gag gat gtg gct cca ggc ccc       1200
Pro Asp Ala Lys Leu Leu Ala Gly Gly Glu Asp Val Ala Pro Gly Pro
385                 390                 395                 400 ctg ggt ctg ggg cag ctg ctg gcc gtg gct agc cag gtc gct gcg ggg       1248
Leu Gly Leu Gly Gln Leu Leu Ala Val Ala Ser Gln Val Ala Ala Gly
                405                 410                 415 atg gtg tac ctg gcg ggt ctg cat ttt gtg cac cgg gac ctg gcc aca       1296
Met Val Tyr Leu Ala Gly Leu His Phe Val His Arg Asp Leu Ala Thr
            420                 425                 430 cgc aac tgt cta gtg ggc cag gga ctg gtg gtc aag att ggt gat ttt       1344
Arg Asn Cys Leu Val Gly Gln Gly Leu Val Val Lys Ile Gly Asp Phe
        435                 440                 445 ggc atg agc agg gat atc tac agc acc gac tat tac cgt gtg gga ggc       1392
Gly Met Ser Arg Asp Ile Tyr Ser Thr Asp Tyr Tyr Arg Val Gly Gly
450                 455                 460 cgc acc atg ctg ccc att cgc tgg atg ccg ccc gag agc atc ctg tac       1440
Arg Thr Met Leu Pro Ile Arg Trp Met Pro Pro Glu Ser Ile Leu Tyr
465                 470                 475                 480 cgt aag ttc acc acc gag agc gac gtg tgg agc ttc ggc gtg gtg ctc       1488
Arg Lys Phe Thr Thr Glu Ser Asp Val Trp Ser Phe Gly Val Val Leu
                485                 490                 495 tgg gag atc ttc acc tac ggc aag cag ccc tgg tac cag ctc tcc aac       1536
Trp Glu Ile Phe Thr Tyr Gly Lys Gln Pro Trp Tyr Gln Leu Ser Asn
            500                 505                 510 acg gag gca atc gac tgc atc acg cag gga cgt gag ttg gag cgg cca       1584
Thr Glu Ala Ile Asp Cys Ile Thr Gln Gly Arg Glu Leu Glu Arg Pro
        515                 520                 525 cgt gcc tgc cca cca gag gtc tac gcc atc atg cgg ggc tgc tgg cag       1632
Arg Ala Cys Pro Pro Glu Val Tyr Ala Ile Met Arg Gly Cys Trp Gln
530                 535                 540 cgg gag ccc cag caa cgc cac agc atc aag gat gtg cac gcc cgg ctg       1680
Arg Glu Pro Gln Gln Arg His Ser Ile Lys Asp Val His Ala Arg Leu
545                 550                 555                 560 caa gcc ctg gcc cag gca cct cct gtc tac ctg gat gtc ctg ggc tag       1728
Gln Ala Leu Ala Gln Ala Pro Pro Val Tyr Leu Asp Val Leu Gly
                565                 570                 575
```

```
<210> SEQ ID NO 10
<211> LENGTH: 575
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Val Ser Phe Ser Pro
                165                 170                 175

Val Asp Thr Asn Ser Thr Ser Gly Asp Pro Val Glu Lys Lys Asp Glu
            180                 185                 190

Thr Pro Phe Gly Val Ser Val Ala Val Gly Leu Ala Val Phe Ala Cys
        195                 200                 205

Leu Phe Leu Ser Thr Leu Leu Leu Val Leu Asn Lys Cys Gly Arg Arg
    210                 215                 220

Asn Lys Phe Gly Ile Asn Arg Pro Ala Val Leu Ala Pro Glu Asp Gly
225                 230                 235                 240

Leu Ala Met Ser Leu His Phe Met Thr Leu Gly Gly Ser Ser Leu Ser
                245                 250                 255

Pro Thr Glu Gly Lys Gly Ser Gly Leu Gln Gly His Ile Ile Glu Asn
            260                 265                 270

Pro Gln Tyr Phe Ser Asp Ala Cys Val His His Ile Lys Arg Arg Asp
        275                 280                 285

Ile Val Leu Lys Trp Glu Leu Gly Glu Gly Ala Phe Gly Lys Val Phe
    290                 295                 300

Leu Ala Glu Cys His Asn Leu Leu Pro Glu Gln Asp Lys Met Leu Val
305                 310                 315                 320

Ala Val Lys Ala Leu Lys Glu Ala Ser Glu Ser Ala Arg Gln Asp Phe
                325                 330                 335

Gln Arg Glu Ala Glu Leu Leu Thr Met Leu Gln His Gln His Ile Val
            340                 345                 350

Arg Phe Phe Gly Val Cys Thr Glu Gly Arg Pro Leu Leu Met Val Phe
        355                 360                 365
```

```
Glu Tyr Met Arg His Gly Asp Leu Asn Arg Phe Leu Arg Ser His Gly
    370                 375                 380

Pro Asp Ala Lys Leu Leu Ala Gly Gly Glu Asp Val Ala Pro Gly Pro
385                 390                 395                 400

Leu Gly Leu Gly Gln Leu Leu Ala Val Ala Ser Gln Val Ala Ala Gly
                405                 410                 415

Met Val Tyr Leu Ala Gly Leu His Phe Val His Arg Asp Leu Ala Thr
            420                 425                 430

Arg Asn Cys Leu Val Gly Gln Gly Leu Val Val Lys Ile Gly Asp Phe
        435                 440                 445

Gly Met Ser Arg Asp Ile Tyr Ser Thr Asp Tyr Tyr Arg Val Gly Gly
    450                 455                 460

Arg Thr Met Leu Pro Ile Arg Trp Met Pro Pro Glu Ser Ile Leu Tyr
465                 470                 475                 480

Arg Lys Phe Thr Thr Glu Ser Asp Val Trp Ser Phe Gly Val Val Leu
                485                 490                 495

Trp Glu Ile Phe Thr Tyr Gly Lys Gln Pro Trp Tyr Gln Leu Ser Asn
            500                 505                 510

Thr Glu Ala Ile Asp Cys Ile Thr Gln Gly Arg Glu Leu Glu Arg Pro
        515                 520                 525

Arg Ala Cys Pro Pro Glu Val Tyr Ala Ile Met Arg Gly Cys Trp Gln
    530                 535                 540

Arg Glu Pro Gln Gln Arg His Ser Ile Lys Asp Val His Ala Arg Leu
545                 550                 555                 560

Gln Ala Leu Ala Gln Ala Pro Pro Val Tyr Leu Asp Val Leu Gly
                565                 570                 575

<210> SEQ ID NO 11
<211> LENGTH: 3813
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(3810)

<400> SEQUENCE: 11 atg gga gcc atc ggg ctc ctg tgg ctc ctg ccg ctg ctg ctt tcc acg      48
Met Gly Ala Ile Gly Leu Leu Trp Leu Leu Pro Leu Leu Leu Ser Thr
1               5                   10                  15 gca gct gtg ggc tcc ggg atg ggg acc ggc cag cgc gcg ggc tcc cca      96
Ala Ala Val Gly Ser Gly Met Gly Thr Gly Gln Arg Ala Gly Ser Pro
            20                  25                  30 gct gcg ggg ccg ccg ctg cag ccc cgg gag cca ctc agc tac tcg cgc     144
Ala Ala Gly Pro Pro Leu Gln Pro Arg Glu Pro Leu Ser Tyr Ser Arg
        35                  40                  45 ctg cag agg aag agt ctg gca gtt gac ttc gtg gtg ccc tcg ctc ttc     192
Leu Gln Arg Lys Ser Leu Ala Val Asp Phe Val Val Pro Ser Leu Phe
    50                  55                  60 cgt gtc tac gcc cgg gac cta ctg ctg cca cca tcc tcc tcg gag ctg     240
Arg Val Tyr Ala Arg Asp Leu Leu Leu Pro Pro Ser Ser Ser Glu Leu
65                  70                  75                  80 aag gct ggc agg ccc gag gcc cgc ggc tcg cta gct ctg gac tgc gcc     288
Lys Ala Gly Arg Pro Glu Ala Arg Gly Ser Leu Ala Leu Asp Cys Ala
                85                  90                  95 ccg ctg ctc agg ttg ctg ggg ccg gcg ccg ggg gtc tcc tgg acc gcc     336
```

```
                Pro Leu Leu Arg Leu Leu Gly Pro Ala Pro Gly Val Ser Trp Thr Ala
                                100                 105                 110 ggt tca cca gcc ccg gca gag gcc cgg acg ctg tcc agg gtg ctg aag        384
Gly Ser Pro Ala Pro Ala Glu Ala Arg Thr Leu Ser Arg Val Leu Lys
        115                 120                 125 ggc ggc tcc gtg cgc aag ctc cgg cgt gcc aag cag ttg gtg ctg gag        432
Gly Gly Ser Val Arg Lys Leu Arg Arg Ala Lys Gln Leu Val Leu Glu
130                 135                 140 ctg ggc gag gag gcg atc ttg gag ggt tgc gtc ggg ccc ccg ggg gag        480
Leu Gly Glu Glu Ala Ile Leu Glu Gly Cys Val Gly Pro Pro Gly Glu
145                 150                 155                 160 gcg gct gtg ggg ctg ctc cag ttc aat ctc agc gag ctg ttc agt tgg        528
Ala Ala Val Gly Leu Leu Gln Phe Asn Leu Ser Glu Leu Phe Ser Trp
            165                 170                 175 tgg att cgc caa ggc gaa ggg cga ctg agg atc cgc ctg atg ccc gag        576
Trp Ile Arg Gln Gly Glu Gly Arg Leu Arg Ile Arg Leu Met Pro Glu
        180                 185                 190 aag aag gcg tcg gaa gtg ggc aga gag gga agg ctg tcc gcg gca att        624
Lys Lys Ala Ser Glu Val Gly Arg Glu Gly Arg Leu Ser Ala Ala Ile
                195                 200                 205 cgc gcc tcc cag ccc cgc ctt ctc ttc cag atc ttc ggg act ggt cat        672
Arg Ala Ser Gln Pro Arg Leu Leu Phe Gln Ile Phe Gly Thr Gly His
210                 215                 220 agc tcc ttg gaa tca cca aca aac atg cct tct cct tct cct gat tat        720
Ser Ser Leu Glu Ser Pro Thr Asn Met Pro Ser Pro Ser Pro Asp Tyr
225                 230                 235                 240 ttt aca tgg aat ctc acc tgg ata atg aaa gac tcc ttc cct ttc ctg        768
Phe Thr Trp Asn Leu Thr Trp Ile Met Lys Asp Ser Phe Pro Phe Leu
            245                 250                 255 tct cat cgc agc cga tat ggt ctg gag tgc agc ttt gac ttc ccc tgt        816
Ser His Arg Ser Arg Tyr Gly Leu Glu Cys Ser Phe Asp Phe Pro Cys
        260                 265                 270 gag ctg gag tat tcc cct cca ctg cat gac ctc agg aac cag agc tgg        864
Glu Leu Glu Tyr Ser Pro Pro Leu His Asp Leu Arg Asn Gln Ser Trp
                275                 280                 285 tcc tgg cgc cgc atc ccc tcg gag gag gcc tcc cag atg gac ttg ctg        912
Ser Trp Arg Arg Ile Pro Ser Glu Glu Ala Ser Gln Met Asp Leu Leu
290                 295                 300 gat ggg cct ggg gca gag cgt tct aag gag atg ccc aga ggc tcc ttt        960
Asp Gly Pro Gly Ala Glu Arg Ser Lys Glu Met Pro Arg Gly Ser Phe
305                 310                 315                 320 ctc ctt ctc aac acc tca gct gac tcc aag cac acc atc ctg agt ccg       1008
Leu Leu Leu Asn Thr Ser Ala Asp Ser Lys His Thr Ile Leu Ser Pro
            325                 330                 335 tgg atg agg agc agc agt gag cac tgc aca ctg gcc gtc tcg gtg cac       1056
Trp Met Arg Ser Ser Ser Glu His Cys Thr Leu Ala Val Ser Val His
        340                 345                 350 agg cac ctg cag ccc tct gga agg tac att gcc cag ctg ctg ccc cac       1104
Arg His Leu Gln Pro Ser Gly Arg Tyr Ile Ala Gln Leu Leu Pro His
                355                 360                 365 aac gag gct gca aga gag atc ctc ctg atg ccc act cca ggg aag cat       1152
Asn Glu Ala Ala Arg Glu Ile Leu Leu Met Pro Thr Pro Gly Lys His
370                 375                 380 ggt tgg aca gtg ctc cag gga aga atc ggg cgt cca gac aac cca ttt       1200
Gly Trp Thr Val Leu Gln Gly Arg Ile Gly Arg Pro Asp Asn Pro Phe
385                 390                 395                 400 cga gtg gcc ctg gaa tac atc tcc agt gga aac cgc agc ttg tct gca       1248
Arg Val Ala Leu Glu Tyr Ile Ser Ser Gly Asn Arg Ser Leu Ser Ala
            405                 410                 415
```

```
gtg gac ttc ttt gcc ctg aag aac tgc agt gaa gga aca tcc cca ggc    1296
Val Asp Phe Phe Ala Leu Lys Asn Cys Ser Glu Gly Thr Ser Pro Gly
            420                 425                 430 tcc aag atg gcc ctg cag agc tcc ttc act tgt tgg aat ggg aca gtc    1344
Ser Lys Met Ala Leu Gln Ser Ser Phe Thr Cys Trp Asn Gly Thr Val
        435                 440                 445 ctc cag ctt ggg cag gcc tgt gac ttc cac cag gac tgt gcc cag gga    1392
Leu Gln Leu Gly Gln Ala Cys Asp Phe His Gln Asp Cys Ala Gln Gly
    450                 455                 460 gaa gat gag agc cag atg tgc cgg aaa ctg cct gtg ggt ttt tac tgc    1440
Glu Asp Glu Ser Gln Met Cys Arg Lys Leu Pro Val Gly Phe Tyr Cys
465                 470                 475                 480 aac ttt gaa gat ggc ttc tgt ggc tgg acc caa ggc aca ctg tca ccc    1488
Asn Phe Glu Asp Gly Phe Cys Gly Trp Thr Gln Gly Thr Leu Ser Pro
                485                 490                 495 cac act cct caa tgg cag gtc agg acc cta aag gat gcc cgg ttc cag    1536
His Thr Pro Gln Trp Gln Val Arg Thr Leu Lys Asp Ala Arg Phe Gln
            500                 505                 510 gac cac caa gac cat gct cta ttg ctc agt acc act gat gtc ccc gct    1584
Asp His Gln Asp His Ala Leu Leu Leu Ser Thr Thr Asp Val Pro Ala
        515                 520                 525 tct gaa agt gct aca gtg acc agt gct acg ttt cct gca ccg atc aag    1632
Ser Glu Ser Ala Thr Val Thr Ser Ala Thr Phe Pro Ala Pro Ile Lys
    530                 535                 540 agc tct cca tgt gag ctc cga atg tcc tgg ctc att cgt gga gtc ttg    1680
Ser Ser Pro Cys Glu Leu Arg Met Ser Trp Leu Ile Arg Gly Val Leu
545                 550                 555                 560 agg gga aac gtg tcc ttg gtg cta gtg gag aac aaa acc ggg aag gag    1728
Arg Gly Asn Val Ser Leu Val Leu Val Glu Asn Lys Thr Gly Lys Glu
                565                 570                 575 caa ggc agg atg gtc tgg cat gtc gcc gcc tat gaa ggc ttg agc ctg    1776
Gln Gly Arg Met Val Trp His Val Ala Ala Tyr Glu Gly Leu Ser Leu
            580                 585                 590 tgg cag tgg atg gtg ttg cct ctc ctc gat gtg tct gac agg ttc tgg    1824
Trp Gln Trp Met Val Leu Pro Leu Leu Asp Val Ser Asp Arg Phe Trp
        595                 600                 605 ctg cag atg gtc gca tgg tgg gga caa gga tcc aga gcc atc gtg gct    1872
Leu Gln Met Val Ala Trp Trp Gly Gln Gly Ser Arg Ala Ile Val Ala
    610                 615                 620 ttt gac aat atc tcc atc agc ctg gac tgc tac ctc acc att agc gga    1920
Phe Asp Asn Ile Ser Ile Ser Leu Asp Cys Tyr Leu Thr Ile Ser Gly
625                 630                 635                 640 gag gac aag atc ctg cag aat aca gca ccc aaa tca aga aac ctg ttt    1968
Glu Asp Lys Ile Leu Gln Asn Thr Ala Pro Lys Ser Arg Asn Leu Phe
                645                 650                 655 gag aga aac cca aac aag gag ctg aaa ccc ggg gaa aat tca cca aga    2016
Glu Arg Asn Pro Asn Lys Glu Leu Lys Pro Gly Glu Asn Ser Pro Arg
            660                 665                 670 cag acc ccc atc ttt gac cct aca gtt cat tgg ctg ttc acc aca tgt    2064
Gln Thr Pro Ile Phe Asp Pro Thr Val His Trp Leu Phe Thr Thr Cys
        675                 680                 685 ggg gcc agc ggg ccc cat ggc ccc acc cag gca cag tgc aac aac gcc    2112
Gly Ala Ser Gly Pro His Gly Pro Thr Gln Ala Gln Cys Asn Asn Ala
    690                 695                 700 tac cag aac tcc aac ctg agc gtg gag gtg ggg agc gag ggc ccc ctg    2160
Tyr Gln Asn Ser Asn Leu Ser Val Glu Val Gly Ser Glu Gly Pro Leu
705                 710                 715                 720 aaa ggc atc cag atc tgg aag gtg cca gcc acc gac acc tac agc atc    2208
Lys Gly Ile Gln Ile Trp Lys Val Pro Ala Thr Asp Thr Tyr Ser Ile
                725                 730                 735
```

-continued

| | | |
|---|---|---|
| tcg ggc tac gga gct gct ggc ggg aaa ggc ggg aag aac acc atg atg<br>Ser Gly Tyr Gly Ala Ala Gly Gly Lys Gly Gly Lys Asn Thr Met Met<br>                  740                      745                  750 | | 2256 |
| cgg tcc cac ggc gtg tct gtg ctg ggc atc ttc aac ctg gag aag gat<br>Arg Ser His Gly Val Ser Val Leu Gly Ile Phe Asn Leu Glu Lys Asp<br>     755                    760                   765 | | 2304 |
| gac atg ctg tac atc ctg gtt ggg cag cag gga gag gac gcc tgc ccc<br>Asp Met Leu Tyr Ile Leu Val Gly Gln Gln Gly Glu Asp Ala Cys Pro<br>770                     775                   780 | | 2352 |
| agt aca aac cag tta atc cag aaa gtc tgc att gga gag aac aat gtg<br>Ser Thr Asn Gln Leu Ile Gln Lys Val Cys Ile Gly Glu Asn Asn Val<br>785                  790               795              800 | | 2400 |
| ata gaa gaa gaa atc cgt gtg aac aga agc gtg cat gag tgg gca gga<br>Ile Glu Glu Glu Ile Arg Val Asn Arg Ser Val His Glu Trp Ala Gly<br>                  805               810              815 | | 2448 |
| ggc gga gga gga ggg ggt gga gcc acc tac gta ttt aag atg aag gat<br>Gly Gly Gly Gly Gly Gly Gly Ala Thr Tyr Val Phe Lys Met Lys Asp<br>            820                   825              830 | | 2496 |
| gga gtg ccg gtg ccc ctg atc att gca gcc gga ggt ggt ggc agg gcc<br>Gly Val Pro Val Pro Leu Ile Ile Ala Ala Gly Gly Gly Gly Arg Ala<br>                835                 840              845 | | 2544 |
| tac ggg gcc aag aca gac acg ttc cac cca gag aga ctg gag aat aac<br>Tyr Gly Ala Lys Thr Asp Thr Phe His Pro Glu Arg Leu Glu Asn Asn<br>850                   855               860 | | 2592 |
| tcc tcg gtt cta ggg cta aac ggc aat tcc gga gcc gca ggt ggt gga<br>Ser Ser Val Leu Gly Leu Asn Gly Asn Ser Gly Ala Ala Gly Gly Gly<br>865                  870              875              880 | | 2640 |
| ggt ggc tgg aat gat aac act tcc ttg ctc tgg gcc gga aaa tct ttg<br>Gly Gly Trp Asn Asp Asn Thr Ser Leu Leu Trp Ala Gly Lys Ser Leu<br>                885                 890              895 | | 2688 |
| cag gag ggt gcc acc gga gga cat tcc tgc ccc cag gcc atg aag aag<br>Gln Glu Gly Ala Thr Gly Gly His Ser Cys Pro Gln Ala Met Lys Lys<br>                     900               905              910 | | 2736 |
| tgg ggg tgg gag aca aga ggg ggt ttc gga ggg ggt gga ggg ggg tgc<br>Trp Gly Trp Glu Thr Arg Gly Gly Phe Gly Gly Gly Gly Gly Gly Cys<br>                 915                 920              925 | | 2784 |
| tcc tca ggt gga gga ggc gga gga tat ata ggc ggc aat gca gcc tca<br>Ser Ser Gly Gly Gly Gly Gly Gly Tyr Ile Gly Gly Asn Ala Ala Ser<br>930                   935               940 | | 2832 |
| aac aat gac ccc gaa atg gat ggg gaa gat ggg gtt tcc ttc atc agt<br>Asn Asn Asp Pro Glu Met Asp Gly Glu Asp Gly Val Ser Phe Ile Ser<br>945                   950               955              960 | | 2880 |
| cca ctg ggc atc ctg tac acc cca gct tta aaa gtg atg gaa ggc cac<br>Pro Leu Gly Ile Leu Tyr Thr Pro Ala Leu Lys Val Met Glu Gly His<br>               965                 970              975 | | 2928 |
| ggg gaa gtg aat att aag cat tat cta aac tgc agt cac tgt gag gta<br>Gly Glu Val Asn Ile Lys His Tyr Leu Asn Cys Ser His Cys Glu Val<br>                   980               985              990 | | 2976 |
| gac gaa tgt cac atg gac cct gaa  agc cac aag gtc atc  tgc ttc tgt<br>Asp Glu Cys His Met Asp Pro Glu  Ser His Lys Val Ile  Cys Phe Cys<br>            995                  1000               1005 | | 3024 |
| gac cac  ggg acg gtg ctg gct  gag gat ggc gtc tcc  tgc att gtg<br>Asp His  Gly Thr Val Leu Ala  Glu Asp Gly Val Ser  Cys Ile Val<br>          1010                 1015               1020 | | 3069 |
| tca ccc  acc ccg gag cca cac  ctg cca ctc tcg ctg  atc ctc tct<br>Ser Pro  Thr Pro Glu Pro His  Leu Pro Leu Ser Leu  Ile Leu Ser<br>          1025                 1030               1035 | | 3114 |
| gtg gtg  acc tct gcc ctc gtg  gcc gcc ctg gtc ctg  gct ttc tcc<br>Val Val  Thr Ser Ala Leu Val  Ala Ala Leu Val Leu  Ala Phe Ser | | 3159 |

| | | |
|---|---|---|
| ggc atc atg att gaa gaa cag cag cga gga gcc atc cct ggg cag<br>Gly Ile Met Ile Glu Glu Gln Gln Arg Gly Ala Ile Pro Gly Gln<br>1055                   1060                  1065 | 3204 |
| gct cca ggg tct gtg cca ggc cca ggg ctg gtg aag gac tca cca<br>Ala Pro Gly Ser Val Pro Gly Pro Gly Leu Val Lys Asp Ser Pro<br>1070                   1075                  1080 | 3249 |
| ctg ctg ctt cag cag atc tct gcc atg agg ctg cac atc tcc cag<br>Leu Leu Leu Gln Gln Ile Ser Ala Met Arg Leu His Ile Ser Gln<br>1085                   1090                  1095 | 3294 |
| ctc cag cat gag aac agc atc ctc aag gga gcc cag atg aag gca<br>Leu Gln His Glu Asn Ser Ile Leu Lys Gly Ala Gln Met Lys Ala<br>1100                   1105                  1110 | 3339 |
| tcc ttg gca tcc ctg ccc cct ctg cat gtt gca aag cta tcc cat<br>Ser Leu Ala Ser Leu Pro Pro Leu His Val Ala Lys Leu Ser His<br>1115                   1120                  1125 | 3384 |
| gag ggc cct ggc agt gag tta cca gct gga gcg ctg tat cgt aag<br>Glu Gly Pro Gly Ser Glu Leu Pro Ala Gly Ala Leu Tyr Arg Lys<br>1130                   1135                  1140 | 3429 |
| acc agc cag ctg ctg gag aca ttg aat caa ttg agc aca cac acg<br>Thr Ser Gln Leu Leu Glu Thr Leu Asn Gln Leu Ser Thr His Thr<br>1145                   1150                  1155 | 3474 |
| cac gta gta gac atc act cgc acc agc cct gct gcc aag agc ccg<br>His Val Val Asp Ile Thr Arg Thr Ser Pro Ala Ala Lys Ser Pro<br>1160                   1165                  1170 | 3519 |
| tcg gcc caa ctt atg gag caa gtg gct cag ctt aag tcc ctg agt<br>Ser Ala Gln Leu Met Glu Gln Val Ala Gln Leu Lys Ser Leu Ser<br>1175                   1180                  1185 | 3564 |
| gac acc gtc gag aag ctc aag gat gag gtc ctc aag gag aca gta<br>Asp Thr Val Glu Lys Leu Lys Asp Glu Val Leu Lys Glu Thr Val<br>1190                   1195                  1200 | 3609 |
| tct cag cgc cct gga gcc aca gta ccc act gac ttt gcc acc ttc<br>Ser Gln Arg Pro Gly Ala Thr Val Pro Thr Asp Phe Ala Thr Phe<br>1205                   1210                  1215 | 3654 |
| cct tca tca gcc ttc ctc agg gcc aag gag gag cag cag gat gac<br>Pro Ser Ser Ala Phe Leu Arg Ala Lys Glu Glu Gln Gln Asp Asp<br>1220                   1225                  1230 | 3699 |
| aca gtc tac atg ggc aaa gtg acc ttc tca tgt gcg gct ggt ttt<br>Thr Val Tyr Met Gly Lys Val Thr Phe Ser Cys Ala Ala Gly Phe<br>1235                   1240                  1245 | 3744 |
| gga cag cga cac cgg ctg gtg ctg acc cag gag cag ctg cac cag<br>Gly Gln Arg His Arg Leu Val Leu Thr Gln Glu Gln Leu His Gln<br>1250                   1255                  1260 | 3789 |
| ctt cac agt cgc ctc atc tcc taa<br>Leu His Ser Arg Leu Ile Ser<br>1265                   1270 | 3813 |

<210> SEQ ID NO 12
<211> LENGTH: 1270
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 12

Met Gly Ala Ile Gly Leu Leu Trp Leu Leu Pro Leu Leu Leu Ser Thr
1              5                  10                 15

Ala Ala Val Gly Ser Gly Met Gly Thr Gly Gln Arg Ala Gly Ser Pro
                 20                  25                 30

Ala Ala Gly Pro Pro Leu Gln Pro Arg Glu Pro Leu Ser Tyr Ser Arg
            35                  40                  45

Leu Gln Arg Lys Ser Leu Ala Val Asp Phe Val Pro Ser Leu Phe
 50                  55                  60

Arg Val Tyr Ala Arg Asp Leu Leu Pro Pro Ser Ser Ser Glu Leu
 65                  70                  75                  80

Lys Ala Gly Arg Pro Glu Ala Arg Gly Ser Leu Ala Leu Asp Cys Ala
                 85                  90                  95

Pro Leu Leu Arg Leu Leu Gly Pro Ala Pro Gly Val Ser Trp Thr Ala
                100                 105                 110

Gly Ser Pro Ala Pro Ala Glu Ala Arg Thr Leu Ser Arg Val Leu Lys
             115                 120                 125

Gly Gly Ser Val Arg Lys Leu Arg Arg Ala Lys Gln Leu Val Leu Glu
         130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
             180                 185                 190

Lys Lys Ala Ser Glu Val Gly Arg Glu Gly Arg Leu Ser Ala Ala Ile
         195                 200                 205

Arg Ala Ser Gln Pro Arg Leu Leu Phe Gln Ile Phe Gly Thr Gly His
    210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
             260                 265                 270

Glu Leu Glu Tyr Ser Pro Pro Leu His Asp Leu Arg Asn Gln Ser Trp
         275                 280                 285

Ser Trp Arg Arg Ile Pro Ser Glu Glu Ala Ser Gln Met Asp Leu Leu
    290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Ser Glu His Cys Thr Leu Ala Val Ser Val His
             340                 345                 350

Arg His Leu Gln Pro Ser Gly Arg Tyr Ile Ala Gln Leu Leu Pro His
         355                 360                 365

Asn Glu Ala Ala Arg Glu Ile Leu Leu Met Pro Thr Pro Gly Lys His
370                 375                 380

Gly Trp Thr Val Leu Gln Gly Arg Ile Gly Arg Pro Asp Asn Pro Phe
385                 390                 395                 400

Arg Val Ala Leu Glu Tyr Ile Ser Ser Gly Asn Arg Ser Leu Ser Ala
                405                 410                 415

Val Asp Phe Phe Ala Leu Lys Asn Cys Ser Glu Gly Thr Ser Pro Gly
             420                 425                 430

Ser Lys Met Ala Leu Gln Ser Ser Phe Thr Cys Trp Asn Gly Thr Val
         435                 440                 445

Leu Gln Leu Gly Gln Ala Cys Asp Phe His Gln Asp Cys Ala Gln Gly

```
                450                 455                 460
Glu Asp Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
                    485                 490                 495

His Thr Pro Gln Trp Gln Val Arg Thr Leu Lys Asp Ala Arg Phe Gln
                500                 505                 510

Asp His Gln Asp His Ala Leu Leu Leu Ser Thr Thr Asp Val Pro Ala
                515                 520                 525

Ser Glu Ser Ala Thr Val Thr Ser Ala Thr Phe Pro Ala Pro Ile Lys
530                 535                 540

Ser Ser Pro Cys Glu Leu Arg Met Ser Trp Leu Ile Arg Gly Val Leu
545                 550                 555                 560

Arg Gly Asn Val Ser Leu Val Leu Val Glu Asn Lys Thr Gly Lys Glu
                565                 570                 575

Gln Gly Arg Met Val Trp His Val Ala Ala Tyr Glu Gly Leu Ser Leu
                580                 585                 590

Trp Gln Trp Met Val Leu Pro Leu Leu Asp Val Ser Asp Arg Phe Trp
                595                 600                 605

Leu Gln Met Val Ala Trp Trp Gly Gln Gly Ser Arg Ala Ile Val Ala
            610                 615                 620

Phe Asp Asn Ile Ser Ile Ser Leu Asp Cys Tyr Leu Thr Ile Ser Gly
625                 630                 635                 640

Glu Asp Lys Ile Leu Gln Asn Thr Ala Pro Lys Ser Arg Asn Leu Phe
                645                 650                 655

Glu Arg Asn Pro Asn Lys Glu Leu Lys Pro Gly Glu Asn Ser Pro Arg
                660                 665                 670

Gln Thr Pro Ile Phe Asp Pro Thr Val His Trp Leu Phe Thr Thr Cys
                675                 680                 685

Gly Ala Ser Gly Pro His Gly Pro Thr Gln Ala Gln Cys Asn Asn Ala
            690                 695                 700

Tyr Gln Asn Ser Asn Leu Ser Val Glu Val Gly Ser Glu Gly Pro Leu
705                 710                 715                 720

Lys Gly Ile Gln Ile Trp Lys Val Pro Ala Thr Asp Thr Tyr Ser Ile
                    725                 730                 735

Ser Gly Tyr Gly Ala Ala Gly Gly Lys Gly Gly Lys Asn Thr Met Met
                740                 745                 750

Arg Ser His Gly Val Ser Val Leu Gly Ile Phe Asn Leu Glu Lys Asp
            755                 760                 765

Asp Met Leu Tyr Ile Leu Val Gly Gln Gln Gly Glu Asp Ala Cys Pro
770                 775                 780

Ser Thr Asn Gln Leu Ile Gln Lys Val Cys Ile Gly Glu Asn Asn Val
785                 790                 795                 800

Ile Glu Glu Glu Ile Arg Val Asn Arg Ser Val His Glu Trp Ala Gly
                    805                 810                 815

Gly Gly Gly Gly Gly Gly Gly Ala Thr Tyr Val Phe Lys Met Lys Asp
                820                 825                 830

Gly Val Pro Val Pro Leu Ile Ile Ala Ala Gly Gly Gly Gly Arg Ala
                835                 840                 845

Tyr Gly Ala Lys Thr Asp Thr Phe His Pro Glu Arg Leu Glu Asn Asn
            850                 855                 860

Ser Ser Val Leu Gly Leu Asn Gly Asn Ser Gly Ala Ala Gly Gly Gly
865                 870                 875                 880
```

```
Gly Gly Trp Asn Asp Asn Thr Ser Leu Leu Trp Ala Gly Lys Ser Leu
            885                 890                 895

Gln Glu Gly Ala Thr Gly Gly His Ser Cys Pro Gln Ala Met Lys Lys
            900                 905                 910

Trp Gly Trp Glu Thr Arg Gly Gly Phe Gly Gly Gly Gly Gly Gly Cys
            915                 920                 925

Ser Ser Gly Gly Gly Gly Gly Gly Tyr Ile Gly Gly Asn Ala Ala Ser
    930                 935                 940

Asn Asn Asp Pro Glu Met Asp Gly Glu Asp Gly Val Ser Phe Ile Ser
945                 950                 955                 960

Pro Leu Gly Ile Leu Tyr Thr Pro Ala Leu Lys Val Met Glu Gly His
            965                 970                 975

Gly Glu Val Asn Ile Lys His Tyr Leu Asn Cys Ser His Cys Glu Val
            980                 985                 990

Asp Glu Cys His Met Asp Pro Glu Ser His Lys Val Ile Cys Phe Cys
            995                 1000                1005

Asp His Gly Thr Val Leu Ala Glu Asp Gly Val Ser Cys Ile Val
            1010                1015                1020

Ser Pro Thr Pro Glu Pro His Leu Pro Leu Ser Leu Ile Leu Ser
            1025                1030                1035

Val Val Thr Ser Ala Leu Val Ala Ala Leu Val Leu Ala Phe Ser
            1040                1045                1050

Gly Ile Met Ile Glu Glu Gln Gln Arg Gly Ala Ile Pro Gly Gln
            1055                1060                1065

Ala Pro Gly Ser Val Pro Gly Pro Gly Leu Val Lys Asp Ser Pro
            1070                1075                1080

Leu Leu Leu Gln Gln Ile Ser Ala Met Arg Leu His Ile Ser Gln
            1085                1090                1095

Leu Gln His Glu Asn Ser Ile Leu Lys Gly Ala Gln Met Lys Ala
            1100                1105                1110

Ser Leu Ala Ser Leu Pro Pro Leu His Val Ala Lys Leu Ser His
            1115                1120                1125

Glu Gly Pro Gly Ser Glu Leu Pro Ala Gly Ala Leu Tyr Arg Lys
            1130                1135                1140

Thr Ser Gln Leu Leu Glu Thr Leu Asn Gln Leu Ser Thr His Thr
            1145                1150                1155

His Val Val Asp Ile Thr Arg Thr Ser Pro Ala Ala Lys Ser Pro
            1160                1165                1170

Ser Ala Gln Leu Met Glu Gln Val Ala Gln Leu Lys Ser Leu Ser
            1175                1180                1185

Asp Thr Val Glu Lys Leu Lys Asp Glu Val Leu Lys Glu Thr Val
            1190                1195                1200

Ser Gln Arg Pro Gly Ala Thr Val Pro Thr Asp Phe Ala Thr Phe
            1205                1210                1215

Pro Ser Ser Ala Phe Leu Arg Ala Lys Glu Glu Gln Gln Asp Asp
            1220                1225                1230

Thr Val Tyr Met Gly Lys Val Thr Phe Ser Cys Ala Ala Gly Phe
            1235                1240                1245

Gly Gln Arg His Arg Leu Val Leu Thr Gln Glu Gln Leu His Gln
            1250                1255                1260

Leu His Ser Arg Leu Ile Ser
            1265                1270
```

```
<210> SEQ ID NO 13
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tgaagccaca tgaactcagt gagaaaacag gcacctgtgg cacagcctga gacactattc      60
agtcctgcct tcctgc                                                     76
```

US 11,098,368 B2

ALK AND NTRK1 FUSION MOLECULES AND USES THEREOF

RELATED APPLICATIONS

This application is a divisional of U.S. Application Ser. No. 14/257,607, filed Apr. 21, 2014, now U.S. Pat. No. 10,000,814, which is a continuation of PCT/US2012/061211, filed Oct. 19, 2012, which claims the benefit of U.S. Provisional Application No. 61/550,327, filed Oct. 21, 2011, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Apr. 17, 2014, is named F2036-703120 Sequence Listing.TXT and is 81.8 kilobytes in size.

BACKGROUND

Cancer represents the phenotypic end-point of multiple genetic lesions that endow cells with a full range of biological properties required for tumorigenesis. Indeed, a hallmark genomic feature of many cancers, including, for example, B cell cancer, lung cancer, breast cancer, ovarian cancer, pancreatic cancer, and colon cancer, is the presence of numerous complex chromosome structural aberrations, including translocations, intra-chromosomal inversions, point mutations, deletions, gene copy number changes, gene expression level changes, and germline mutations, among others.

The need still exists for identifying novel genetic lesions associated with cancer. Such genetic lesions can be an effective approach to develop compositions, methods and assays for evaluating and treating cancer patients.

SUMMARY

The invention is based, at least in part, on the discovery of novel translocation events that include a fragment of an ALK gene ("Anaplastic lymphoma kinase") and a fragment of a DCTN1 gene ("Dynactin-1") referred to herein as "DCTN1-ALK." The term "DCTN1-ALK" or "DCTN1-ALK fusion" is used generically herein, and includes any fusion molecule (e.g., gene, gene product (e.g., cDNA, mRNA, or polypeptide), and variant thereof) that includes a fragment of DCTN1 and a fragment of ALK, including, e.g., a DCTN1-ALK. Expression of DCTN1-ALK was detected in a Spitz tumor, which is a family of neoplasms that can range from benign Spitz nevi to Spitzoid melanomas. Expression of DCTN1-ALK was also detected in a non-Langerhans cell histiocytosis.

The invention is also based, in part, on the discovery of a novel deletion resulting in the formation of an LMNA-NTRK1 fusion. The term "LMNA-NTRK1" or "LMNA-NTRK1 fusion" is used generically herein, and includes any fusion molecule (e.g., gene, gene product (e.g., cDNA, mRNA, or polypeptide), and variant thereof) that includes a fragment of NTRK1 ("neurotrophic tyrosine kinase receptor, type 1") and a fragment of LMNA ("lamin A/C"), including, e.g., a LMNA-NTRK1. Expression of LMNA-NTRK1 was detected in Spitz tumors.

ALK and NTRK1 receptor tyrosine kinase domains have been associated with cancerous phenotypes, including lung, thyroid, non-Hodgkin's lymphoma, neuroblastoma, among others. Expression of the fusion molecules described herein in Spitz tumors and histiocytosis suggests a further association with neoplastic growth (including benign, pre-malignant, or malignant and/or metastatic growth (e.g., a cancer), including, for example, melanocytic neoplasms, melanoma and metastatic disease. Accordingly, the invention provides methods of: identifying, assessing or detecting a DCTN1-ALK and/or LMNA-NTRK1 fusion; methods of identifying, assessing, evaluating, and/or treating a subject having a cancer, e.g., a cancer having a DCTN1-ALK and/or LMNA-NTRK1 fusion; isolated DCTN1-ALK and/or LMNA-NTRK1 nucleic acid molecules, nucleic acid constructs, host cells containing the nucleic acid molecules; purified DCTN1-ALK and/or LMNA-NTRK1 polypeptides and binding agents; detection reagents (e.g., probes, primers, antibodies, kits, capable, e.g., of specific detection of a DCTN1-ALK and/or LMNA-NTRK1 nucleic acid or protein); screening assays for identifying molecules that interact with, e.g., inhibit, 5'DCTN1-3'ALK and/or 5'LMNA-3'NTRK1 fusions, e.g., novel kinase inhibitors; as well as assays and kits for evaluating, identifying, assessing and/or treating a subject having a cancer, e.g., a cancer having a DCTN1-ALK and/or LMNA-NTRK1 fusion. The compositions and methods identified herein can be used, for example, to identify new DCTN1-ALK and/or LMNA-NTRK1 inhibitors; to evaluate, identify or select a subject, e.g., a patient, having a cancer; and to treat or prevent a cancer.

Each of these fusion molecules is described herein in more detail.

DCTN1-ALK Fusions:

In one embodiment, a DCTN1-ALK fusion includes an in-frame fusion of an exon of DCTN1 (e.g., one more exons of DCTN1, such as exons 1-26 or a fragment thereof) and an exon of ALK (e.g., one or more exons encoding the ALK receptor tyrosine kinase or a fragment thereof). For example, the DCTN1-ALK fusion can occur in chromosome 2 and include an in-frame fusion within an intron of DCTN (e.g., intron 26) or a fragment thereof, with an intron of ALK (e.g., intron 19) or a fragment thereof. In one embodiment, the fusion junction of the DCTN1-ALK fusion comprises a nucleotide sequence of: GTTTTGGCTTGGCCTGGGC-TGCCCTAATCACCACCCCACCCAATTCACAGT GTC-CAAGCAGAGAAGCAATCAA (SEQ ID NO: 5), or a fragment thereof. The sequence of SEQ ID NO:5 is the reference genome orientation.

In certain embodiments, the DCTN1-ALK fusion is in a 5'-DCTN1 to 3'-ALK configuration referred to herein as "5' DCTN1-ALK." A DCTN1-ALK fusion polypeptide encoded by a 5'DCTN1-3'ALK nucleic acid is sometimes referred to herein as a 5'DCTN1-3'ALK polypeptide. In an embodiment, the 5'DCTN1-3'ALK fusion comprises sufficient DCTN1 and sufficient ALK sequence such that the 5'DCTN1-3'ALK fusion has kinase activity, e.g., has elevated activity, e.g., ALK tyrosine kinase activity, as compared with wild type ALK, e.g., in a cell of a cancer referred to herein (e.g., melanoma). In one embodiment, the 5'DCTN1-3'ALK fusion comprises at least 1, 2, 3, 4, 5, 6, 7, 9, 10, or more exons from DCTN1 and at least 1, 2, 3, 4, 5, 6, 7, 9, 10, or more, ALK exons. In one embodiment, the 5'DCTN1-3'ALK fusion polypeptide includes an ALK receptor tyrosine kinase domain or a functional fragment thereof. In one embodiment, the DCTN1-ALK fusion comprises a nucleotide sequence shown in FIG. 2 (SEQ ID NO: 6), or a fragment thereof. In another embodiment, the DCTN1-ALK fusion comprises an amino acid sequence shown in FIG. 2 (SEQ ID NO:7).

The ALK receptor tyrosine kinase is known to be associated with cancerous phenotypes including inflammatory myofibroblastic tumors, neuroblastoma, lung cancer, non-Hodgkin's lymphoma, and anaplastic large cell lymphoma, among others. For example, a chromosomal rearrangement that generates a fusion gene resulting in the juxtaposition of the N-terminal region of nucleophosmin (NPM) with the kinase domain of ALK are known to be associated with non-Hodgkin's lymphoma (Morris, S W (1994) Science 263:1281-1284).

In other embodiments, the DCTN1-ALK fusion includes an in-frame fusion having a breakpoint in an intron of DCTN1 (e.g., intron 26) or a fragment thereof and a breakpoint in an intron of ALK (e.g., intron 19) or a fragment thereof. In certain embodiments, the DCTN1-ALK fusion is in a 5'-ALK to 3'-DCTN1 configuration referred to herein as "5'ALK-3'DCTN1"). For example, the ALK-DCTN1 fusion can occur in chromosome 2 and include an in-frame fusion within an intron of DCTN (e.g., intron 26) or a fragment thereof, with an intron of ALK (e.g., intron 19) or a fragment thereof. In one embodiment, the fusion junction of the ALK-DCTN1 fusion comprises a nucleotide sequence of: TGAAGCCACATGAACTCAGTGAGAAAAICAGGCA-CCTGTGGCACAGCCTGAGACACTATTCAGTCCTG-CCTTCCTGC (SEQ ID NO: 13), or a fragment thereof. The sequence of SEQ ID NO:5 is the reference genome orientation.

An ALK-DCTN1 fusion polypeptide encoded by a 5'ALK-3'DCTN1 nucleic acid is sometimes referred to herein as a 5'ALK-3'DCTN1 polypeptide. In one embodiment, the 5'ALK-3'DCTN1 fusion comprises at least 1, 2, 3, 4, 5, 6, 7, 9, 10, or more exons from ALK and at least 1, 2, 3, 4, 5, or 6, or more, DCTN1 exons. In one embodiment, the ALK-DCTN1 fusion comprises a nucleotide sequence shown in FIGS. 4A-4D (SEQ ID NO:11), or a fragment thereof. In another embodiment, the ALK-DCTN1 fusion comprises an amino acid sequence shown in FIGS. 4A-4D (SEQ ID NO:12).

LMNA-NTRK1 Fusion:

Certain aspects featured in the invention include LMNA-NTRK1 fusion nucleic acids and polypeptides. An LMNA-NTRK1 fusion includes an in-frame fusion of at least exon 2 of LMNA (e.g., one or more of exons 1-2 or a fragment thereof) and exon 11 of NTRK1 (e.g., one more exons encoding a tyrosine kinase domain or a fragment thereof) (FIG. 6). For example, the LMNA-NTRK1 fusion can include an in-frame fusion within an intron of NTRK1 (e.g., intron 10) or a fragment thereof, with an intron of LMNA (e.g., intron 2) or a fragment thereof. In certain embodiments, the LMNA-NTRK1 fusion is in a 5'-LMNA to 3'-NTRK1 configuration referred to herein as "5' LMNA-3'NTRK1." In one embodiment, the LMNA-NTRK1 fusion has a breakpoint comprising the nucleotide sequence of: ATAAAAATTTAAAGAAATTAGCTGGGCATAGGGGT-CCCCAGGGGAGGATGA GGCAGGTCTGGAGACCT (SEQ ID NO:8), or a fragment thereof (FIG. 6). The sequence of SEQ ID NO:8 is presented in the reference genome orientation.

In one embodiment, the LMNA-NTRK1 fusion has a nucleotide sequence as shown in FIGS. 7A-7B (SEQ ID NO: 9), or a fragment thereof. In another embodiment, the LMNA-NTRK1 fusion has an amino acid sequence as shown in FIGS. 7A-7B (SEQ ID NO:10), or a fragment thereof.

An LMNA-NTRK1 fusion polypeptide encoded by a 5'LMNA-3'NTRK nucleic acid is sometimes referred to herein as a 5'LMNA-3'NTRK1 polypeptide. In an embodiment, the 5'LMNA-3'NTRK1 fusion comprises sufficient LMNA and sufficient NTRK1 sequence such that the 5'LMNA-3'NTRK1 fusion has kinase activity, e.g., has elevated activity, e.g., receptor tyrosine kinase activity, as compared with wild type NTRK1, e.g., in a cell of a cancer referred to herein (e.g., melanoma). In one embodiment, the 5'LMNA-3'NTRK1 fusion comprises at least 1, 2, 3, 4, 5, 6, 7, 9, 10, or more exons from LMNA and at least 1, 2, 3, 4, 5, 6, 7, 9, 10, or more, NTRK1 exons. In one embodiment, the 5'LMNA-3'NTRK1 fusion polypeptide includes e.g., an NTRK1 receptor tyrosine kinase domain or a functional fragment thereof.

The NTRK1 receptor tyrosine kinase (also referred to as the TrkA receptor) is known to be associated with cancerous phenotypes including colon tumors and papillary thyroid carcinomas, among others. For example, a chromosomal rearrangement that generates a fusion gene resulting in the juxtaposition of the TFG gene with the kinase binding domain of NTRK1 are known to be associated with papillary thyroid carcinomas. Other NTRK1 rearrangements resulting in fusions include, e.g., NTRK1-TPM3 and TPR-NTRK1. NTRK1 fusion genes are reviewed in, e.g., Greco, A. et al., *Mol Cell Endocrinol* (2010) 321(1):44-49.

In other embodiments, the LMNA-NTRK1 fusion includes an in-frame fusion having a breakpoint in an intron of LMNA (e.g., intron 2) or a fragment thereof and a breakpoint in an intron of NTRK1 (e.g., intron 10) or a fragment thereof. In another embodiment, the LMNA-NTRK1 is an in-frame fusion comprising at least exon 2 or LMNA and at least exon 11 of NTRK1. In certain embodiments, the LMNA-NTRK1 fusion is in a 5'-LMNA to 3'-NTRK1 configuration referred to herein as "5'LMNA-3'NTRK1").

Accordingly, the invention provides, methods of: identifying, assessing or detecting a LMNA-NTRK1 fusion; isolated LMNA-NTRK1 nucleic acid molecules, nucleic acid constructs, host cells containing the nucleic acid molecules; purified LMNA-NTRK1 polypeptides and binding agents; detection reagents (e.g., probes, primers, antibodies, kits, capable, e.g., of specific detection of a LMNA-NTRK1 nucleic acid or protein); screening assays for identifying molecules that interact with, e.g., inhibit, LMNA-NTRK1 fusions, e.g., novel kinase inhibitors.

Nucleic Acid Molecules

In one aspect, the invention features an isolated nucleic acid molecule, or an isolated preparation of nucleic acid molecules, that includes a genetic alteration disclosed herein. Such nucleic acid molecules or preparations thereof can include a genetic alteration described herein or can be used to detect, e.g., sequence, a genetic alteration disclosed herein.

In certain embodiments, the alteration in the nucleic acid molecule, isolated preparation, or tumor member, is chosen from one or more of:

(i) a rearrangement (e.g., translocation) of a fragment of a Dynactin-1 gene (DCTN1) and a fragment of an Anaplastic Lymphoma receptor tyrosine Kinase (ALK) gene (a "DCTN1-ALK fusion"); and (ii) a rearrangement (e.g., deletion) of a fragment of a lamin A/C gene (LMNA) and a fragment of an NRTK1 (neurotrophic tyrosine kinase receptor, type 1) gene ("a "LMNA-NRTK1 fusion").

DCTN1-ALK Nucleic Acid Molecules

In one aspect, the invention features a nucleic acid molecule (e.g., an isolated or purified) nucleic acid molecule that includes a fragment of a DCTN1 gene and a fragment of an ALK receptor tyrosine kinase. In one embodiment, the nucleic acid molecule includes a fusion, e.g., an in-frame fusion, between an intron of DCTN1 (e.g., intron 26, or a fragment thereof), and an intron of ALK (e.g., intron 19, or a fragment thereof).

In another embodiment, the nucleic acid molecule includes a fusion, e.g., an in-frame fusion, of at least exon 26 of DCTN1 or a fragment thereof (e.g., exons 1-26 of DCTN1 or a fragment thereof), and at least exon 20 or a fragment thereof (e.g., exons 20-29 of ALK or a fragment thereof). In one embodiment, the nucleic acid molecule includes the nucleotides sequence of 1-3195 of SEQ ID NO:6 (corresponding to exons 1-26 of a DCTN1 gene) or a fragment thereof, or a sequence substantially identical thereto. In another embodiment, the nucleic acid molecule includes the nucleotide sequence of 3196-4907 of SEQ ID NO:6 (corresponding to exons 20-29 of the ALK gene) or a fragment thereof, or a sequence substantially identical thereto. In yet other embodiments, the nucleic acid molecule includes the nucleotide sequence shown in FIGS. 2A-2F (e.g., SEQ ID NO:6) or a fragment thereof, or a sequence substantially identical thereto. In one embodiment, the nucleic acid molecule is complementary to at least a portion of a nucleotide sequence disclosed herein, e.g., is capable of hybridizing under a stringency condition described herein to SEQ ID NO:6 or a fragment thereof. In yet another embodiment, the nucleic acid molecule hybridizes to a nucleotide sequence that is complementary to at least a portion of a nucleotide sequence disclosed herein, e.g., is capable of hybridizing under a stringency condition to a nucleotide sequence complementary to SEQ ID NO:6 or a fragment thereof. The nucleotide sequence of a cDNA encoding an exemplary 5'DCTN1-3'ALK fusion is shown in SEQ ID NO:6, and the predicted amino acid sequence is shown in SEQ ID ID NO:7.

In an embodiment the 5'DCTN1-3'ALK nucleic acid molecule comprises sufficient DCTN1 and sufficient ALK sequence such that the encoded 5'DCTN1-3'ALK fusion has kinase activity, e.g., has elevated activity, e.g., ALK kinase activity, as compared with wild type ALK, e.g., in a cell of a cancer referred to herein. In an embodiment the encoded 5'DCTN-3'ALK fusion comprises at least 1, 2, 3, 4, 5, 6, 7, 9, 10, or 11 exons from DCTN1 and at least 1, 2, 3, 4, 5, 6, 7, 9, or 10, ALK exons. In one embodiment, the encoded 5'DCTN1-3'ALK fusion polypeptide includes an ALK tyrosine kinase domain or a functional fragment thereof.

In one embodiment, the nucleic acid molecule includes a nucleotide sequence that has an in-frame fusion of intron 26 of DCTN1 (e.g., NM_004082) with intron 19 of ALK (e.g., NM_004304). In other embodiments, the nucleic acid molecules includes a nucleotide sequence in the region of nucleotides 29,447,851-29,448,653 of chromosome 2 coupled to (e.g., juxtaposed to) nucleotides in the region of nucleotides 74,591,512-74,592,314 of chromosome 2 (FIG. 5). In another embodiment, the nucleic acid molecule includes a nucleotide sequence that includes a breakpoint, e.g., a breakpoint identified in FIG. 1. For example, the nucleic acid molecule includes a nucleotide sequence that includes the fusion junction between the DCTN1 gene and the ALK gene, e.g., a nucleotide sequence that includes a portion of SEQ ID NO:5 (e.g., the breakpoint between intron 26 of DCTN1 and intron 19 of ALK).

In other embodiments, the nucleic acid molecule includes a DCTN1-ALK fusion having a configuration shown in FIG. 1. For example, the DCTN1-ALK fusion can include an in-frame fusion resulting from a break-point of at least intron 26 of DCTN1 or a fragment thereof with at least intron 19 of ALK or a fragment thereof. In certain embodiments, the DCTN1-ALK fusion is in a 5'-DCTN1 to 3'-ALK configuration referred to herein as "5'DCTN1-3'ALK"). In one embodiment, the nucleic acid molecule includes the nucleotide sequence of SEQ ID NO:5 (corresponding to the breakpoint of a DCTN1-ALK fusion), or a fragment thereof, or a sequence substantially identical thereto. In another embodiment, the nucleic acid molecule includes the nucleotide sequence of nucleotides 1-27 of SEQ ID NO:5 (e.g., corresponding to intron 26 of DCTN1), or a fragment thereof, or a sequence substantially identical thereto. In another embodiment, the nucleic acid molecule includes the nucleotide sequence of nucleotides 28-73 of SEQ ID NO:5 (e.g., corresponding to intron 19 of ALK), or a fragment thereof, or a sequence substantially identical thereto. In yet other embodiments, the nucleic acid molecule includes the nucleotide sequence shown in FIGS. 2A-2F (e.g., SEQ ID NO:6) or a fragment thereof, or a sequence substantially identical thereto. In one embodiment, the nucleic acid molecule is complementary to at least a portion of a nucleotide sequence disclosed herein, e.g., is capable of hybridizing under a stringency condition described herein to SEQ ID NO:6 or a fragment thereof. In yet other embodiment, the nucleic acid molecule hybridizes to a nucleotide sequence that is complementary to at least a portion of a nucleotide sequence disclosed herein, e.g., is capable of hybridizing under a stringency condition described herein to a nucleotide sequence complementary to SEQ ID NO:6 or a fragment thereof. The nucleotide sequence of a cDNA encoding an exemplary breakpoint for a 5'DCTN1-3'ALK fusion is shown in SEQ ID NO:6.

In other embodiments, the nucleic acid molecule includes a nucleotide sequence encoding a DCTN1-ALK fusion polypeptide that includes a fragment of a DCTN1 gene and a fragment of an ALK receptor tyrosine kinase. In one embodiment, the nucleotide sequence encodes a DCTN1-ALK fusion polypeptide that includes e.g., an ALK tyrosine kinase domain or a functional fragment thereof. In another embodiment, the nucleotide sequence encodes a fragment of the DCTN1 polypeptide including the amino acid sequence of amino acids 1062-1069 of SEQ ID NO:7 or a fragment thereof, or a sequence substantially identical thereto. For example, the nucleic acid molecule can include a nucleotide sequence encoding an ALK kinase domain of a DCTN1-ALK fusion polypeptide that includes amino acids 1124-1370 of SEQ ID NO:7 or a fragment thereof. In yet other embodiments, the nucleic acid molecule includes a nucleotide sequence encoding the amino acid sequence shown in FIGS. 2A-2F (e.g., SEQ ID NO:7) or a fragment thereof, or a sequence substantially identical thereto.

In another embodiment, the nucleic acid molecule includes a DCTN1-ALK fusion having the configuration shown in FIG. 1. In one embodiment, the nucleic acid molecule includes a nucleotide sequence that includes a fusion junction between the DCTN1 transcript and the ALK transcript, e.g., a nucleotide sequence within SEQ ID NO:6.

In another embodiment, the nucleic acid molecule includes a fusion, e.g., an in-frame fusion, of at least exon 19 of ALK or a fragment thereof (e.g., exons 1-19 of ALK or a fragment thereof), and at least exon 27 or a fragment thereof (e.g., exons 27-32 of DCTN1 or a fragment thereof). In certain embodiments, the DCTN1-ALK fusion is in a 5'-ALK to 3'-DCTN1 configuration referred to herein as "5'ALK-3'DCTN1"). In one embodiment, the nucleic acid molecule includes the nucleotides sequence of 1-3172 of SEQ ID NO:11 (corresponding to exons 1-19 of an ALK gene) or a fragment thereof, or a sequence substantially identical thereto. In another embodiment, the nucleic acid molecule includes the nucleotides sequence of 3173-3831 of SEQ ID NO:11 (corresponding to exons 27-32 of the a DCTN1 gene) or a fragment thereof, or a sequence substantially identical thereto. In yet other embodiments, the nucleic acid molecule includes the nucleotide sequence shown in FIGS. 4A-4D (e.g., SEQ ID NO:11) or a fragment thereof, or a sequence substantially identical thereto. In one embodiment, the nucleic acid molecule is complementary to at least a portion of a nucleotide sequence disclosed herein, e.g., is capable of hybridizing under a stringency condition described herein to SEQ ID NO:11 or a fragment thereof. In yet another embodiment, the nucleic acid molecule hybridizes to a nucleotide sequence that is complementary to at least a portion of a nucleotide sequence disclosed herein, e.g., is capable of hybridizing under a stringency condition to a nucleotide sequence complementary to SEQ ID NO:11 or a fragment thereof. The nucleotide sequence of a cDNA encoding an exemplary 5' ALK-3'DCTN1 fusion is shown in SEQ ID NO:11, and the predicted amino acid sequence is shown in SEQ ID ID NO:12.

In a related aspect, the invention features nucleic acid constructs that include the DCTN1-ALK nucleic acid molecules described herein. In certain embodiments, the nucleic acid molecules are operatively linked to a native or a heterologous regulatory sequence. Also included are vectors and host cells that include the DCTN1-ALK nucleic acid molecules described herein, e.g., vectors and host cells suitable for producing the nucleic acid molecules and polypeptides described herein.

In a related aspect, methods of producing the nucleic acid molecules and polypeptides described herein are also described.

In another aspect, the invention features nucleic acid molecules that reduce or inhibit the expression of a nucleic acid molecule that encodes a DCTN1-ALK fusion described herein. Examples of such nucleic acid molecules include, for example, antisense molecules, ribozymes, RNAi, triple helix molecules that hybridize to a nucleic acid encoding DCTN1-ALK, or a transcription regulatory region of DCTN1-ALK, and blocks or reduces mRNA expression of DCTN1-ALK.

LMNA-NTRK1 Nucleic Acid Molecules

In one aspect, the invention features a nucleic acid molecule (e.g., an isolated or purified) nucleic acid molecule that includes a fragment of a LMNA gene and a fragment of an NTRK1 receptor tyrosine kinase. In one embodiment, the nucleic acid molecule includes a fusion, e.g., an in-frame fusion, of an intron of LMNA (e.g., expressing one more exons of LMNA, e.g., at least exon 2, or a fragment thereof), and an intron of NTRK1 (e.g., expressing one or more exons encoding an NRTK1 tyrosine kinase domain, e.g., at least exon 11 or a fragment thereof).

In one embodiment, the nucleic acid molecule includes a fusion, e.g., an in-frame fusion, of at least exon 2 of LMNA or a fragment thereof (e.g., exons 1 and 2 of LMNA or a fragment thereof), and at least exon 11 or a fragment thereof (e.g., exons 11-19 of NTRK1 or a fragment thereof). In one embodiment, the nucleic acid molecule includes the nucleotides sequence of 1-513 of SEQ ID NO:9 (corresponding to exons 1-2 of an LMNA gene) or a fragment thereof, or a sequence substantially identical thereto. In another embodiment, the nucleic acid molecule includes the nucleotide sequence of 514-1740 of SEQ ID NO:9 (corresponding to exons 11-19 of the an NTRK1 gene) or a fragment thereof, or a sequence substantially identical thereto. In yet other embodiments, the nucleic acid molecule includes the nucleotide sequence shown in FIGS. 7A-7B (e.g., SEQ ID NO:9) or a fragment thereof, or a sequence substantially identical thereto. In one embodiment, the nucleic acid molecule is complementary to at least a portion of a nucleotide sequence disclosed herein, e.g., is capable of hybridizing under a stringency condition described herein to SEQ ID NO:9 or a fragment thereof. In yet another embodiment, the nucleic acid molecule hybridizes to a nucleotide sequence that is complementary to at least a portion of a nucleotide sequence disclosed herein, e.g., is capable of hybridizing under a stringency condition to a nucleotide sequence complementary to SEQ ID NO:9 or a fragment thereof. The nucleotide sequence of a cDNA encoding an exemplary 5'LMNA-3'NTRK1 fusion is shown in SEQ ID NO:9, and the predicted amino acid sequence is shown in SEQ ID ID NO:10.

In an embodiment the 5'LMNA-3'NTRK1 nucleic acid molecule comprises sufficient LMNA and sufficient NTRK1 sequence such that the encoded 5'LMNA-3'NTRK1 fusion has kinase activity, e.g., has elevated activity, e.g., NTRK1 kinase activity, as compared with wild type NTRK1, e.g., in a cell of a cancer referred to herein. In an embodiment the encoded 5'LMNA-3'NTRK1 fusion comprises at least 1 or 2 exons or more from LMNA and at least 1, 2, 3, 4, 5, 6, 7, or 9 NTRK1 exons. In one embodiment, the encoded 5'LMNA-3'NTRK1 fusion polypeptide includes an NTRK1 tyrosine kinase domain or a functional fragment thereof.

In one embodiment, the nucleic acid molecule includes a nucleotide sequence that has an in-frame fusion of intron 2 of LMNA (e.g., NM_005572) with intron 10 of NTRK1 (e.g., NM_002529). In other embodiments, the nucleic acid molecules includes a nucleotide sequence in the region of 156,100,970-156,101,459 of chromosome 1 coupled to (e.g., juxtaposed to) nucleotides in the region of nucleotides 156,844,390-156,844,879 of chromosome 1 (FIG. 8). In another embodiment, the nucleic acid molecule includes a nucleotide sequence that includes a breakpoint, e.g., a breakpoint identified in FIG. 6. For example, the nucleic acid molecule includes a nucleotide sequence that includes the fusion junction between the LMNA gene and the NTRK1 gene, e.g., a nucleotide sequence that includes a portion of SEQ ID NO:8 (e.g., the breakpoint between intron 2 of LMNA and intron 10 of NTRK1).

In other embodiments, the nucleic acid molecule includes a LMNA-NTRK1 fusion having a configuration shown in FIG. 6. For example, the LMNA-NTRK1 fusion can include an in-frame fusion of at least intron 2 of LMNA or a fragment thereof with at least intron 10 of NTRK1 or a fragment thereof. In one embodiment, the LMNA-NTRK2 fusion comprises a fusion of at least exon 2 of LMNA and at least exon 11 of NTRK1. In certain embodiments, the LMNA-NTRK1 fusion is in a 5'-LMNA to 3'-NTRK1 configuration referred to herein as "5'LMNA-3'NTRK1"). In one embodiment, the nucleic acid molecule includes the nucleotide sequence of SEQ ID NO:8 (corresponding to the breakpoint of a LMNA-NTRK1 fusion), or a fragment thereof, or a sequence substantially identical thereto. In another embodiment, the nucleic acid molecule includes the nucleotide sequence of nucleotides 1-29 of SEQ ID NO:8 (e.g., corresponding to intron 2 of LMNA), or a fragment thereof, or a sequence substantially identical thereto. In another embodiment, the nucleic acid molecule includes the nucleotide sequence of nucleotides 30-68 of SEQ ID NO:8

(e.g., corresponding to intron 10 of NTRK1), or a fragment thereof, or a sequence substantially identical thereto. In yet other embodiments, the nucleic acid molecule includes the nucleotide sequence shown in FIG. 6 (e.g., SEQ ID NO:8) or a fragment thereof, or a sequence substantially identical thereto. In one embodiment, the nucleic acid molecule is complementary to at least a portion of a nucleotide sequence disclosed herein, e.g., is capable of hybridizing under a stringency condition described herein to SEQ ID NO:8 or a fragment thereof. In yet other embodiment, the nucleic acid molecule hybridizes to a nucleotide sequence that is complementary to at least a portion of a nucleotide sequence disclosed herein, e.g., is capable of hybridizing under a stringency condition described herein to a nucleotide sequence complementary to SEQ ID NO:9 or a fragment thereof. The nucleotide sequence of a cDNA encoding an exemplary breakpoint for a 5'LMNA-3'NTRK1 fusion is shown in SEQ ID NO:9.

In other embodiments, the nucleic acid molecule includes a nucleotide sequence encoding a LMNA-NTRK1 fusion polypeptide that includes a fragment of a LMNA gene and a fragment of an NTRK1 receptor tyrosine kinase. In one embodiment, the nucleotide sequence encodes a LMNA-NTRK1 fusion polypeptide that includes e.g., an NTRK1 tyrosine kinase domain or a functional fragment thereof. In another embodiment, the nucleotide sequence encodes a fragment of the LMNA polypeptide including the amino acid sequence of amino acids 168-175 of SEQ ID NO:10 or a fragment thereof, or a sequence substantially identical thereto. For example, the nucleic acid molecule can include a nucleotide sequence encoding a LMNA kinase domain of a to LMNA-NTRK1 fusion polypeptide that includes amino acids 289-560 of SEQ ID NO:10 or a fragment thereof. In yet other embodiments, the nucleic acid molecule includes a nucleotide sequence encoding the amino acid sequence shown in FIG. 4 (e.g., SEQ ID NO:10) or a fragment thereof, or a sequence substantially identical thereto.

In another embodiment, the nucleic acid molecule includes the nucleotides sequence of 1-513 of SEQ ID NO:9 (corresponding to exons 1-2 of an LMNA gene) or a fragment thereof, or a sequence substantially identical thereto. In another embodiment, the nucleic acid molecule includes the nucleotide sequence of 514-1740 of SEQ ID NO:9 (corresponding to exons 11-19 of an NTRK1 gene) or a fragment thereof, or a sequence substantially identical thereto. In yet other embodiments, the nucleic acid molecule includes the nucleotide sequence shown in FIGS. 7A-7B (e.g., SEQ ID NO:9) or a fragment thereof, or a sequence substantially identical thereto. In one embodiment, the nucleic acid molecule is complementary to at least a portion of a nucleotide sequence disclosed herein, e.g., is capable of hybridizing under a stringency condition described herein to SEQ ID NO:9 or a fragment thereof. In yet other embodiments, the nucleic acid molecule hybridizes to a nucleotide sequence that is complementary to at least a portion of a nucleotide sequence disclosed herein, e.g., is capable of hybridizing under a stringency condition to a nucleotide sequence complementary to SEQ ID NO:9 or a fragment thereof. The nucleotide sequence of a cDNA encoding an exemplary 5'LMNA-3'NTRK1 fusion is shown in SEQ ID NO:9, and the predicted amino acid sequence is shown in SEQ ID ID NO:10.

In a related aspect, the invention features nucleic acid constructs that include the LMNA-NTRK1 nucleic acid molecules described herein. In certain embodiments, the nucleic acid molecules are operatively linked to a native or a heterologous regulatory sequence. Also included are vectors and host cells that include the LMNA-NTRK1 nucleic acid molecules described herein, e.g., vectors and host cells suitable for producing the nucleic acid molecules and polypeptides described herein.

In a related aspect, methods of producing the nucleic acid molecules and polypeptides described herein are also described.

In another aspect, the invention features nucleic acid molecules that reduce or inhibit the expression of a nucleic acid molecule that encodes a LMNA-NTRK1 fusion described herein. Examples of such nucleic acid molecules include, for example, antisense molecules, ribozymes, RNAi, triple helix molecules that hybridize to a nucleic acid encoding LMNA-NTRK1, or a transcription regulatory region of LMNA-NTRK1, and blocks or reduces mRNA expression of LMNA-NTRK1.

Nucleic Acid Detection and Capturing Reagents

The invention also features a nucleic acid molecule, e.g., nucleic acid fragment, suitable as probe, primer, bait or library member that includes, flanks, hybridizes to, which are useful for identifying, or are otherwise based on, the DCTN1-ALK or LMNA-NTRK1 fusions described herein. In certain embodiments, the probe, primer or bait molecule is an oligonucleotide that allows capture, detection or isolation of a DCTN1-ALK or an LMNA-NTRK1 fusion nucleic acid molecule described herein. The oligonucleotide can comprise a nucleotide sequence substantially complementary to a fragment of the DCTN1-ALK or LMNA-NTRK1 fusion nucleic acid molecules described herein. The sequence identity between the nucleic acid fragment, e.g., the oligonucleotide, and the target DCTN1-ALK or LMNA-NTRK1 sequence need not be exact, so long as the sequences are sufficiently complementary to allow the capture, detection or isolation of the target sequence. In one embodiment, the nucleic acid fragment is a probe or primer that includes an oligonucleotide between about 5 and 25, e.g., between 10 and 20, or 10 and 15 nucleotides in length. In other embodiments, the nucleic acid fragment is a bait that includes an oligonucleotide between about 100 to 300 nucleotides, 130 and 230 nucleotides, or 150 and 200 nucleotides, in length.

In one embodiment, the nucleic acid fragment can be used to identify or capture, e.g., by hybridization, a DCTN1-ALK fusion or a LMNA-NTRK1 fusion. For example, the nucleic acid fragment can be a probe, a primer, or a bait, for use in identifying or capturing, e.g., by hybridization, a DCTN1-ALK fusion or an LMNA-NTRK1 fusion described herein. In one embodiment, the nucleic acid fragment can be useful for identifying or capturing a DCTN1-ALK breakpoint, e.g., as identified in FIG. 1 (e.g., SEQ ID NO:5). In one embodiment, the nucleic acid fragment hybridizes to a nucleotide sequence within a chromosomal rearrangement that creates an in-frame fusion of intron 26 of DCTN1 with intron 19 of ALK. In one embodiment, the nucleic acid fragment hybridizes to a nucleotide sequence in the region of 29,447,851-29,448,653 of chromosome 2 coupled to (e.g., juxtaposed to) nucleotides in the region of nucleotides 74,591,512-74,592,314 of chromosome 2. In one embodiment, the nucleic acid fragment hybridizes to a nucleotide sequence that includes a breakpoint, e.g., a breakpoint as identified in FIG. 1. For example, the nucleic acid fragment can hybridize to a nucleotide sequence that includes the fusion junction between the DCTN1 gene and the ALK gene, e.g., a nucleotide sequence that includes a portion of SEQ ID NO:6 (e.g., a nucleotide sequence within introns 26 of a DCTN1 gene and 19 of an ALK gene).

In another embodiment, the nucleic acid fragment can be useful for identifying or capturing a LMNA-NTRK1 breakpoint, e.g., as identified in FIG. 6 (e.g., SEQ ID NO:8). In one embodiment, the nucleic acid fragment hybridizes to a nucleotide sequence within a chromosomal rearrangement that creates an in-frame fusion of intron 2 of LMNA with intron 10 of NTRK1. In other embodiments, the nucleic acid molecules includes a nucleotide sequence in the region of 156,100,970-156,101,459 of chromosome 1 coupled to (e.g., juxtaposed to) nucleotides in the region of nucleotides 156,844,390-156,844,879 of chromosome 1. In one embodiment, the nucleic acid fragment hybridizes to a nucleotide sequence that includes a breakpoint, e.g., a breakpoint as identified in FIG. 6. For example, the nucleic acid fragment can hybridize to a nucleotide sequence that includes the fusion junction between the LMNA transcript and the NRTK1 transcript, e.g., a nucleotide sequence that includes a portion of SEQ ID NO:8 (e.g., a nucleotide sequence within introns 2 of a LMNA gene and 10 of an NRTK1 gene).

The probes or primers described herein can be used, for example, for FISH detection or PCR amplification. In one exemplary embodiment where detection is based on PCR, amplification of the DCTN1-ALK fusion junction or the LMNA-NTRK1 fusion junction can be performed using a primer or a primer pair, e.g., for amplifying a sequence flanking the fusion junctions described herein, e.g., the mutations or the junction of a chromosomal rearrangement described herein, e.g., DCTN1-ALK or LMNA-NTRK1.

In one embodiment, a pair of isolated oligonucleotide primers can amplify a region containing or adjacent to a position in the ALK-DCTN1 fusion or the NTRK1-LMNA fusion. For example, reverse primers can be designed to hybridize to a nucleotide sequence within ALK genomic or mRNA sequence (e.g., a nucleotide sequence within exon 20 of ALK, or to a sequence corresponding to nucleotides 3196-3231 of SEQ ID NO:6), and the forward primers can be designed to hybridize to a nucleotide sequence within DCTN1 (e.g., a nucleotide sequence within exon 26 of DCTN1, or a sequence corresponding to nucleotides 3163-3195 of SEQ ID NO:6). Also, forward primers can be designed to hybridize to a nucleotide sequence within LMNA genomic or mRNA sequence (e.g., a nucleotide sequence within exon 2 of LMNA or a sequence corresponding to nucleotides 484-514 of SEQ ID NO:9), and the reverse primers can be designed to hybridize to a nucleotide sequence of NTRK1 (e.g., a nucleotide sequence within exon 11 of NTRK1, or nucleotides 514-540 of SEQ ID NO:9).

In another embodiment, the nucleic acid fragments can be used to identify, e.g., by hybridization, a 5'DCTN1-3'ALK fusion or the 5'LMNA-3'NTRK1 fusion. In one embodiment, the nucleic acid fragment hybridizes to a nucleotide sequence that includes a fusion junction between the DCTN1 transcript and the ALK transcript or a fusion junction between the LMNA transcript and the NTRK1 transcript.

In other embodiments, the nucleic acid fragment includes a bait that comprises a nucleotide sequence that hybridizes to a DCTN1-ALK or LMNA-NTRK1 fusion nucleic acid molecule described herein, and thereby allows the capture or isolation said nucleic acid molecule. In one embodiment, a bait is suitable for solution phase hybridization. In other embodiments, a bait includes a binding entity, e.g., an affinity tag, that allows capture and separation, e.g., by binding to a binding entity, of a hybrid formed by a bait and a nucleic acid hybridized to the bait.

In other embodiments, the nucleic acid fragment includes a library member comprising a DCTN1-ALK or LMNA-NTRK1 nucleic acid molecule described herein. In one embodiment, the library member includes a rearrangement that results in a DCTN1-ALK or LMNA-NTRK1 fusion described herein.

The nucleic acid fragment can be detectably labeled with, e.g., a radiolabel, a fluorescent label, a bioluminescent label, a chemiluminescent label, an enzyme label, a binding pair label, or can include an affinity tag; a tag, or identifier (e.g., an adaptor, barcode or other sequence identifier).

DCTN1-ALK Fusion Polypeptides

In another aspect, the invention features a DCTN1-ALK fusion polypeptide (e.g., a purified DCTN1-ALK fusion polypeptide), a biologically active or antigenic fragment thereof, as well as reagents (e.g., antibody molecules that bind to a DCTN1-ALK fusion polypeptide), methods for modulating a DCTN1-ALK polypeptide activity and detection of a DCTN1-ALK polypeptide.

In one embodiment, the DCTN1-ALK fusion polypeptide has at least one biological activity, e.g., an ALK kinase activity, dynein binding activity, kinesin binding activity, and/or a dimerizing or multimerizing activity. In one embodiment, at least one biological activity of the DCTN1-ALK fusion polypeptide is reduced or inhibited by an anti-cancer drug, e.g., a kinase inhibitor (e.g., a multikinase inhibitor or an ALK-specific inhibitor). In one embodiment, at least one biological activity of the DCTN1-ALK fusion polypeptide is reduced or inhibited by an ALK kinase inhibitor chosen from e.g., TAE-684 (also referred to herein as "NVP-TAE694"), PF02341066 (also referred to herein as "crizotinib" or "1066"), AF-802, LDK-378, ASP-3026, CEP-37440, CEP-28122, CEP-18050 and AP26113.

In other embodiments, the nucleic acid molecule includes a nucleotide sequence encoding a DCTN-ALK fusion polypeptide that includes a fragment of a DCNT1 gene and a fragment of an ALK gene. In one embodiment, the nucleotide sequence encodes a DCTN1-ALK fusion polypeptide that includes a dynein associated domain or a functional fragment thereof, and an ALK tyrosine kinase domain or a functional fragment thereof. In another embodiment, the nucleotide sequence encodes a fragment of the DCTN1 polypeptide including the amino acid sequence of amino acids 1-1065 of SEQ ID NO:7 or a fragment thereof, or a sequence substantially identical thereto. For example, the nucleic acid molecule can include a nucleotide sequence encoding a dynein association domain of a DCTN1-ALK fusion polypeptide that includes amino acids 526-805 of SEQ ID NO:7 or a fragment thereof. In other embodiments, the nucleic acid molecule includes a fragment of the ALK gene encoding the amino acid sequence of amino acids 1066-1640 of SEQ ID NO:7 or a fragment thereof, or a sequence substantially identical thereto. For example, the nucleic acid molecule can include a nucleotide sequence encoding an ALK kinase domain of a DCTN1-ALK fusion polypeptide that includes amino acids 1116-1362 of SEQ ID NO:7 or a fragment thereof. In yet other embodiments, the nucleic acid molecule includes a nucleotide sequence encoding the amino acid sequence shown in FIGS. 2A-2F (e.g., SEQ ID NO:7) or a fragment thereof, or a sequence substantially identical thereto.

In another embodiment, the nucleic acid molecule includes a DCTN1-ALK fusion having the configuration shown in FIGS. 1 and 2A-2F. In one embodiment, the nucleic acid molecule includes a nucleotide sequence that includes a fusion junction between the DCTN1 transcript and the ALK transcript, e.g., a nucleotide sequence within SEQ ID NO:6 (e.g., a sequence comprising nucleotides 3181-3220, 3184-3210, or 3178-3213 of SEQ ID NO:6 (see FIG. 2D)). In another embodiment, the nucleic acid molecule includes a fusion, e.g., an in-frame fusion, of at least exon 20 of ALK or a fragment thereof (e.g., exons 20-29 ALK or a fragment thereof), and at least exon 26 or a fragment thereof (e.g., exons 1-26 of DCNT1 or a fragment thereof).

In certain embodiments, the DCNT1-ALK fusion is in a 5'-ALK to 3'-DCTN1 configuration referred to herein as "5'ALK 3'DCTN1"). In one embodiment, the nucleic acid molecule includes the nucleotides sequence of 1-3172 of SEQ ID NO:11 (corresponding to exons 1-19 of ALK gene) or a fragment thereof, or a sequence substantially identical thereto. In another embodiment, the nucleic acid molecule includes the nucleotides sequence of 3173-3813 of SEQ ID NO:11 (corresponding to exons 27-32 of the a DCTN1 gene) or a fragment thereof, or a sequence substantially identical thereto. In yet other embodiments, the nucleic acid molecule includes the nucleotide sequence shown in FIGS. 4A-4D (e.g., SEQ ID NO:11) or a fragment thereof, or a sequence substantially identical thereto. In one embodiment, the nucleic acid molecule is complementary to at least a portion of a nucleotide sequence disclosed herein, e.g., is capable of hybridizing under a stringency condition described herein to SEQ ID NO:11 or a fragment thereof. In yet other embodiment, the nucleic acid molecule hybridizes to a nucleotide sequence that is complementary to at least a portion of a nucleotide sequence disclosed herein, e.g., is capable of hybridizing under a stringency condition to a nucleotide sequence complementary to SEQ ID NO:11 or a fragment thereof. The nucleotide sequence of a cDNA encoding an exemplary 5'ALK-3'DCTN1 fusion is shown in SEQ ID NO:11, and the predicted amino acid sequence is shown in SEQ ID ID NO:12.

In yet other embodiments, the DCTN1-ALK fusion polypeptide is encoded by a nucleic acid molecule described herein. In one embodiment, the DCTN1-ALK fusion polypeptide is encoded by an in-frame fusion of intron 26 of DCTN1 with intron 19 of ALK (e.g., a sequence on chromosome 2). In other embodiments, the DCTN1-ALK fusion polypeptide is encoded by a nucleotide sequence in the region of Ser. No. 29/447,851-29,448,653 of chromosome 2 coupled to (e.g., juxtaposed to) nucleotides in the region of nucleotides 74,591,512-74,592,314 of chromosome 2. In another embodiment, the DCTN1-ALK fusion polypeptide includes an amino acid sequence encoded by a nucleotide sequence comprising a fusion junction between the DCTN transcript and the ALK transcript, e.g., a nucleotide sequence that includes a portion of SEQ ID NO:6 (e.g., a nucleotide sequence within exon 26 of a DCTN1 and exon 20 of an ALK gene).

In an embodiment, the 5'DCTN1-3'ALK fusion polypeptide comprises sufficient DCTN1 and sufficient ALK sequence such that it has kinase activity, e.g., has elevated activity, e.g., ALK kinase activity, as compared with wild type ALK, e.g., in a cell of a cancer referred to herein. In an embodiment the 5'DCTN1-3'ALK fusion polypeptide comprises at least 1, 2, 3, 4, 5, 6, 7, 9, 10, or 11 exons from DCTN1 and at least 1, 2, 3, 4, 5, 6, 7, 9, or 10, ALK exons. In one embodiment, the 5'DCTN1-3'ALK fusion polypeptide includes a dynein or kinesin II binding domain or a functional fragment thereof, and an ALK tyrosine kinase domain or a functional fragment thereof. In a related aspect, the invention features DCTN1-ALK fusion polypeptide or fragments operatively linked to heterologous polypeptides to form fusion proteins.

In another embodiment, the DCTN1-ALK fusion polypeptide or fragment is a peptide, e.g., an immunogenic peptide or protein, that contains a fusion junction described herein. Such immunogenic peptides or proteins can be used to raise antibodies specific to the fusion protein. In other embodiments, such immunogenic peptides or proteins can be used for vaccine preparation. The vaccine preparation can include other components, e.g., an adjuvant.

In another aspect, the invention features antibody molecules that bind to a DCTN1-ALK fusion polypeptide or fragment described herein. In embodiments the antibody can distinguish wild type ALK (or DCTN1) from DCTN1-ALK.

LMNA-NTRK1 Fusion Polypeptides

In another aspect, the invention features a LMNA-NTRK1 fusion polypeptide (e.g., a purified LMNA-NTRK1 fusion polypeptide), a biologically active or antigenic fragment thereof, as well as reagents (e.g., antibody molecules that bind to a LMNA-NTRK1 fusion polypeptide), and detection of an LMNA-NTRK1 polypeptide.

In one embodiment, the LMNA-NTRK1 fusion polypeptide has at least one biological activity, e.g., an NTRK1 kinase activity, lamin matrix activity, and/or a dimerizing or multimerizing activity.

In other embodiments, the LMNA-NTRK1 fusion polypeptide includes a fragment of a LMNA polypeptide and a fragment of an NTRK1 polypeptide. In one embodiment, the LMNA-NTRK1 fusion polypeptide includes amino acids 167-175 of SEQ ID NO:10 or a fragment thereof (e.g., amino acids 1-175 of SEQ ID NO:10 or a fragment thereof), and amino acids 168-176 of SEQ ID NO:10 or a fragment thereof (e.g., amino acids 168-580 of SEQ ID NO:10 or a fragment thereof). In yet other embodiments, the LMNA-NTRK1 fusion polypeptide includes an amino acid sequence substantially identical to an in-frame fusion of amino acids 168-176 of SEQ ID NO:10 or a fragment thereof (e.g., amino acids 1-176 of SEQ ID NO:10 or a fragment thereof), and amino acids 168-176 of SEQ ID NO:10 or a fragment thereof (e.g., amino acids 168-580 of SEQ ID NO:10 or a fragment thereof).

In other embodiments, the LMNA-NTRK1 fusion polypeptide includes a LMNA dynein association domain or a fragment thereof, and an NTRK1 tyrosine kinase domain or a fragment thereof. In another embodiment, the LMNA-NTRK1 fusion polypeptide includes the amino acid sequence of amino acids 1-176 of SEQ ID NO:10 or a fragment thereof, or a sequence substantially identical thereto. For example, the LMNA-TRK1 fusion polypeptide can include a laminin binding domain of LMNA or a fragment thereof. In other embodiments, the LMNA-NTRK1 fusion polypeptide includes the amino acid sequence of amino acids 289-560 of SEQ ID NO:10 or a fragment thereof, or a sequence substantially identical thereto. For example, the LMNA-NTRK1 fusion polypeptide can include an NTRK1 kinase domain that includes amino acids 269-560 of SEQ ID NO:10 or a fragment thereof. In yet other embodiments, the LMNA-NTRK1 fusion polypeptide includes the amino acid sequence shown in FIGS. 7A-7B (e.g., SEQ ID NO:10) or a fragment thereof, or a sequence substantially identical thereto.

In yet other embodiments, the LMNA-NTRK1 fusion polypeptide is encoded by a nucleic acid molecule described herein. In one embodiment, the LMNA-NTRK1 fusion polypeptide is encoded by an in-frame fusion of intron 2 of LMNA with intron 10 of NTRK1. In other embodiments, the nucleic acid molecules includes a nucleotide sequence in the region of 156,100,970-156,101,459 of chromosome 1 coupled to (e.g., juxtaposed to) nucleotides in the region of nucleotides 156,844,390-156,844,879 of chromosome 1. In another embodiment, the LMNA-NTRK1 fusion polypeptide includes an amino acid sequence encoded by a nucleotide sequence comprising a fusion junction between the LMNA transcript and the NTRK1 transcript, e.g., a nucleotide sequence that includes a portion of SEQ ID NO:8 (e.g., a nucleotide sequence within introns 2 of an LMNA gene and 10 of an NTRK1 gene) (e.g., SEQ ID NO:10).

In yet other embodiments, the LMNA-NTRK1 fusion polypeptide is encoded by a 5'-LMNA to 3'-NTRK1 nucleic acid molecule described herein. In one embodiment, the LMNA-NTRK1 fusion polypeptide is encoded by a nucleotide sequence that includes a fusion junction between the LMNA transcript and the NTRK1 transcript, e.g., a sequence comprising nucleotides 502-525 of SEQ ID NO:9. In yet other embodiments, the LMNA-TRK1 fusion polypeptide is encoded by the nucleotide sequence shown in FIGS. 7A-7B (e.g., SEQ ID NO:9) or a fragment thereof, or a sequence substantially identical thereto.

In an embodiment, the 5'LMNA-3'NTRK1 fusion polypeptide comprises sufficient LMNA and sufficient NTRK1 sequence such that it has kinase activity, e.g., has elevated activity, e.g., NTRK1 kinase activity, as compared with wild type NTRK1, e.g., in a cell of a cancer referred to herein. In an embodiment the 5'LMNA-3'NTRK1 fusion polypeptide comprises at least 1, 2, 3, 4, 5, 6, 7, 9, 10, or 11 exons from LMNA and at least 1, 2, 3, 4, 5, 6, 7, 9, or 10, NTRK1 exons. In one embodiment, the 5'LMNA-3'NTRK1 fusion polypeptide includes a CAAX farnesylation motif, an autophosphorylation site, or a functional fragment thereof, and an NRTK1 tyrosine kinase domain or a functional fragment thereof. In a related aspect, the invention features LMNA-NTRK1 fusion polypeptide or fragments operatively linked to heterologous polypeptides to form fusion proteins.

In another embodiment, the LMNA-NTRK1 fusion polypeptide or fragment is a peptide, e.g., an immunogenic peptide or protein that contains a fusion junction described herein. Such immunogenic peptides or proteins can be used to raise antibodies specific to the fusion protein. In other embodiments, such immunogenic peptides or proteins can be used for vaccine preparation. The vaccine preparation can include other components, e.g., an adjuvant.

In another aspect, the invention features antibody molecules that bind to a LMNA-NTRK1 fusion polypeptide or fragment described herein. In embodiments the antibody can distinguish wild type NRTK1 (or LMNA) from LMNA-NTRK1.

Detection Reagents and Detection of Mutations

In another aspect, the invention features a detection reagent, e.g., a purified or an isolated preparation thereof. Detection reagents can distinguish a nucleic acid, or protein sequence, having a breakpoint, e.g., a DCTN1-ALK breakpoint, e.g., as identified in FIG. 1 (e.g., SEQ ID NO:5); or an LMNA-NTRK1 breakpoint, e.g., as identified in FIG. 6 (e.g., SEQ ID NO:8), from a reference sequence. In one embodiment, the detection reagent detects (e.g., specifically detects) a DCTN1-ALK fusion nucleic acid or a polypeptide (e.g., distinguishes a wild type ALK or another ALK fusion (or DCTN1) from a DCTN1-ALK nucleic acid (e.g., as described herein in FIG. 2 (SEQ ID NO:6); or a DCTN1-ALK polypeptide (e.g., as described herein in FIG. 2 (SEQ ID NO:7). In another embodiment, the detection reagent detects (e.g., specifically detects) an LMNA-NTRK1 fusion nucleic acid or polypeptide (e.g., distinguishes a wild type NTRK1 or another NTRK1 fusion (or LMNA) from LMNA-NTRK1 nucleic acid (e.g., as described herein in FIG. 7 (SEQ ID NO:9); or LMNA-NTRK1 polypeptide (e.g., as described herein in FIG. 7 (SEQ ID NO:10).

Detection reagents, e.g., nucleic acid-based detection reagents, can be used to identify mutations in a target nucleic acid, e.g., DNA, e.g., genomic DNA or cDNA, or RNA, e.g., in a sample, e.g., a sample of nucleic acid derived from a neoplastic or tumor cell, e.g., a melanocytic neoplasm, melanoma or metastatic cell. Detection reagents, e.g., antibody-based detection reagents, can be used to identify mutations in a target protein, e.g., in a sample, e.g., a sample of protein derived from, or produced by, a neoplastic or tumor cell, e.g., a melanocytic neoplasm, melanoma or metastatic cell.

Nucleic Acid-Based Detection Reagents

In an embodiment, the detection reagent comprises a nucleic acid molecule, e.g., a DNA, RNA or mixed DNA/RNA molecule, comprising sequence which is complementary with a nucleic acid sequence on a target nucleic acid (the sequence on the target nucleic acid that is bound by the detection reagent is referred to herein as the "detection reagent binding site" and the portion of the detection reagent that corresponds to the detection reagent binding site is referred to as the "target binding site"). In an embodiment, the detection reagent binding site is disposed in relationship to the interrogation position such that binding (or in embodiments, lack of binding) of the detection reagent to the detection reagent binding site allows differentiation of mutant and reference sequences for a mutant described herein (e.g., a translocation having a breakpoint, e.g., a DCTN1-ALK breakpoint, e.g., as identified in FIG. 1 (e.g., SEQ ID NO:5); or an LMNA-NTRK1 breakpoint, e.g., as identified in FIG. 6 (e.g., SEQ ID NO:8)), from a reference sequence. The detection reagent can be modified, e.g., with a label or other moiety, e.g., a moiety that allows capture.

In an embodiment, the detection reagent comprises a nucleic acid molecule, e.g., a DNA, RNA or mixed DNA/RNA molecule, which, e.g., in its target binding site, includes the interrogation position and which can distinguish (e.g., by affinity of binding of the detection reagent to a target nucleic acid or the ability for a reaction, e.g., a ligation or extension reaction with the detection reagent) between a mutation, e.g., a translocation described herein, and a reference sequence. In embodiments, the interrogation position can correspond to a terminal, e.g., to a 3' or 5' terminal nucleotide, a nucleotide immediately adjacent to a 3' or 5' terminal nucleotide, or to another internal nucleotide, of the detection reagent or target binding site.

In embodiments, the difference in the affinity of the detection reagent for a target nucleic acid comprising the mutant and that for a target nucleic acid comprising the reference sequence allows determination of the presence or absence of the mutation (or reference) sequence. Typically, such detection reagents, under assay conditions, will exhibit substantially higher levels of binding only to the mutant or only to the reference sequence, e.g., will exhibit substantial levels of binding only to the mutant or only to the reference sequence.

In embodiments, binding allows (or inhibits) a subsequent reaction, e.g., a subsequent reaction involving the detection reagent or the target nucleic acid. E.g., binding can allow ligation, or the addition of one or more nucleotides to a nucleic acid, e.g., the detection reagent, e.g., by DNA polymerase, which can be detected and used to distinguish mutant from reference. In embodiments, the interrogation position is located at the terminus, or sufficiently close to the terminus, of the detection reagent or its target binding site, such that hybridization, or a chemical reaction, e.g., the addition of one or more nucleotides to the detection reagent, e.g., by DNA polymerase, only occurs, or occurs at a substantially higher rate, when there is a perfect match between the detection reagent and the target nucleic acid at the interrogation position or at a nucleotide position within 1, 2, or 3 nucleotides of the interrogation position.

In an embodiment, the detection reagent comprises a nucleic acid, e.g., a DNA, RNA or mixed DNA/RNA molecule wherein the molecule, or its target binding site, is adjacent (or flanks), e.g., directly adjacent, to the interrogation position, and which can distinguish between a mutation, e.g., a translocation described herein, and a reference sequence, in a target nucleic acid.

In embodiments, the detection reagent binding site is adjacent to the interrogation position, e.g., the 5' or 3'terminal nucleotide of the detection reagent, or its target binding site, is adjacent, e.g., between 0 (directly adjacent) and 1,000, 500, 400, 200, 100, 50, 10, 5, 4, 3, 2, or 1 nucleotides from the interrogation position. In embodiments, the outcome of a reaction will vary with the identity of the nucleotide at the interrogation position allowing one to distinguish between mutant and reference sequences. E.g., in the presence of a first nucleotide at the interrogation position a first reaction will be favored over a second reaction. E.g., in a ligation or primer extension reaction, the product will differ, e.g., in charge, sequence, size, or susceptibility to a further reaction (e.g., restriction cleavage) depending on the identity of the nucleotide at the interrogation position. In embodiments the detection reagent comprises paired molecules (e.g., forward and reverse primers), allowing for amplification, e.g., by PCR amplification, of a duplex containing the interrogation position. In such embodiments, the presence of the mutation can be determined by a difference in the property of the amplification product, e.g., size, sequence, charge, or susceptibility to a reaction, resulting from a sequence comprising the interrogation position and a corresponding sequence having a reference nucleotide at the interrogation positions. In embodiments, the presence or absence of a characteristic amplification product is indicative of the identity of the nucleotide at the interrogation site and thus allows detection of the mutation.

In embodiments, the detection reagent, or its target binding site, is directly adjacent to the interrogation position, e.g., the 5' or 3'terminal nucleotide of the detection reagent is directly adjacent to the interrogation position. In embodiments, the identity of the nucleotide at the interrogation position will determine the nature of a reaction, e.g., a reaction involving the detection reagent, e.g., the modification of one end of the detection reagent. E.g., in the presence of a first nucleotide at the interrogation position a first reaction will be favored over a second reaction. By way of example, the presence of a first nucleotide at the interrogation position, e.g., a nucleotide associated with a mutation, can promote a first reaction, e.g., the addition of a complementary nucleotide to the detection reagent. By way of example, the presence of an A at the interrogation position will cause the incorporation of a T, having, e.g., a first colorimetric label, while the presence of a G and the interrogation position will cause the incorporation for a C, having, e.g., a second colorimetric label. In an embodiment, the presence of a first nucleotide at the nucleotide will result in ligation of the detection reagent to a second nucleic acid. E.g., a third nucleic acid can be hybridized to the target nucleic acid sufficiently close to the interrogation site that if the third nucleic acid has an exact match at the interrogation site it will be ligated to the detection reagent. Detection of the ligation product, or its absence, is indicative of the identity of the nucleotide at the interrogation site and thus allows detection of the mutation.

A variety of readouts can be employed. E.g., binding of the detection reagent to the mutant or reference sequence can be followed by a moiety, e.g., a label, associated with the detection reagent, e.g., a radioactive or enzymatic label. In embodiments the label comprises a quenching agent and a signaling agent and hybridization results in altering the distance between those two elements, e.g., increasing the distance and un-quenching the signaling agent. In embodiments, the detection reagent can include a moiety that allows separation from other components of a reaction mixture. In embodiments, binding allows cleavage of the bound detection reagent, e.g., by an enzyme, e.g., by the nuclease activity of the DNA polymerase or by a restriction enzyme. The cleavage can be detected by the appearance or disappearance of a nucleic acid or by the separation of a quenching agent and a signaling agent associated with the detection reagent. In embodiments, binding protects, or renders the target susceptible, to further chemical reaction, e.g., labeling or degradation, e.g., by restriction enzymes. In embodiments binding with the detection reagent allows capture separation or physical manipulation of the target nucleic acid to thereby allow for identification. In embodiments binding can result in a detectable localization of the detection reagent or target, e.g., binding could capture the target nucleic acid or displace a third nucleic acid. Binding can allow for determination of the presence of mutant or reference sequences with FISH, particularly in the case of rearrangements. Binding can allow for the extension or other size change in a component, e.g., the detection reagent, allowing distinction between mutant and reference sequences. Binding can allow for the production, e.g., by PCR, of an amplicon that distinguishes mutant from reference sequence.

In an embodiment the detection reagent, or the target binding site, is between 5 and 500, 5 and 300, 5 and 250, 5 and 200, 5 and 150, 5 and 100, 5 and 50, 5 and 25, 5 and 20, 5 and 15, or 5 and 10 nucleotides in length. In an embodiment the detection reagent, or the target binding site, is between 10 and 500, 10 and 300, 10 and 250, 10 and 200, 10 and 150, 10 and 100, 10 and 50, 10 and 25, 10 and 20, or 10 and 15, nucleotides in length. In an embodiment the detection reagent, or the target binding site, is between 20 and 500, 20 and 300, 20 and 250, 20 and 200, 20 and 150, 20 and 100, 20 and 50, or 20 and 25 nucleotides in length. In an embodiment the detection reagent, or the target binding site, is sufficiently long to distinguish between mutant and reference sequences and is less than 100, 200, 300, 400, or 500 nucleotides in length.

Preparations of Mutant Nucleic Acid and Uses Thereof

In another aspect, the invention features purified or isolated preparations of a neoplastic or tumor cell nucleic acid, e.g., DNA, e.g., genomic DNA or cDNA, or RNA, containing an interrogation position described herein, useful for determining if a mutation disclosed herein is present. The nucleic acid includes the interrogation position, and typically additional fusion sequence on one or both sides of the interrogation position. In addition the nucleic acid can contain heterologous sequences, e.g., adaptor or priming sequences, typically attached to one or both terminus of the nucleic acid. The nucleic acid also includes a label or other moiety, e.g., a moiety that allows separation or localization.

In embodiments, the nucleic acid is between 20 and 1,000, 30 and 900, 40 and 800, 50 and 700, 60 and 600, 70 and 500, 80 and 400, 90 and 300, or 100 and 200 nucleotides in length (with or without heterologous sequences). In one embodiment, the nucleic acid is between 40 and 1,000, 50 and 900, 60 and 800, 70 and 700, 80 and 600, 90 and 500, 100 and 400, 110 and 300, or 120 and 200 nucleotides in length (with or without heterologous sequences). In another embodiment, the nucleic acid is between 50 and 1,000, 50 and 900, 50 and 800, 50 and 700, 50 and 600, 50 and 500, 50 and 400, 50 and 300, or 50 and 200 nucleotides in length (with or without heterologous sequences). In embodiments, the nucleic acid is of sufficient length to allow sequencing (e.g., by chemical sequencing or by determining a difference in $T_m$ between mutant and reference preparations) but is optionally less than 100, 200, 300, 400, or 500 nucleotides in length (with or without heterologous sequences).

Such preparations can be used to sequence nucleic acid from a sample, e.g., a neoplastic or tumor sample. In an embodiment the purified preparation is provided by in situ amplification of a nucleic acid provided on a substrate. In embodiments the purified preparation is spatially distinct from other nucleic acids, e.g., other amplified nucleic acids, on a substrate.

In an embodiment, the purified or isolated preparation of nucleic acid is derived from a neoplasm or tumor of a type described herein, e.g., neoplasm and/or cancer, e.g., a melanocytic neoplasm, melanoma or metastatic cancer. In one embodiment, the fusion nucleic acid is derived from a histiocytoses, e.g., a non-Langerhans cell histiocytosis.

Such preparations can be used to determine if a sample comprises mutant sequence, e.g., a translocation as described herein. In one embodiment, the translocation includes a breakpoint, e.g., a DCTN1-ALK breakpoint, e.g., as identified in FIG. 1 (e.g., SEQ ID NO:5). In other embodiments, the translocation includes an LMNA-NTRK1 breakpoint, e.g., as identified in FIG. 6 (e.g., SEQ ID NO:8). Nucleic acids that include the aforesaid breakpoints, e.g., a DCTN1-ALK breakpoint or an LMNA-NTRK1 breakpoint, are collectively referred to herein as fusion nucleic acids.

In another aspect, the invention features, a method of determining the sequence of an interrogation position for a mutation described herein, comprising:

providing a purified or isolated preparations of nucleic acid or fusion nucleic acid, e.g., DNA, e.g., genomic DNA or cDNA, or RNA, containing an interrogation position described herein, sequencing, by a method that breaks or forms a chemical bond, e.g., a covalent or non-covalent chemical bond, e.g., in a detection reagent or a target sequence, the nucleic acid so as to determine the identity of the nucleotide at an interrogation position. The method allows determining if a mutation described herein is present.

In an embodiment, sequencing comprises contacting the fusion nucleic acid with a detection reagent described herein.

In an embodiment, sequencing comprises determining a physical property, e.g., stability of a duplex form of the fusion nucleic acid, e.g., $T_m$, that can distinguish mutant from reference sequence.

In an embodiment, the fusion nucleic acid is derived from a neoplasm or a tumor of a type described herein, e.g., a melanocytic neoplasm, melanoma or metastatic cancer. In one embodiment, the fusion nucleic acid is derived from a histiocytoses, e.g., a non-Langerhans cell histiocytosis.

Reaction Mixtures and Devices

In another aspect, the invention features, purified or isolated preparations of a fusion nucleic acid, e.g., DNA, e.g., genomic DNA or cDNA, or RNA, containing an interrogation position described herein, useful for determining if a mutation disclosed herein is present, disposed in sequencing device, or a sample holder for use in such a device. In an embodiment, the fusion nucleic acid is derived from a neoplasm or a tumor of a type described herein, e.g., a melanocytic neoplasm, melanoma or metastatic cancer. In one embodiment, the fusion nucleic acid is derived from a histiocytoses, e.g., a non-Langerhans cell histiocytosis.

In another aspect, the invention features, purified or isolated preparations of a fusion nucleic acid, e.g., DNA, e.g., genomic DNA or cDNA, or RNA, containing an interrogation position described herein, useful for determining if a mutation disclosed herein is present, disposed in a device for determining a physical or chemical property, e.g., stability of a duplex, e.g., $T_m$ or a sample holder for use in such a device. In an embodiment, the device is a calorimeter. In an embodiment the fusion nucleic acid is derived from a neoplasm or a tumor of a type described herein, e.g., a melanocytic neoplasm, melanoma or metastatic cancer. In one embodiment, the fusion nucleic acid is derived from a histiocytoses, e.g., a non-Langerhans cell histiocytosis.

The detection reagents described herein can be used to determine if a mutation described herein is present in a sample. In embodiments, the sample comprises a nucleic acid that is derived from a neoplastic or a tumor cell. The cell can be from a neoplastic or a tumor sample, e.g., a biopsy taken from the neoplasm or the tumor; from circulating tumor cells, e.g., from peripheral blood; or from a blood or plasma sample. In an embodiment, the fusion nucleic acid is derived from a neoplasm or a tumor of a type described herein, e.g., a melanocytic neoplasm, melanoma or metastatic cancer. In one embodiment, the fusion nucleic acid is derived from a histiocytoses, e.g., a non-Langerhans cell histiocytosis.

Accordingly, in one aspect, the invention features a method of making a reaction mixture, comprising:

combining a detection reagent, or purified or isolated preparation thereof, described herein with a target nucleic acid derived from a neoplastic or a tumor cell which comprises a sequence having an interrogation position for a mutation described herein.

In another aspect, the invention features a reaction mixture, comprising:

a detection reagent, or purified or isolated preparation thereof, described herein; and a target nucleic acid derived from a neoplastic or tumor cell which comprises a sequence having an interrogation position for a mutation described herein.

In an embodiment of the reaction mixture, or the method of making the reaction mixture:

the detection reagent comprises a nucleic acid, e.g., a DNA, RNA or mixed DNA/RNA, molecule which is complementary with a nucleic acid sequence on a target nucleic acid (the detection reagent binding site) wherein the detection reagent binding site is disposed in relationship to the interrogation position such that binding of the detection reagent to the detection reagent binding site allows differentiation of mutant and reference sequences for a mutant described herein.

In an embodiment of the reaction mixture, or the method of making the reaction mixture, the neoplasm or a tumor is as described herein.

In an embodiment of the reaction mixture, or the method of making the reaction mixture:

the mutation is a mutation described herein, including: a translocation event, e.g., a translocation as described herein. In one embodiment, the mutation is a breakpoint, e.g., a DCTN1-ALK breakpoint, e.g., as identified in FIG. 1 (e.g., SEQ ID NO:5); or an LMNA-NTRK1 breakpoint, e.g., as identified in FIG. 6 (e.g., SEQ ID NO:8). In another embodiment, the mutation is a DCTN1-ALK fusion nucleic acid or polypeptide (e.g., as described herein in FIG. 2 (SEQ ID NO:6); or DCTN1-ALK polypeptide (e.g., as described herein in FIG. 2 (SEQ ID NO:7). In another embodiment, the mutation is an LMNA-NTRK1 fusion nucleic acid or polypeptide (e.g., as described herein in FIG. 7 (SEQ ID NO:9); or LMNA-NTRK1 polypeptide (e.g., as described herein in FIG. 7 (SEQ ID NO:10)).

A mutation described herein, can be distinguished from a reference, e.g., a non-mutant or wildtype sequence, by reaction with an enzyme that reacts differentially with the mutation and the reference. E.g., they can be distinguished by cleavage with a restriction enzyme that has differing activity for the mutant and reference sequences. E.g., the invention includes a method of contacting a nucleic acid comprising a mutation described herein with such an enzyme and determining if a product of that cleavage which can distinguish mutant form reference sequence is present.

In one aspect the inventions provides, a purified preparation of a restriction enzyme cleavage product which can distinguish between mutant and reference sequence, wherein one end of the cleavage product is defined by an enzyme that cleaves differentially between mutant and reference sequence. In an embodiment, the cleavage product includes the interrogation position.

Protein-Based Detection Reagents, Methods, Reaction Mixtures and Devices

A mutant protein described herein can be distinguished from a reference, e.g., a non-mutant or wild-type protein, by reaction with a reagent, e.g., a substrate, e.g, a substrate for catalytic activity, e.g., phosphorylation or other ALK or NTRK1 activity, or an antibody, that reacts differentially with the mutant and reference protein. In one aspect, the invention includes a method of contacting a sample comprising a mutant protein described herein with such reagent and determining if the mutant protein is present in the sample.

In another embodiment, the invention features, an antibody that can distinguish a mutant protein described herein, e.g., a mutant protein corresponding to a junction shown FIG. 2 or FIG. 4, or an associated mutation from a reference, e.g., a non-mutant or wildtype protein.

Accordingly, in one aspect, the invention features a method of making a reaction mixture comprising:

combining a detection reagent, or purified or isolated preparation thereof, e.g., a substrate, e.g., a substrate for phosphorylation or other activity, or an antibody, described herein with a target fusion protein derived from a neoplastic or a tumor cell which comprises a sequence having an interrogation position for a mutation described herein.

In another aspect, the invention features a reaction mixture comprising:

a detection reagent, or purified or isolated preparation thereof, e.g., a substrate, e.g., a substrate for phosphorylation or other activity, or an antibody, described herein; and a target fusion protein derived from a neoplastic or a tumor cell which comprises a sequence having an interrogation position for a mutation described herein.

In an embodiment of the reaction mixture, or the method of making the reaction mixture:

the detection reagent comprises an antibody specific for a mutant fusion protein described herein.

In an embodiment of the reaction mixture, or the method of making the reaction mixture:

the neoplastic or a tumor cell is a cell described herein, e.g., a melanocytic neoplasm, melanoma or metastatic cell.

In an embodiment of the reaction mixture, or the method of making the reaction mixture:

the mutation is a mutation described herein, including: a translocation, e.g., a translocation as described herein. In one embodiment, the mutation is a breakpoint, e.g., a DCTN1-ALK breakpoint, e.g., as identified in FIG. 1 (e.g., SEQ ID NO:5); or an LMNA-NTRK1 breakpoint, e.g., as identified in FIG. 6 (e.g., SEQ ID NO:8). In another embodiment, the mutation is a DCTN1-ALK fusion nucleic acid or polypeptide (e.g., as described herein in FIG. 2 (SEQ ID NO:6); or DCTN1-ALK polypeptide (e.g., as described herein in FIG. 2 (SEQ ID NO:7). In another embodiment, the mutation is an LMNA-NTRK1 fusion nucleic acid or polypeptide (e.g., as described herein in FIG. 7 (SEQ ID NO:9); or LMNA-NTRK1 polypeptide (e.g., as described herein in FIG. 7 (SEQ ID NO:10)).

Kits

In another aspect, the invention features a kit comprising a detection reagent as described herein.

Methods Reducing a DCTN1-ALK Activity

In another aspect, the invention features a method of reducing an activity of a DCTN1-ALK fusion. The method includes contacting the DCTN1-ALK fusion, or a DCTN1-ALK-expressing cell, with an agent that inhibits an activity or expression of DCTN1-ALK (e.g., a kinase inhibitor). In one embodiment, the contacting step can be effected in vitro, e.g., in a cell lysate or in a reconstituted system. Alternatively, the method can be performed on cells in culture, e.g., in vitro or ex vivo. In other embodiments, the method can be performed on DCTN1-ALK-expressing cells present in a subject, e.g., as part of an in vivo (e.g., therapeutic or prophylactic) protocol. In an embodiment the method is practiced on an animal subject (e.g., an in vivo animal model). In certain embodiments, the DCTN1-ALK fusion is a nucleic acid molecule or a polypeptide as described herein.

In a related aspect, a method of inhibiting, reducing, or treating a hyperproliferative disorder, e.g., a neoplasm (including benign, pre-malignant or malignant (e.g., a cancer), in a subject is provided. The method includes administering to the subject a preselected therapeutic agent, e.g., an anti-cancer agent (e.g., a kinase inhibitor), as a single agent, or in combination, in an amount sufficient to reduce, inhibit or treat the activity or expression of DCTN1-ALK (e.g., a DCTN1-ALK fusion described herein), thereby inhibiting, reducing, or treating the hyperproliferative disorder in the subject. "Treatment" as used herein includes, but is not limited to, inhibiting tumor growth, reducing tumor mass, reducing size or number of metastatic lesions, inhibiting the development of new metastatic lesions, prolonged survival, prolonged progression-free survival, prolonged time to progression, and/or enhanced quality of life.

In one embodiment, the kinase inhibitor is administered based on a determination that a DCTN1-ALK fusion is present in a subject, e.g., based on its present in a subject's sample. Thus, treatment can be combined with a DCTN1-ALK detection or evaluation method, e.g., as described herein, or administered in response to a determination made by a DCTN1-ALK detection or evaluation method, e.g., as described herein. In certain embodiments, the kinase inhibitor is administered responsive to acquiring knowledge or information of the presence of the DCTN1-ALK fusion in a subject. In one embodiment, the kinase inhibitor is administered responsive to acquiring knowledge or information on the subject's genotype, e.g., acquiring knowledge or information that the patient's genotype has a DCTN1-ALK fusion. In other embodiments, the kinase inhibitor is administered responsive to receiving a communication (e.g., a report) of the presence of the DCTN1-ALK fusion in a subject (e.g., a subject's sample). In yet other embodiments, the kinase inhibitor is administered responsive to information obtained from a collaboration with another party that identifies the presence of the DCTN1-ALK fusion in a subject (e.g., a subject's sample). In other embodiments, the kinase inhibitor is administered responsive to a determination that the DCTN1-ALK fusion is present in a subject. In one embodiment, the determination of the presence of the DCTN1-ALK fusion is carried out using one or more of the methods, e.g., the sequencing methods, described herein. In other embodiments, the determination of the presence of the DCTN1-ALK fusion includes receiving information on the subject's DCTN1-ALK fusion genotype, e.g., from another party or source.

The methods can, optionally, further include the step(s) of identifying (e.g., evaluating, diagnosing, screening, and/or selecting) a subject at risk of having, or having, a DCTN1-ALK fusion. In one embodiment, the method further includes one or more of: acquiring knowledge or information of the presence of the DCTN1-ALK fusion in a subject (e.g., a subject's sample); acquiring knowledge or information on the subject's genotype, e.g., acquiring knowledge or information that the patient's genotype has a DCTN1-ALK fusion; receiving a communication (e.g., a report) of the presence of the DCTN1-ALK fusion in a subject (e.g., a subject's sample); or collaborating with another party that identifies the presence of the DCTN1-ALK fusion in a subject.

In one embodiment, the subject treated has a DCTN1-ALK fusion; e.g., the subject has a tumor or cancer harboring a DCTN1-ALK fusion. In other embodiments, the subject has been previously identified as having a DCTN1-ALK fusion. In yet other embodiments, the subject has been previously identified as being likely or unlikely to respond to treatment with a protein kinase inhibitor, e.g., a subject that has previously participated in a clinical trial. In other embodiments, the subject has been previously identified as being likely or unlikely to respond to treatment with a protein kinase inhibitor, based on the presence of the DCTN1-ALK fusion. In one embodiment, the subject is a mammal, e.g., a human. In one embodiment, the subject has, or at risk of having a cancer at any stage of disease. In other embodiments, the subject is a patient, e.g., a cancer patient.

In other embodiments, the subject treated is a cancer patient who has participated in a clinical trial. For example, the subject participated in a clinical trial that evaluated a kinase inhibitor (e.g., a multikinase inhibitor, an ALK kinase inhibitor). In other embodiment, the subject participated in a clinical trial that evaluates upstream or downstream targets of ALK. In one embodiment, said cancer patient responded to the kinase inhibitor evaluated.

In certain embodiments, the neoplasm or neoplastic cell is a benign, pre-malignant, malignant (cancer) or metastasis. In certain embodiments, the cancer is a solid tumor, a soft tissue tumor, or a metastatic lesion. In one embodiment, the cancer is chosen from a lung cancer, a pancreatic cancer, melanoma, a colorectal cancer, an esophageal-gastric cancer, a thyroid cancer, or an adenocarcinoma. In other embodiment, the lung cancer is chosen from one or more of the following: non-small cell lung cancer (NSCLC), small cell lung cancer (SCLC), squamous cell carcinoma (SCC), adenocarcinoma of the lung, bronchogenic carcinoma, or a combination thereof. In one embodiment, the lung cancer is NSCLC or SCC. In one embodiment, the neoplasm or cancer is a melanocytic neoplasm, a Spitz nevi, a Spitz tumor, a Spitzoid melanoma, a metastatic Spitz tumor, or a melanoma. In one embodiment, the Spitz tumor is metastatic, e.g., localized to lymph nodes or widespread disease.

In one embodiment, the anti-cancer agent is a kinase inhibitor. For example, the kinase inhibitor is a multi-kinase inhibitor or an ALK-specific inhibitor. In one embodiment, the kinase inhibitor is an ALK inhibitor including, but not limited to, TAE-684 (also referred to herein as "NVP-TAE694"), PF02341066 (also referred to herein as "crizotinib" or "1066"), AF-802, LDK-378, ASP-3026, CEP-37440, CEP-28122, CEP-108050 and AP26113. Additional examples of ALK kinase inhibitors are described in examples 3-39 of WO 2005016894 by Garcia-Echeverria C, et al.

In other embodiments, the anti-cancer agent is a DCTN1-ALK antagonist inhibits the expression of nucleic acid encoding DCTN1-ALK. Examples of such DCTN1-ALK antagonists include nucleic acid molecules, for example, antisense molecules, ribozymes, RNAi, triple helix molecules that hybridize to a nucleic acid encoding DCTN1-ALK, or a transcription regulatory region, and blocks or reduces mRNA expression of DCTN1-ALK.

In other embodiments, the kinase inhibitor is administered in combination with a second therapeutic agent or a different therapeutic modality, e.g., anti-cancer agents, and/or in combination with surgical and/or radiation procedures. For example, the second therapeutic agent can be a cytotoxic or a cytostatic agent. Exemplary cytotoxic agents include antimicrotubule agents, topoisomerase inhibitors, or taxanes, antimetabolites, mitotic inhibitors, alkylating agents, intercalating agents, agents capable of interfering with a signal transduction pathway, agents that promote apoptosis and radiation. In yet other embodiments, the methods can be used in combination with immunodulatory agents, e.g., IL-1, 2, 4, 6, or 12, or interferon alpha or gamma, or immune cell growth factors such as GM-CSF.

Screening Methods

In another aspect, the invention features a method, or assay, for screening for agents that modulate, e.g., inhibit, the expression or activity of a DCTN1-ALK fusion, e.g., a DCTN1-ALK fusion as described herein. The method includes contacting a DCTN1-ALK fusion, or a cell expressing a DCTN1-ALK fusion, with a candidate agent; and detecting a change in a parameter associated with a DCTN1-ALK fusion, e.g., a change in the expression or an activity of the DCTN1-ALK fusion. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the DCTN1-ALK fusion is detected, the candidate agent is identified as an inhibitor. In another embodiment, if an increase in expression or activity of the DCTN1-ALK fusion is detected, the candidate agent is identified as an activator. In certain embodiments, the DCTN1-ALK fusion is a nucleic acid molecule or a polypeptide as described herein.

In one embodiment, the contacting step is effected in a cell-free system, e.g., a cell lysate or in a reconstituted system. In other embodiments, the contacting step is effected in a cell in culture, e.g., a cell expressing a DCTN1-ALK fusion (e.g., a mammalian cell, a tumor cell or cell line, a recombinant cell). In yet other embodiments, the contacting step is effected in a cell in vivo (a DCTN1-ALK-expressing cell present in a subject, e.g., an animal subject (e.g., an in vivo animal model).

Exemplary parameters evaluated include one or more of:

(i) a change in binding activity, e.g., direct binding of the candidate agent to a DCTN1-ALK fusion polypeptide; a binding competition between a known ligand and the candidate agent to a DCTN1-ALK fusion polypeptide;

(ii) a change in kinase activity, e.g., phosphorylation levels of a DCTN1-ALK fusion polypeptide (e.g., an increased or decreased autophosphorylation); or a change in phosphorylation of a target of an ALK kinase, e.g., Akt, In certain embodiments, a change in kinase activity, e.g., phosphorylation, is detected by any of Western blot (e.g., using an anti-DCTN1 or anti-ALK antibody; a phosphor-specific antibody, detecting a shift in the molecular weight of a DCTN1-ALK fusion polypeptide), mass spectrometry, immunoprecipitation, immunohistochemistry, immunomagnetic beads, among others;

(iii) a change in an activity of a cell containing a DCTN1-ALK fusion (e.g., a tumor cell or a recombinant cell), e.g., a change in proliferation, morphology or tumorigenicity of the cell;

(iv) a change in tumor present in an animal subject, e.g., size, appearance, proliferation, of the tumor; or (v) a change in the level, e.g., expression level, of a DCTN1-ALK fusion polypeptide or nucleic acid molecule.

In one embodiment, a change in a cell free assay in the presence of a candidate agent is evaluated. For example, an activity of a DCTN1-ALK fusion, or interaction of a DCTN1-ALK fusion with a downstream ligand can be detected. In one embodiment, a DCTN1-ALK fusion polypeptide is contacted with a ligand, e.g., in solution, and a candidate agent is monitored for an ability to modulate, e.g., inhibit, an interaction, e.g., binding, between the DCTN1-ALK fusion polypeptide and the ligand.

In other embodiments, a change in an activity of a cell is detected in a cell in culture, e.g., a cell expressing a DCTN1-ALK fusion (e.g., a mammalian cell, a tumor cell or cell line, a recombinant cell). In one embodiment, the cell is a recombinant cell that is modified to express a DCTN1-ALK fusion nucleic acid, e.g., is a recombinant cell transfected with a DCTN1-ALK fusion nucleic acid. The transfected cell can show a change in response to the expressed DCTN1-ALK fusion, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, transformed morphology, in the presence of the candidate agent can be indicative of an inhibitor of a DCTN1-ALK fusion. In other embodiments, a change in binding activity or phosphorylation as described herein is detected.

In yet other embodiment, a change in a tumor present in an animal subject (e.g., an in vivo animal model) is detected. In one embodiment, the animal model is a tumor containing animal or a xenograft comprising cells expressing a DCTN1-ALK fusion (e.g., tumorigenic cells expressing a DCTN1-ALK fusion). The candidate agent can be administered to the animal subject and a change in the tumor is detected. In one embodiment, the change in the tumor includes one or more of a tumor growth, tumor size, tumor burden, survival, is evaluated. A decrease in one or more of tumor growth, tumor size, tumor burden, or an increased survival is indicative that the candidate agent is an inhibitor.

In other embodiments, a change in expression of a DCTN1-ALK fusion can be monitored by detecting the nucleic acid or protein levels, e.g., using the methods described herein.

In certain embodiments, the screening methods described herein can be repeated and/or combined. In one embodiment, a candidate agent that is evaluated in a cell-free or cell-based described herein can be further tested in an animal subject.

In one embodiment, the candidate agent is a small molecule compound, e.g., a kinase inhibitor, a nucleic acid (e.g., antisense, siRNA, aptamer, ribozymes, microRNA), an antibody molecule (e.g., a full antibody or antigen binding fragment thereof that binds to DCTN1 or ALK). The candidate agent can be obtained from a library (e.g., a commercial library of kinase inhibitors) or rationally designed (e.g., based on the ALK kinase domain).

Methods for Detecting Fusions

In another aspect, the invention features a method of determining the presence of a fusion as described herein, e.g., a DCTN1-ALK fusion or an LMNA-NTRK1 as described herein. In one embodiment, the fusion (e.g., DCTN1-ALK or LMNA-NTRK1) is detected in a nucleic acid molecule or a polypeptide. The method includes detecting whether a fusion nucleic acid molecule or polypeptide is present in a cell (e.g., a circulating cell), a tissue (e.g., a tumor), or a sample, e.g., a tumor sample, from a subject. In one embodiment, the sample is a nucleic acid sample. In one embodiment, the nucleic acid sample comprises DNA, e.g., genomic DNA or cDNA, or RNA, e.g., mRNA. In other embodiments, the sample is a protein sample.

In one embodiment, the sample is, or has been, classified as non-malignant using other diagnostic techniques, e.g., immunohistochemistry.

In one embodiment, the sample is acquired from a subject (e.g., a subject having or at risk of having a cancer, e.g., a patient), or alternatively, the method further includes acquiring a sample from the subject. The sample can be chosen from one or more of: tissue, e.g., cancerous tissue (e.g., a tissue biopsy), whole blood, serum, plasma, buccal scrape, sputum, saliva, cerebrospinal fluid, urine, stool, circulating tumor cells, circulating nucleic acids, or bone marrow. In certain embodiments, the sample is a tissue (e.g., a tumor biopsy), a circulating tumor cell or nucleic acid.

In embodiments, the tumor is from a cancer described herein, e.g., is chosen from a lung cancer, a colorectal cancer, an esophageal-gastric cancer, a thyroid cancer, an adenocarcinoma or a melanoma. In one embodiment, the tumor is from a lung cancer, e.g., a NSCLC, a SCLC, a SCC, or a combination thereof.

In one embodiment, the subject is at risk of having, or has a cancer (e.g., a patient with a cancer described herein).

In other embodiments, the DCTN1-ALK fusion or LMNA-NTRK1 fusion is detected in a nucleic acid molecule by a method chosen from one or more of: nucleic acid hybridization assay, amplification-based assays (e.g., polymerase chain reaction (PCR)), PCR-RFLP assay, real-time PCR, sequencing, screening analysis (including metaphase cytogenetic analysis by standard karyotype methods, FISH (e.g., break away FISH), spectral karyotyping or MFISH, comparative genomic hybridization), in situ hybridization, SSP, HPLC or mass-spectrometric genotyping.

In one embodiment, the method includes: contacting a nucleic acid sample, e.g., a genomic DNA sample (e.g., a chromosomal sample or a fractionated, enriched or otherwise pre-treated sample) or a gene product (mRNA, cDNA), obtained from the subject, with a nucleic acid fragment (e.g., a probe or primer as described herein (e.g., an exon-specific probe or primer) under conditions suitable for hybridization, and determining the presence or absence of the DCTN1-

ALK or LMNA-NTRK1 nucleic acid molecule. The method can, optionally, include enriching a sample for the gene or gene product.

In a related aspect, a method for determining the presence of a DCTN1-ALK or LMNA-NTRK1 fusion nucleic acid molecule is provided. The method includes: acquiring a sequence for a position in a nucleic acid molecule, e.g., by sequencing at least one nucleotide of the nucleic acid molecule (e.g., sequencing at least one nucleotide in the nucleic acid molecule that comprises the fusion), thereby determining that the DCTN1-ALK or LMNA-NTRK1 fusion is present in the nucleic acid molecule. Optionally, the sequence acquired is compared to a reference sequence, or a wild type reference sequence. In one embodiment, the nucleic acid molecule is from a cell (e.g., a circulating cell), a tissue (e.g., a tumor), or any sample from a subject (e.g., blood or plasma sample). In other embodiments, the nucleic acid molecule from a tumor sample (e.g., a tumor or cancer sample) is sequenced. In one embodiment, the sequence is determined by a next generation sequencing method. The method further can further include acquiring, e.g., directly or indirectly acquiring, a sample, e.g., a tumor or cancer sample, from a subject (e.g., a patient). In certain embodiments, the cancer is chosen from a lung cancer, colorectal cancer, esophageal-gastric cancer or melanoma.

In another aspect, the invention features a method of analyzing a tumor or a circulating tumor cell. The method includes acquiring a nucleic acid sample from the tumor or the circulating cell; and sequencing, e.g., by a next generation sequencing method, a nucleic acid molecule, e.g., a nucleic acid molecule that includes a DCTN1-ALK fusion or a LMNA-NTRK1 as described herein.

In yet other embodiment, a fusion polypeptide is detected. The method includes: contacting a protein sample with a reagent which specifically binds to a fusion polypeptide (e.g., DCTN1-ALK or LMNA-NTRK1); and detecting the formation of a complex of the fusion polypeptide and the reagent. In one embodiment, the reagent is labeled with a detectable group to facilitate detection of the bound and unbound reagent. In one embodiment, the reagent is an antibody molecule, e.g., is selected from the group consisting of an antibody, and antibody derivative, and an antibody fragment.

In yet another embodiment, the level (e.g., expression level) or activity the DCTN1-ALK or LMNA-NTRK1 fusion is evaluated. For example, the level (e.g., expression level) or activity of the DCTN1-ALK fusion (e.g., mRNA or polypeptide) is detected and (optionally) compared to a pre-determined value, e.g., a reference value (e.g., a control sample). Similarly, the level (e.g., expression level) or activity of the LMNA-NTRK1 fusion (e.g., mRNA or polypeptide) is detected and (optionally compared to a pre-determined value, e.g., a reference value (e.g., a control sample).

In yet another embodiment, the fusion is detected prior to initiating, during, or after, a treatment in a subject having an ALK fusion, such as a DCTN1-ALK fusion, e.g., treatment with an ALK kinase inhibitor.

In one embodiment, the DCTN1-ALK fusion or LMNA-NTRK1 fusion is detected at the time of diagnosis with a cancer. In other embodiment, the fusion is detected at a pre-determined interval, e.g., a first point in time and at least at a subsequent point in time.

In certain embodiments, responsive to a determination of the presence of the DCTN1-ALK fusion, the method further includes one or more of:

(1) stratifying a patient population (e.g., assigning a subject, e.g., a patient, to a group or class);

(2) identifying or selecting the subject as likely or unlikely to respond to a treatment, e.g., a kinase inhibitor treatment as described herein;

(3) selecting a treatment option, e.g., administering or not administering a preselected therapeutic agent, e.g., a kinase inhibitor as described herein; or (4) prognosticating the time course of the disease in the subject (e.g., evaluating the likelihood of increased or decreased patient survival).

In certain embodiments, the kinase inhibitor is a multi-kinase inhibitor or an ALK-specific inhibitor. In one embodiment, the kinase inhibitor an ALK inhibitor including, but not limited to, TAE-684 (also referred to herein as "NVP-TAE694"), PF02341066 (also referred to herein as "crizotinib" or "1066"), AF-802, LDK-378, ASP-3026, CEP-37440, CEP-28122, CEP-108050 and AP26113. Additional examples of ALK kinase inhibitors are described, e.g., in examples 3-39 of WO 2005016894 by Garcia-Echeverria C, et al.

In certain embodiments, responsive to the determination of the presence of a DCTN1-ALK fusion, the subject is classified as a candidate to receive treatment with a kinase inhibitor, e.g., a kinase inhibitor as described herein. In one embodiment, responsive to the determination of the presence of a DCTN1-ALK fusion, the subject, e.g., a patient, can further be assigned to a particular class if a fusion is identified in a sample of the patient. For example, a patient identified as having a DCTN1-ALK fusion can be classified as a candidate to receive treatment with a kinase inhibitor, e.g., an ALK kinase inhibitor as described herein. In one embodiment, the subject, e.g., a patient, is assigned to a second class if the mutation is not present. For example, a patient who has a lung tumor that does not contain a DCTN1-ALK fusion, may be determined as not being a candidate to receive a kinase inhibitor, e.g., an ALK kinase inhibitor as described herein.

In another embodiment, responsive to the determination of the presence of the DCTN1-ALK fusion, the subject is identified as likely to respond to a treatment that comprises a kinase inhibitor e.g., a kinase inhibitor as described herein.

In yet another embodiment, responsive to the determination of the presence of the DCTN1-ALK fusion, the method includes administering a kinase inhibitor, e.g., a kinase inhibitor as described herein, to the subject.

Method of Evaluating a Tumor or a Subject

In another aspect, the invention features a method of evaluating a subject (e.g., a patient), e.g., for risk of having or developing a cancer, e.g., a lung cancer, colorectal cancer or skin cancer. The method includes: acquiring information or knowledge of the presence of a fusion as described herein (e.g., DCTN1-ALK or LMNA-NTRK1) in a subject (e.g., acquiring genotype information of the subject that identifies a fusion as being present in the subject); acquiring a sequence for a nucleic acid molecule identified herein (e.g., a nucleic acid molecule that includes a DCTN1-ALK or LMNA-NTRK1 fusion sequence); or detecting the presence of a fusion nucleic acid or polypeptide in the subject), wherein the presence of the fusion (e.g., DCTN1-ALK, or LMNA-NTRK1) is positively correlated with increased risk for, or having, a cancer associated with such a fusion.

The method can further include acquiring, e.g., directly or indirectly, a sample from a patient and evaluating the sample for the present of a DCTN1-ALK fusion or a LMNA-NTRK1 fusion as described herein.

The method can further include the step(s) of identifying (e.g., evaluating, diagnosing, screening, and/or selecting) the subject as being positively correlated with increased risk for, or having, a cancer associated with the DCTN1-ALK fusion or the LMNA-NTRK1 fusion.

In another embodiment, a subject identified has having a DCTN1-ALK fusion is identified or selected as likely or unlikely to respond to a treatment, e.g., a kinase inhibitor treatment as described herein. The method can further include treating the subject with a kinase inhibitor, e.g., a kinase inhibitor as described herein.

In certain embodiments, the subject is a patient or patient population that has participated in a clinical trial. In one embodiment, the subject has participated in a clinical trial for evaluating a kinase inhibitor (e.g., a multi-kinase inhibitor or an ALK inhibitor). In one embodiment, the clinical trial is discontinued or terminated. In other embodiments, the subject has participated in a clinical trial that evaluates an ALK kinase, a DCTN1 inhibitor (e.g., a kinesin inhibitor), an upstream or downstream component of DCTN1 or ALK. In one embodiment, the subject responded favorably to the clinical trial, e.g., experience an improvement in at least one symptom of a cancer (e.g., decreased in tumor size, rate of tumor growth, increased survival). In other embodiments, the subject did not respond in a detectable way to the clinical trial.

In a related aspect, a method of evaluating a patient or a patient population is provided. The method includes: identifying, selecting, or obtaining information or knowledge that the patient or patient population has participated in a clinical trial; acquiring information or knowledge of the presence of a DCTN1-ALK fusion in the patient or patient population (e.g., acquiring genotype information of the subject that identifies a DCTN1-ALK fusion as being present in the subject); acquiring a sequence for a nucleic acid molecule identified herein (e.g., a nucleic acid molecule that includes a fusion sequence); or detecting the presence of a DCTN1-ALK fusion nucleic acid or polypeptide in the subject), wherein the presence of the fusion identifies the patient or patient population as having an increased risk for, or having, a cancer associated with the DCTN1-ALK.

In some embodiments, the method further includes treating the subject with a kinase inhibitor, e.g., a kinase inhibitor as described herein.

Reporting

Methods described herein can include providing a report, such as, in electronic, web-based, or paper form, to the patient or to another person or entity, e.g., a caregiver, e.g., a physician, e.g., an oncologist, a hospital, clinic, third-party payor, insurance company or government office. The report can include output from the method, e.g., the identification of nucleotide values, the indication of presence or absence of a DCTN1-ALK fusion or an LMNA-NTRK1 fusion as described herein, or wildtype sequence. In one embodiment, a report is generated, such as in paper or electronic form, which identifies the presence or absence of an alteration described herein, and optionally includes an identifier for the patient from which the sequence was obtained.

The report can also include information on the role of a DCTN1-ALK fusion as described herein, or wildtype sequence, in disease. Such information can include information on prognosis, resistance, or potential or suggested therapeutic options. The report can include information on the likely effectiveness of a therapeutic option, the acceptability of a therapeutic option, or the advisability of applying the therapeutic option to a patient, e.g., a patient having a sequence, alteration or mutation identified in the test, and in embodiments, identified in the report. For example, the report can include information, or a recommendation on, the administration of a drug, e.g., the administration at a preselected dosage or in a preselected treatment regimen, e.g., in combination with other drugs, to the patient. In an embodiment, not all mutations identified in the method are identified in the report. For example, the report can be limited to mutations in genes having a preselected level of correlation with the occurrence, prognosis, stage, or susceptibility of the cancer to treatment, e.g., with a preselected therapeutic option. The report can be delivered, e.g., to an entity described herein, within 7, 14, or 21 days from receipt of the sample by the entity practicing the method.

In another aspect, the invention features a method for generating a report, e.g., a personalized cancer treatment report, by obtaining a sample, e.g., a tumor sample, from a subject, detecting a DCTN1-ALK fusion as described herein in the sample, and selecting a treatment based on the mutation identified. In one embodiment, a report is generated that annotates the selected treatment, or that lists, e.g., in order of preference, two or more treatment options based on the mutation identified. In another embodiment, the subject, e.g., a patient, is further administered the selected method of treatment.

Unless otherwise defined, all technical and scientific terms used herein have the same meaning as commonly understood by one of ordinary skill in the art to which this invention belongs. Although methods and materials similar or equivalent to those described herein can be used in the practice or testing the invention, suitable methods and materials are described below. All publications, patent applications, patents, and other references mentioned herein are incorporated by reference in their entirety. In case of conflict, the present specification, including definitions, will control. In addition, the materials, methods, and the example are illustrative only and not intended to be limiting.

The details of one or more embodiments featured in the invention are set forth in the accompanying drawings and the description below. Other features, objects, and advantages featured in the invention will be apparent from the description and drawings, and from the claims.

BRIEF DESCRIPTION OF DRAWINGS

FIGS. 2A-2F is the mRNA and amino acid sequence of the DCTN1-ALK protein fusion (SEQ ID NO:6 (nucleotide) and SEQ ID NO:7 (amino acid)). The amino acid and mRNA sequences of DCTN1 are underlined. The ALK kinase domain (amino acids 1116-1362) is indicated in bold letters.

FIGS. 4A-4D are the sequences of the ALK-DCTN1 fusion mRNA (SEQ ID NO:11, nucleotide) and protein (SEQ ID NO:12). The DCTN1 mRNA and protein sequences are underlined.

FIGS. 7A and 7B are the sequences of the LMNA-NTRK1 fusion mRNA (SEQ ID NO:9, nucleotide) and protein (SEQ ID NO:10, amino acid). The LMNA mRNA and protein sequences are underlined. The NTRK1 kinase domain (amino acids 289-560) is indicated in bold letters.

DETAILED DESCRIPTION

Figure 1:
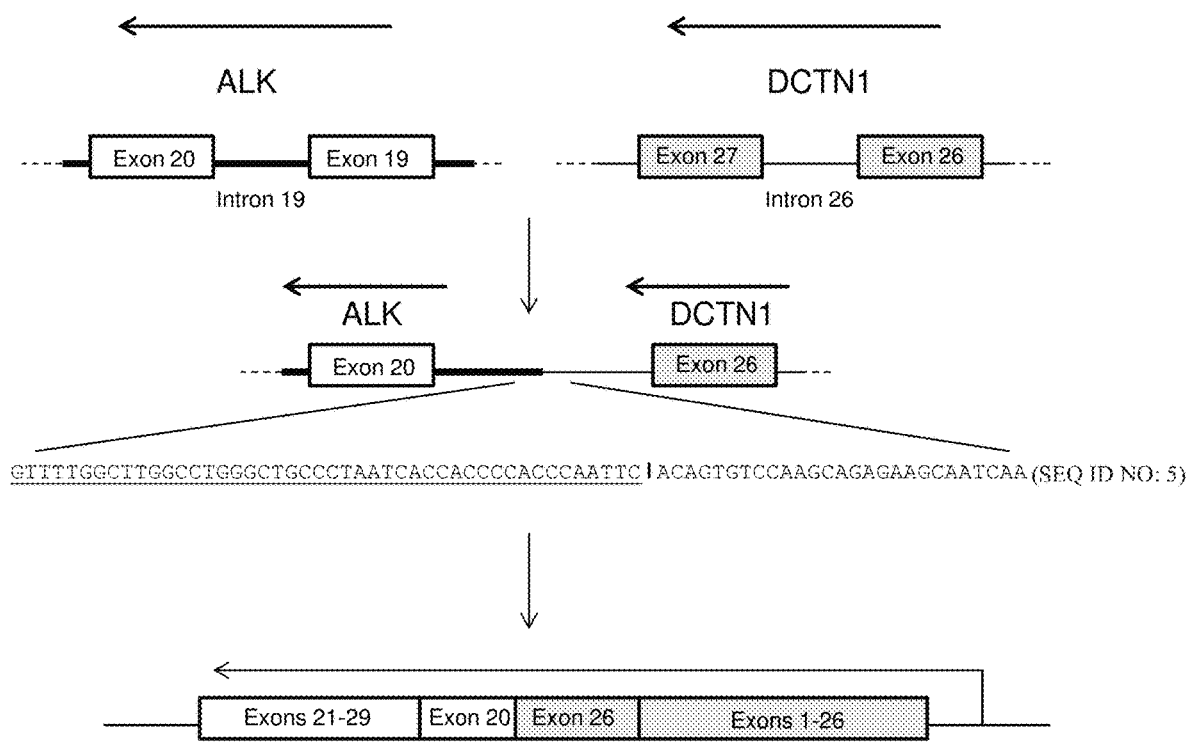
FIG. 1 is a schematic of a balanced translocation with breakpoints in intron 26 of DCTN1 and intron 19 of ALK. The sequence at the breakpoint region is indicated (SEQ ID NO:5). The intron 19 sequence of ALK is indicated by underlining, and the fusion junction is indicated by a vertical line. The sequence of SEQ ID NO:5 is shown in the reference genome orientation.

The invention is based, at least in part, on the discovery of novel translocation and deletion events, and their association with cancer, e.g., melanoma. In one embodiment, balanced translocation on chromosome 2 that results in an in-frame fusion of a fragment of a DCTN1 gene and a fragment of an ALK gene was discovered. In another embodiment, a chromosomal deletion resulting in an in-frame fusion of the LMNA gene and the NRTK1 gene was discovered.

DCTN1-ALK Fusions

The term "DCTN1-ALK" or "DCTN1-ALK fusion" is used generically herein, and includes any fusion molecule (e.g., gene, gene product (e.g., cDNA, mRNA, polypeptide), and variant thereof) that includes a fragment of DCTN1 and a fragment of ALK, in any configuration, including, e.g., a 5'DCTN1-3'ALK or a 5'ALK-3'DCTN1 fusion molecule.

In one embodiment, a DCTN1-ALK fusion includes an in-frame fusion of an exon of DCTN1 (e.g., one more of exons 1-26) and an exon of ALK (e.g., one or more exons encoding an ALK tyrosine kinase domain or a fragment thereof). In one embodiment, the fusion is produced by a translocation on chromosome 2 having a breakpoint in intron 26 of DCTN1 and in intron 19 of ALK. For example, the DCTN1-ALK fusion can include an in-frame fusion of at least exon 26 of DCTN1 or a fragment thereof (e.g., exons 1-26 of DCTN1 or a fragment thereof) with at least exon 10 of ALK or a fragment thereof (e.g., exons 20-34 of ALK or a fragment thereof). In certain embodiments, the DCTN1-ALK fusion is in a 5'-DCTN1 to 3'-ALK configuration referred to herein as "5'DCTN1-3'ALK."

The ALK receptor tyrosine kinase is known to be associated with cancerous phenotypes including inflammatory myofibroblastic tumors, neuroblastoma, lung cancer, non-Hodgkin's lymphoma, and anaplastic large cell lymphoma, among others. For example, a chromosomal rearrangement that generates a fusion gene resulting in the juxtaposition of the N-terminal region of nucleophosmin (NPM) with the kinase domain of ALK are known to be associated with non-Hodgkin's lymphoma (Morris, SW (1994) Science 263: 1281-1284). Thus, the DCTN1-ALK fusions disclosed herein (e.g., the 5'-DCTN1 to 3'-ALK fusions that include an ALK tyrosine kinase domain) are likely to be associated with cancers, e.g., lung cancer.

Accordingly, the invention provides, at least in part, isolated DCTN1-ALK nucleic acid molecules, nucleic acid constructs, host cells containing the nucleic acid molecules; purified DCTN1-ALK polypeptides and binding agents; detection reagents (e.g., probes, primers, antibodies, kits); screening assays for identifying novel kinase inhibitors; as well as methods, assays and kits for evaluating, identifying, assessing and/or treating a subject having a cancer, e.g., a cancer having a DCTN1-ALK fusion disclosed herein. The compositions and methods identified herein can be used, for example, to identify new DCTN1-ALK inhibitors; to treat or prevent a cancer; as well as in methods or assays for evaluating a cancer (e.g., evaluating one or more of: cancer progression, cancer treatment response or resistance to cancer treatment; selecting a treatment option, stratifying a patient population, and/or more effectively monitoring, treating or preventing a cancer).

LMNA-NTRK1 Fusions

The term "LMNA-NTRK1" or "LMNA-NTRK1 fusion" is used generically herein, and includes any fusion molecule (e.g., gene, gene product (e.g., cDNA, mRNA, polypeptide), and variant thereof) that includes a fragment of LMNA and a fragment of NTRK1, in any configuration, including, e.g., a 5'LMNA-3'NTRK1 or a 5'NTRK1-3'LMNA fusion molecule.

In one embodiment, a LMNA-NTRK1 fusion includes an in-frame fusion of an exon of LMNA (e.g., one more exons of LMNA, such as exons 1 or 2, or a fragment thereof) and an exon of NTRK1 (e.g., one or more exons encoding an NTRK1 tyrosine kinase domain or a fragment thereof). In one embodiment, the fusion is produced by a translocation having a breakpoint in intron 2 of LMNA and in intron 10 of NTRK1. For example, the LMNA-NTRK1 fusion can include an in-frame fusion of at least exon 2 of LMNA or a fragment thereof (e.g., one or more of exons 1-2 of LMNA or a fragment thereof) with at least exon 11 of LMNA or a fragment thereof (e.g., one or more of exons 11-41 of NTRK1 or a fragment thereof).

In certain embodiments, the LMNA-NTRK1 fusion is in a 5'-LMNA to 3'-NTRK1 configuration referred to herein as "5'LMNA-3'NTRK."

The NTRK1 receptor tyrosine kinase (also referred to as the TrkA receptor) is known to be associated with cancerous phenotypes including colon tumors and papillary thyroid carcinomas, among others. For example, a chromosomal rearrangement that generates a fusion gene resulting in the juxtaposition of the TFG gene with the kinase binding domain of NTRK1 are known to be associated with papillary thyroid carcinomas. Other NTRK1 rearrangements resulting in fusions include, e.g., NTRK1-TPM3 and TPR-NTRK1. NTRK1 fusion genes are reviewed in e.g., Greco, A. et al., *Mol Cell Endocrinol* (2010) 321(1):44-49.

Accordingly, the invention provides, at least in part, isolated LMNA-NTRK1 nucleic acid molecules, nucleic acid constructs, host cells containing the nucleic acid molecules; purified LMNA-NTRK1 polypeptides and binding agents; detection reagents (e.g., probes, primers, antibodies, kits); screening assays for identifying novel kinase inhibitors; as well as methods, assays and kits for evaluating, identifying, and/or assessing a subject having a cancer, e.g., a cancer having a LMNA-NTRK1 fusion disclosed herein.

Certain terms are first defined. Additional terms are defined throughout the specification.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

"Acquire" or "acquiring" as the terms are used herein, refer to obtaining possession of a physical entity, or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

"Acquiring a sequence" as the term is used herein, refers to obtaining possession of a nucleotide sequence or amino acid sequence, by "directly acquiring" or "indirectly acquiring" the sequence. "Directly acquiring a sequence" means performing a process (e.g., performing a synthetic or analytical method) to obtain the sequence, such as performing a sequencing method (e.g., a Next Generation Sequencing (NGS) method). "Indirectly acquiring a sequence" refers to receiving information or knowledge of, or receiving, the sequence from another party or source (e.g., a third party laboratory that directly acquired the sequence). The sequence acquired need not be a full sequence, e.g., sequencing of at least one nucleotide, or obtaining information or knowledge, that identifies a DCTN1-ALK fusion or LMNA-NTRK1 fusion disclosed herein as being present in a subject constitutes acquiring a sequence.

Directly acquiring a sequence includes performing a process that includes a physical change in a physical substance, e.g., a starting material, such as a tissue sample, e.g., a biopsy, or an isolated nucleic acid (e.g., DNA or RNA) sample. Exemplary changes include making a physical entity from two or more starting materials, shearing or fragmenting a substance, such as a genomic DNA fragment; separating or purifying a substance (e.g., isolating a nucleic acid sample from a tissue); combining two or more separate entities into a mixture, performing a chemical reaction that includes breaking or forming a covalent or non-covalent bond. Directly acquiring a value includes performing a process that includes a physical change in a sample or another substance as described above.

"Acquiring a sample" as the term is used herein, refers to obtaining possession of a sample, e.g., a tissue sample or nucleic acid sample, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material, dissecting or scraping a tissue; separating or purifying a substance (e.g., a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above.

"Binding entity" means any molecule to which molecular tags can be directly or indirectly attached that is capable of specifically binding to an analyte. The binding entity can be an affinity tag on a nucleic acid sequence. In certain embodiments, the binding entity allows for separation of the nucleic acid from a mixture, such as an avidin molecule, or an antibody that binds to the hapten or an antigen-binding fragment thereof. Exemplary binding entities include, but are not limited to, a biotin molecule, a hapten, an antibody, an antibody binding fragment, a peptide, and a protein.

"Complementary" refers to sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In certain embodiments, the first region comprises a first portion and the second region comprises a second portion, whereby, when the first and second portions are arranged in an antiparallel fashion, at least about 50%, at least about 75%, at least about 90%, or at least about 95% of the nucleotide residues of the first portion are capable of base pairing with nucleotide residues in the second portion.

In other embodiments, all nucleotide residues of the first portion are capable of base pairing with nucleotide residues in the second portion.

The term "cancer" or "tumor" is used interchangeably herein. These terms refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. These terms include a solid tumor, a soft tissue tumor, or a metastatic lesion. As used herein, the term "cancer" includes premalignant, as well as malignant cancers. In certain embodiments, the cancer is a solid tumor, a soft tissue tumor, or a metastatic lesion.

The term "neoplasm" or "neoplastic" cell refers to an abnormal proliferative stage, e.g., a hyperproliferative stage, in a cell or tissue that can include a benign, pre-malignant, malignant (cancer) or metastatic stage.

Cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

"Chemotherapeutic agent" means a chemical substance, such as a cytotoxic or cytostatic agent, that is used to treat a condition, particularly cancer.

As used herein, "cancer therapy" and "cancer treatment" are synonymous terms.

As used herein, "chemotherapy" and "chemotherapeutic" and "chemotherapeutic agent" are synonymous terms.

The terms "homology" or "identity," as used interchangeably herein, refer to sequence similarity between two polynucleotide sequences or between two polypeptide sequences, with identity being a more strict comparison. The phrases "percent identity or homology" and "% identity or homology" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value there between. Identity or similarity can be determined by comparing a position in each sequence that can be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences. The term "substantially identical," as used herein, refers to an identity or homology of at least 75%, at least 80%, at least 85%, at least 90%, 91%, 92%, 93%, 94%, 95%, 96%, 97%, 98%, 99%, or more.

"Likely to" or "increased likelihood," as used herein, refers to an increased probability that an item, object, thing or person will occur. Thus, in one example, a subject that is likely to respond to treatment with a kinase inhibitor, alone or in combination, has an increased probability of responding to treatment with the inhibitor alone or in combination, relative to a reference subject or group of subjects.

"Unlikely to" refers to a decreased probability that an event, item, object, thing or person will occur with respect to a reference. Thus, a subject that is unlikely to respond to treatment with a kinase inhibitor, alone or in combination, has a decreased probability of responding to treatment with a kinase inhibitor, alone or in combination, relative to a reference subject or group of subjects.

"Sequencing" a nucleic acid molecule requires determining the identity of at least 1 nucleotide in the molecule. In embodiments, the identity of less than all of the nucleotides in a molecule are determined. In other embodiments, the identity of a majority or all of the nucleotides in the molecule is determined.

"Next-generation sequencing or NGS or NG sequencing" as used herein, refers to any sequencing method that determines the nucleotide sequence of either individual nucleic acid molecules (e.g., in single molecule sequencing) or clonally expanded proxies for individual nucleic acid molecules in a highly parallel fashion (e.g., greater than $10^5$ molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference. Next generation sequencing can detect a variant present in less than 5% of the nucleic acids in a sample.

"Sample," "tissue sample," "patient sample," "patient cell or tissue sample" or "specimen" each refers to a collection of similar cells obtained from a tissue of a subject or patient. The source of the tissue sample can be solid tissue as from a fresh, frozen and/or preserved organ, tissue sample, biopsy, or aspirate; blood or any blood constituents; bodily fluids such as cerebral spinal fluid, amniotic fluid, peritoneal fluid or interstitial fluid; or cells from any time in gestation or development of the subject. The tissue sample can contain compounds that are not naturally intermixed with the tissue in nature such as preservatives, anticoagulants, buffers, fixatives, nutrients, antibiotics or the like. In one embodiment, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample.

A "tumor nucleic acid sample" as used herein, refers to nucleic acid molecules from a tumor or cancer sample. Typically, it is DNA, e.g., genomic DNA, or cDNA derived from RNA, from a tumor or cancer sample. In certain embodiments, the tumor nucleic acid sample is purified or isolated (e.g., it is removed from its natural state).

A "control" or "reference" "nucleic acid sample" as used herein, refers to nucleic acid molecules from a control or reference sample. Typically, it is DNA, e.g., genomic DNA, or cDNA derived from RNA, not containing the alteration or variation in the gene or gene product, e.g., not containing a DCTN1-ALK fusion. In certain embodiments, the reference or control nucleic acid sample is a wild type or a non-mutated sequence. In certain embodiments, the reference nucleic acid sample is purified or isolated (e.g., it is removed from its natural state). In other embodiments, the reference nucleic acid sample is from a non-tumor sample, e.g., a blood control, a normal adjacent tumor (NAT), or any other non-cancerous sample from the same or a different subject.

"Adjacent to the interrogation position," as used herein, means that a site sufficiently close such that a detection reagent complementary with the site can be used to distinguish between a mutation, e.g., a mutation described herein, and a reference sequence, e.g., a non-mutant or wild-type sequence, in a target nucleic acid. Directly adjacent, as used herein, is where 2 nucleotides have no intervening nucleotides between them.

"Associated mutation," as used herein, refers to a mutation within a preselected distance, in terms of nucleotide or primary amino acid sequence, from a definitional mutation, e.g., a mutant as described herein, e.g., a translocation, breakpoint or fusion molecule described herein. In embodiments, the associated mutation is within n, wherein n is 2, 5, 10, 20, 30, 50, 100, or 200 nucleotides from the definitional mutation (n does not include the nucleotides defining the associated and definitional mutations). In embodiments, the associated mutation is a translocation mutation.

"Interrogation position," as used herein, comprises at least one nucleotide (or, in the case of polypeptides, an amino acid residue) which corresponds to a nucleotide (or amino acid residue) that is mutated in a mutation of interest, e.g., a mutation being identified, or in a nucleic acid (or protein) being analyzed, e.g., sequenced, or recovered. By way of example, the interrogation position in the breakpoint shown in FIG. 1 (SEQ ID NO:5), includes one, two, or more nucleotide positions at the junction site. In other embodiments, the interrogation position in the breakpoint shown in FIG. 3 (SEQ ID NO:13), includes one, two, or more nucleotide positions at the junction site.

A "reference sequence," as used herein, e.g., as a comparator for a mutant sequence, is a sequence which has a different nucleotide or amino acid at an interrogation position than does the mutant(s) being analyzed. In an embodiment, the reference sequence is wild-type for at least the interrogation position.

Headings, e.g., (a), (b), (i) etc, are presented merely for ease of reading the specification and claims. The use of headings in the specification or claims does not require the steps or elements be performed in alphabetical or numerical order or the order in which they are presented.

Various aspects featured in the invention are described in further detail below. Additional definitions are set out throughout the specification.

Isolated Nucleic Acid Molecules

One aspect featured in the invention pertains to isolated nucleic acid molecules that include a DCTN1-ALK fusion or an LMNA-NTRK1 fusion, including nucleic acids which encode a DCTN1-ALK or LMNA-NTRK1 fusion polypeptide or a portion of such a polypeptide. The nucleic acid molecules include those nucleic acid molecules which reside in genomic regions identified herein. As used herein, the term "nucleic acid molecule" includes DNA molecules (e.g., cDNA or genomic DNA) and RNA molecules (e.g., mRNA) and analogs of the DNA or RNA generated using nucleotide analogs. The nucleic acid molecule can be single-stranded or double-stranded; in certain embodiments the nucleic acid molecule is double-stranded DNA.

Isolated nucleic acid molecules also include nucleic acid molecules sufficient for use as hybridization probes or primers to identify nucleic acid molecules that correspond to a DCTN1-ALK fusion or an LMNA-NTRK1 fusion, e.g., those suitable for use as PCR primers for the amplification or mutation of nucleic acid molecules.

An "isolated" nucleic acid molecule is one which is separated from other nucleic acid molecules which are present in the natural source of the nucleic acid molecule. In certain embodiments, an "isolated" nucleic acid molecule is free of sequences (such as protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, less than about 4 kB, less than about 3 kB, less than about 2 kB, less than about 1 kB, less than about 0.5 kB or less than about 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

The language "substantially free of other cellular material or culture medium" includes preparations of nucleic acid molecule in which the molecule is separated from cellular components of the cells from which it is isolated or recombinantly produced. Thus, nucleic acid molecule that is substantially free of cellular material includes preparations of nucleic acid molecule having less than about 30%, less than about 20%, less than about 10%, or less than about 5% (by dry weight) of other cellular material or culture medium.

A fusion nucleic acid molecule can be isolated using standard molecular biology techniques and the sequence information in the database records described herein. Using all or a portion of such nucleic acid sequences, fusion nucleic acid molecules as described herein can be isolated using standard hybridization and cloning techniques (e.g., as described in Sambrook et al., ed., *Molecular Cloning: A Laboratory Manual*, 2nd ed., Cold Spring Harbor Laboratory Press, Cold Spring Harbor, N.Y., 1989).

A fusion nucleic acid molecule (e.g., DCTN1-ALK or LMNA-NTRK1 fusion) can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule featured in the invention can be prepared by standard synthetic techniques, e.g., using an automated DNA synthesizer.

In another embodiment, a fusion nucleic acid molecule (e.g., DCTN1-ALK or LMNA-NTRK1 fusion) comprises a nucleic acid molecule which has a nucleotide sequence complementary to the nucleotide sequence of the fusion nucleic acid molecule or to the nucleotide sequence of a nucleic acid encoding a fusion protein. A nucleic acid molecule which is complementary to a given nucleotide sequence is one which is sufficiently complementary to the given nucleotide sequence that it can hybridize to the given nucleotide sequence thereby forming a stable duplex.

Moreover, a DCTN1-ALK or LMNA-NTRK1 fusion nucleic acid molecule can comprise only a portion of a nucleic acid sequence, wherein the full length nucleic acid sequence or which encodes a DCTN1-ALK or LMNA-NTRK1 fusion polypeptide. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, at least about 15, at least about 25, at least about 50, at least about 75, at least about 100, at least about 125, at least about 150, at least about 175, at least about 200, at least about 250, at least about 300, at least about 350, at least about 400, at least about 500, at least about 600, at least about 700, at least about 800, at least about 900, at least about 1 kb, at least about 2 kb, at least about 3 kb, at least about 4 kb, at least about 5 kb, at least about 6 kb, at least about 7 kb, at least about 8 kb, at least about 9 kb, at least about 10 kb, at least about 15 kb, at least about 20 kb, at least about 25 kb, at least about 30 kb, at least about 35 kb, at least about 40 kb, at least about 45 kb, at least about 50 kb, at least about 60 kb, at least about 70 kb, at least about 80 kb, at least about 90 kb, at least about 100 kb, at least about 200 kb, at least about 300 kb, at least about 400 kb, at least about 500 kb, at least about 600 kb, at least about 700 kb, at least about 800 kb, at least about 900 kb, at least about 1 mb, at least about 2 mb, at least about 3 mb, at least about 4 mb, at least about 5 mb, at least about 6 mb, at least about 7 mb, at least about 8 mb, at least about 9 mb, at least about 10 mb or more consecutive nucleotides of a DCTN1-ALK fusion nucleic acid.

The invention further encompasses nucleic acid molecules that are substantially identical to the gene mutations and/or gene products described herein, e.g., DCTN1-ALK fusion having a nucleotide sequence of SEQ ID NO:6, or an amino acid sequence of SEQ ID NO:7, such that they are at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5% or greater. The invention further encompasses nucleic acid molecules that are substantially identical to the gene mutations and/or gene products described herein, e.g., LMNA-NTRK1 fusion having a nucleotide sequence of SEQ ID NO:9, or an amino acid sequence of SEQ ID NO:10, such that they are at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5% or greater.

In other embodiments, the invention further encompasses nucleic acid molecules that are substantially homologous to the DCTN1-ALK or LMNA-NTRK1 fusion gene mutations and/or gene products described herein, such that they differ by only or at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 30, at least 40, at least 50, at least 60, at least 70, at least 80, at least 90, at least 100, at least 200, at least 300, at least 400, at least 500, at least 600 nucleotides or any range in between.

In another embodiment, an isolated DCTN1-ALK fusion nucleic acid molecule or LMNA-NTRK1 fusion nucleic acid molecule is at least 7, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, at least 300, at least 350, at least 400, at least 450, at least 550, at least 650, at least 700, at least 800, at least 900, at least 1000, at least 1200, at least 1400, at least 1600, at least 1800, at least 2000, at least 2200, at least 2400, at least 2600, at least 2800, at least 3000, or more nucleotides in length and hybridizes under stringent conditions to a DCTN1-ALK or LMNA-NTRK1 fusion nucleic acid molecule or to a nucleic acid molecule encoding a protein corresponding to a marker featured in the invention.

As used herein, the term "hybridizes under stringent conditions" is intended to describe conditions for hybridization and washing under which nucleotide sequences at least 60%, at least 65%, at least 70%, at least 75%, at least 80%, or at least 85% identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). Another, non-limiting example of stringent hybridization conditions are hybridization in 6× sodium chloride/sodium citrate (SSC) at about 45° C., followed by one or more washes in 0.2×SSC, 0.1% SDS at 50-65° C.

The invention also includes molecular beacon nucleic acid molecules having at least one region which is complementary to a DCTN1-ALK fusion or LMNA-NTRK1 fusion nucleic acid molecule, such that the molecular beacon is useful for quantitating the presence of the nucleic acid molecule featured in the invention in a sample. A "molecular beacon" nucleic acid is a nucleic acid molecule comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid molecules are not annealed with one another, fluorescence of the fluorophore is quenched to a lesser degree. Molecular beacon nucleic acid molecules are described, for example, in U.S. Pat. No. 5,876,930.

Probes

The invention also provides isolated nucleic acid molecules useful as probes. Such nucleic acid probes can be designed based on the sequence of a DCTN1-ALK fusion or a LMNA-NTRK1 fusion.

Probes based on the sequence of a fusion nucleic acid molecule as described herein can be used to detect transcripts or genomic sequences corresponding to one or more markers featured in the invention. The probe comprises a label group attached thereto, e.g., a radioisotope, a fluorescent compound, an enzyme, or an enzyme co-factor. Such probes can be used as part of a test kit for identifying cells or tissues which express the fusion protein (e.g., DCTN1-ALK or LMNA-NTRK1), such as by measuring levels of a nucleic acid molecule encoding the protein in a sample of cells from a subject, e.g., detecting mRNA levels or determining whether a gene encoding the protein has been mutated or deleted.

Probes featured in the invention include those that will specifically hybridize to a gene sequence described in the Example, e.g., a DCTN1-ALK fusion or a LMNA-NTRK1 fusion. Typically these probes are 12 to 20, e.g., 17 to 20 nucleotides in length (longer for large insertions) and have the nucleotide sequence corresponding to the region of the mutations at their respective nucleotide locations on the gene sequence. Such molecules can be labeled according to any technique known in the art, such as with radiolabels, fluorescent labels, enzymatic labels, sequence tags, biotin, other ligands, etc. As used herein, a probe that "specifically hybridizes" to a fusion gene sequence will hybridize under high stringency conditions.

A probe will typically contain one or more of the specific mutations described herein. Typically, a nucleic acid probe will encompass only one mutation. Such molecules may be labeled and can be used as allele-specific probes to detect the mutation of interest.

In one aspect, the invention features a probe or probe set that specifically hybridizes to a nucleic acid comprising an inversion resulting in a DCTN1-ALK fusion. In another aspect, the invention features a probe or probe set that specifically hybridizes to a nucleic acid comprising a deletions resulting in an LMNA-NTRK1 fusion.

Isolated pairs of allele specific oligonucleotide probes are also provided, where the first probe of the pair specifically hybridizes to the mutant allele, and the second probe of the pair specifically hybridizes to the wildtype allele. For example, in one exemplary probe pair, one probe will recognize the fusion junction in the DCTN1-ALK fusion, and the other probe will recognize a sequence downstream or upstream of DCTN1 or ALK, neither of which includes the fusion junction. These allele-specific probes are useful in detecting an ALK somatic mutation in a tumor sample, e.g., melanoma sample. In a similar manner, probe pairs can be designed and produced for the LMNA-NTRK1 fusion and are useful in detecting an NTRK1 somatic mutation in a tumor sample.

Primers

The invention also provides isolated nucleic acid molecules useful as primers.

The term "primer" as used herein refers to a sequence comprising two or more deoxyribonucleotides or ribonucleotides, e.g., more than three, and more than eight, or at least 20 nucleotides of a gene described in the Example, where the sequence corresponds to a sequence flanking one of the mutations or a wild type sequence of a gene identified in the Example, e.g., a DCTN1, ALK, LMNA, or NRTK1 gene. Primers may be used to initiate DNA synthesis via the PCR (polymerase chain reaction) or a sequencing method. Primers featured in the invention include the sequences recited and complementary sequences which would anneal to the opposite DNA strand of the sample target. Since both strands of DNA are complementary and mirror images of each other, the same segment of DNA will be amplified.

Primers can be used to sequence a nucleic acid, e.g., an isolated nucleic acid described herein, such as by an NGS method, or to amplify a gene described in the Example, such as by PCR. The primers can specifically hybridize, for example, to the ends of the exons or to the introns flanking the exons. The amplified segment can then be further analyzed for the presence of the mutation such as by a sequencing method. The primers are useful in directing amplification of a target polynucleotide prior to sequencing. In another aspect, the invention features a pair of oligonucleotide primers that amplify a region that contains or is adjacent to a fusion junction identified in the Example. Such primers are useful in directing amplification of a target region that includes a fusion junction identified in the Example, e.g., prior to sequencing. The primer typically contains 12 to 20, or 17 to 20, or more nucleotides, although a primer may contain fewer nucleotides.

A primer is typically single stranded, e.g., for use in sequencing or amplification methods, but may be double stranded. If double stranded, the primer may first be treated to separate its strands before being used to prepare extension products. A primer must be sufficiently long to prime the synthesis of extension products in the presence of the inducing agent for polymerization. The exact length of primer will depend on many factors, including applications (e.g., amplification method), temperature, buffer, and nucleotide composition. A primer typically contains 12-20 or more nucleotides, although a primer may contain fewer nucleotides.

Primers are typically designed to be "substantially" complementary to each strand of a genomic locus to be amplified. Thus, the primers must be sufficiently complementary to specifically hybridize with their respective strands under conditions which allow the agent for polymerization to perform. In other words, the primers should have sufficient complementarity with the 5' and 3' sequences flanking the mutation to hybridize therewith and permit amplification of the genomic locus.

The term "substantially complementary to" or "substantially the sequence" refers to sequences that hybridize to the sequences provided under stringent conditions and/or sequences having sufficient homology with a sequence comprising a fusion junction identified in the Example, or the wildtype counterpart sequence, such that the allele specific oligonucleotides hybridize to the sequence. In one embodiment, a sequence is substantially complementary to a fusion junction in an inversion event, e.g., to a fusion junction in SEQ ID NO:6. "Substantially the same" as it refers to oligonucleotide sequences also refers to the functional ability to hybridize or anneal with sufficient specificity to distinguish between the presence or absence of the mutation. This is measurable by the temperature of melting being sufficiently different to permit easy identification of whether the oligonucleotide is binding to the normal or mutant gene sequence identified in the Example.

In one aspect, the invention features a primer or primer set for amplifying a nucleic acid comprising an inversion resulting in a DCTN1-ALK fusion. In another aspect, the invention features a primer or primer set for amplifying a nucleic acid comprising a deletion resulting in an LMNA-NTRK1 fusion.

Isolated pairs of allele specific oligonucleotide primer are also provided, where the first primer of the pair specifically hybridizes to the mutant allele, and the second primer of the pair specifically hybridizes to a sequence upstream or downstream of a mutation, or a fusion junction resulting from, e.g., an inversion, duplication, deletion, insertion or translocation. For example, in one exemplary primer pair, one probe will recognize a DCTN1-ALK translocation, such as by hybridizing to a sequence at the fusion junction between the DCTN1 and ALK transcripts, and the other primer will recognize a sequence upstream or downstream of the fusion junction. These allele-specific primers are useful for amplifying a DCTN1-ALK fusion sequence from a tumor sample, e.g., a skin biopsy, such as a skin biopsy from a suspected melanoma. Similarly, in one exemplary primer pair, one probe will recognize a LMNA-NTRK1 fusion, such as by hybridizing to a sequence at the fusion junction between the LMNA and NTRK1 transcripts, and the other primer will recognize a sequence upstream or downstream of the fusion junction. These allele-specific primers are useful for amplifying a LMNA-NTRK1 fusion sequence from a tumor sample, e.g., a skin biopsy, such as a skin biopsy from a suspected melanoma.

In another exemplary primer pair, one primer can recognize an ALK-DCTN1 translocation (e.g., the reciprocal of the DCTN1-ALK translocation), such as by hybridizing to a sequence at the fusion junction between the ALK and DCTN1 transcripts, and the other primer will recognize a sequence upstream or downstream of the fusion junction. These allele-specific primers are useful for amplifying a ALK-DCTN1 fusion sequence from a tumor sample, e.g., a melanoma or skin biopsy sample.

In addition, an exemplary primer pair can be designed such that one primer recognizes an NTRK1-LMNA fusion (e.g., the reciprocal of the LMNA-NTRK1 fusion), such as by hybridizing to a sequence at the fusion junction between the NTRK1 and LMNA transcripts, and the other primer will recognize a sequence upstream or downstream of the fusion junction. These allele-specific primers are useful for amplifying a NTRK1-LMNA fusion sequence from a tumor sample, e.g., a melanoma or skin biopsy sample.

Primers can be prepared using any suitable method, such as conventional phosphotriester and phosphodiester methods or automated embodiments thereof. In one such automated embodiment, diethylphosphoramidites are used as starting materials and may be synthesized as described by Beaucage, et al., Tetrahedron Letters, 22:1859-1862, (1981). One method for synthesizing oligonucleotides on a modified solid support is described in U.S. Pat. No. 4,458,066.

An oligonucleotide probe or primer that hybridizes to a mutant or wildtype allele is said to be the complement of the allele. As used herein, a probe exhibits "complete complementarity" when every nucleotide of the probe is complementary to the corresponding nucleotide of the allele. Two polynucleotides are said to be "minimally complementary" if they can hybridize to one another with sufficient stability to permit them to remain annealed to one another under at least conventional "low-stringency" conditions. Similarly, the polynucleotides are said to be "complementary" if they can hybridize to one another with sufficient stability to permit them to remain annealed to one another under conventional "high-stringency" conditions. Conventional stringency conditions are known to those skilled in the art and can be found, for example in *Molecular Cloning: A Laboratory Manual*, 3rd edition Volumes 1, 2, and 3. J. F. Sambrook, D. W. Russell, and N. Irwin, Cold Spring Harbor Laboratory Press, 2000.

Departures from complete complementarity are therefore permissible, as long as such departures do not completely preclude the capacity of a probe to hybridize to an allele. Thus, in order for a polynucleotide to serve as a primer or probe it need only be sufficiently complementary in sequence to be able to form a stable double-stranded structure under the particular solvent and salt concentrations employed. Appropriate stringency conditions which promote DNA hybridization are, for example, 6.0× sodium chloride/sodium citrate (SSC) at about 45° C., followed by a wash of 2.0×SSC at 50° C. Such conditions are known to those skilled in the art and can be found, for example in *Current Protocols in Molecular Biology*, John Wiley & Sons, N.Y. (1989). Salt concentration and temperature in the wash step can be adjusted to alter hybridization stringency. For example, conditions may vary from low stringency of about 2.0×SSC at 40° C. to moderately stringent conditions of about 2.0×SSC at 50° C. to high stringency conditions of about 0.2×SSC at 50° C.

Fusion Proteins and Antibodies

One aspect featured in the invention pertains to purified fusion polypeptides, and biologically active portions thereof. In one embodiment, the native DCTN1-ALK or NTRK1-LMNA fusion polypeptide can be isolated from cells or tissue sources by an appropriate purification scheme using standard protein purification techniques. In another embodiment, a DCTN1-ALK or NTRK1-LMNA fusion polypeptide is produced by recombinant DNA techniques. Alternative to recombinant expression, a DCTN1-ALK or NTRK1-LMNA fusion polypeptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, less than about 20%, less than about 10%, or less than about 5% (by dry weight) of heterologous protein (also referred to herein as a "contaminating protein"). When the protein or biologically active portion thereof is recombinantly produced, it can be substantially free of culture medium, i.e., culture medium represents less than about 20%, less than about 10%, or less than about 5% of the volume of the protein preparation. When the protein is produced by chemical synthesis, it can substantially be free of chemical precursors or other chemicals, i.e., it is separated from chemical precursors or other chemicals which are involved in the synthesis of the protein. Accordingly such preparations of the protein have less than about 30%, less than about 20%, less than about 10%, less than about 5% (by dry weight) of chemical precursors or compounds other than the polypeptide of interest.

Biologically active portions of a fusion polypeptide include polypeptides comprising amino acid sequences sufficiently identical to or derived from the amino acid sequence of the fusion protein, which include fewer amino acids than the full length protein, and exhibit at least one activity of the corresponding full-length protein, e.g., a kinase activity e.g., an ALK kinase or NTRK1 kinase activity. A biologically active portion of a protein featured in the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide.

In certain embodiments, the DCTN1-ALK fusion polypeptide or the NTRK1-LMNA fusion polypeptide has an amino acid sequence of a protein encoded by a nucleic acid molecule disclosed herein. Other useful proteins are substantially identical (e.g., at least 60, at least 65, at least 70, at least 75, at least 80, at least 85, at least 86, at least 87, at least 88, at least 89, at least 90, at least 91, at least 92, at least 93, at least 94, at least 95, at least 96, at least 97, at least 98, at least 99, at least 99.5% or greater) to one of these sequences and retain the functional activity of the protein of the corresponding full-length protein yet differ in amino acid sequence.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. Another, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules featured in the invention. BLAST protein searches can be performed with the XBLAST program, score=50, word length=3 to obtain amino acid sequences homologous to protein molecules featured in the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. Another non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

An isolated fusion polypeptide (e.g., DCTN1-ALK or LMNA-NTRK1), or a fragment thereof, can be used as an immunogen to generate antibodies using standard techniques for polyclonal and monoclonal antibody preparation. The full-length fusion polypeptide can be used or, alternatively, the invention provides antigenic peptide fragments for use as immunogens. The antigenic peptide of a protein featured in the invention comprises at least 8 (or at least 10, at least 15, at least 20, or at least 30 or more) amino acid residues of the amino acid sequence of one of the polypeptides featured in the invention, and encompasses an epitope of the protein such that an antibody raised against the peptide forms a specific immune complex with a marker featured in the invention to which the protein corresponds. Exemplary epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions.

An immunogen typically is used to prepare antibodies by immunizing a suitable (i.e., immunocompetent) subject such as a rabbit, goat, mouse, or other mammal or vertebrate. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

Accordingly, another aspect featured in the invention pertains to antibodies directed against a DCTN1-ALK fusion polypeptide. In one embodiment, the antibody molecule specifically binds to DCTN1-ALK fusion, e.g., specifically binds to an epitope formed by the DCTN1-ALK fusion. In embodiments the antibody can distinguish wild type ALK (or DCTN1) from DCTN1-ALK.

Another aspect featured in the invention provides antibodies directed against a LMNA-NTRK1 fusion polypeptide are contemplated. In one embodiment, the antibody molecule specifically binds to LMNA-NTRK1fusion, e.g., specifically binds to an epitope formed by the LMNA-NTRK1fusion. In embodiments the antibody can distinguish wild type NTRK1 (or LNMA) from LMNA-NTRK1.

The terms "antibody" and "antibody molecule" as used interchangeably herein refer to immunoglobulin molecules and immunologically active portions of immunoglobulin molecules, i.e., molecules that contain an antigen binding site which specifically binds an antigen, such as a polypeptide featured in the invention. A molecule which specifically binds to a given polypeptide featured in the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies. The term "monoclonal antibody" or "monoclonal antibody composition," as used herein, refers to a population of antibody molecules that contain only one species of an antigen binding site capable of immunoreacting with a particular epitope.

Polyclonal antibodies can be prepared as described above by immunizing a suitable subject with a fusion polypeptide as an immunogen. Antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (see Kozbor et al., 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., John Wiley & Sons, New York, 1994). Hybridoma cells producing a monoclonal antibody are detected by screening the hybridoma culture supernatants for antibodies that bind the polypeptide of interest, e.g., using a standard ELISA assay.

Alternative to preparing monoclonal antibody-secreting hybridomas, a monoclonal antibody can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System,* Catalog No. 27-9400-01; and the Stratagene *SurfZAP Phage Display Kit,* Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Additionally, recombinant antibodies, such as chimeric and humanized monoclonal antibodies, comprising both human and non-human portions can be made using standard recombinant DNA techniques. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559; Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

Completely human antibodies can be produced using transgenic mice which are incapable of expressing endogenous immunoglobulin heavy and light chains genes, but which can express human heavy and light chain genes. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

An antibody directed against a DCTN1-ALK fusion polypeptide or a LMNA-NTRK1 fusion polypeptide (e.g., a monoclonal antibody) can be used to isolate the polypeptide by standard techniques, such as affinity chromatography or immunoprecipitation. Moreover, such an antibody can be used to detect the marker (e.g., in a cellular lysate or cell supernatant) in order to evaluate the level and pattern of expression of the marker. Detection can be facilitated by coupling the antibody to a detectable substance. Examples of detectable substances include, but are not limited to, various enzymes, prosthetic groups, fluorescent materials, luminescent materials, bioluminescent materials, and radioactive materials. Examples of suitable enzymes include, but are not limited to, horseradish peroxidase, alkaline phosphatase, β-galactosidase, or acetylcholinesterase; examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, but are not limited to, luciferase, luciferin, and aequorin, and examples of suitable radioactive materials include, but are not limited to, $^{125}I$, $^{131}I$, $^{35}S$ or $^{3}H$.

An antibody directed against a DCTN1-ALK fusion polypeptide can also be used diagnostically to monitor protein levels in tissues or body fluids (e.g., in a tumor cell-containing body fluid) as part of a clinical testing procedure, e.g., to, for example, determine the efficacy of a given treatment regimen.

Antigens and Vaccines

Embodiments featured in the invention include preparations, e.g., antigenic preparations, of the entire fusion or a fragment thereof, e.g., a fragment capable of raising antibodies specific to the fusion protein, e.g., a fusion junction containing fragment (collectively referred to herein as a fusion specific polypeptides or FSP). The preparation can include an adjuvant or other component.

An FSP can be used as an antigen or vaccine. For example, an FSP can be used as an antigen to immunize an animal, e.g., a rodent, e.g., a mouse or rat, rabbit, horse, goat, dog, or non-human primate, to obtain antibodies, e.g., fusion protein specific antibodies. In an embodiment a fusion specific antibody molecule is an antibody molecule described herein, e.g., a polyclonal. In other embodiments a fusion specific antibody molecule is monospecific, e.g., monoclonal, human, humanized, chimeric or other monospecific antibody molecule. An anti-DCTN1-ALK fusion protein specific antibody molecule can be used to treat a subject having a cancer, e.g., a cancer described herein, such as a melanoma.

Embodiments featured in the invention include vaccine preparations that comprise an FSP capable of stimulating an immune response in a subject, e.g., by raising, in the subject, antibodies specific to the fusion protein. The vaccine preparation can include other components, e.g., an adjuvant. The vaccine preparations can be used to treat a subject having cancer, e.g., a cancer described herein.

Expression Vectors, Host Cells and Recombinant Cells

In another aspect, the invention includes vectors (e.g., expression vectors), containing a nucleic acid encoding a DCTN1-ALK fusion polypeptide or encoding an LMNA-NTRK1 fusion polypeptide as described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a fusion nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors can be introduced into host cells to thereby produce a fusion polypeptide, including fusion proteins or polypeptides encoded by nucleic acids as described herein, mutant forms thereof, and the like).

The term "recombinant host cell" (or simply "host cell" or "recombinant cell"), as used herein, is intended to refer to a cell into which a recombinant expression vector has been introduced. It should be understood that such terms are intended to refer not only to the particular subject cell, but to the progeny of such a cell. Because certain modifications may occur in succeeding generations due to either mutation or environmental influences, such progeny may not, in fact, be identical to the parent cell, but are still included within the scope of the term "host cell" as used herein.

The recombinant expression vectors can be designed for expression of a fusion polypeptide (e.g., LMNA-NTRK1 or DCTN1-ALK) in prokaryotic or eukaryotic cells. For example, polypeptides featured in the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRITS (Pharmacia, Piscataway, N.J.) which fuse glutathione S-transferase (GST), maltose E binding protein, or protein A, respectively, to the target recombinant protein.

Purified DCTN1-ALK or LMNA-NTRK1 fusion polypeptides can be used in activity assays (e.g., direct assays or competitive assays described in detail below), or to generate antibodies specific for DCTN1-ALK or LMNA-NTRK1 fusion polypeptides.

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences can be carried out by standard DNA synthesis techniques.

The fusion polypeptide expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule featured in the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a DCTN1-ALK or LMNA-NTRK1 fusion nucleic acid molecule within a recombinant expression vector or a DCTN1-ALK or LMNA-NTRK1 fusion nucleic acid molecule containing sequences which allow it to homologous recombination into a specific site of the host cell's genome.

A host cell can be any prokaryotic or eukaryotic cell. For example, a fusion polypeptide can be expressed in bacterial cells (such as *E. coli*), insect cells, yeast or mammalian cells (such as Chinese hamster ovary cells (CHO) or COS cells, e.g., COS-7 cells, CV-1 origin SV40 cells; Gluzman (1981) *Cell* 23:175-182). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell can be used to produce (e.g., express) a fusion polypeptide (e.g., DCTN1-ALK or LMNA-NTRK1). Accordingly, the invention further provides methods for producing a fusion polypeptide using the host cells. In one embodiment, the method includes culturing the host cell (into which a recombinant expression vector encoding a polypeptide has been introduced) in a suitable medium such that the fusion polypeptide is produced. In another embodiment, the method further includes isolating a fusion polypeptide from the medium or the host cell.

In another aspect, the invention features, a cell or purified preparation of cells which include a DCTN1-ALK fusion transgene, or which otherwise misexpress DCTN1-ALK fusion. In another aspect, the invention features, a cell or purified preparation of cells which include a LMNA-NTRK1fusion transgene, or which otherwise misexpress LMNA-NTRK1fusion.

The cell preparation can consist of human or non-human cells, e.g., rodent cells, e.g., mouse or rat cells, rabbit cells, or pig cells. In embodiments, the cell or cells include a DCTN1-ALK fusion transgene, e.g., a heterologous form of a DCTN1-ALK fusion, e.g., a gene derived from humans (in the case of a non-human cell) or a LMNA-NTRK1 fusion transgene, e.g., a heterologous form of a LMNA-NTRK1 fusion. The fusion transgene can be misexpressed, e.g., overexpressed or underexpressed. In other preferred embodiments, the cell or cells include a gene that misexpresses an endogenous fusion, e.g., a gene the expression of which is disrupted, e.g., a knockout. Such cells can serve as a model for studying disorders that are related to mutated or mis-expressed fusion alleles (e.g., cancers) or for use in drug screening, as described herein.

Therapeutic Methods

Alternatively, or in combination with the methods described herein, the invention features a method of treating a neoplasm, a cancer or a tumor harboring a DCTN1-ALK fusion described herein. The methods include administering an anti-cancer agent, e.g., a kinase inhibitor, alone or in combination, e.g., in combination with other chemotherapeutic agents or procedures, in an amount sufficient to reduce or inhibit the tumor cell growth, and/or treat or prevent the cancer(s), in the subject.

"Treat," "treatment," and other forms of this word refer to the administration of a kinase inhibitor, alone or in combination with a second agent to impede growth of a cancer, to cause a cancer to shrink by weight or volume, to extend the expected survival time of the subject and or time to progression of the tumor or the like. In those subjects, treatment can include, but is not limited to, inhibiting tumor growth, reducing tumor mass, reducing size or number of metastatic lesions, inhibiting the development of new metastatic lesions, prolonged survival, prolonged progression-free survival, prolonged time to progression, and/or enhanced quality of life.

As used herein, unless otherwise specified, the terms "prevent," "preventing" and "prevention" contemplate an action that occurs before a subject begins to suffer from the re-growth of the cancer and/or which inhibits or reduces the severity of the cancer.

As used herein, and unless otherwise specified, a "therapeutically effective amount" of a compound is an amount sufficient to provide a therapeutic benefit in the treatment or management of the cancer, or to delay or minimize one or more symptoms associated with the cancer. A therapeutically effective amount of a compound means an amount of therapeutic agent, alone or in combination with other therapeutic agents, which provides a therapeutic benefit in the treatment or management of the cancer. The term "therapeutically effective amount" can encompass an amount that improves overall therapy, reduces or avoids symptoms or causes of the cancer, or enhances the therapeutic efficacy of another therapeutic agent.

As used herein, and unless otherwise specified, a "prophylactically effective amount" of a compound is an amount sufficient to prevent re-growth of the cancer, or one or more symptoms associated with the cancer, or prevent its recurrence. A prophylactically effective amount of a compound means an amount of the compound, alone or in combination with other therapeutic agents, which provides a prophylactic benefit in the prevention of the cancer. The term "prophylactically effective amount" can encompass an amount that improves overall prophylaxis or enhances the prophylactic efficacy of another prophylactic agent.

As used herein, the term "patient" or "subject" refers to an animal, typically a human (i.e., a male or female of any age group, e.g., a pediatric patient (e.g, infant, child, adolescent) or adult patient (e.g., young adult, middle-aged adult or senior adult) or other mammal, such as a primate (e.g., cynomolgus monkey, rhesus monkey); commercially relevant mammals such as cattle, pigs, horses, sheep, goats, cats, and/or dogs; and/or birds, including commercially relevant birds such as chickens, ducks, geese, and/or turkeys, that will be or has been the object of treatment, observation, and/or experiment. When the term is used in conjunction with administration of a compound or drug, then the patient has been the object of treatment, observation, and/or administration of the compound or drug.

In certain embodiments, the cancer includes, but is not limited to, a solid tumor, a soft tissue tumor, and a metastatic lesion (e.g., a cancer as described herein). In one embodiment, the cancer is chosen from a lung cancer, a pancreatic cancer, melanoma, a colorectal cancer, an esophageal-gastric cancer, a thyroid cancer, or an adenocarcinoma. In other embodiment, the lung cancer is chosen from one or more of the following: non-small cell lung cancer (NSCLC), small cell lung cancer (SCLC), squamous cell carcinoma (SCC), adenocarcinoma of the lung, bronchogenic carcinoma, or a combination thereof. In one embodiment, the lung cancer is NSCLC or SCC.

In other embodiments, the cancer is chosen from lung cancer, thyroid cancer, colorectal cancer, adenocarcinoma, melanoma, B cell cancer, breast cancer, bronchus cancer, cancer of the oral cavity or pharynx, cancer of hematological tissues, cervical cancer, colon cancer, esophageal cancer, esophageal-gastric cancer, gastric cancer, kidney cancer, liver cancer, multiple myeloma, ovarian cancer, pancreatic cancer, prostate cancer, salivary gland cancer, small bowel or appendix cancer, stomach cancer, testicular cancer, urinary bladder cancer, uterine or endometrial cancer, inflammatory myofibroblastic tumors, gastrointestinal stromal tumor (GIST), and the like.

In certain embodiments, the neoplasm or neoplastic cell is a benign, pre-malignant, malignant (cancer) or metastasis. In one embodiment, the neoplasm or cancer is a melanocytic neoplasm, a Spitz nevi, a Spitz tumor, a Spitzoid melanoma, a metastatic Spitz tumor, or a melanoma. In one embodiment, the Spitz tumor is metastatic, e.g., localized to lymph nodes or widespread disease.

In one embodiment, the anti-cancer agent is a kinase inhibitor. For example, the kinase inhibitor is a multi-kinase inhibitor or an ALK-specific inhibitor. Exemplary kinase inhibitors include, but are not limited to, axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib, vatalanib (PTK787, PTK/ZK), sorafenib (NEXAVAR®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and XL228.

DCTN1-ALK

In one embodiment, the kinase inhibitor is an ALK inhibitor including, but not limited to, TAE-684 (also referred to herein as "NVP-TAE694"), PF02341066 (also referred to herein as "crizotinib" or "1066"), AF-802, LDK-378, ASP-3026, CEP-37440, CEP-28122, CEP-108050, and AP26113. Additional examples of ALK kinase inhibitors are described in examples 3-39 of WO 2005016894 by Garcia-Echeverria C, et al.

In other embodiments, the anti-cancer agent is a DCTN1-ALK antagonist inhibits the expression of nucleic acid encoding DCTN1-ALK. Examples of such DCTN1-ALK antagonists include nucleic acid molecules, for example, antisense molecules, ribozymes, RNAi, triple helix molecules that hybridize to a nucleic acid encoding DCTN1-ALK, or a transcription regulatory region, and blocks or reduces mRNA expression of DCTN1-ALK.

In other embodiments, the kinase inhibitor is administered in combination with a second therapeutic agent or a different therapeutic modality, e.g., anti-cancer agents, and/or in combination with surgical and/or radiation procedures.

By "in combination with," it is not intended to imply that the therapy or the therapeutic agents must be administered at the same time and/or formulated for delivery together, although these methods of delivery are within the scope of the invention. The pharmaceutical compositions can be administered concurrently with, prior to, or subsequent to, one or more other additional therapies or therapeutic agents. In general, each agent will be administered at a dose and/or on a time schedule determined for that agent. In will further be appreciated that the additional therapeutic agent utilized in this combination can be administered together in a single composition or administered separately in different compositions. The particular combination to employ in a regimen will take into account compatibility of the inventive pharmaceutical composition with the additional therapeutically active agent and/or the desired therapeutic effect to be achieved.

For example, the second therapeutic agent can be a cytotoxic or a cytostatic agent. Exemplary cytotoxic agents include antimicrotubule agents, topoisomerase inhibitors, or taxanes, antimetabolites, mitotic inhibitors, alkylating agents, intercalating agents, agents capable of interfering with a signal transduction pathway, agents that promote apoptosis and radiation. In yet other embodiments, the methods can be used in combination with immunodulatory agents, e.g., IL-1, 2, 4, 6, or 12, or interferon alpha or gamma, or immune cell growth factors such as GM-CSF.

Anti-cancer agents, e.g., kinase inhibitors, used in therapeutic methods can be evaluated using the screening assays described herein. In one embodiment, the anti-cancer agents are evaluated in a cell-free system, e.g., a cell lysate or in a reconstituted system. In other embodiments, the anti-cancer agents are evaluated in a cell in culture, e.g., a cell expressing a DCTN1-ALK fusion (e.g., a mammalian cell, a tumor cell or cell line, a recombinant cell). In yet other embodiments, the anti-cancer agents are evaluated cell in vivo (a DCTN1-ALK-expressing cell present in a subject, e.g., an animal subject (e.g., an in vivo animal model).

Exemplary parameters evaluated include one or more of:

(i) a change in binding activity, e.g., direct binding of the candidate agent to a DCTN1-ALK fusion polypeptide; a binding competition between a known ligand and the candidate agent to a DCTN1-ALK fusion polypeptide;

(ii) a change in kinase activity, e.g., phosphorylation levels of a DCTN1-ALK fusion polypeptide (e.g., an increased or decreased autophosphorylation); or a change in phosphorylation of a target of an ALK kinase, e.g., Akt/Protein kinase B;

(iii) a change in an activity of a cell containing a DCTN1-ALK fusion (e.g., a tumor cell or a recombinant cell), e.g., a change in proliferation, morphology or tumorigenicity of the cell;

(iv) a change in tumor present in an animal subject, e.g., size, appearance, proliferation, of the tumor; or (v) a change in the level, e.g., expression level, of a DCTN1-ALK fusion polypeptide or nucleic acid molecule.

In one embodiment, a change in a cell free assay in the presence of a candidate agent is evaluated. For example, an activity of a DCTN1-ALK fusion, or interaction of a DCTN1-ALK fusion with a downstream ligand can be detected.

In other embodiments, a change in an activity of a cell is detected in a cell in culture, e.g., a cell expressing a DCTN1-ALK fusion (e.g., a mammalian cell, a tumor cell or cell line, a recombinant cell). In one embodiment, the cell is a recombinant cell that is modified to express a DCTN1-ALK fusion nucleic acid, e.g., is a recombinant cell transfected with a DCTN1-ALK fusion nucleic acid. The transfected cell can show a change in response to the expressed DCTN1-ALK fusion, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, transformed morphology, in the presence of the candidate agent can be indicative of an inhibitor of a DCTN1-ALK fusion. In other embodiments, a change in binding activity or phosphorylation as described herein is detected.

In yet other embodiment, a change in a tumor present in an animal subject (e.g., an in vivo animal model) is detected. In one embodiment, the animal model is a tumor containing animal or a xenograft comprising cells expressing a DCTN1-ALK fusion (e.g., tumorigenic cells expressing a DCTN1-ALK fusion). The anti-cancer agents can be administered to the animal subject and a change in the tumor is detected. In one embodiment, the change in the tumor includes one or more of a tumor growth, tumor size, tumor burden, survival, is evaluated. A decrease in one or more of tumor growth, tumor size, tumor burden, or an increased survival is indicative that the candidate agent is an inhibitor.

The screening methods and assays are described in more detail herein below.

Screening Methods

In another aspect, the invention features a method, or assay, for screening for agents that modulate, e.g., inhibit, the expression or activity of a DCTN1-ALK fusion, e.g., a DCTN1-ALK fusion as described herein. The method includes contacting a DCTN1-ALK fusion, or a cell expressing a DCTN1-ALK fusion, with a candidate agent; and detecting a change in a parameter associated with a DCTN1-ALK fusion, e.g., a change in the expression or an activity of the DCTN1-ALK fusion. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the DCTN1-ALK fusion is detected, the candidate agent is identified as an inhibitor. In another embodiment, if an increase in expression or activity of the DCTN1-ALK fusion is detected, the candidate agent is identified as an activator. In certain embodiments, the DCTN1-ALK fusion is a nucleic acid molecule or a polypeptide as described herein.

In one embodiment, the contacting step is effected in a cell-free system, e.g., a cell lysate or in a reconstituted system. In other embodiments, the contacting step is effected in a cell in culture, e.g., a cell expressing a DCTN1-ALK fusion (e.g., a mammalian cell, a tumor cell or cell line, a recombinant cell). In yet other embodiments, the contacting step is effected in a cell in vivo (a DCTN1-ALK-expressing cell present in a subject, e.g., an animal subject (e.g., an in vivo animal model).

Exemplary parameters evaluated include one or more of:

(i) a change in binding activity, e.g., direct binding of the candidate agent to a DCTN1-ALK fusion polypeptide; a binding competition between a known ligand and the candidate agent to a DCTN1-ALK fusion polypeptide;

(ii) a change in kinase activity, e.g., phosphorylation levels of a DCTN1-ALK fusion polypeptide (e.g., an increased or decreased autophosphorylation); or a change in phosphorylation of a target of an ALK kinase, e.g., Protein kinase B/Akt. In certain embodiments, a change in kinase activity, e.g., phosphorylation, is detected by any of Western blot (e.g., using an anti-DCTN1 or anti-ALK antibody; a phosphor-specific antibody, detecting a shift in the molecular weight of a DCTN1-ALK fusion polypeptide), mass spectrometry, immunoprecipitation, immunohistochemistry, immunomagnetic beads, among others;

(iii) a change in an activity of a cell containing a DCTN1-ALK fusion (e.g., a tumor cell or a recombinant cell), e.g., a change in proliferation, morphology or tumorigenicity of the cell;

(iv) a change in tumor present in an animal subject, e.g., size, appearance, proliferation, of the tumor; or (v) a change in the level, e.g., expression level, of a DCTN1-ALK fusion polypeptide or nucleic acid molecule.

In one embodiment, a change in a cell free assay in the presence of a candidate agent is evaluated. For example, an activity of a DCTN1-ALK fusion, or interaction of a DCTN1-ALK fusion with a downstream ligand can be detected. In one embodiment, a DCTN1-ALK fusion polypeptide is contacted with a ligand, e.g., in solution, and a candidate agent is monitored for an ability to modulate, e.g., inhibit, an interaction, e.g., binding, between the DCTN1-ALK fusion polypeptide and the ligand. In one exemplary assay, purified DCTN1-ALK fusion protein is contacted with a ligand, e.g., in solution, and a candidate agent is monitored for an ability to inhibit interaction of the fusion protein with the ligand, or to inhibit phosphorylation of the ligand by the fusion protein. An effect on an interaction between the fusion protein and a ligand can be monitored by methods known in the art, such as by absorbance, and an effect on phosphorylation of the ligand can be assayed, e.g., by Western blot, immunoprecipitation, or immunomagnetic beads.

In other embodiments, a change in an activity of a cell is detected in a cell in culture, e.g., a cell expressing a DCTN1-ALK fusion (e.g., a mammalian cell, a tumor cell or cell line, a recombinant cell). In one embodiment, the cell is a recombinant cell that is modified to express a DCTN1-ALK fusion nucleic acid, e.g., is a recombinant cell transfected with a DCTN1-ALK fusion nucleic acid. The transfected cell can show a change in response to the expressed K DCTN1-ALK fusion, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, transformed morphology, in the presence of the candidate agent can be indicative of an inhibitor of a DCTN1-ALK fusion. In other embodiments, a change in binding activity or phosphorylation as described herein is detected.

In an exemplary cell-based assay, a nucleic acid comprising a DCTN1-ALK fusion can be expressed in a cell, such as a cell (e.g., a mammalian cell) in culture. The cell containing a nucleic acid expressing the DCTN1-ALK fusion can be contacted with a candidate agent, and the cell is monitored for an effect of the candidate agent. A candidate agent that causes decreased cell proliferation or cell death can be determined to be a candidate for treating a tumor (e.g., a cancer) that carries a DCTN1-ALK fusion.

In one embodiment, a cell containing a nucleic acid expressing a DCTN1-ALK fusion can be monitored for expression of the DCTN1-ALK fusion protein. Protein expression can be monitored by methods known in the art, such as by, e.g., mass spectrometry (e.g., tandem mass spectrometry), a reporter assay (e.g., a fluorescence-based assay), Western blot, and immunohistochemistry. By one method, decreased DCTN1-ALK expression is detected. A candidate agent that causes decreased expression of the DCTN1-ALK fusion protein as compared to a cell that does not contain the DCTN1-ALK nucleic acid fusion can be determined to be a candidate for treating a tumor (e.g., a cancer) that carries a DCTN1-ALK fusion.

A cell containing a nucleic acid expressing a DCTN1-ALK fusion can be monitored for altered ALK kinase activity Kinase activity can be assayed by measuring the effect of a candidate agent on a known ALK kinase target protein, such as e.g., protein kinase B/Akt.

In yet other embodiment, a change in a tumor present in an animal subject (e.g., an in vivo animal model) is detected. In one embodiment, the animal model is a tumor containing animal or a xenograft comprising cells expressing a DCTN1-ALK fusion (e.g., tumorigenic cells expressing a DCTN1-ALK fusion). The candidate agent can be administered to the animal subject and a change in the tumor is detected. In one embodiment, the change in the tumor includes one or more of a tumor growth, tumor size, tumor burden, survival, is evaluated. A decrease in one or more of tumor growth, tumor size, tumor burden, or an increased survival is indicative that the candidate agent is an inhibitor.

In one exemplary animal model, a xenograft is created by injecting cells into mouse. A candidate agent is administered to the mouse, e.g., by injection (such as subcutaneous, intraperitoneal, or tail vein injection, or by injection directly into the tumor) or oral delivery, and the tumor is observed to determine an effect of the candidate anti-cancer agent. The health of the animal is also monitored, such as to determine if an animal treated with a candidate agent survives longer. A candidate agent that causes growth of the tumor to slow or stop, or causes the tumor to shrink in size, or causes decreased tumor burden, or increases survival time, can be considered to be a candidate for treating a tumor (e.g., a cancer) that carries a DCTN1-ALK fusion.

In another exemplary animal assay, cells expressing a DCTN1-ALK fusion are injected into the tail vein, e.g., of a mouse, to induce metastasis. A candidate agent is administered to the mouse, e.g., by injection (such as subcutaneous, intraperitoneal, or tail vein injection, or by injection directly into the tumor) or oral delivery, and the tumor is observed to determine an effect of the candidate anti-cancer agent. A candidate agent that inhibits or prevents or reduces metastasis, or increases survival time, can be considered to be a candidate for treating a tumor (e.g., a cancer) that carries a DCTN1-ALK fusion.

Cell proliferation can be measured by methods known in the art, such as PCNA (Proliferating cell nuclear antigen) assay, 5-bromodeoxyuridine (BrdUrd) incorporation, Ki-67 assay, mitochondrial respiration, or propidium iodide staining. Cells can also be measured for apoptosis, such as by use of a TUNEL (Terminal Deoxynucleotide Transferase dUTP Nick End Labeling) assay. Cells can also be assayed for presence of angiogenesis using methods known in the art, such as by measuring endothelial tube formation or by measuring the growth of blood vessels from subcutaneous tissue, such as into a solid gel of basement membrane.

In other embodiments, a change in expression of a DCTN1-ALK fusion can be monitored by detecting the nucleic acid or protein levels, e.g., using the methods described herein.

In certain embodiments, the screening methods described herein can be repeated and/or combined. In one embodiment, a candidate agent that is evaluated in a cell-free or cell-based described herein can be further tested in an animal subject.

In one embodiment, the candidate agent is identified and re-tested in the same or a different assay. For example, a test compound is identified in an in vitro or cell-free system, and re-tested in an animal model or a cell-based assay. Any order or combination of assays can be used. For example, a high throughput assay can be used in combination with an animal model or tissue culture.

Candidate agents suitable for use in the screening assays described herein include, e.g., small molecule compounds, nucleic acids (e.g., siRNA, aptamers, short hairpin RNAs, antisense oligonucleotides, ribozymes, antagomirs, microRNA mimics or DNA, e.g., for gene therapy) or polypeptides, e.g., antibodies (e.g., full length antibodies or antigen-binding fragments thereof, Fab fragments, or scFv fragments). The candidate anti-cancer agents can be obtained from a library (e.g., a commercial library), or can be rationally designed, such as to target an active site in a functional domain of ALK (e.g., the kinase domain of ALK), or a functional domain of DCTN1 (e.g., the dynein or kinesin II binding domain).

In other embodiments, the method, or assay, includes providing a step based on proximity-dependent signal generation, e.g., a two-hybrid assay that includes a first fusion protein (e.g., a DCTN1-ALK fusion protein), and a second fusion protein (e.g., a ligand), contacting the two-hybrid assay with a test compound, under conditions wherein said two hybrid assay detects a change in the formation and/or stability of the complex, e.g., the formation of the complex initiates transcription activation of a reporter gene.

In one non-limiting example, the three-dimensional structure of the active site of DCTN1-ALK fusion is determined by crystallizing the complex formed by the DCTN1-ALK fusion and a known inhibitor. Rational drug design is then used to identify new test agents by making alterations in the structure of a known inhibitor or by designing small molecule compounds that bind to the active site of the DCTN1-ALK fusion.

The candidate agents can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means known in the art (e.g., using a fluorimeter).

In another embodiment, determining the ability of the DCTN1-ALK fusion protein to bind to a target molecule can be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Nucleic Acid Inhibitors

In yet another embodiment, the DCTN1-ALK fusion inhibitor inhibits the expression of nucleic acid encoding the fusion. Examples of such fusion inhibitors include nucleic acid molecules, for example, antisense molecules, ribozymes, siRNA, triple helix molecules that hybridize to a nucleic acid encoding a DCTN1-ALK fusion, or a transcription regulatory region, and blocks or reduces mRNA expression of the fusion.

In one embodiment, the nucleic acid antagonist is a siRNA that targets mRNA encoding a DCTN1-ALK fusion. Other types of antagonistic nucleic acids can also be used, e.g., a dsRNA, a ribozyme, a triple-helix former, or an antisense nucleic acid. Accordingly, isolated nucleic acid molecules that are nucleic acid inhibitors, e.g., antisense, RNAi, to a DCTN1-ALK fusion-encoding nucleic acid molecule are provided.

An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire fusion coding strand, or to only a portion thereof. In another embodiment, the antisense nucleic acid molecule is antisense to a "noncoding region" of the coding strand of a nucleotide sequence encoding fusion (e.g., the 5' and 3' untranslated regions). Anti-sense agents can include, for example, from about 8 to about 80 nucleobases (i.e., from about 8 to about 80 nucleotides), e.g., about 8 to about 50 nucleobases, or about 12 to about 30 nucleobases. Anti-sense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA can interfere with one or more of the normal functions of mRNA. The functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

Exemplary antisense compounds include DNA or RNA sequences that specifically hybridize to the target nucleic acid, e.g., the mRNA encoding DCTN1-ALK fusion. The complementary region can extend for between about 8 to about 80 nucleobases. The compounds can include one or more modified nucleobases. Modified nucleobases are known in the art. Descriptions of modified nucleic acid agents are also available. See, e.g., U.S. Pat. Nos. 4,987,071; 5,116,742; and 5,093,246; Woolf et al. (1992) *Proc Natl Acad Sci USA; Antisense RNA and DNA*, D. A. Melton, Ed., Cold Spring Harbor Laboratory, Cold Spring Harbor, N.Y. (1988); 89:7305-9; Haselhoff and Gerlach (1988) *Nature* 334:585-59; Helene, C. (1991) *Anticancer Drug Des.* 6:569-84; Helene (1992) *Ann. N.Y. Acad. Sci.* 660:27-36; and Maher (1992) *Bioassays* 14:807-15.

The antisense nucleic acid molecules are typically administered to a subject (e.g., by direct injection at a tissue site), or generated in situ such that they hybridize with or bind to cellular mRNA and/or genomic DNA encoding a DCTN1-NTRK1 fusion to thereby inhibit expression of the protein, e.g., by inhibiting transcription and/or translation. Alternatively, antisense nucleic acid molecules can be modified to target selected cells and then be administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

siRNAs are small double stranded RNAs (dsRNAs) that optionally include overhangs. For example, the duplex region of an siRNA is about 18 to 25 nucleotides in length, e.g., about 19, 20, 21, 22, 23, or 24 nucleotides in length. Typically, the siRNA sequences are exactly complementary to the target mRNA. dsRNAs and siRNAs in particular can be used to silence gene expression in mammalian cells (e.g., human cells). siRNAs also include short hairpin RNAs (shRNAs) with 29-base-pair stems and 2-nucleotide 3' overhangs. See, e.g., Clemens et al. (2000) *Proc. Natl. Acad. Sci. USA* 97:6499-6503; Billy et al. (2001) *Proc. Natl. Sci. USA* 98:14428-14433; Elbashir et al. (2001) *Nature.* 411:494-8; Yang et al. (2002) *Proc. Natl. Acad. Sci. USA* 99:9942-9947; Siolas et al. (2005), *Nat. Biotechnol.* 23(2):227-31; 20040086884; U.S. 20030166282; 20030143204; 20040038278; and 20030224432.

In still another embodiment, an antisense nucleic acid featured in the invention is a ribozyme. A ribozyme having specificity for a DCTN1-ALK fusion-encoding nucleic acid can include one or more sequences complementary to the nucleotide sequence of a fusion cDNA disclosed herein (i.e., SEQ ID NO:6), and a sequence having known catalytic sequence responsible for mRNA cleavage (see U.S. Pat. No. 5,093,246 or Haselhoff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in a DCTN1-ALK fusion-encoding mRNA. See, e.g., Cech et al. U.S. Pat. No. 4,987,071; and Cech et al. U.S. Pat. No. 5,116,742. Alternatively, fusion mRNA can be used to select a catalytic RNA having a specific ribonuclease activity from a pool of RNA molecules. See, e.g., Bartel, D. and Szostak, J. W. (1993) Science 261:1411-1418.

Inhibition of a DCTN1-ALK fusion gene can be accomplished by targeting nucleotide sequences complementary to the regulatory region of the fusion to form triple helical structures that prevent transcription of the DCTN1-ALK fusion gene in target cells. See generally, Helene, C. (1991) Anticancer Drug Des. 6:569-84; Helene, C. i (1992) Ann. N.Y. Acad. Sci. 660:27-36; and Maher, L. J. (1992) Bioassays 14:807-15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A fusion nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) Nature Biotech. 19:17 and Faria et al. (2001) Nature Biotech. 19:40-44. Such phosphoramidite oligonucleotides can be effective antisense agents.

For example, the deoxyribose phosphate backbone of the nucleic acid molecules can be modified to generate peptide nucleic acids (see Hyrup B. et al. (1996) Bioorganic & Medicinal Chemistry 4: 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. Proc. Natl. Acad. Sci. 93: 14670-675.

PNAs of DCTN1-ALK fusion nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of fusion nucleic acid molecules can also be used in the analysis of single base pair mutations in a gene, (e.g., by PNA-directed PCR clamping); as 'artificial restriction enzymes' when used in combination with other enzymes, (e.g., 51 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; WO88/09810) or the blood-brain barrier (see, e.g., WO 89/10134).

In addition, oligonucleotides can be modified with hybridization-triggered cleavage agents (see, e.g., Krol et al. (1988) Bio-Techniques 6:958-976) or intercalating agents (See, e.g., Zon (1988) Pharm. Res. 5:539-549). To this end, the oligonucleotide may be conjugated to another molecule, (e.g., a peptide, hybridization triggered cross-linking agent, transport agent, or hybridization-triggered cleavage agent).

In some embodiments, a nucleic acid inhibitor described herein is provided for the inhibition of expression of an LMNA1-NTRK1 nucleic acid in vitro.

Evaluation of Subjects

Subjects, e.g., patients, can be evaluated for the presence of a DCTN1-ALK fusion or a LMNA-NTRK1 fusion. A patient can be evaluated, for example, by determining the genomic sequence of the patient, e.g., by an NGS method. Alternatively, or in addition, evaluation of a patient can include directly assaying for the presence of a DCTN1-ALK fusion or an LMNA-NTRK1 fusion in the patient, such as by an assay to detect a fusion nucleic acid (e.g., DNA or RNA), such as by, Southern blot, Northern blot, or RT-PCR, e.g., qRT-PCR. Alternatively, or in addition, a patient can be evaluated for the presence of a protein fusion, such as by immunohistochemistry, Western blot, immunoprecipitation, or immunomagnetic bead assay.

Evaluation of a patient can also include a cytogenetic assay, such as by fluorescence in situ hybridization (FISH), to identify the chromosomal rearrangement resulting in the DCTN1-ALK or LMNA-NTRK1 fusion. For example, to perform FISH, at least a first probe tagged with a first detectable label can be designed to target DCTN1, such as in one or more exons of DCTN1 and at least a second probe tagged with a second detectable label can be designed to target ALK, such as in one or more exons of ALK (e.g., the exons containing the part of the protein that includes the tyrosine kinase domain). The at least one first probe and the at least one second probe will be closer together in patients who carry the DCTN1-ALK fusion than in patients who do not carry the DCTN1-ALK fusion. These methods can be utilized in a similar manner for the LMNA-NTRK1 fusion.

Additional methods for fusion detection are provided below.

In one aspect, the results of a clinical trial, e.g., a successful or unsuccessful clinical trial, can be repurposed to identify agents that target a DCTN1-ALK fusion. By one exemplary method, a candidate agent used in a clinical trial can be reevaluated to determine if the agent in the trial targets a fusion, or is effective to treat a tumor containing a particular fusion. For example, subjects who participated in a clinical trial for an agent, such as a kinase inhibitor, can be identified. Patients who experienced an improvement in symptoms, e.g., cancer (e.g., lung cancer) symptoms, such as decreased tumor size, or decreased rate of tumor growth, can be evaluated for the presence of a DCTN1-ALK fusion. Patients who did not experience an improvement in cancer symptoms can also be evaluated for the presence of a DCTN1-ALK fusion. Where patients carrying a DCTN1-ALK fusion are found to have been more likely to respond to the test agent than patients who did not carry such a fusion, then the agent is determined to be an appropriate treatment option for a patient carrying the fusion.

"Reevaluation" of patients can include, for example, determining the genomic sequence of the patients, or a subset of the clinical trial patients, e.g., by an NGS method. Alternatively, or in addition, reevaluation of the patients can include directly assaying for the presence of a DCTN1-ALK fusion in the patient, such as by an assay to detect a DCTN1-ALK nucleic acid (e.g., RNA), such as by RT-PCR, e.g., qRT-PCR. Alternatively, or in addition, a patient can be evaluated for the presence of a DCTN1-ALK protein fusion, such as by immunohistochemistry, Western blot, immunoprecipitation, or immunomagnetic bead assay.

Clinical trials suitable for repurposing as described above include trials that tested ALK inhibitors, tyrosine kinase inhibitors, multikinase inhibitors, and drugs purported to act upstream or downstream of ALK in a pathway involving ALK. Other clinical trials suitable for repurposing as described above include trials that tested DCTN1 inhibitors, kinesin inhibitors, inhibitors of cell trafficking and drugs purported to act upstream or downstream of DCTN1 in a pathway involving DCTN1.

Methods for Detection of Fusion Nucleic Acids and Polypeptides

Methods for evaluating a fusion gene, mutations and/or gene products are known to those of skill in the art. In one embodiment, the fusion is detected in a nucleic acid molecule by a method chosen from one or more of: nucleic acid hybridization assay, amplification-based assays (e.g., polymerase chain reaction (PCR)), PCR-RFLP assay, real-time PCR, sequencing, screening analysis (including metaphase cytogenetic analysis by standard karyotype methods, FISH (e.g., break away FISH), spectral karyotyping or MFISH, comparative genomic hybridization), in situ hybridization, SSP, HPLC or mass-spectrometric genotyping.

Additional exemplary methods include, traditional "direct probe" methods such as Southern blots or in situ hybridization (e.g., fluorescence in situ hybridization (FISH) and FISH plus SKY), and "comparative probe" methods such as comparative genomic hybridization (CGH), e.g., cDNA-based or oligonucleotide-based CGH, can be used. The methods can be used in a wide variety of formats including, but not limited to, substrate (e.g., membrane or glass) bound methods or array-based approaches.

In certain embodiments, the evaluation methods include the probes/primers described herein.

In one embodiment, probes/primers can be designed to detect a DCTN1-ALK fusion or a reciprocal thereof. The DCTN1 probes/primers can be from nucleotides 47-78 of SEQ ID NO:6 (e.g., can hybridize to the nucleotides encoding one or more exons of the DCTN1 protein). These probes/primers are suitable, e.g., for FISH or PCR amplification. The ALK probes/primers can be from nucleotides 3196-4907 of SEQ ID NO:6 (e.g., can hybridize to the nucleotides encoding one or more exons of the ALK protein). These probes/primers are suitable, e.g., for FISH or PCR amplification.

For PCR, e.g., to amply a region including a DCTN1-ALK fusion junction, forward primers can be designed to hybridize to a DCTN1 sequence from nucleotides corresponding to DCTN1 in SEQ ID NO:6, and reverse primers can be designed to hybridize to an ALK sequence from nucleotides corresponding to ALK in SEQ ID NO:6.

For example, probes/primers can be designed to detect a DCTN1-ALK fusion or a reciprocal thereof. The ALK probes/primers can be from nucleotides 3196-4907 of SEQ ID NO:6 (e.g., can hybridize to the nucleotides encoding one or more exons of the ALK protein). The DCNT1 probes/primers can be from nucleotides 1-3195 of SEQ ID NO:6 (e.g., can hybridize to the nucleotides encoding one or more exons of the DCTN1 protein). These probes/primers are suitable, e.g., for FISH or PCR amplification.

For PCR, e.g., to amply a region including an LMNA-NTRK1 fusion junction (or reciprocal thereof), forward primers can be designed to hybridize to an LMNA sequence from nucleotides corresponding to LMNA in SEQ ID NO:9, and reverse primers can be designed to hybridize to an NTRK1 sequence from nucleotides corresponding to NTRK1 in SEQ ID NO:9.

For example, probes/primers can be designed to detect an LMNA-NTRK1 fusion junction (or a reciprocal thereof). The NTRK1 probes/primers can be from nucleotides 514-1740 of SEQ ID NO:9 (e.g., can hybridize to the nucleotides encoding one or more exons of the NTRK1 protein). The LMNA probes/primers can be from nucleotides 1-513 of SEQ ID NO:9 (e.g., can hybridize to the nucleotides encoding one or more exons of the LMNA protein). These probes/primers are suitable, e.g., for FISH or PCR amplification.

In one embodiment, FISH analysis is used to identify the chromosomal rearrangement resulting in the fusions as described above. For example, to perform FISH, at least a first probe tagged with a first detectable label can be designed to target DCTN1, such as in one or more exons of DCTN1 and at least a second probe tagged with a second detectable label can be designed to target ALK, such as in one or more exons of ALK (e.g., the exons containing the part of the protein that includes the tyrosine kinase domain). The at least one first probe and the at least one second probe will be closer together in a subject who carries the ALK-DCTN1 fusion compared to a subject who does not carry the fusion.

In one approach, a variation of a FISH assay, e.g., "break-away FISH", is used to evaluate a patient. By this method, at least one probe targeting the ALK intron 19/DCTN1 intron 26 junction and at least one probe targeting DCNT1 (or ALK), e.g., at one or more exons and or introns of DCTN1 or ALK, are utilized. In normal cells, both probes will be observed (or a secondary color will be observed due to the close proximity of the DCTN1 and ALK genes), and only the DCTN1 probe will be observed when the translocation occurs. Other variations of the FISH method known in the art are suitable for evaluating a patient.

The FISH methods described herein above use DCTN1-ALK as an example, and such methods can be readily applied to the LMNA-NTRK1 fusion by one of skill in the art.

Probes are used that contain DNA segments that are essentially complementary to DNA base sequences existing in different portions of chromosomes. Examples of probes useful according to the invention, and labeling and hybridization of probes to samples are described in two U.S. patents to Vysis, Inc. U.S. Pat. Nos. 5,491,224 and 6,277,569 to Bittner, et al.

Additional protocols for FISH detection are described below.

Chromosomal probes are typically about 50 to about $10^5$ nucleotides in length. Longer probes typically comprise smaller fragments of about 100 to about 500 nucleotides in length. Probes that hybridize with centromeric DNA and locus-specific DNA are available commercially, for example, from Vysis, Inc. (Downers Grove, Ill.), Molecular Probes, Inc. (Eugene, Oreg.) or from Cytocell (Oxfordshire, UK). Alternatively, probes can be made non-commercially from chromosomal or genomic DNA through standard techniques. For example, sources of DNA that can be used include genomic DNA, cloned DNA sequences, somatic cell hybrids that contain one, or a part of one, chromosome (e.g., human chromosome) along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, Biotechnic Histochem., 1998, 73(1):6-22, Wheeless et al., Cytometry 1994, 17:319-326, and U.S. Pat. No. 5,491,224.

The probes to be used hybridize to a specific region of a chromosome to determine whether a cytogenetic abnormality is present in this region. One type of cytogenetic abnormality is a deletion. Although deletions can be of one or more entire chromosomes, deletions normally involve loss of part of one or more chromosomes. If the entire region of a chromosome that is contained in a probe is deleted from a cell, hybridization of that probe to the DNA from the cell will normally not occur and no signal will be present on that chromosome. If the region of a chromosome that is partially contained within a probe is deleted from a cell, hybridization of that probe to the DNA from the cell can still occur, but less of a signal can be present. For example, the loss of a signal is compared to probe hybridization to DNA from control cells that do not contain the genetic abnormalities which the probes are intended to detect. In some embodiments, at least 1, 5, 10, 20, 30, 40, 50, 60, 70, 80, 90, 100, 110, 120, 130, 140, 150, 160, 170, 180, 190, 200, or more cells are enumerated for presence of the cytogenetic abnormality.

Cytogenetic abnormalities to be detected can include, but are not limited to, non-reciprocal translocations, balanced translocations, intra-chromosomal inversions, point mutations, deletions, gene copy number changes, gene expression level changes, and germ line mutations. In particular, one type of cytogenetic abnormality is a duplication. Duplications can be of entire chromosomes, or of regions smaller than an entire chromosome. If the region of a chromosome that is contained in a probe is duplicated in a cell, hybridization of that probe to the DNA from the cell will normally produce at least one additional signal as compared to the number of signals present in control cells with no abnormality of the chromosomal region contained in the probe.

Chromosomal probes are labeled so that the chromosomal region to which they hybridize can be detected. Probes typically are directly labeled with a fluorophore, an organic molecule that fluoresces after absorbing light of lower wavelength/higher energy. The fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, U.S. Pat. No. 5,491,224.

U.S. Pat. No. 5,491,224 describes probe labeling as a number of the cytosine residues having a fluorescent label covalently bonded thereto. The number of fluorescently labeled cytosine bases is sufficient to generate a detectable fluorescent signal while the individual so labeled DNA segments essentially retain their specific complementary binding (hybridizing) properties with respect to the chromosome or chromosome region to be detected. Such probes are made by taking the unlabeled DNA probe segment, transaminating with a linking group a number of deoxycytidine nucleotides in the segment, covalently bonding a fluorescent label to at least a portion of the transaminated deoxycytidine bases.

Probes can also be labeled by nick translation, random primer labeling or PCR labeling. Labeling is done using either fluorescent (direct)- or hapten (indirect)-labeled nucleotides. Representative, non-limiting examples of labels include: AMCA-6-dUTP, CascadeBlue-4-dUTP, Fluorescein-12-dUTP, Rhodamine-6-dUTP, TexasRed-6-dUTP, Cy3-6-dUTP, Cy5-dUTP, Biotin(BIO)-11-dUTP, Digoxygenin(DIG)-11-dUTP or Dinitrophenyl (DNP)-11-dUTP.

Probes also can be indirectly labeled with biotin or digoxygenin, or labeled with radioactive isotopes such as $^{32}P$ and $^{3}H$, although secondary detection molecules or further processing then is required to visualize the probes. For example, a probe labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Probes can also be prepared such that a fluorescent or other label is not part of the DNA before or during the hybridization, and is added after hybridization to detect the probe hybridized to a chromosome. For example, probes can be used that have antigenic molecules incorporated into the DNA. After hybridization, these antigenic molecules are detected using specific antibodies reactive with the antigenic molecules. Such antibodies can themselves incorporate a fluorochrome, or can be detected using a second antibody with a bound fluorochrome.

However treated or modified, the probe DNA is commonly purified in order to remove unreacted, residual products (e.g., fluorochrome molecules not incorporated into the DNA) before use in hybridization.

Prior to hybridization, chromosomal probes are denatured according to methods well known in the art. Probes can be hybridized or annealed to the chromosomal DNA under hybridizing conditions. "Hybridizing conditions" are conditions that facilitate annealing between a probe and target chromosomal DNA. Since annealing of different probes will vary depending on probe length, base concentration and the like, annealing is facilitated by varying probe concentration, hybridization temperature, salt concentration and other factors well known in the art.

Hybridization conditions are facilitated by varying the concentrations, base compositions, complexities, and lengths of the probes, as well as salt concentrations, temperatures, and length of incubation. For example, in situ hybridizations are typically performed in hybridization buffer containing 1-2×SSC, 50-65% formamide and blocking DNA to suppress non-specific hybridization. In general, hybridization conditions, as described above, include temperatures of about 25° C. to about 55° C., and incubation lengths of about 0.5 hours to about 96 hours.

Non-specific binding of chromosomal probes to DNA outside of the target region can be removed by a series of washes. Temperature and concentration of salt in each wash are varied to control stringency of the washes. For example, for high stringency conditions, washes can be carried out at about 65° C. to about 80° C., using 0.2× to about 2×SSC, and about 0.1% to about 1% of a non-ionic detergent such as Nonidet P-40 (NP40). Stringency can be lowered by decreasing the temperature of the washes or by increasing the concentration of salt in the washes. In some applications it is necessary to block the hybridization capacity of repetitive sequences. Thus, in some embodiments, tRNA, human genomic DNA, or Cot-I DNA is used to block non-specific hybridization. After washing, the slide is allowed to drain and air dry, then mounting medium, a counterstain such as DAPI, and a coverslip are applied to the slide. Slides can be viewed immediately or stored at −20° C. before examination.

For fluorescent probes used in fluorescence in situ hybridization (FISH) techniques, fluorescence can be viewed with a fluorescence microscope equipped with an appropriate filter for each fluorophore, or by using dual or triple bandpass filter sets to observe multiple fluorophores. See, for example, U.S. Pat. No. 5,776,688. Alternatively, techniques such as flow cytometry can be used to examine the hybridization pattern of the chromosomal probes.

In CGH methods, a first collection of nucleic acids (e.g., from a sample, e.g., a possible tumor) is labeled with a first label, while a second collection of nucleic acids (e.g., a control, e.g., from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number. Array-based CGH can also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays.

Hybridization protocols suitable for use with the methods featured in the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; Methods in Molecular Biology, Vol. 33: In situ Hybridization Protocols, Choo, ed., Humana Press, Totowa, N.J. (1994), etc. In one embodiment, the hybridization protocol of Pinkel, et al. (1998) *Nature Genetics* 20: 207-211, or of Kallioniemi (1992) *Proc. Natl Acad Sci USA* 89:5321-5325 (1992) is used. Array-based CGH is described in U.S. Pat. No. 6,455,258, the contents of each of which are incorporated herein by reference.

In still another embodiment, amplification-based assays can be used to measure presence/absence and copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g., healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that can be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR can also be used. In fluorogenic quantitative PCR, quantitation is based on amount of fluorescence signals, e.g., TaqMan and sybr green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Nucleic Acid Samples

A variety of tissue samples can be the source of the nucleic acid samples used in the present methods. Genomic or subgenomic DNA fragments can be isolated from a subject's sample (e.g., a tumor sample, a normal adjacent tissue (NAT), a blood sample or any normal control)). In certain embodiments, the tissue sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample. The isolating step can include flow-sorting of individual chromosomes; and/or micro-dissecting a subject's sample (e.g., a tumor sample, a NAT, a blood sample).

Protocols for DNA isolation from a tissue sample are known in the art. Additional methods to isolate nucleic acids (e.g., DNA) from formaldehyde- or paraformaldehyde-fixed, paraffin-embedded (FFPE) tissues are disclosed, e.g., in Cronin M. et al., (2004) *Am J Pathol.* 164(1):35-42; Masuda N. et al., (1999) *Nucleic Acids Res.* 27(22):4436-4443; Specht K. et al., (2001) *Am J Pathol.* 158(2):419-429, Ambion RecoverAll™ Total Nucleic Acid Isolation Protocol (Ambion, Cat. No. AM1975, September 2008), and QIAamp® DNA FFPE Tissue Handbook (Qiagen, Cat. No. 37625, October 2007). RecoverAll™ Total Nucleic Acid Isolation Kit uses xylene at elevated temperatures to solubilize paraffin-embedded samples and a glass-fiber filter to capture nucleic acids. QIAamp® DNA FFPE Tissue Kit uses QIAamp® DNA Micro technology for purification of genomic and mitochondrial DNA.

The isolated nucleic acid samples (e.g., genomic DNA samples) can be fragmented or sheared by practicing routine techniques. For example, genomic DNA can be fragmented by physical shearing methods, enzymatic cleavage methods, chemical cleavage methods, and other methods well known to those skilled in the art. The nucleic acid library can contain all or substantially all of the complexity of the genome. The term "substantially all" in this context refers to the possibility that there can in practice be some unwanted loss of genome complexity during the initial steps of the procedure. The methods described herein also are useful in cases where the nucleic acid library is a portion of the genome, i.e., where the complexity of the genome is reduced by design. In some embodiments, any selected portion of the genome can be used with the methods described herein. In certain embodiments, the entire exome or a subset thereof is isolated.

Methods can further include isolating a nucleic acid sample to provide a library (e.g., a nucleic acid library). In certain embodiments, the nucleic acid sample includes whole genomic, subgenomic fragments, or both. The isolated nucleic acid samples can be used to prepare nucleic acid libraries. Thus, in one embodiment, the methods featured in the invention further include isolating a nucleic acid sample to provide a library (e.g., a nucleic acid library as described herein). Protocols for isolating and preparing libraries from whole genomic or subgenomic fragments are known in the art (e.g., Illumina's genomic DNA sample preparation kit). In certain embodiments, the genomic or subgenomic DNA fragment is isolated from a subject's sample (e.g., a tumor sample, a normal adjacent tissue (NAT), a blood sample or any normal control)). In one embodiment, the sample (e.g., the tumor or NAT sample) is a preserved. For example, the sample is embedded in a matrix, e.g., an FFPE block or a frozen sample. In certain embodiments, the isolating step includes flow-sorting of individual chromosomes; and/or microdissecting a subject's sample (e.g., a tumor sample, a NAT, a blood sample). In certain embodiments, the nucleic acid sample used to generate the nucleic acid library is less than 5, less than 1 microgram, less than 500 ng, less than 200 ng, less than 100 ng, less than 50 ng or less than 20 ng (e.g., 10 ng or less).

In still other embodiments, the nucleic acid sample used to generate the library includes RNA or cDNA derived from RNA. In some embodiments, the RNA includes total cellular RNA. In other embodiments, certain abundant RNA sequences (e.g., ribosomal RNAs) have been depleted. In some embodiments, the poly(A)-tailed mRNA fraction in the total RNA preparation has been enriched. In some embodiments, the cDNA is produced by random-primed cDNA synthesis methods. In other embodiments, the cDNA synthesis is initiated at the poly(A) tail of mature mRNAs by priming by oligo(dT)-containing oligonucleotides. Methods for depletion, poly(A) enrichment, and cDNA synthesis are well known to those skilled in the art.

The method can further include amplifying the nucleic acid sample (e.g., DNA or RNA sample) by specific or non-specific nucleic acid amplification methods that are well known to those skilled in the art. In some embodiments, certain embodiments, the nucleic acid sample is amplified, e.g., by whole-genome amplification methods such as random-primed strand-displacement amplification.

In other embodiments, the nucleic acid sample is fragmented or sheared by physical or enzymatic methods and ligated to synthetic adapters, size-selected (e.g., by preparative gel electrophoresis) and amplified (e.g., by PCR). In other embodiments, the fragmented and adapter-ligated group of nucleic acids is used without explicit size selection or amplification prior to hybrid selection.

In other embodiments, the isolated DNA (e.g., the genomic DNA) is fragmented or sheared. In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA.

In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA. Protocols for isolating and preparing libraries from whole genomic or subgenomic fragments are known in the art (e.g., Illumina's genomic DNA sample preparation kit). Alternative DNA shearing methods can be more automatable and/or more efficient (e.g., with degraded FFPE samples). Alternatives to DNA shearing methods can also be used to avoid a ligation step during library preparation.

The methods described herein can be performed using a small amount of nucleic acids, e.g., when the amount of source DNA is limiting (e.g., even after whole-genome amplification). In one embodiment, the nucleic acid comprises less than about 5 µg, 4 µg, 3 µg, 2 µg, 1 µg, 0.8 µg, 0.7 µg, 0.6 µg, 0.5 µg, or 400 ng, 300 ng, 200 ng, 100 ng, 50 ng, or 20 ng or less of nucleic acid sample. For example, to prepare 500 ng of hybridization-ready nucleic acids, one typically begins with 3 µg of genomic DNA. One can start with less, however, if one amplifies the genomic DNA (e.g., using PCR) before the step of solution hybridization. Thus it is possible, but not essential, to amplify the genomic DNA before solution hybridization.

In some embodiments, a library is generated using DNA (e.g., genomic DNA) from a sample tissue, and a corresponding library is generated with RNA (or cDNA) isolated from the same sample tissue.

Design of Baits

A bait can be a nucleic acid molecule, e.g., a DNA or RNA molecule, which can hybridize to (e.g., be complementary to), and thereby allow capture of a target nucleic acid. In one embodiment, a bait is an RNA molecule. In other embodiments, a bait includes a binding entity, e.g., an affinity tag, that allows capture and separation, e.g., by binding to a binding entity, of a hybrid formed by a bait and a nucleic acid hybridized to the bait. In one embodiment, a bait is suitable for solution phase hybridization.

Baits can be produced and used by methods and hybridization conditions as described in US 2010/0029498 and Gnirke, A. et al. (2009) *Nat Biotechnol.* 27(2):182-189, and U.S. Ser. No. 61/428,568, filed Dec. 30, 2010, incorporated herein by reference. For example, biotinylated RNA baits can be produced by obtaining a pool of synthetic long oligonucleotides, originally synthesized on a microarray, and amplifying the oligonucleotides to produce the bait sequences. In some embodiments, the baits are produced by adding an RNA polymerase promoter sequence at one end of the bait sequences, and synthesizing RNA sequences using RNA polymerase. In one embodiment, libraries of synthetic oligodeoxynucleotides can be obtained from commercial suppliers, such as Agilent Technologies, Inc., and amplified using known nucleic acid amplification methods.

Each bait sequence can include a target-specific (e.g., a member-specific) bait sequence and universal tails on each end. As used herein, the term "bait sequence" can refer to the target-specific bait sequence or the entire oligonucleotide including the target-specific "bait sequence" and other nucleotides of the oligonucleotide. In one embodiment, a target-specific bait hybridizes to a nucleic acid sequence comprising a nucleic acid sequence in intron 26 of DCTN1, in intron 19 of ALK, or a fusion junction joining introns 26 of DCTN1 and 19 of ALK. In another embodiment, a target-specific bait hybridizes to a nucleic acid sequence comprising a nucleic acid sequence in intron 2 of LMNA, in intron 10 of NTRK1, or a fusion junction joining intron 2 of LMNA and intron 10 of NTRK1.

In one embodiment, the bait is an oligonucleotide about 200 nucleotides in length, of which 170 nucleotides are target-specific "bait sequence". The other 30 nucleotides (e.g., 15 nucleotides on each end) are universal arbitrary tails used for PCR amplification. The tails can be any sequence selected by the user. For example, the pool of synthetic oligonucleotides can include oligonucleotides of the sequence of 5'-ATCGCACCAGCGTGTN$_{170}$CACTGCGGCTCCTCA-3' with N$_{170}$ indicating the target-specific bait sequences.

The bait sequences described herein can be used for selection of exons and short target sequences. In one embodiment, the bait is between about 100 nucleotides and 300 nucleotides in length. In another embodiment, the bait is between about 130 nucleotides and 230 nucleotides in length. In yet another embodiment, the bait is between about 150 nucleotides and 200 nucleotides in length. The target-specific sequences in the baits, e.g., for selection of exons and short target sequences, are between about 40 nucleotides and 1000 nucleotides in length. In one embodiment, the target-specific sequence is between about 70 nucleotides and 300 nucleotides in length. In another embodiment, the target-specific sequence is between about 100 nucleotides and 200 nucleotides in length. In yet another embodiment, the target-specific sequence is between about 120 nucleotides and 170 nucleotides in length.

Sequencing

The invention also includes methods of sequencing nucleic acids. In one embodiment, any of a variety of sequencing reactions known in the art can be used to directly sequence at least a portion of a DCTN1-ALK or LMNA-NTRK1 fusion. In one embodiment, the DCTN1-ALK or LMNA-NTRK1fusion sequence is compared to a corresponding reference (control) sequence.

In one embodiment, the sequence of the fusion nucleic acid molecule is determined by a method that includes one or more of: hybridizing an oligonucleotide, e.g., an allele specific oligonucleotide for one alteration described herein to said nucleic acid; hybridizing a primer, or a primer set (e.g., a primer pair), that amplifies a region comprising the mutation or a fusion junction of the allele; amplifying, e.g., specifically amplifying, a region comprising the mutation or a fusion junction of the allele; attaching an adapter oligonucleotide to one end of a nucleic acid that comprises the mutation or a fusion junction of the allele; generating an optical, e.g., a colorimetric signal, specific to the presence of the one of the mutation or fusion junction; hybridizing a nucleic acid comprising the mutation or fusion junction to a second nucleic acid, e.g., a second nucleic acid attached to a substrate; generating a signal, e.g., an electrical or fluorescent signal, specific to the presence of the mutation or fusion junction; and incorporating a nucleotide into an oligonucleotide that is hybridized to a nucleic acid that contains the mutation or fusion junction.

In another embodiment, the sequence is determined by a method that comprises one or more of: determining the nucleotide sequence from an individual nucleic acid molecule, e.g., where a signal corresponding to the sequence is derived from a single molecule as opposed, e.g., from a sum of signals from a plurality of clonally expanded molecules; determining the nucleotide sequence of clonally expanded proxies for individual nucleic acid molecules; massively parallel short-read sequencing; template-based sequencing; pyrosequencing; real-time sequencing comprising imaging the continuous incorporation of dye-labeling nucleotides during DNA synthesis; nanopore sequencing; sequencing by hybridization; nano-transistor array based sequencing; polony sequencing; scanning tunneling microscopy (STM) based sequencing; or nanowire-molecule sensor based sequencing.

Any method of sequencing known in the art can be used. Exemplary sequencing reactions include those based on techniques developed by Maxam and Gilbert (*Proc. Natl Acad Sci USA* (1977) 74:560) or Sanger (Sanger et al. (1977) *Proc. Nat. Acad. Sci* 74:5463). Any of a variety of automated sequencing procedures can be utilized when performing the assays (*Biotechniques* (1995) 19:448), including sequencing by mass spectrometry (see, for example, U.S. Pat. No. 5,547,835 and international patent application Publication Number WO 94/16101, entitled *DNA Sequencing by Mass Spectrometry* by H. Köster; U.S. Pat. No. 5,547,835 and international patent application Publication Number WO 94/21822 entitled *DNA Sequencing by Mass Spectrometry Via Exonuclease Degradation* by H. Köster), and U.S. Pat. No. 5,605,798 and International Patent Application No. PCT/US96/03651 entitled *DNA Diagnostics Based on Mass Spectrometry* by H. Köster; Cohen et al. (1996) *Adv Chromatogr* 36:127-162; and Griffin et al. (1993) *Appl Biochem Biotechnol* 38:147-159).

Sequencing of nucleic acid molecules can also be carried out using next-generation sequencing (NGS). Next-generation sequencing includes any sequencing method that determines the nucleotide sequence of either individual nucleic acid molecules or clonally expanded proxies for individual nucleic acid molecules in a highly parallel fashion (e.g., greater than $10^5$ molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference.

In one embodiment, the next-generation sequencing allows for the determination of the nucleotide sequence of an individual nucleic acid molecule (e.g., Helicos BioSciences' HeliScope Gene Sequencing system, and Pacific Biosciences' PacBio RS system). In other embodiments, the sequencing method determines the nucleotide sequence of clonally expanded proxies for individual nucleic acid molecules (e.g., the Solexa sequencer, Illumina Inc., San Diego, Calif.; 454 Life Sciences (Branford, Conn.), and Ion Torrent). e.g., massively parallel short-read sequencing (e.g., the Solexa sequencer, Illumina Inc., San Diego, Calif.), which generates more bases of sequence per sequencing unit than other sequencing methods that generate fewer but longer reads. Other methods or machines for next-generation sequencing include, but are not limited to, the sequencers provided by 454 Life Sciences (Branford, Conn.), Applied Biosystems (Foster City, Calif.; SOLiD sequencer), and Helicos BioSciences Corporation (Cambridge, Mass.).

Platforms for next-generation sequencing include, but are not limited to, Roche/454's Genome Sequencer (GS) FLX System, Illumina/Solexa's Genome Analyzer (GA), Life/APG's Support Oligonucleotide Ligation Detection (SOLiD) system, Polonator's G.007 system, Helicos BioSciences' HeliScope Gene Sequencing system, and Pacific Biosciences' PacBio RS system.

NGS technologies can include one or more of steps, e.g., template preparation, sequencing and imaging, and data analysis.

Template Preparation

Methods for template preparation can include steps such as randomly breaking nucleic acids (e.g., genomic DNA or cDNA) into smaller sizes and generating sequencing templates (e.g., fragment templates or mate-pair templates). The spatially separated templates can be attached or immobilized to a solid surface or support, allowing massive amounts of sequencing reactions to be performed simultaneously. Types of templates that can be used for NGS reactions include, e.g., clonally amplified templates originating from single DNA molecules, and single DNA molecule templates.

Methods for preparing clonally amplified templates include, e.g., emulsion PCR (emPCR) and solid-phase amplification.

EmPCR can be used to prepare templates for NGS. Typically, a library of nucleic acid fragments is generated, and adapters containing universal priming sites are ligated to the ends of the fragment. The fragments are then denatured into single strands and captured by beads. Each bead captures a single nucleic acid molecule. After amplification and enrichment of emPCR beads, a large amount of templates can be attached or immobilized in a polyacrylamide gel on a standard microscope slide (e.g., Polonator), chemically crosslinked to an amino-coated glass surface (e.g., Life/APG; Polonator), or deposited into individual PicoTiterPlate (PTP) wells (e.g., Roche/454), in which the NGS reaction can be performed.

Solid-phase amplification can also be used to produce templates for NGS. Typically, forward and reverse primers are covalently attached to a solid support. The surface density of the amplified fragments is defined by the ratio of the primers to the templates on the support. Solid-phase amplification can produce hundreds of millions spatially separated template clusters (e.g., Illumina/Solexa). The ends of the template clusters can be hybridized to universal sequencing primers for NGS reactions.

Other methods for preparing clonally amplified templates also include, e.g., Multiple Displacement Amplification (MDA) (Lasken R. S. *Curr Opin Microbiol.* 2007; 10(5): 510-6). MDA is a non-PCR based DNA amplification technique. The reaction involves annealing random hexamer primers to the template and DNA synthesis by high fidelity enzyme, typically Φ29 at a constant temperature. MDA can generate large sized products with lower error frequency.

Template amplification methods such as PCR can be coupled with NGS platforms to target or enrich specific regions of the genome (e.g., exons). Exemplary template enrichment methods include, e.g., microdroplet PCR technology (Tewhey R. et al., *Nature Biotech.* 2009, 27:1025-1031), custom-designed oligonucleotide microarrays (e.g., Roche/NimbleGen oligonucleotide microarrays), and solution-based hybridization methods (e.g., molecular inversion probes (MIPs) (Porreca G. J. et al., *Nature Methods,* 2007, 4:931-936; Krishnakumar S. et al., *Proc. Natl. Acad. Sci. USA,* 2008, 105:9296-9310; Turner E. H. et al., *Nature Methods,* 2009, 6:315-316), and biotinylated RNA capture sequences (Gnirke A. et al., *Nat. Biotechnol.* 2009; 27(2): 182-9)

Single-molecule templates are another type of templates that can be used for NGS reaction. Spatially separated single molecule templates can be immobilized on solid supports by various methods. In one approach, individual primer molecules are covalently attached to the solid support. Adapters are added to the templates and templates are then hybridized to the immobilized primers. In another approach, single-molecule templates are covalently attached to the solid support by priming and extending single-stranded, single-molecule templates from immobilized primers. Universal primers are then hybridized to the templates. In yet another approach, single polymerase molecules are attached to the solid support, to which primed templates are bound.

Sequencing and Imaging

Exemplary sequencing and imaging methods for NGS include, but are not limited to, cyclic reversible termination (CRT), sequencing by ligation (SBL), single-molecule addition (pyrosequencing), and real-time sequencing.

CRT uses reversible terminators in a cyclic method that minimally includes the steps of nucleotide incorporation, fluorescence imaging, and cleavage. Typically, a DNA polymerase incorporates a single fluorescently modified nucleotide corresponding to the complementary nucleotide of the template base to the primer. DNA synthesis is terminated after the addition of a single nucleotide and the unincorporated nucleotides are washed away. Imaging is performed to determine the identity of the incorporated labeled nucleotide. Then in the cleavage step, the terminating/inhibiting group and the fluorescent dye are removed. Exemplary NGS platforms using the CRT method include, but are not limited to, Illumina/Solexa Genome Analyzer (GA), which uses the clonally amplified template method coupled with the four-color CRT method detected by total internal reflection fluorescence (TIRF); and Helicos BioSciences/HeliScope, which uses the single-molecule template method coupled with the one-color CRT method detected by TIRF.

SBL uses DNA ligase and either one-base-encoded probes or two-base-encoded probes for sequencing. Typically, a fluorescently labeled probe is hybridized to its complementary sequence adjacent to the primed template. DNA ligase is used to ligate the dye-labeled probe to the primer. Fluorescence imaging is performed to determine the identity of the ligated probe after non-ligated probes are washed away. The fluorescent dye can be removed by using cleavable probes to regenerate a 5'-$PO_4$ group for subsequent ligation cycles. Alternatively, a new primer can be hybridized to the template after the old primer is removed. Exemplary SBL platforms include, but are not limited to, Life/APG/SOLiD (support oligonucleotide ligation detection), which uses two-base-encoded probes.

Pyrosequencing method is based on detecting the activity of DNA polymerase with another chemiluminescent enzyme. Typically, the method allows sequencing of a single strand of DNA by synthesizing the complementary strand along it, one base pair at a time, and detecting which base was actually added at each step. The template DNA is immobile, and solutions of A, C, G, and T nucleotides are sequentially added and removed from the reaction. Light is produced only when the nucleotide solution complements the first unpaired base of the template. The sequence of solutions which produce chemiluminescent signals allows the determination of the sequence of the template. Exemplary pyrosequencing platforms include, but are not limited to, Roche/454, which uses DNA templates prepared by emPCR with 1-2 million beads deposited into PTP wells.

Real-time sequencing involves imaging the continuous incorporation of dye-labeled nucleotides during DNA synthesis. Exemplary real-time sequencing platforms include, but are not limited to, Pacific Biosciences platform, which uses DNA polymerase molecules attached to the surface of individual zero-mode waveguide (ZMW) detectors to obtain sequence information when phospholinked nucleotides are being incorporated into the growing primer strand; Life/VisiGen platform, which uses an engineered DNA polymerase with an attached fluorescent dye to generate an enhanced signal after nucleotide incorporation by fluorescence resonance energy transfer (FRET); and LI-COR Biosciences platform, which uses dye-quencher nucleotides in the sequencing reaction.

Other sequencing methods for NGS include, but are not limited to, nanopore sequencing, sequencing by hybridization, nano-transistor array based sequencing, polony sequencing, scanning tunneling microscopy (STM) based sequencing, and nanowire-molecule sensor based sequencing.

Nanopore sequencing involves electrophoresis of nucleic acid molecules in solution through a nano-scale pore which provides a highly confined space within which single-nucleic acid polymers can be analyzed. Exemplary methods of nanopore sequencing are described, e.g., in Branton D. et al., *Nat Biotechnol.* 2008; 26(10):1146-53.

Sequencing by hybridization is a non-enzymatic method that uses a DNA microarray. Typically, a single pool of DNA is fluorescently labeled and hybridized to an array containing known sequences. Hybridization signals from a given spot on the array can identify the DNA sequence. The binding of one strand of DNA to its complementary strand in the DNA double-helix is sensitive to even single-base mismatches when the hybrid region is short or is specialized mismatch detection proteins are present. Exemplary methods of sequencing by hybridization are described, e.g., in Hanna G. J. et al., *J. Clin. Microbiol.* 2000; 38 (7): 2715-21; and Edwards J. R. et al., *Mut. Res.* 2005; 573 (1-2): 3-12.

Polony sequencing is based on polony amplification and sequencing-by-synthesis via multiple single-base-extensions (FISSEQ). Polony amplification is a method to amplify DNA in situ on a polyacrylamide film. Exemplary polony sequencing methods are described, e.g., in US Patent Application Publication No. 2007/0087362.

Nano-transistor array based devices, such as Carbon NanoTube Field Effect Transistor (CNTFET), can also be used for NGS. For example, DNA molecules are stretched and driven over nanotubes by micro-fabricated electrodes. DNA molecules sequentially come into contact with the carbon nanotube surface, and the difference in current flow from each base is produced due to charge transfer between the DNA molecule and the nanotubes. DNA is sequenced by recording these differences. Exemplary Nano-transistor array based sequencing methods are described, e.g., in U.S. Patent Application Publication No. 2006/0246497.

Scanning tunneling microscopy (STM) can also be used for NGS. STM uses a piezo-electric-controlled probe that performs a raster scan of a specimen to form images of its surface. STM can be used to image the physical properties of single DNA molecules, e.g., generating coherent electron tunneling imaging and spectroscopy by integrating scanning tunneling microscope with an actuator-driven flexible gap. Exemplary sequencing methods using STM are described, e.g., in U.S. Patent Application Publication No. 2007/0194225.

A molecular-analysis device which is comprised of a nanowire-molecule sensor can also be used for NGS. Such device can detect the interactions of the nitrogenous material disposed on the nanowires and nucleic acid molecules such as DNA. A molecule guide is configured for guiding a molecule near the molecule sensor, allowing an interaction and subsequent detection. Exemplary sequencing methods using nanowire-molecule sensor are described, e.g., in U.S. Patent Application Publication No. 2006/0275779.

Double ended sequencing methods can be used for NGS. Double ended sequencing uses blocked and unblocked primers to sequence both the sense and antisense strands of DNA. Typically, these methods include the steps of annealing an unblocked primer to a first strand of nucleic acid; annealing a second blocked primer to a second strand of nucleic acid; elongating the nucleic acid along the first strand with a polymerase; terminating the first sequencing primer; deblocking the second primer; and elongating the nucleic acid along the second strand. Exemplary double ended sequencing methods are described, e.g., in U.S. Pat. No. 7,244,567.

Data Analysis

After NGS reads have been generated, they can be aligned to a known reference sequence or assembled de novo.

For example, identifying genetic variations such as single-nucleotide polymorphism and structural variants in a sample (e.g., a tumor sample) can be accomplished by aligning NGS reads to a reference sequence (e.g., a wild-type sequence). Methods of sequence alignment for NGS are described e.g., in Trapnell C. and Salzberg S. L. *Nature Biotech.*, 2009, 27:455-457.

Examples of de novo assemblies are described, e.g., in Warren R. et al., *Bioinformatics*, 2007, 23:500-501; Butler J. et al., *Genome Res.*, 2008, 18:810-820; and Zerbino D. R. and Birney E., *Genome Res.*, 2008, 18:821-829.

Sequence alignment or assembly can be performed using read data from one or more NGS platforms, e.g., mixing Roche/454 and Illumina/Solexa read data.

Algorithms and methods for data analysis are described in U.S. Ser. No. 61/428,568, filed Dec. 30, 2010, incorporated herein by reference.

Fusion Expression Level

In certain embodiments, DCTN1-ALK or LMNA-NTRK1 fusion expression level can also be assayed. Fusion expression can be assessed by any of a wide variety of methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In certain embodiments, activity of a particular gene is characterized by a measure of gene transcript (e.g., mRNA), by a measure of the quantity of translated protein, or by a measure of gene product activity. DCTN1-ALK or LMNA-NTRK1 fusion expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

Methods of detecting and/or quantifying the fusion gene transcript (mRNA or cDNA made therefrom) using nucleic acid hybridization techniques are known to those of skill in the art (see Sambrook et al. supra). For example, one method for evaluating the presence, absence, or quantity of cDNA involves a Southern transfer as described above. Briefly, the mRNA is isolated (e.g., using an acid guanidinium-phenol-chloroform extraction method, Sambrook et al. supra.) and reverse transcribed to produce cDNA. The cDNA is then optionally digested and run on a gel in buffer and transferred to membranes. Hybridization is then carried out using the nucleic acid probes specific for the DCTN1-ALK fusion cDNA or the LMNA-NTRK1 fusion cDNA, e.g., using the probes and primers described herein.

In other embodiments, DCTN1-ALK or LMNA-NTRK1 expression is assessed by preparing genomic DNA or mRNA/cDNA (i.e., a transcribed polynucleotide) from cells in a subject sample, and by hybridizing the genomic DNA or mRNA/cDNA with a reference polynucleotide which is a complement of a polynucleotide comprising the DCTN1-ALK fusion or the LMNA-NTRK1 fusion, and fragments thereof. cDNA can, optionally, be amplified using any of a variety of polymerase chain reaction methods prior to hybridization with the reference polynucleotide. Expression of a fusion as described herein can likewise be detected using quantitative PCR (QPCR) to assess the level of expression.

Detection of Fusion Polypeptide

The activity or level of a fusion polypeptide (e.g., DCTN1-ALK or LMNA-NTRK1) can also be detected and/or quantified by detecting or quantifying the expressed polypeptide. The fusion polypeptide can be detected and quantified by any of a number of means known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, immunohistochemistry (IHC) and the like. A skilled artisan can adapt known protein/antibody detection methods.

Another agent for detecting a fusion polypeptide is an antibody molecule capable of binding to a polypeptide corresponding to a marker, e.g., an antibody with a detectable label. Techniques for generating antibodies are described herein. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In another embodiment, the antibody is labeled, e.g., a radio-labeled, chromophore-labeled, fluorophore-labeled, or enzyme-labeled antibody. In another embodiment, an antibody derivative (e.g., an antibody conjugated with a substrate or with the protein or ligand of a protein-ligand pair {e.g., biotin-streptavidin}), or an antibody fragment (e.g., a single-chain antibody, an isolated antibody hypervariable domain, etc.) which binds specifically with a DCTN1-ALK or LMNA-NTRK1 fusion protein, is used.

Fusion polypeptides from cells can be isolated using techniques that are known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

Means of detecting proteins using electrophoretic techniques are well known to those of skill in the art (see generally, R. Scopes (1982) *Protein Purification*, Springer-Verlag, N.Y.; Deutscher, (1990) *Methods in Enzymology* Vol. 182: *Guide to Protein Purification*, Academic Press, Inc., N.Y.).

In another embodiment, Western blot (immunoblot) analysis is used to detect and quantify the presence of a polypeptide in the sample.

In another embodiment, the polypeptide is detected using an immunoassay. As used herein, an immunoassay is an assay that utilizes an antibody to specifically bind to the analyte. The immunoassay is thus characterized by detection of specific binding of a polypeptide to an anti-antibody as opposed to the use of other physical or chemical properties to isolate, target, and quantify the analyte.

The fusion polypeptide is detected and/or quantified using any of a number of immunological binding assays (see, e.g., U.S. Pat. Nos. 4,366,241; 4,376,110; 4,517,288; and 4,837,168). For a review of the general immunoassays, see also Asai (1993) *Methods in Cell Biology* Volume 37: *Antibodies in Cell Biology*, Academic Press, Inc. New York; Stites & Terr (1991) *Basic and Clinical Immunology* 7th Edition.

Kits

In one aspect, the invention features, a kit, e.g., containing an oligonucleotide having a mutation described herein, e.g., a DCTN1-ALK fusion or a LMNA-NTRK1 fusion. Optionally, the kit can also contain an oligonucleotide that is the wildtype counterpart of the mutant oligonucleotide.

A kit featured in the invention can include a carrier, e.g., a means being compartmentalized to receive in close confinement one or more container means. In one embodiment the container contains an oligonucleotide, e.g., a primer or probe as described above. The components of the kit are useful, for example, to diagnose or identify a mutation in a tumor sample in a patient. The probe or primer of the kit can be used in any sequencing or nucleotide detection assay known in the art, e.g., a sequencing assay, e.g., an NGS method, RT-PCR, or in situ hybridization.

In some embodiments, the components of the kit are useful, for example, to diagnose or identify a DCTN1-ALK fusion in a tumor sample in a patient, and to accordingly identify an appropriate therapeutic agent to treat the cancer.

A kit featured in the invention can include, e.g., assay positive and negative controls, nucleotides, enzymes (e.g., RNA or DNA polymerase or ligase), solvents or buffers, a stabilizer, a preservative, a secondary antibody, e.g., an anti-HRP antibody (IgG) and a detection reagent.

An oligonucleotide can be provided in any form, e.g., liquid, dried, semi-dried, or lyophilized, or in a form for storage in a frozen condition.

Typically, an oligonucleotide, and other components in a kit are provided in a form that is sterile. An oligonucleotide, e.g., an oligonucleotide that contains an ALK mutation, e.g., a DCTN1-ALK fusion, described herein, or an oligonucleotide complementary to a LMNA-NTRK1 fusion described herein, is provided in a liquid solution, the liquid solution generally is an aqueous solution, e.g., a sterile aqueous solution. When the oligonucleotide is provided as a dried form, reconstitution generally is accomplished by the addition of a suitable solvent. The solvent, e.g., sterile buffer, can optionally be provided in the kit.

The kit can include one or more containers for the composition containing an oligonucleotide in a concentration suitable for use in the assay or with instructions for dilution for use in the assay. In some embodiments, the kit contains separate containers, dividers or compartments for the oligonucleotide and assay components, and the informational material. For example, the oligonucleotides can be contained in a bottle or vial, and the informational material can be contained in a plastic sleeve or packet. In other embodiments, the separate elements of the kit are contained within a single, undivided container. For example, an oligonucleotide composition is contained in a bottle or vial that has attached thereto the informational material in the form of a label. In some embodiments, the kit includes a plurality (e.g., a pack) of individual containers, each containing one or more unit forms (e.g., for use with one assay) of an oligonucleotide. For example, the kit includes a plurality of ampoules, foil packets, or blister packs, each containing a single unit of oligonucleotide for use in sequencing or detecting a mutation in a tumor sample. The containers of the kits can be air tight and/or waterproof. The container can be labeled for use.

For antibody-based kits, the kit can include: (1) a first antibody (e.g., attached to a solid support) which binds to a fusion polypeptide; and, optionally, (2) a second, different antibody which binds to either the polypeptide or the first antibody and is conjugated to a detectable agent.

In one embodiment, the kit can include informational material for performing and interpreting the sequencing or diagnostic. In another embodiment, the kit can provide guidance as to where to report the results of the assay, e.g., to a treatment center or healthcare provider. The kit can include forms for reporting the results of a sequencing or diagnostic assay described herein, and address and contact information regarding where to send such forms or other related information; or a URL (Uniform Resource Locator) address for reporting the results in an online database or an online application (e.g., an app). In another embodiment, the informational material can include guidance regarding whether a patient should receive treatment with a particular chemotherapeutic drug, depending on the results of the assay.

The informational material of the kits is not limited in its form. In many cases, the informational material, e.g., instructions, is provided in printed matter, e.g., a printed text, drawings, and/or photographs, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about the sequencing or diagnostic assay and/or its use in the methods described herein. The informational material can also be provided in any combination of formats.

In some embodiments, a biological sample is provided to an assay provider, e.g., a service provider (such as a third party facility) or a healthcare provider, who evaluates the sample in an assay and provides a read out. For example, in one embodiment, an assay provider receives a biological sample from a subject, such as a blood or tissue sample, e.g., a biopsy sample, and evaluates the sample using an assay described herein, e.g., a sequencing assay or in situ hybridization assay, and determines that the sample contains a DCTN1-ALK fusion. The assay provider, e.g., a service provider or healthcare provider, can then conclude that the subject is, or is not, a candidate for a particular drug or a particular cancer treatment regimen.

The assay provider can provide the results of the evaluation, and optionally, conclusions regarding one or more of diagnosis, prognosis, or appropriate therapy options to, for example, a healthcare provider, or patient, or an insurance company, in any suitable format, such as by mail or electronically, or through an online database. The information collected and provided by the assay provider can be stored in a database.

The invention is further illustrated by the following example, which should not be construed as further limiting.

EXAMPLES

Example 1: DCTN1-ALK Fusion

The following exemplifies the use of massively parallel sequencing assays to identify novel alterations, such as DCTN1-ALK fusions. Based on the results shown herein, additional alterations, e.g., ALK translocations, can be screened using, e.g., either qRT-PCR analysis of cDNA prepared from a pre-selected tumor sample.

Figure 5:
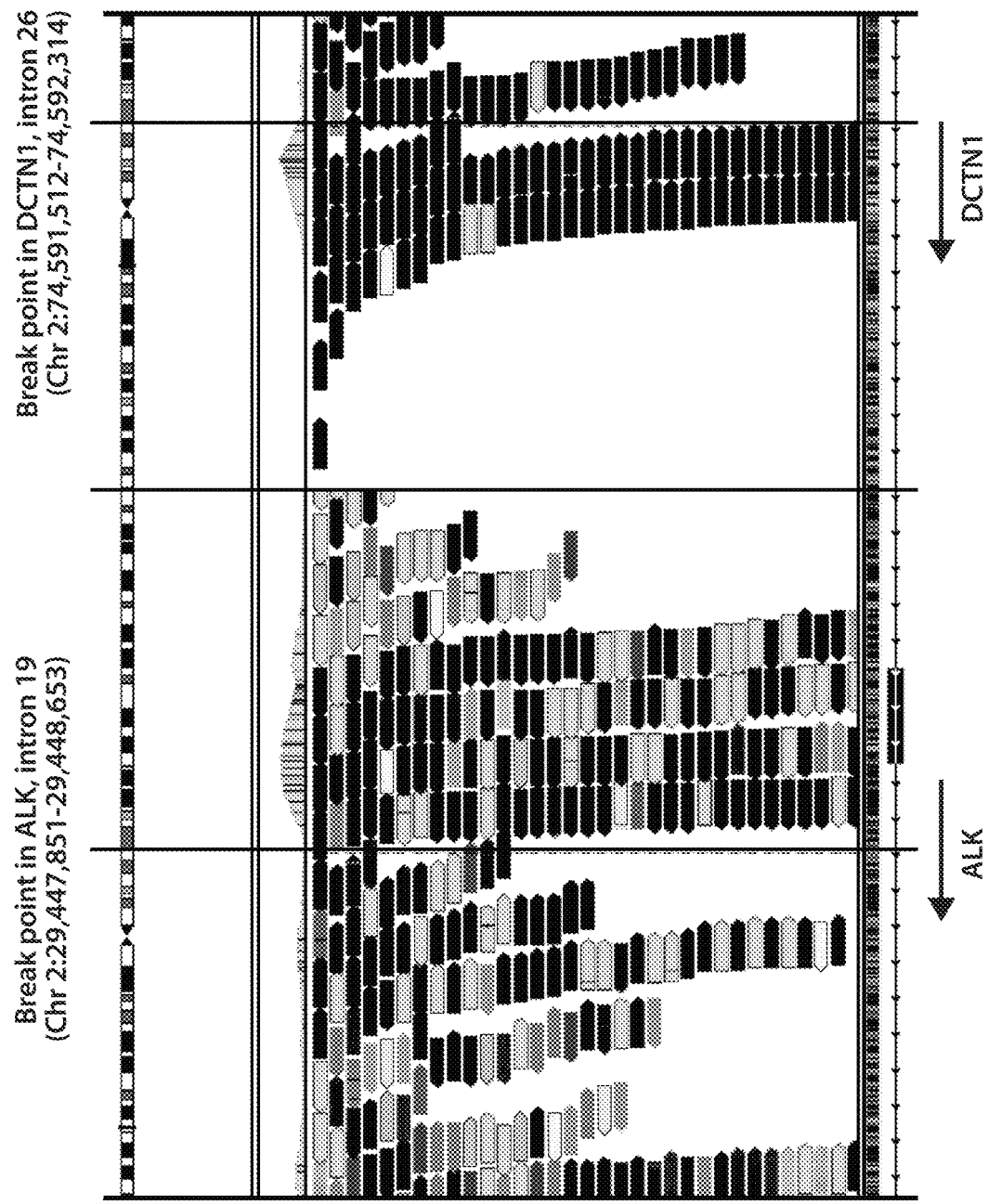
FIG. 5 is a snapshot of the sequencing reads illustrating the read pairs arising from the two fused constructs, mapped to the reference genome. Inward-pointing reads are pairs corresponding to the DCTN1-ALK fusion, whereas outward-pointing reads are pairs corresponding to the ALK-DCTN1 fusion.

A pan-cancer diagnostic assay based on massively parallel sequencing technology was used to identify genetic alterations in a series of colorectal cancer (CRC), non-small cell lung cancer (NSCLC) and melanoma samples. A novel ALK translocation was identified in one melanoma sample. The resulting DCNT1-ALK fusion is the product of a balanced translocation between two parts of chromosome 2. A snapshot of the sequencing reads is presented in FIG. 5. Both breakpoints are in introns and the predicted mRNA is in frame. ALK ("Anaplastic Lymphoma receptor tyrosine Kinase" RefSeq No. NM_004304, GenBank Record dated Oct. 2, 2011) is a known oncogene. DCTN1 ("dynactin 1" NM_004082, RefSeq No. NM_004082, GenBank record dated Aug. 14, 2011) is involved in intracellular transport. The ALK breakpoint is in the canonical intron 19, and the DCTN1 breakpoint is in intron 26. The translocation juxtaposes DCTN1 (exons 1 to 26) with the ALK kinase domain (exons 20-26) (FIG. 1). The nucleotide sequence (SEQ ID NO:6) and polypeptide sequence (SEQ ID NO:7) of the fusion protein are shown in FIGS. 2A to 2F. This fusion may permit the use of a kinase inhibitor or an ALK inhibitor in the treatment of melanoma or other cancers.

A BLAT sequence was performed on the fused construct to identify the coordinates of the ends within both partners. It was determined that the end coordinates are at chromosome 2 position 29,448,216 in the DCTN1 gene and at chromosome 2 position 74,591,795 of the ALK gene. The sequence of the DCTN1-ALK fusion breakpoint (SEQ ID NO:5) is shown in FIG. 1.

Figure 3:
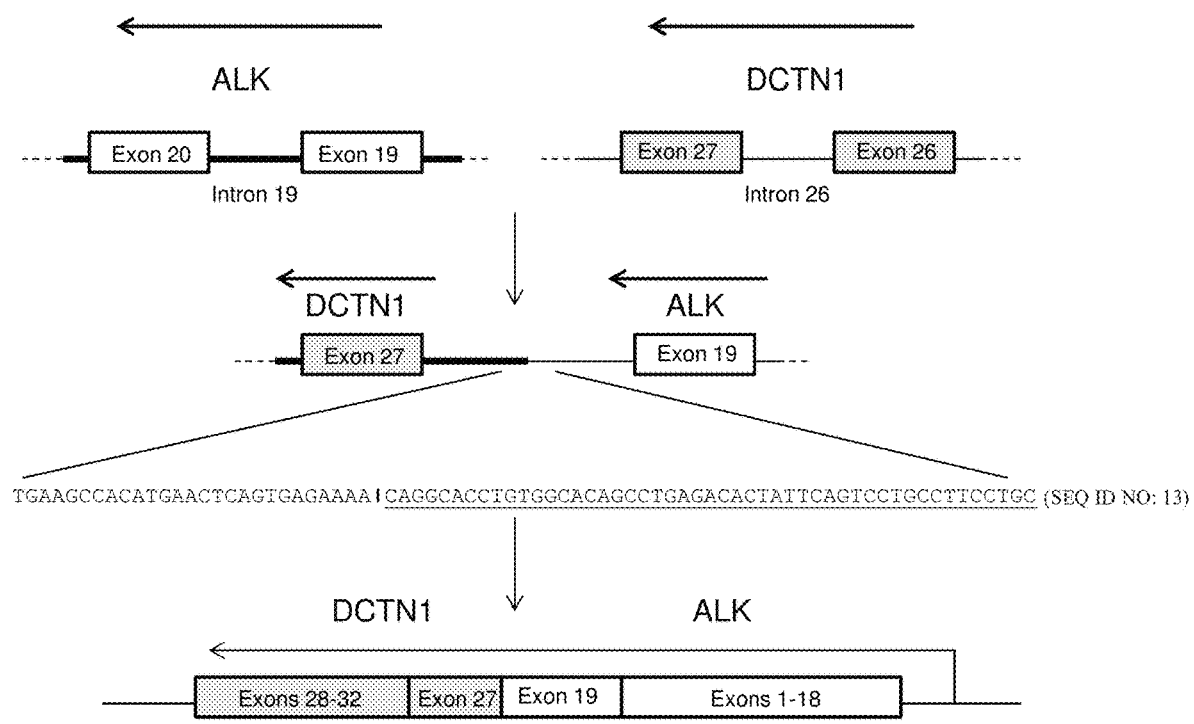
FIG. 3 is a schematic diagram of the reciprocal translocation shown in FIG. 1, which creates an ALK-DCTN1 fusion. As a result of the translocation, ALK intron 19 is fused to DCTN1 intron 26, and the sequence at the fusion junction is shown (SEQ ID NO:13). The sequence of SEQ ID NO:13 is shown in the reference genome orientation.

A reciprocol fusion construct (ALK-DCTN1) caused by the translocation was also identified. This fusion is illustrated in FIG. 3, and the nucleotide sequence (SEQ ID NO:11, and the amino acid sequence (SEQ ID NO:12) are presented in FIGS. 4A-4D. The sequence of the ALK-DCTN1 breakpoint (SEQ ID NO:13) is shown in FIG. 3. It is not been determined whether the ALK-DCTN1 polypeptide is expressed, and it is not expected that the ALK-DCTN1 polypeptide is relevant to oncogenesis.

The ALK segment of the DCTN1-ALK fusion starts at the exon 19 recombination site previously reported for the majority of ALK fusion genes and contains the same intracellular domain as other ALK rearrangements including EML4-ALK, known to be ALK kinase inhibitor sensitive (Soda, M., et al. Nature 448, 561-566 (2007); Kwak, E. L., et al. *N Engl J Med* 363, 1693-1703 (2010)). Clinical detection of ALK rearrangements is commonly performed using fluorescence in situ hybridization (FISH) with ALK break-apart probes (Kwak, E. L., et al. *N Engl J Med* 363, 1693-1703 (2010)) or by RT-PCR (Takeuchi, K., et al. *Clin Cancer Res* 14, 6618-6624 (2008)) using primers for specific ALK rearrangement partners.

Translocations in the region of ALK are previously known to be associated with certain types of cancer. For example, an inversion resulting in an EML4 (Echinoderm Microtubule associated protein Like 4)-ALK fusion is associated with lung cancer (e.g., non-small cell lung cancer), and these cancers respond to treatment with the ALK inhibitor crizotinib. A translocation that results in an NPM (Nucleophosmin)-ALK fusion is associated with lymphoma, and translocations that result in TPM3 (Tropomyosin3)-ALK and TPM4-ALK fusions are associated with myofibroblastic tumors.

Expression of DCTN1-ALK was detected in a Spitz tumor, which is a family of neoplasms that can range from benign Spitz nevi to Spitzoid melanomas. Expression of DCTN1-ALK was also detected in a non-Langerhans cell histiocytosis.

These findings suggest that Spitz tumor patients (e.g., patients with melanocytic neoplasms) and patients with histiocytosis, as well as patients with melanomas or other cancers carrying the identified rearrangement may be candidates for therapy with crizotinib or other ALK kinase inhibitors.

Example 2: LMNA-NTRK1 Fusion

Figure 6:
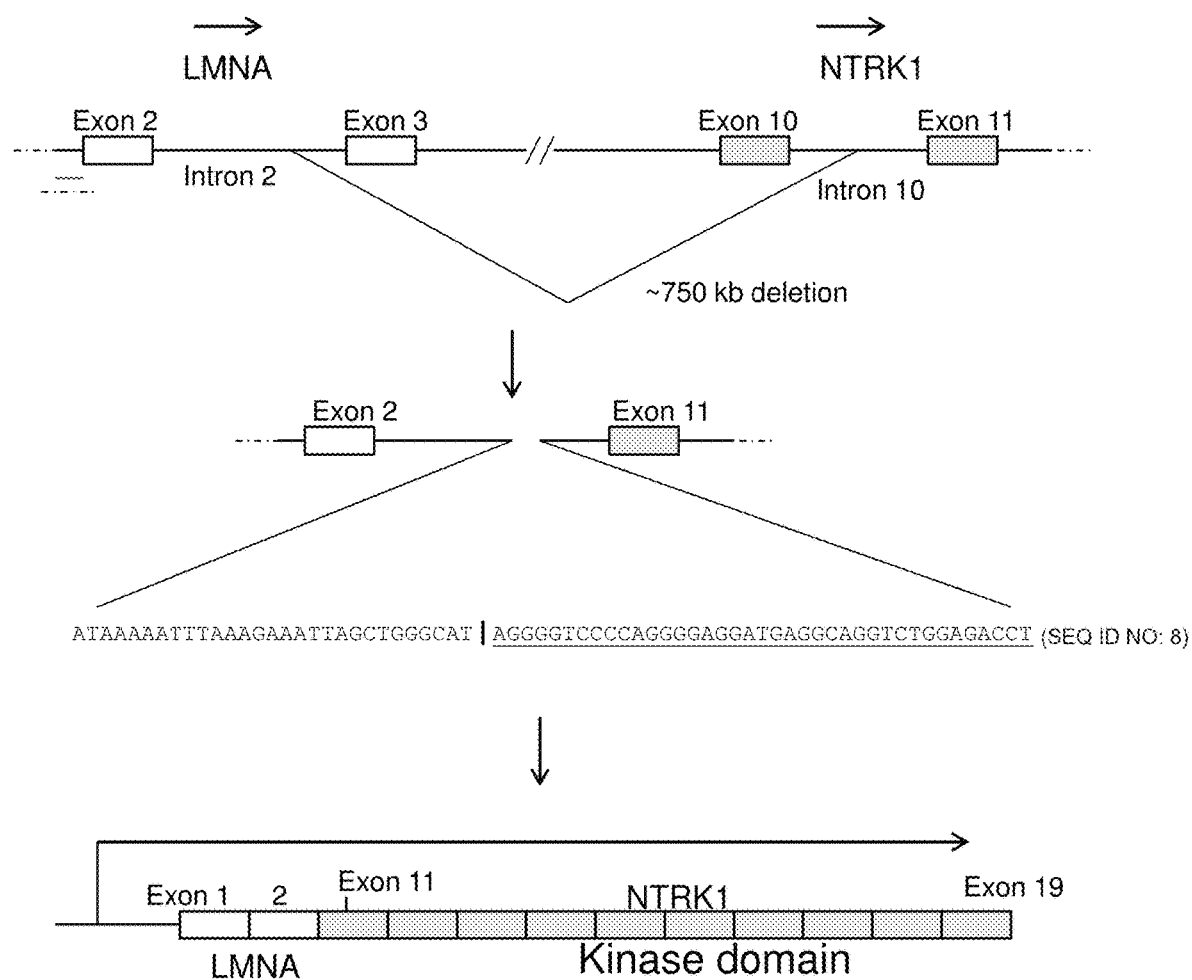
FIG. 6 is a schematic of a ~750 bp deletion with breakpoints in intron 2 of LMNA and intron 10 of NTRK1. The sequence at the breakpoint region is indicated (SEQ ID NO:8). The intron 10 sequence of NTRK1 is indicated by underlining, and the fusion junction is indicated by a vertical line. The sequence of SEQ ID NO:8 is shown in the reference genome orientation.
Figure 8:
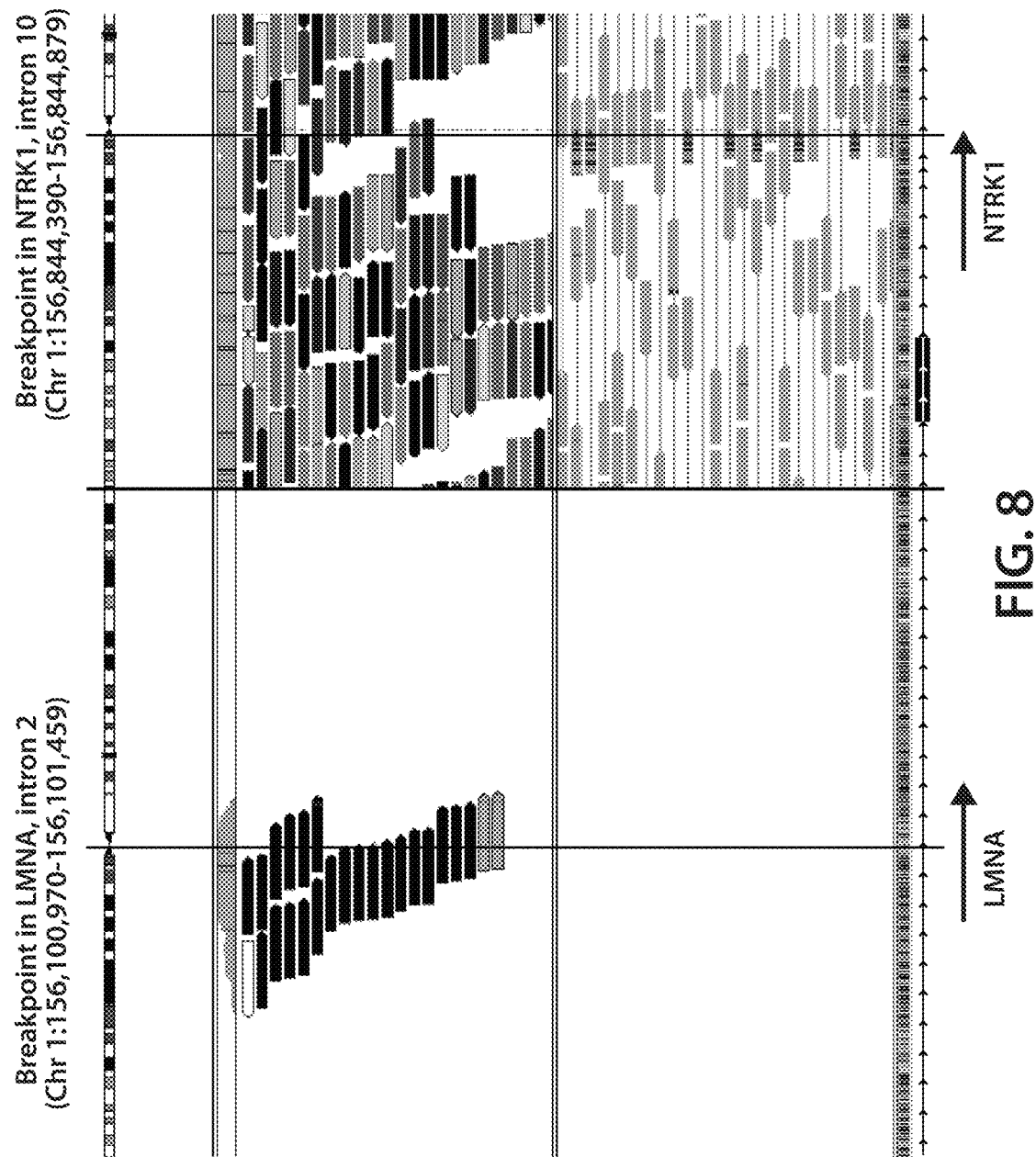
FIG. 8 is a snapshot of the sequencing reads arising from the fused construct, including members of LMNA-NTRK1 read-pairs mapping to LMNA and clipped reads in read-pairs mapping within NTRK1 that capture the fusion breakpoint.

A novel fusion between LMNA and NTRK1 was also found in a single melanoma sample. The fusion is the result of a ~750 kb deletion between intron 2 of LMNA and intron 10 of NTRK1, and the fusion product is in-frame (FIG. 6). The nucleotide sequence (SEQ ID NO:9) and polypeptide sequence (SEQ ID NO:10) of the fusion protein are shown in FIGS. 7A-7B. The sequence at the fusion junction (SEQ ID NO:8) is presented in FIG. 6. A snapshot of the sequencing reads is presented in FIG. 8.

LMNA ("Lamin A/C," RefSeq NM_005572, GenBank Record dated Oct. 16, 2011) is a gene involved in the formation of the nuclear lamina, a two dimensional matrix of proteins known to be involved in nuclear stability, chromatin structure, and gene expression. LMNA has previously been shown to be overexpressed in cancer.

NTRK1 ("neurotrophic tyrosine kinase" RefSeq NM_002529; GenBank record dated Oct. 16, 2011) is a receptor tyrosine kinase known to be an occasional target of re-arrangement in papillary thyroid carcinomas. The kinase domain is preserved in the fusion gene described in FIGS. 7A-7B, and is in the region of NTRK1 where fusions have previously been observed (see e.g., Greco, A. et al., *Mol Cell Endocrin* (2010) 321(1): 44-49).

NTRK1 fusions have been observed across a relatively large expanse of NTRK1 (see e.g., Greco, A. et al., *Mol Cell Endocrin* (2010) 321(1): 44-49). We observed one fusion event on the shorter side, but other versions are possible. Some LMNA-NTRK1 fusions may have different length pieces of LMNA attached at the 5' end of the fusion gene, and different length pieces of NTRK1 attached at the 3' end of the fusion gene, provided that the tyrosine kinase domain or a functional portion thereof is preserved.

Expression of LMNA-NTRK1 was detected in a Spitz tumor, which is a family of neoplasms that can range from benign Spitz nevi to Spitzoid melanomas.

We also observed an NTRK1 mutation in an unrelated colorectal sample set using similar NGS sequencing methods.

Incorporated by reference herein in their entirety are any polynucleotide and polypeptide sequences which reference an accession number correlating to an entry in a public database, such as those maintained by the COSMIC database, available on the worldwide web; and the Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments described herein. Such equivalents are intended to be encompassed by the following claims.

We claim:

1. A method of treating a subject having cancer, comprising:
   identifying the subject as having a DCTN1-ALK fusion polypeptide or a nucleic acid molecule encoding a DCTN1-ALK fusion polypeptide in said subject; and
   administering to the identified subject an effective amount of an anti-cancer agent that reduces or inhibits activity or expression of the DCTN1-ALK fusion polypeptide, thereby treating the cancer in the subject,
   wherein the DCTN1-ALK fusion polypeptide comprises the amino acid sequence of SEQ ID NO:7 or a fragment thereof, or a sequence at least 85% identical thereto.

2. The method of claim 1, wherein said anti-cancer agent is a kinase inhibitor.

3. The method of claim 1, wherein the subject is identified as having the nucleic acid molecule encoding the DCTN1-ALK fusion polypeptide by a sequencing method.

4. The method of claim 1, wherein said cancer is an inflammatory myofibroblastic tumor, a Spitz tumor, a melanoma, a colorectal cancer, a lung cancer, a pancreatic cancer, an esophageal-gastric cancer, a thyroid cancer, or an adenocarcinoma.

5. The method of claim 1, wherein said cancer is a lung cancer, and said lung cancer is a small cell lung cancer (SCLC), a non-small cell lung cancer (NSCLC), an adenocarcinoma of the lung, a bronchogenic carcinoma, a squamous cell carcinoma (SCC), or a combination thereof.

6. The method of claim 1, wherein the anti-cancer agent comprises:
   LDK-378, PF-02341066, XL228, an ALK-specific inhibitor, TAE-684, PF02341066 (crizotinib), AF-802, ASP-3026, CEP-37440, CEP-28122, or AP26113; or
   an inhibitor comprising an antisense molecule, a ribozyme, an RNAi molecule, or a triple helix molecule that hybridizes to the nucleic acid molecule encoding the DCTN1-ALK fusion polypeptide or a transcription regulatory region, thereby blocking or reducing mRNA expression of the nucleic acid molecule encoding the DCTN1-ALK fusion polypeptide.

7. The method of claim 2, wherein the kinase inhibitor is administered in combination with a second therapeutic agent or a different therapeutic modality.

8. The method of claim 7, wherein the second therapeutic agent is a cytotoxic agent or a cytostatic agent.

9. The method of claim 8, wherein the cytotoxic agent comprises an antimicrotubule agent, a topoisomerase inhibitor, a taxane, an antimetabolite, a mitotic inhibitor, an alkylating agent, an intercalating agent, an agent capable of interfering with a signal transduction pathway, or an agent that promotes apoptosis.

10. The method of claim 7, wherein the second therapeutic agent is an immunomodulatory agent.

11. The method of claim 10, wherein the immunomodulatory agent comprises IL-1, IL-2, IL-4, IL-6, IL-12, interferon alpha, interferon gamma, an immune cell growth factor, or GM-CSF.

12. The method of claim 1, wherein the nucleic acid molecule encoding the DCTN1-ALK fusion polypeptide comprises an in-frame fusion of the nucleotide sequence of one or more of exons 1-26 of DCTN1 of SEQ ID NO: 6 or a fragment thereof, or a nucleotide sequence at least 85% identical thereto, and the nucleotide sequence of one or more of exons 20-29 of ALK of SEQ ID NO: 6 or a fragment thereof, or a nucleotide sequence at least 85% identical thereto.

13. The method of claim 1, wherein the nucleic acid molecule encoding the DCTN1-ALK fusion polypeptide comprises an in-frame fusion of at least the nucleotide sequence of exon 26 of DCTN1 of SEQ ID NO: 6, and at least the nucleotide sequence of exon 20 of ALK of SEQ ID NO: 6.

14. The method of claim 1, wherein the nucleic acid molecule encoding the DCTN1-ALK fusion polypeptide comprises a break point comprising the nucleotide sequence of SEQ ID NO: 5 or a fragment thereof.

15. The method of claim 1, wherein the DCTN1-ALK fusion polypeptide comprises amino acids 1062-1069 or 1116-1362 of the amino acid sequence of SEQ ID NO: 7.

16. A method of treating a subject having a cancer, comprising:
   identifying the subject as having a nucleic acid molecule encoding a DCTN1-ALK fusion polypeptide in a tumor nucleic acid sample from said subject; and
   administering to the identified subject an effective amount of a kinase inhibitor that reduces or inhibits ALK activity, thereby treating the cancer in the subject,
   wherein the DCTN1-ALK fusion polypeptide comprises the amino acid sequence of SEQ ID NO:7 or a fragment thereof, or a sequence at least 85% identical thereto.

17. The method of claim 16, wherein the subject is identified as having the nucleic acid molecule encoding the DCTN1-ALK fusion polypeptide by a sequencing method.

18. The method of claim 16, wherein said cancer comprises an inflammatory myofibroblastic tumor, a Spitz tumor, a melanoma, a colorectal cancer, a lung cancer, a pancreatic cancer, an esophageal-gastric cancer, a thyroid cancer, or an adenocarcinoma.

19. The method of claim 16, wherein said cancer is a lung cancer, and said lung cancer is a small cell lung cancer (SCLC), a non-small cell lung cancer (NSCLC), an adenocarcinoma of the lung, a bronchogenic carcinoma, a squamous cell carcinoma (SCC), or a combination thereof.

20. The method of claim 16, wherein the kinase inhibitor comprises:

LDK-378, PF-02341066, XL228, an ALK-specific inhibitor, TAE-684, PF02341066 (crizotinib), AF-802, ASP-3026, CEP-37440, CEP-28122, or AP26113; or an inhibitor comprising an antisense molecule, a ribozyme, an RNAi molecule, or a triple helix molecule that hybridizes to the nucleic acid molecule encoding the DCTN1-ALK fusion polypeptide, or a transcription regulatory region that blocks or reduces mRNA expression of the nucleic acid molecule encoding the DCTN1-ALK fusion polypeptide.

21. The method of claim 16, wherein the nucleic acid molecule encoding the DCTN1-ALK fusion polypeptide comprises an in-frame fusion of the nucleotide sequence of one or more of exons 1-26 of DCTN1 of SEQ ID NO: 6 or a fragment thereof, or a nucleotide sequence at least 85% identical thereto, and the nucleotide sequence of one or more of exons 20-29 of ALK of SEQ ID NO: 6 or a fragment thereof, or a nucleotide sequence at least 85% identical thereto.

22. The method of claim 16, wherein the nucleic acid molecule encoding the DCTN1-ALK fusion polypeptide comprises an in-frame fusion of at least the nucleotide sequence of exon 26 of DCTN1 of SEQ ID NO: 6, and at least the nucleotide sequence of exon 20 of ALK of SEQ ID NO: 6.

23. The method of claim 16, wherein the nucleic acid molecule encoding the DCTN1-ALK fusion polypeptide comprises a break point comprising the nucleotide sequence of SEQ ID NO: 5 or a fragment thereof.

24. The method of claim 16, wherein the DCTN1-ALK fusion polypeptide comprises amino acids 1062-1069 or 1116-1362 of the amino acid sequence of SEQ ID NO: 7.

25. A method of treating a subject having an inflammatory myofibroblastic tumor, comprising:

identifying the subject as having a DCTN1-ALK fusion polypeptide or a nucleic acid molecule encoding a DCTN1-ALK fusion polypeptide in said subject;

administering to the identified subject an effective amount of LDK-378, thereby treating the inflammatory myofibroblastic tumor in the subject, wherein the DCTN1-ALK fusion polypeptide comprises the amino acid sequence of SEQ ID NO: 7 or a fragment thereof, or an amino acid sequence at least 85% identical thereto.

26. The method of claim 25, wherein the subject is identified as having the nucleic acid molecule encoding the DCTN1-ALK fusion polypeptide by a sequencing method.

27. The method of claim 25, wherein the nucleic acid molecule encoding the DCTN1-ALK fusion polypeptide comprises an in-frame fusion of the nucleotide sequence of one or more of exons 1-26 of DCTN1 of SEQ ID NO: 6 or a fragment thereof, or a nucleotide sequence at least 85% identical thereto, and the nucleotide sequence of one or more of exons 20-29 of ALK of SEQ ID NO: 6 or a fragment thereof, or a nucleotide sequence at least 85% identical thereto.

28. The method of claim 25, wherein the nucleic acid molecule encoding the DCTN1-ALK fusion polypeptide comprises an in-frame fusion of at least the nucleotide sequence of exon 26 of DCTN1 of SEQ ID NO: 6, and at least the nucleotide sequence of exon 20 of ALK of SEQ ID NO: 6.

29. The method of claim 25, wherein the nucleic acid molecule encoding the DCTN1-ALK fusion polypeptide comprises a break point comprising the nucleotide sequence of SEQ ID NO: 5 or a fragment thereof.

30. The method of claim 25, wherein the DCTN1-ALK fusion polypeptide comprises amino acids 1062-1069 or 1116-1362 of the amino acid sequence of SEQ ID NO: 7.

* * * * *